(12) United States Patent
Gomis et al.

(10) Patent No.: US 9,702,878 B2
(45) Date of Patent: Jul. 11, 2017

(54) METHOD FOR THE PROGNOSIS AND TREATMENT OF CANCER METASTASIS

(71) Applicants: Fundació Institut de Recerca Biomèdica (IRB Barcelona), Barcelona (ES); Institució Catalana de Recerca i Estudis Avançats, Barcelona (ES)

(72) Inventors: Roger Gomis, Barcelona (ES); Milica Pavlovic, Lajkovac (RS); Evarist Planet, Barcelona (ES); Anna Arnal, Barcelona (ES); Maria Tarragona, Barcelona (ES)

(73) Assignees: Fundació Institut de Recera Biomèdica (IRB Barcelona), Barcelona (ES); Institució Catalana de Recerca I Estudis Avançats, Barcelona (ES)

( * ) Notice: Subject to any disclaimer, the term of this patent is extended or adjusted under 35 U.S.C. 154(b) by 0 days.

(21) Appl. No.: 14/391,085

(22) PCT Filed: Mar. 15, 2013

(86) PCT No.: PCT/IB2013/001204
§ 371 (c)(1),
(2) Date: Oct. 7, 2014

(87) PCT Pub. No.: WO2013/153458
PCT Pub. Date: Oct. 17, 2013

(65) Prior Publication Data
US 2015/0293100 A1    Oct. 15, 2015
US 2016/0139126 A9    May 19, 2016

Related U.S. Application Data

(60) Provisional application No. 61/732,175, filed on Nov. 30, 2012, provisional application No. 61/724,807, filed on Nov. 9, 2012, provisional application No. 61/621,949, filed on Apr. 9, 2012.

(30) Foreign Application Priority Data

Apr. 9, 2012    (EP) .................................... 123821399

(51) Int. Cl.
C12Q 1/68      (2006.01)
G01N 33/574    (2006.01)
C07K 16/28     (2006.01)

(52) U.S. Cl.
CPC ..... *G01N 33/5748* (2013.01); *C07K 16/2875* (2013.01); *C12Q 1/6886* (2013.01); *G01N 33/57407* (2013.01); *G01N 33/57415* (2013.01); *C07K 2317/21* (2013.01); *C07K 2317/76* (2013.01); *C12Q 2600/112* (2013.01); *C12Q 2600/118* (2013.01); *C12Q 2600/158* (2013.01); *G01N 2333/4706* (2013.01)

(58) Field of Classification Search
None
See application file for complete search history.

(56) References Cited

U.S. PATENT DOCUMENTS

| | | |
|---|---|---|
| 6,274,338 B1 | 8/2001 | Glimcher et al. |
| 6,740,522 B2 | 5/2004 | Anderson |
| 7,019,028 B2 | 3/2006 | Eder et al. |
| 7,097,834 B1 | 8/2006 | Boyle |
| 7,364,736 B2 | 4/2008 | Boyle et al. |
| 7,411,050 B2 | 8/2008 | Anderson |
| 8,642,270 B2 | 2/2014 | Leyland-Jones et al. |
| 2004/0138313 A1 | 7/2004 | Eder et al. |
| 2005/0181375 A1 | 8/2005 | Aziz et al. |
| 2008/0219996 A1 | 9/2008 | Kalebic et al. |
| 2009/0029378 A1 | 1/2009 | Connelly et al. |
| 2009/0048117 A1 | 2/2009 | Glimcher et al. |
| 2009/0220955 A1 | 9/2009 | Verrant |
| 2010/0113297 A1 | 5/2010 | Lidereau et al. |
| 2011/0130296 A1 | 6/2011 | Benz et al. |

(Continued)

FOREIGN PATENT DOCUMENTS

| | | |
|---|---|---|
| EP | 1 961 825 A1 | 8/2008 |
| EP | 2626431 A2 | 8/2013 |
| EP | 2650682 A1 | 10/2013 |
| WO | WO 00/55126 A2 | 9/2000 |
| WO | WO 01/49288 A1 | 7/2001 |

(Continued)

OTHER PUBLICATIONS

Largo et al (haematologica/the hematology journal, 2006, 91(2): 184-191).*

(Continued)

*Primary Examiner* — Sean Aeder
(74) *Attorney, Agent, or Firm* — Sterne, Kessler, Goldstein & Fox P.L.L.C.

(57) ABSTRACT

The present invention relates to a method for the prognosis of bone metastasis in triple negative (including basal-like) breast cancer or, alternatively, ER+ breast cancer (including luminal A and B) which comprises determining if the c-MAF gene is amplified in a primary tumor sample. Likewise, the invention also relates to a method for determining the tendency to develop bone metastasis with respect to metastasis in other organs, which comprise determining the c-MAF gene expression level, amplification or translocation. The invention also relates to a method for predicting early bone metastasis in a subject suffering breast cancer. The invention also relates to a c-MAF inhibitor as therapeutic agent for use in the treatment of triple negative (including basal-like) breast cancer metastasis or, alternatively, ER+ breast cancer (including luminal A and B) metastasis. The invention relates to kits for predicting bone metastasis and predicting the clinical outcome of a subject suffering from bone metastasis. Finally, the invention relates to a method for typing of a subject suffering breast cancer and for classifying a subject from breast cancer into a cohort.

19 Claims, 22 Drawing Sheets

(56) References Cited

U.S. PATENT DOCUMENTS

| | | |
|---|---|---|
| 2011/0150979 A1 | 6/2011 | Ray et al. |
| 2011/0152113 A1 | 6/2011 | Escudero et al. |
| 2014/0057796 A1 | 2/2014 | Gomis et al. |
| 2014/0105918 A1 | 4/2014 | Gomis et al. |
| 2014/0314792 A1 | 10/2014 | Gomis et al. |
| 2015/0152506 A1 | 6/2015 | Gomis et al. |
| 2015/0293100 A1 | 10/2015 | Gomis et al. |
| 2015/0362495 A1 | 12/2015 | Gomis et al. |
| 2016/0032399 A1 | 2/2016 | Gomis et al. |
| 2016/0032400 A1 | 2/2016 | Gomis et al. |
| 2016/0040247 A1 | 2/2016 | Gomis et al. |

FOREIGN PATENT DOCUMENTS

| | | |
|---|---|---|
| WO | WO 03/020278 A1 | 3/2003 |
| WO | WO 03/020721 A1 | 3/2003 |
| WO | WO 03/059249 A2 | 7/2003 |
| WO | WO 2004/000843 | 12/2003 |
| WO | WO 2004/014888 A1 | 2/2004 |
| WO | WO 2005/046731 A1 | 5/2005 |
| WO | WO 2005/063252 A1 | 7/2005 |
| WO | WO 2005/086891 A2 | 9/2005 |
| WO | WO 2006/012221 A2 | 2/2006 |
| WO | WO 2006/135436 A2 | 12/2006 |
| WO | WO 2008/098351 | 8/2008 |
| WO | WO-2008104543 A2 | 9/2008 |
| WO | WO 2008/142164 A2 | 11/2008 |
| WO | WO-2008145125 A1 | 12/2008 |
| WO | WO 2009/049410 A1 | 4/2009 |
| WO | WO 2009/146546 A1 | 12/2009 |
| WO | WO 2010/000907 A1 | 1/2010 |
| WO | WO 2012/045905 A2 | 4/2012 |
| WO | WO 2013/153458 A2 | 10/2013 |
| WO | WO 2013/182912 A2 | 12/2013 |
| WO | WO 2014/057357 | 5/2014 |
| WO | WO 2014/140933 A2 | 9/2014 |
| WO | WO-2014140896 A2 | 9/2014 |
| WO | WO 2014/184679 A2 | 11/2014 |
| WO | WO-2015052583 A2 | 4/2015 |
| WO | WO-2016092524 A1 | 6/2016 |

OTHER PUBLICATIONS

Al-Mulla, F., et al., "Expressive Genomic Hybridisation: Gene Expression Profiling at the Cytogenetic Level," Journal of Clinical Pathology: Molecular Pathology 56(4):210-217, BMJ Publishing Group, England (2003).

Badve, S., et al. "Basal-like and Triple-negative Breast Cancers: A Critical Review with an Emphasis on the Implications for Pathologists and Oncologists," Modern Pathology 24(2):157-167, USCAP, Inc., United States (2011).

Bogado, C.E., et al., "Denosumab: An Update," Drug of Today 47(8):605-613, Prous Science, United States (2011).

Bohn, O.L., et al., "Biomarker Profile in Breast Carcinomas Presenting with Bone Metastasis," International Journal of Clinical and Experimental Pathology 3(2):139-146, E-Century Publishing Corporation, United States (2010).

Co-Pending Application, U.S. Appl. No. 15/014,916, inventors Gomis, R., et al., filed Feb. 3, 2016 (Not Published).

Co-Pending Application, U.S. Appl. No. 15/027,946, inventors Gomis, R., et al. (Not Published).

Dean-Colomb, W., et al., "Elevated Serum P1NP Predicts Development of Bone Metastasis and Survival in Early-Stage Breast Cancer," Breast Cancer Research and Treatment 137(2):631-636, Springer Science+Business Media, United States (2012).

Extended European Search Report for EP Application No. 12382139.9, European Patent Office, Munich, Germany, dated Sep. 20, 2012, 8 pages.

Fili, S., et al., "Therapeutic Implications of Osteoprotegerin," Cancer Cell International 9:26:1-8, BioMed Central Ltd., England (2009).

Giancotti, V., "Breast Cancer Markers," Cancer Letters, 243(2):145-159, Elsevier Ireland Ltd., Ireland (2006).

Gnant, M., et al., "Adjuvant Bisphosphonates in Endocrine-responsive Breast Cancer: What is their Place in Therapy?" Therapeutic Advances in Medical Oncology 1(3):123-136, Sage, England (2009).

Goss, P.E., and Chambers, A.F., "Does Tumour Dormancy Offer a Therapeutic Target?," Nature Reviews. Cancer 10(12):871-877, Macmillan Publishers Ltd., England (2010).

Henry, D.H., et al., "Randomized, Double-Blind Study of Denosumab Versus Zoledronic Acid in the Treatment of Bone Metastases in Patients with Advanced Cancer (Excluding Breast and Prostate Cancer) or Multiple Myeloma," Journal of Clinical Onocology 29(9):1125-1132 , American Society of Clinical Oncology, United States (2011).

Huang, Q. and Ouyang, X., "Biochemical-Markers for the Diagnosis of Bone Metastasis: A Clinical Review," Cancer Epidemiology 36(1):94-98, Elsevier Ltd., Netherlands (2012).

Hurt, E.M., et al., "Overexpression of c-maf is a Frequent Oncogenic Event in Multiple Myeloma that Promotes Proliferation and Pathological Interactions with Bone Marrow Strome," Cancer Cell 5(2):191-199, Cell Press, United States (2004).

International Preliminary Report on Patentability for International Application No. PCT/IB2014/002675, The International Bureau of WIPO, Geneva, Switzerland, issued Apr. 12, 2016, 12 pages.

International Search Report and Written Opinion for International Application No. PCT/IB2014/002675, European Patent Office, Netherlands, mailed on Jun. 3, 2015, 17 pages.

Kang, Y., et al., "A Multigenic Program Mediating Breast Cancer Metastasis to Bone," Cancer Cell 3(6):537-549, Cell Press, United States (2003).

Kharaishvili, G., et al., "Collagen Triple Helix Repeat Containing 1 Protein, Periostin and Versican in Primary and Metastatic Breast Cancer: An Immunohistochemical Study," Journal of Clinical Pathology 64(11):977-982, BMJ Publishing Group, England (2011).

Klopocki, E. and Mundlos, S., "Copy-number Variations, Noncoding Sequences, and Human Phenotypes," Annual Review of Genomics and Human Genetics 12:53-72, Annual Reviews, United States (2011).

Lipton, A., et al., "The science and practice of bone health in oncology: managing bone loss and metastasis in patients with solid tumors," J Natl Compr Canc Netw 7(Suppl 7):S1-S30, Jones and Bartlett Publishers, United States (2009).

Maisano, R., et al, , "Novel Therapeutic Approaches to Cancer Patients with Bone Metastasis," Critical Reviews in Oncology/Hematology 40(3):239-250, Elsevier Science Ireland Ltd., Ireland (2001).

Mystakidou, K., et al., "Randomized, Open Label, Prospective Study on the Effect of Zoledronic Acid on the Prevention of Bone Metastases in Patients with Recurrent Solid Tumors That Did Not Present with Bone Metastases at Baseline," Medical Oncology 22(2):195-201, Humana Press Inc., United States (2005).

Neville-Webbe H.L. and Coleman R.E., "Bisphosphonates and RANK Ligand Inhibitors for the Treatment and Prevention of Metastatic Bone Disease," European Journal of Cancer 46(7):1211-1222, Elsevier Science Ltd., England (2010).

Washam, C.L., et al., "Identification of PTHrP(12-48) as a Plasma Biomarker Associated with Breast Cancer Bone Metastasis," Cancer Epidemiology, Biomarkers and Prevention 22(5):972-983, American Association for Cancer Research, United States (2013).

Weber-Mangal, S., et al., "Breast Cancer in Young Women (≤35 years): Genomic Aberrations Detected by Comparative Genomic Hybridization," International Journal of Cancer 107(4):583-592, Wiley-Liss, Inc., United States (2003).

Pavlovic, M., et al., "Enhanced MAF Oncogene Expression and Breast Cancer Bone Metastasis," Journal of the National Cancer Institute 107(12):djv256:1-12, Oxford University Press, United States (2015).

Polascik, T.J., "Bisphosphonates in Oncology: Evidence for the Prevention of Skeletal Events in Patients with Bone Metastases," Drug Design, Development and Therapy 3:27-40, Dove Medical Press Ltd., New Zealand (2009).

(56) References Cited

OTHER PUBLICATIONS

Santana-Codina, N., et al., "A Transcriptome-proteome Integrated Network Identifies Endoplasmic Reticulum Thiol Oxidoreductase (ERp57) as a Hub that Mediates Bone Metastasis," Molecular and Cellular Proteomics 12(8):2111-2125, The American Society for Biochemistry and Molecular Biology, Inc., United States (2013).
Sutherland, R.L., et al., "Expression and Regulation of Cyclin Genes in Breast Cancer," Acta Oncologica 34(5):651-656, Scandinavian University Press, England (1995).
Abbott Molecular, "Vysis LSI IGH/MAF Dual Color Dual Fusion Probe," accessed at http://abbottmolecular.com/us/products/analyte-specific-reagent/fish/vysis-lsi-igh-maf-dual-color-dual-fusion-probe.html, accessed on Oct. 16, 2014, 2 pages.
Abnova, "MAF FISH Probe," accessed at http://abnova.com/products/products_detail.asp?sCatalog_id=FA0375, accessed on Oct. 16, 2014, 2 pages.
Afinitor.com, "AFINITOI (everolimus) tablets," accessed at http://alinitor.com/sega-tuberous-sclerosis/patient/sega-information.jsp, accessed on Oct. 16, 2014, 5 pages.
Agilent Technologies, "Probes for Chromosome 16," accessed at http://genomics.agilent.com/productSearch.jsp?chr=16&start=79483700&end=79754340&_requestid=78075, accessed on Oct. 16, 2014, 3 pages.
Altschul, S.F., et al., "Basic Local Alignment Search Tool," J Mol Biol 215:403-410, Academic Press Limited, United States (1990).
Andrews, N.C., et al., "The ubiquitous subunit of erythroid transcription factor NF-E2 is a small basic-leucine zipper protein related to the v-maf oncogene," Proc Natl Acad Sci USA 90:11488-11492, National Academy of Sciences, United States (1993).
Arup Laboratories, "Multiple Myeloma (MM) by FISH: Detection of Prognostically Significant Genomic Aberrations in Multiple Myeloma (MM) by Fluorescence in situ Hybridization (FISH)," accessed at http://aruplab.com, accessed on Oct. 16, 2014, 2 pages.
Barrett, T., et al., "NCBI GEO: mining tens of millions of expression profiles—database and tools update," Nucleic Acids Research 35(Database Issue):D760-D765, Oxford University Press, England (2007).
Baselga. J., et al.,"Everolimus in postmenopausal hormone-receptor-positive advanced breast cancer," N Engl J Med 366(6):520-529, Massachusetts Medical Society, United States (Feb. 2012).
Bertucci, F., et al., "How basal are triple-negative breast cancers?," Int J Cancer 123(1):236-240, Wiley-Liss. Inc., United States (2008).
Bos, P.D., et al., "Genes that mediate breast cancer metastasis to the brain," Nature 459(7249):1005-1009, Nature Publishing Group, England (2009).
Brufsky. A..M., "The evolving role of bone-conserving therapy in patients with breast cancer," Semin Oncol 37(Suppl 1 ):S12-S19, Elsevier Inc., United States (2010).
Cancer Genome Atlas Network, "Comprehensive molecular portraits of human breast tumors," Nature 490(7418):61-70, Nature Publishing Group, England (Oct. 2012).
Carey, L.A., "Triple-negative (basal-like) breast cancer: a new entity," Breast Cancer Research 9(Suppl 1):S13, VII Madrid Breast Cancer Conference: Changes in the treatment of breast cancer, held Jun. 20-22, 2007, BioMed Central Ltd., England (2007).
CGI Italia. "IGH/MAF Two Color, Two Fusion Translocation Probe," accessed at http:// cancergeneticsitalia.com/dna-fish-probe/ighmaf/, accessed on Oct. 16, 2014, 1 page.
Choi, M., et al., "Genetic diagnosis by whole exome capture and massively parallel DNA sequencing," Proc Natl Acad Sci USA 106(45):19096-19101, National Academy of Sciences, United States (2009).
Coleman, R.E., et al., "Breast-Cancer Adjuvant Therapy with Zoledronic Acid," New England Journal of Medicine 365:1396-1405, Massachusetts Medical Society, United States (Oct. 2011).

Creative Bioarray, "Products," accessed at http://creative-bioarray.com/Products.htm, accessed on Oct. 16, 2014, 2 pages.
Curtis, C., et al., "The genomic and transcriptomic architecture of 2,000 breast tumours reveals novel subgroups," Nature 486(7403):346-352, Macmillan Publishers Limited, England (Apr. 2012).
Cytocell, "Oncology and Constitutional FISH Probe Catalogue 2012/2013," accessed at http://zentech.be/uploads/docs/products_info/prenatalogy/cytocell%202012-2013%20catalogue%5B3%5D.pdf, accessed on Oct. 16, 2014, 134 pages.
Dako, "SureFISH Probes," accessed at http://dako.com/us/ar42/psg42806000/baseproducts_surefish.htm?setCountry=true&purl=ar42/psg42806000/baseproducts_surefish.htm?undefined&submit=Accept%20country, accessed on Oct. 16, 2014, 2 pages.
Dannhardt, G. and Kiefer, W., "Cyclooxygenase inhibitors-current status and future prospects," Eur J Med Chem 36(2):109-126, Éditions Scientifiques et Médicales Elsevier SAS, France (2001).
Demarest, J.F., et al., "Update on Aplaviroc: An HIV Entry Inhibitor Targeting CCR5," Retrovirology 2(Suppl 1):S13. BioMed Central, England (2005).
Ettenberg, S.A., et al., "BHQ880, a novel anti-DKK1 neutralizing antibody, inhibits tumor-induced osteolytic bone disease," Proceedings of the American Association for Cancer Research 49:947, Proceedings of the American Association for Cancer Research, United States (2008) (Abstract #3987).
Eychéne, A., et al., "A new MAFia in cancer," Nat Rev Cancer 8(9):683-693, Nature Pub. Group, England (2008).
Fujiwara, K.T., et al., "Two new members of the maf oncogene family, mafK and mafF, encode nuclear b-Zip proteins lacking putative trans-activator domain," Oncogene 8:2371-2380, Macmillan Press Ltd., England (1993).
GenBank Accession No. NG_016440, accessed at https://www.ncbi.nlm.nih.gov/nuccore/NG_016440, accessed on Apr. 3, 2015, 5 pages.
GenBank Accession No. NM_005360.4, accessed as https://www.ncbi.nlm.nih.gov/nuccore/NM_005360.4, accessed on Apr. 3, 2015, 5 pages.
GenBank Accession No. NM_001031804.2, accessed at https://www.ncbi.nlm.nih.gov/nuccore/NM_001031804.2, accessed on Apr. 3, 2015, 6 pages.
GenPept Accession No. NP_005351.2, accessed at https://www.ncbi.nlm.nih.gov/protein/NP_005351.2, accessed on Apr. 3, 2015, 4 pages.
GenPept Accession No. NP_001026974.1, accessed at https://www.ncbi.nlm.nih.gov/protein/NP_001026974.1, accessed on Apr. 3, 2015, 4 pages.
GenBank Database, NCBI Reference Sequence NT_010498, accessed on Jun. 20, 2013, accessed at http://www.ncbi.nlm.nih.gov/nuccore/NT_010498.15.
GenBank Database, NCBI Reference Sequence NT_010542, accessed on Jun. 20, 2013, accessed at http://www.ncbi.nlm.nih.gov/nuccore/NT_010542.15.
GenPept Accession No. O75444.2, accessed at https://www.ncbi.nlm.nih.gov/protein/o75444, accessed on Apr. 3, 2015, 6 pages.
Gene Expression Omnibus Database, Accession No. GSE 2603, made public on Jul. 28, 2005, accessed on Jun. 20, 2013, accessed at http://www.ncbi.nlm.nih.gov/geo/query/acc.cgi?acc=GSE+2603.
Gene Expression Omnibus Database, Accession No. GSE 2034, made public on Feb. 23, 2005, accessed on Jun. 20, 2013, accessed at http://www.ncbi.nlm.nih.gov/geo/query/acc.cgi?acc=GSE+2034.
Gene Expression Omnibus Database, Accession No. GSE 12276, made public on Jun. 13, 2009, accessed on Jun. 20, 2013, accessed at http://www.ncbi.nlm.nih.gov/geo/query/acc.cgi?acc=GSE12276.
Gene Expression Omnibus Database, Accession No. GSE 14020, made public on May 1, 2009, accessed on Jun. 20, 2013, accessed at http://www.ncbi.nlm.nih.gov/geo/query/acc.cgi?acc=GSE14020.
Gentleman, R.C., et al., "Bioconductor: open software development for computational biology and bioinformatics," Genome Biology 5(10):R80, 16 pages, BioMed Central Ltd., England (2005).

(56) References Cited

OTHER PUBLICATIONS

Genycell Biotech, "Fish Mieloma Multiple," accessed at http://google.com/url?sa=t&rct=j&q=&esrc=s&source=web&cd=1&ved=CCQQFjAA&url=http%3A%2F%2Fwww.genycell.es%2Fimages%2Fproductos%2Fbrochures%2Flphmie6_86.ppt&ei=MhFYUOi3GKWH0QGlt4DoDw&usg=AFQjCNEqQMbT8vQGjJbi9riEf31VgoFTFQ&sig2=V5IS8juEMVHB18Mv2Xx...Ww, accessed on Oct. 16, 2014, 1 page.

Gur-Dedeoglu, B., et al., "A resampling-based meta-analysis for detection of differential gene expression in breast cancer," *BMC Cancer* 8(396):16 pages, BioMed Central Ltd., England (2008).

Hammond, M.E.H., et al., "American Society of Clinical Oncology/College of American Pathologists Guideline Recommendations for Immunohistochemical Testing of Estrogen and Progesterone Receptors in Breast Cancer," *Journal of Clinical Oncology* 28(16):2784-2795, American Society of Clinical Oncology, United States (2010).

Hu, G., et al., "MTDH activation by 8q22 genomic gain promotes chemoresistance and metastasis of poor-prognosis breast cancer," *Cancer Cell* 15(1):9-20, Cell Press, United States (2009).

Igarashi, K., et al., Activity and Expression of Murine Small Maf Family Protein MafK, *The Journal of Biological Chemistry* 270(13):7615-7624, The American Society for Biochemistry and Molecular Biology, Inc., United States (1995).

Kataoka, K., et al., "Small Maf proteins heterodimerize with Fos and may act as competitive repressors of the NF-E2 transcription factor," *Mol Cell Biol* 15(4):2180-2190, American Society for Microbiology, United States (1995).

Kataoka, K., et al., "Transactivation activity of Maf nuclear oncoprotein is modulated by Jun, Fos and small Maf proteins," *Oncogene* 12:53-62, Stockton Press, England (1996).

Knight, W.A., et al., "Estrogen Receptor as an Independent Prognostic Factor for Early Recurrence in Breast Cancer," *Cancer Res* 37:4669-4671, American Association for Cancer Research, United States (1977).

Köhler, G. and Milstein, C., "Continuous cultures of fused cells secreting antibody of predefined specificity," *Nature* 256(5517):495-497, Nature Publishing Group, England (1975).

Kuritzkes, D.R., "HIV-1 Entry Inhibitors: An Overview," *Curr Opin HIV AIDS* 4(2):82-87, Lippincott Williams & Wilkins, United States (2009).

Leica Biosystems, "Kreatech™ Fish Probes," accessed at http://leicabiosystems.com/ihc-ish/kreatech-fish-probes/, accessed on Oct. 16, 2014, 2 pages.

MetaSystems, "24XCyte," http://metasystems-international.com/index.php?option=com_joodb&view=article&joobase=5*id=12%3Ad-5029-100-og&Itemid=272, accessed on Oct. 16, 2014, 2 pages.

Ng, P.C. and Kirkness, E.F., "Whole genome sequencing," *Methods Mol Biol* 628:215-226, Springer Science+Business Media, LLC, Netherlands (2010).

Nguyen, D.X. and Massagué, J., "Genetic determinants of cancer metastasis," *Nat Rev Genet* 8(5):341-352, Nature Publishing Group. England (2007).

Nguyen, D.X., et al., "Metastasis: from dissemination to organ-specific colonization," *Nat Rev Cancer* 9(4):274-284, Macmillan Publishers Limited, England (2009).

Pageau, S.C., "Denosumab," *mAbs* 1(3);210-215, Landes Bioscience, United States (2009).

Paik, S., et al.,"A Multigene Assay to Predict Recurrence of Tamoxifen-Treated, Node-Negative Breast Cancer," *The New England Journal of Medicine* 351(27):2817-2826, Massachusetts Medical Society, United States (2004).

Pollack, J.R. et al., "Microarray analysis reveals a major direct role of DNA copy number alteration in the transcriptional program of human breast tumors," *Proc Natl Acad Sci USA* 99(20): 12963-12968, National Academy of Sciences, United States (2002).

Rocques, N., et al.. "GSK-3-mediated phosphorylation enhances Maf-transforming activity," *Mol Cell* 28(4):584-597, Elsevier Inc., United States (2007).

Rojo, F., et al., "Nuclear PARP-1 protein overexpression is associated with poor overall survival in early breast cancer," *Annals of Oncology* 23:1156-1164, Oxford University Press, England (May 2012).

Rotstein, D.M., et al.,"Spiropiperidine CCR5 antagonists," *Bioorganic & Medicinal Chemistry Letters* 19(18):5401-5406, Elsevier Ltd., England (2009).

Sen, B. and Johnson, F.M., "Regulation of Src Family Kinases in Human Cancers," *Journal of Signal Transduction* 2011(865819):1-14, Hindawi Publishing Corporation, United States (Apr. 2011).

Swennenhuis, J.F., et al., "Construction of repeat-free fluorescence in situ hybridization probes," *Nucleic Acids Research* 40(3):e20:1-8, Oxford University Press, England (Feb. 2012).

Théry, C., et al., "Isolation and characterization of exosomes from cell culture supernatants and biological fluids," *Curr Protoc Cell Biol Chapter* 3:3.22.1-3.22.29, John Wiley & Sons, Inc., United States (2006).

Velasco-Veláquez, M., et al., "CCR5 Antagonist Blocks Metastasis of Basal Breast Cancer Cells," *Cancer Res* 72:3839-3850, American Association for Cancer Research, United States (May 2012).

Winer, E.P., et al., "Activity of Cabozantinib (XL184) in Metastatic Breast Cancer (MBC): Results From a Phase 2 Randomized Discontinuation Trial (RDT)," Annual Meeting of the American Society of Clinical Oncology, Chicago, United States (Jun. 1-5, 2012).

Zeiss, "Fish Probes: XL Haematology," accessed at https://microshop.zeiss.com/?440675675dedc6&1=en&p=uk&f=r&i=5000&o=&h=25&n=1&sd=000000-528-231-uk, accessed on Oct. 16, 2014, 3 pages.

Zhang, X.H.F., et al., "Latent bone metastasis in breast cancer tied to Src-dependent survival signals," *Cancer Cell* 16(1):67-78, Elsevier Inc., United States (2009).

Zhou, H., et al, "Updates of mTOR inhibitors," *Anticancer Agents Med Chem* 10(7):571-581, Bentham Science Publishers, Netherlands (2010).

Zometa®, "About Zometa® (zoledronic acid) 4 mg/5mL injection," accessed at http://www.us.zometa.com/index.jsp?usertrack.filter_applied=true&NovaId=29353769344676433633, accessed on Apr. 3, 2015, 2 pages.

International Search Report and the Written Opinion for International Application No. PCT/ES2011/070693, mailed on Apr. 2, 2012, European Patent Office, Netherlands.

International Preliminary Report on Patentability for International Application No. PCT/ES2011/070693, issued on Apr. 9, 2013, The International Bureau of WIPO, Sweden.

International Search Report and Written Opinion for International Patent Application No. PCT/IB2013/001204, European Patent Office, Rijswijk, Netherlands, mailed Dec. 17, 2013.

International Preliminary Report on Patentability for International Patent Application No. PCT/IB2013/001204, European Patent Office, Rijswijk, Netherlands. completed Aug. 11, 2014.

U.S. Appl. No. 61/888,984, filed Oct. 9, 2013, inventors Gomis et al.

U.S. Appl. No. 61/801,769, filed Mar. 15, 2013, inventor Gomis.

Co-Pending Application, U.S. Appl. No. 15/183,419, inventors Gomis, R. et al., filed Jun. 15, 2016 (Not Published).

Extended European Search Report for EP Application No. 15180897.9, European Patent Office, Munich, Germany, mailed Sep. 29, 2016, 9 pages.

Hiraga, T., "Role of Cyclooxygenase-2 in the Bone Metastasis of the Breast Cancer [Nyugan No Honeteni Ni Okeru Shikurookishigenaze-2 No Yakuwari]," *Bone* 20(5):563-566, Japan (2006).

Takahashi, S., "Anti-RANKL Antibody for Treatment of Patients with Bone Metastasis from Breast Cancer," *Jpn J Cancer Chemotherapy* 39(1):89-94, Gan To Kagaku Ryohosha, Tokyo, Japan (2012).

* cited by examiner

SEQUENCE LISTING

```
<160> NUMBER OF SEQ ID NOS: 13

<210> SEQ ID NO 1
<211> LENGTH: 6878
<212> TYPE: DNA
<213> ORGANISM: Homo sapiens

<400> SEQUENCE: 1
agaggcttta aaatcttttt tcatcttcta gctgtagctc gggctgcttg tcggcttggc      60
ctccccctcc cccctttgct ctctgcctcg tctttcccca ggacttcgct attttgcttt     120
tttaaaaaaa ggcaagaaag aactaaactc cccctccct ctcctccagt cgggctgcac      180
ctctgccttg cactttgcac agaggtagag agcgcgcgag ggagagagag gaaagaaaaa     240
aaataataaa gagagccaag cagaagagga ggcgagaagc atgaagtgtt aactccccg      300 tgccaaggcc cgcgccgccc ggacagacgc ccgccgcgcc tccagccccg agcggacgcc     360
gcgcgcgccc tgcctgcagc ccgggccggc gaggcgagcc cttccttatg caaagcgcgc     420
agcggagcgg cgagcggggg acgccgcgca ccgggccggg ctcctccagc ttcgccgccg     480
cagccaccac cgccgccacc gcagctcgcg gaggatcttc ccgagcctga agccgccggc     540
tcggcgcgca aggaggcgag cgagcaagga ggggccgggg cgagcgaggg agcacattgg     600
```

```
cgtgagcagg ggggagggag ggcgggcgcg gggggcgcgg gcagggcggg ggggtgtgtg    660
tgtgagcgcg ctcggaggtt tcgggccagc caccgccgcg caagctagaa gcgcccagc    720 ccggcaagct ggctcacccg ctggccaccc agcacagccc gctggcccct ctcctgcagc    780
ccatctggcg gagcggcggc ggcggcgcg cggcggcag gagaatggca tcagaactgg    840
caatgagcaa ctccgacctg cccaccagtc ccctggccat ggaatatgtt aatgacttcg    900
atctgatgaa gtttgaagtg aaaaaggaac cggtggagac cgaccgcatc atcagccagt    960
gcggccgtct catcgccggg ggctcgctgt cctccacccc catgagcacg ccgtgcagct   1020
cggtgccccc ttcccccagc ttctcggcgc ccagcccggg ctcggcagc gagcagaagg   1080 cgcacctgga agactactac tggatgaccg gctacccgca gcagctgaac cccgaggcgc   1140
tgggcttcag ccccgaggac gcggtcgagg cgctcatcag caacagccac cagctccagg   1200
gcggcttcga tggctacgcg cgcggggcgc agcagctggc cgcggcggcc ggggccggtg   1260
ccggcgcctc cttgggcggc agcggcgagg agatgggccc cgccgccgcc gtggtgtccg   1320
ccgtgatcgc cgcggccgcc gcgcagagcg gcgcgggccc gcactaccac caccaccacc   1380
accacgccgc cggccaccac caccacccga cggccggcgc gccccggcgcc gcgggcagcg   1440 cggccgcctc ggccggtggc gctggggcg cgggcggcg tggcccggcc agcgctgggg   1500
gcggcggcgg cggcggcggc ggcggaggcg gcggggcgc ggcggggcg ggggcgccc   1560 tgcacccgca ccacgccgcc ggcggcctgc acttcgacga ccgcttctcc gacgagcagc   1620
tggtgaccat gtctgtgcgc gagctgaacc ggcagctgcg cggggtcagc aaggaggagg   1680
tgatccggct gaagcagaag aggcggaccc tgaaaaaccg cggctatgcc cagtcctgcc   1740
gcttcaagag ggtgcagcag agacacgtcc tggagtcgga gaagaaccag ctgctgcagc   1800
aagtcgacca cctcaagcag gagatctcca ggctggtgcg cgagagggac gcgtacaagg   1860
agaaatacga gaagttggtg agcagcggct tccgagaaaa cggctcgagc agcgacaacc   1920
cgtcctctcc cgagttttc atgtgagtct gacacgcgat tccagctagc caccctgata   1980
agtgctccgc gggggtccgg ctcgggtgtg gcttgctag ttctagagcc atgctcgcca   2040
ccacctcacc acccccaccc ccaccgagtt tggccccctt ggcccctac acacacacaa   2100 acccgcacgc acacaccaca cacacacaca cacacacaca cacccccac accctgctcg   2160 agtttgtggt ggtggtggct gttttaaact ggggagggaa tgggtgtctg gctcatggat   2220
tgccaatctg aaattctcca taacttgcta gcttgttttt ttttttttt tacacccccc   2280 cgccccaccc ccggacttgc acaatgttca atgatctcag cagagttctt catgtgaaac   2340
gttgatcacc tttgaagcct gcatcattca catattttt cttcttcttc cccttcagtt   2400
catgaactgg tgttcatttt ctgtgtgtgt gtgtgtttta ttttgtttgg atttttttt   2460 ttaattttac ttttagagct tgctgtgttg cccaccttt ttccaacctc cacccctcact   2520 ccttctcaac ccatctcttc cgagatgaaa gaaaaaaaa agcaaagttt tttttcttc   2580 tcctgagttc ttcatgtgag attgagcttg caaaggaaaa aaaatgtga atgttatag   2640 acttgcagcg tgccgagttc catcgggttt ttttttttagc attgttatgc taaatagag   2700 aaaaaaatcc tcatgaacct tccacaatca agcctgcatc aaccttctgg gtgtgacttg   2760
tgagttttgg ccttgtgatg ccaaatctga gagtttagtc tgccattaaa aaaactcatt   2820
ctcatctcat gcattattat gcttgctact ttgtcttagc aacaatgaac tataactgtt   2880
tcaaagactt tatggaaaag agacattata ttaataaaaa aaaaagcct gcatgctgga   2940 catgtatggt ataattattt tttccttttt ttttcctttt ggcttggaaa tggacgttcg   3000
```

```
aagacttata gcatggcatt catacttttg ttttattgcc tcatgacttt tttgagttta  3060
gaacaaaaca gtgcaaccgt agagccttct tcccatgaaa ttttgcatct gctccaaaac  3120
tgctttgagt tactcagaac ttcaacctcc caatgcactg aaggcattcc ttgtcaaaga  3180
taccagaatg ggttacacat ttaacctggc aaacattgaa gaactcttaa tgttttcttt  3240
ttaataagaa tgacgcccca ctttggggac taaaattgtg ctattgccga gaagcagtct  3300
aaaatttatt ttttaaaaag agaaactgcc ccattatttt tggtttgttt tattttattt  3360
ttatatttt  tggcttttgg tcattgtcaa atgtggaatg ctctgggttt ctagtatata  3420
atttaattct agttttttata atctgttagc ccagttaaaa tgtatgctac agataaagga  3480
atgttataga taaatttgaa agagttaggt ctgtttagct gtagatttt  taaacgattg  3540
atgcactaaa ttgttactta ttgtgatgtt aaggggggta gagtttgcaa ggggactgtt  3600
taaaaaagt  agcttataca gcatgtgctt gcaacttaaa tataagttgg gtatgtgtag  3660
tctttgctat accactgact gtattgaaaa ccaaagtatt aagagggaa  acgccctgt   3720
ttatatctgt aggggtattt tacattcaaa aatgtatgtt ttttttcttt ttcaaaatta  3780
aagtatttgg gactgaattg cactaagata taacctgcaa gcatataata caaaaaaaa   3840
ttgcaaaact gtttagaacg ctaataaaat ttatgcagtt ataaaaatgg cattactgca  3900
cagttttaag atgatgcaga tttttttaca gttgtattgt ggtgcagaac tggattttct  3960
gtaacttaaa aaaaaatcca cagttttaaa ggcaataatc agtaaatgtt attttcaggg  4020
actgacatcc tgtctttaaa aagaaatgaa aagtaaatct taccacaata aatataaaaa  4080
aatcttgtca gttactttc  ttttacatat tttgctgtgc aaaattgttt tatatcttga  4140
gttactaact aaccacgcgt gttgttccta tgtgcttttc tttcattttc aattctggtt  4200
atatcaagaa aagaataatc tacaataata acggcatttt ttttttgatt ctgtactcag  4260
tttcttagtg tacagtttaa ctgggcccaa caacctcgtt aaaagtgtaa aatgcatcct  4320
tttctccagt ggaaggattc ctggaggaat agggagacag taattcaggg tgaaattata  4380
ggctgttttt tgaagtgagg aggctggccc catatactga ttagcaatat ttaatataga  4440
tgtaaattat gacctcattt ttttctcccc aaagttttca gttttcaaat gagttgagcc  4500
ataattgccc ttggtaggaa aaacaaaaca aaacagtgga actaggcttc ctgagcatgg  4560
ccctacactt ctgatcagga gcaaagccat ccatagacag aggagccgga caaatatggc  4620
gcatcagagg tggcttgcgc acatatgcat tgaacggtaa agagaaacag cgcttgcctt  4680
ttcactaaag ttgactattt ttccttcttc tcttacacac cgagattttc ttgttagcaa  4740
ggcctgacaa gatttaacat aaacatgaca aatcatagtt gtttgtttg  ttttgctttt   4800
ctctttaaca ctgaagatca tttgtcttaa ataggaaaaa gaaatccac  tccttacttc  4860
catatttcca agtacatatc tggtttaaac tatgttatca aatcatattt caccgtgaat  4920
attcagtgga gaacttctct acctggatga gctagtaatg atttcagatc atgctatccc  4980
cagaaataaa agcaaaaaat aatacctgtg tggaatatag gctgtgcttt gatttactgg  5040
tatttacccc aaaataggct gtgtatgggg gctgacttaa agatcccttg gaaagactca  5100
aaactacctt cactagtagg actcctaagc gctgacctat ttttaaatga cacaaattca  5160
tgaaactaat gttacaaatt catgcagttt gcactcttag tcatcttccc ctagcacacc  5220
aatagaatgt tagacaaagc cagcactgtt ttgaaaatac agccaaacac gatgactttt  5280
gttttgtttt ctgccgttct taaaagaaaa aagataata  ttgcaactct gactgaaaga  5340
cttattttta agaaaacagg ttgtgtttgg tgctgctaag ttctggccag tttatcatct  5400
```

| | |
|---|---|
| ggccttcctg cctatttttt acaaaacacg aagacagtgt gtaacctcga cattttgacc | 5460 |
| ttcctttatg tgctagttta gacaggctcc tgaatccaca cttaattttg cttaacaaaa | 5520 |
| gtcttaatag taaacctccc ctcatgagct tgaagtcaag tgttcttgac ttcagatatt | 5580 |
| tctttccttt tttttttttt ttcctcatca caactaagag atacacaaac tctgaagaag | 5640 |
| cagaaatgga gagaatgctt ttaacaaaaa agcatctgat gaaagatttt aggcaaacat | 5700 |
| tctcaaaata agagtgatat tctggatgta gttattgcag ttatctcatg acaaatgagg | 5760 |
| cctggattgg aaggaaaata tagttgtgta gaattaagca ttttgatagg aatctacaag | 5820 |
| gtagttgaat ataataagca ggtttgggcc cccaactttt agaaaatcaa atgcaaaggt | 5880 |
| gctggcaaaa atgaggtttg agtggctggc tgtaagagaa ggttaactcc tagtaaaagg | 5940 |
| cattttaga aataacaatt actgaaaact ttgaagtata gtgggagtag caaacaaata | 6000 |
| catgtttttt ttttcttaca aagaactcct aaatcctgag taagtgccat tcattacaat | 6060 |
| aagtctctaa atttaaaaaa aaaaaaatca tatgaggaaa tctagctttc ccctttacgc | 6120 |
| tgcgtttgat ctttgtctaa atagtgttaa aattcctttc attccaatta cagaactgag | 6180 |
| cccactcgca agttggagcc atcagtggga tacgccacat tttggaagcc ccagcatcgt | 6240 |
| gtacttacca gtgtgttcac aaaatgaaat ttgtgtgaga gctgtacatt aaaaaaaatc | 6300 |
| atcattatta ttattatttg cagtcatgga gaaccaccta cccctgactt ctgtttagtc | 6360 |
| tccttttaa ataaaaatta ctgtgttaga gaagaaggct attaaatgta gtagttaact | 6420 |
| atgcctcttg tctgggggtt tcatagagac cggtaggaaa gcgcactcct gcttttcgat | 6480 |
| ttatggtgtg tgcaagtaaa caggtgcatt gctttcaacc tgccatacta gttttaaaaa | 6540 |
| ttcactgaaa ttacaaagat acatatatat gcatatatat aatggaaagt ttcccggaat | 6600 |
| gcaacaatta gcatttttaaa atcatatata ggcatgcaca ttctaaatag tacttttca | 6660 |
| tgcttcattg tttctctggc agataatttt actaagaaga aaaatagata ttcgactccc | 6720 |
| cttccctaaa caaatccacg ggcagaggct ccagcggagc cgagcccct ggttttctcg | 6780 |
| taggccctag acggtgttgc atttatcagt gatgtcaaac gtgctcattt gtcagacata | 6840 |
| gctgtaaatg aaaacaatgt gtggcaaaat acaaagtt | 6878 |

<210> SEQ ID NO 2
<211> LENGTH: 2656
<212> TYPE: DNA
<213> ORGANISM: Homo sapiens

<400> SEQUENCE: 2

| | |
|---|---|
| gaggctttaa aatcttttt catcttctag ctgtagctcg ggctgcttgt cggcttggcc | 60 |
| tcccctccc cccttgctc tctgcctcgt ctttccccag gacttcgcta ttttgctttt | 120 |
| ttaaaaaaag gcaagaaaga actaaactcc cccctccctc tcctccagtc gggctgcacc | 180 |
| tctgccttgc actttgcaca gaggtagaga gcgcgcgagg gagagagagg aaagaaaaaa | 240 |
| aataataaag agagccaagc agaagaggag gcagagaagca tgaagtgtta actccccgt | 300 |
| gccaaggccc gcgccgcccg gacagacgcc cgccgcgcct ccagcccga gcggacgccg | 360 |
| cgcgcgccct gcctgcagcc cgggccggcg aggcgagccc ttccttatgc aaagcgcgca | 420 |
| gcggagcggc gagcggggga cgccgcgcac cgggccgggc tcctccagct tcgccgccgc | 480 |
| agccaccacc gccgccaccg cagctcgcgg aggatcttcc cgagcctgaa gccgccggct | 540 |
| cggcgcgcaa ggaggcgagc gagcaaggag gggccggggc gagcgaggga gcacattggc | 600 |
| gtgagcaggg gggagggagg gcgggcgcgg ggggcgcggg cagggcgggg gggtgtgtgt | 660 |

-continued

```
gtgagcgcgc tcggaggttt cgggccagcc accgccgcgc aagctagaag cgccccagcc      720
cggcaagctg gctcacccgc tggccaccca gcacagcccg ctggcccctc tcctgcagcc      780
catctggcgg agcggcggcg gcggcggcgg cggcggcagg agaatggcat cagaactggc      840
aatgagcaac tccgacctgc ccaccagtcc cctggccatg gaatatgtta atgacttcga      900
tctgatgaag tttgaagtga aaaggaacc ggtggagacc gaccgcatca tcagccagtg      960
cggccgtctc atcgccgggg gctcgctgtc ctccacccc atgagcacgc cgtgcagctc     1020
ggtgccccct tcccccagct tctcggcgcc cagcccgggc tcgggcagcg agcagaaggc     1080
gcacctggaa gactactact ggatgaccgg ctacccgcag cagctgaacc ccgaggcgct     1140
gggcttcagc cccgaggacg cggtcgaggc gctcatcagc aacagccacc agctccaggg     1200
cggcttcgat ggctacgcgc gcgggcgca gcagctggcc gcggcggccg gggccggtgc     1260
cggcgcctcc ttgggcggca gcggcgagga gatgggcccc gccgccgccg tggtgtccgc     1320
cgtgatcgcc gcggccgccg cgcagagcgg cgcgggcccg cactaccacc accaccacca     1380
ccacgccgcc ggccaccacc acacccgac ggccggcgcg cccggcgccg cgggcagcgc     1440
ggccgcctcg gccggtggcg ctgggggcgc gggcggcggt ggcccggcca gcgctggggg     1500
cggcggcggc ggcggcggcg gcggaggcgg cggggcgcg gcggggcgg ggggcgccct     1560
gcacccgcac cacgccgccg gcggcctgca cttcgacgac cgcttctccg acgagcagct     1620
ggtgaccatg tctgtgcgcg agctgaaccg gcagctgcgc ggggtcagca aggaggaggt     1680
gatccggctg aagcagaaga ggcggaccct gaaaaaccgc ggctatgccc agtcctgccg     1740
cttcaagagg gtgcagcaga gacacgtcct ggagtcggag aagaaccagc tgctgcagca     1800
agtcgaccac ctcaagcagg agatctccag gctggtgcgc gagagggacg cgtacaagga     1860
gaaatacgaa aagttggtga gcagcggctt ccgagaaaac ggctcgagca gcgacaaccc     1920
gtcctctccc gagttttca taactgagcc cactcgcaag ttggagccat cagtgggata     1980
cgccacattt tggaagcccc agcatcgtgt acttaccagt gtgttcacaa atgaaatt      2040
gtgtgagagc tgtacattaa aaaaaatcat cattattatt attattgca gtcatggaga     2100
accacctacc cctgacttct gtttagtctc cttttaaat aaaaattact gtgttagaga     2160
agaaggctat taaatgtagt agttaactat gcctcttgtc tgggggtttc atagagaccg     2220
gtaggaaagc gcactcctgc ttttcgattt atggtgtgtg caagtaaaca ggtgcattgc     2280
tttcaacctg ccatactagt tttaaaaatt cactgaaatt acaaagatac atatatatgc     2340
atatatataa tggaaagttt cccggaatgc aacaattagc attttaaaat catatatagg     2400
catgcacatt ctaaatagta ctttttcatg cttcattgtt tctctggcag ataattttac     2460
taagaagaaa aatagatatt cgactcccct tccctaaaca aatccacggg cagaggctcc     2520
agcggagccg agcccctgg ttttctcgta ggccctagac ggtgttgcat ttatcagtga     2580
tgtcaaacgt gctcatttgt cagacatagc tgtaaatgaa acaatgtgt ggcaaaatac     2640
aaagttaaaa aaaaaa                                                     2656
```

<210> SEQ ID NO 3
<211> LENGTH: 6887
<212> TYPE: DNA
<213> ORGANISM: Homo sapiens

<400> SEQUENCE: 3

```
gaggctttaa aatctttttt catcttctag ctgtagctcg gctgcttgt cggcttggcc       60
tcccctccc cctttgctc tctgcctcgt cttccccag gacttcgcta ttttgctttt      120
```

| | |
|---|---|
| ttaaaaaag gcaagaaaga actaaactcc ccctccctc tcctccagtc gggctgcacc | 180 |
| tctgccttgc actttgcaca gaggtagaga gcgcgcgagg gagagagagg aaagaaaaaa | 240 |
| aataataaag agagccaagc agaagaggag gcgagaagca tgaagtgtta actccccgt | 300 |
| gccaaggccc gcgccgcccg gacagacgcc cgccgcgcct ccagcccga gcggacgccg | 360 |
| cgcgcgccct gcctgcagcc cgggccggcg aggcgagccc ttccttatgc aaagcgcgca | 420 |
| gcggagcggc gagcggggga cgccgcgcac cgggccgggc tcctccagct tcgccgccgc | 480 |
| agccaccacc gccgccaccg cagctcgcgg aggatcttcc cgagcctgaa gccgccggct | 540 |
| cggcgcgcaa ggaggcgagc gagcaaggag gggccggggc gagcgaggga gcacattggc | 600 |
| gtgagcaggg gggagggagg gcgggcgcgg ggggcgcggg cagggcgggg gggtgtgtgt | 660 |
| gtgagcgcgc tcggaggttt cgggccagcc accgccgcgc aagctagaag cgccccagcc | 720 |
| cggcaagctg gctcacccgc tggccaccca gcacagcccg ctggcccctc tcctgcagcc | 780 |
| catctggcgg agcggcggcg gcggcggcgg cggcggcagg agaatggcat cagaactggc | 840 |
| aatgagcaac tccgacctgc ccaccagtcc cctggccatg gaatatgtta atgacttcga | 900 |
| tctgatgaag tttgaagtga aaaggaacc ggtggagacc gaccgcatca tcagccagtg | 960 |
| cggccgtctc atcgccgggg gctcgctgtc ctccaccccc atgagcacgc cgtgcagctc | 1020 |
| ggtgcccct tccccagct tctcggcgcc cagcccgggc tcgggcagcg agcagaaggc | 1080 |
| gcacctggaa gactactact ggatgaccgg ctacccgcag cagctgaacc ccgaggcgct | 1140 |
| gggcttcagc cccgaggacg cggtcgaggc gctcatcagc aacagccacc agctccaggg | 1200 |
| cggcttcgat ggctacgcgc gcggggcgca gcagctggcc gcggcggccg gggccggtgc | 1260 |
| cggcgcctcc ttgggcggca gcggcgagga gatgggcccc gccgcgccg tggtgtccgc | 1320 |
| cgtgatcgcc gcggccgccg cgcagagcgg cgcgggcccg cactaccacc accaccacca | 1380 |
| ccacgccgcc ggccaccacc accacccgac ggccggcgcg cccggcgccg cgggcagcgc | 1440 |
| ggccgcctcg gccggtggcg ctgggggcgc gggcggcggt ggcccggcca gcgctggggg | 1500 |
| cggcggcggc ggcggcggcg gcggaggcgg cggggcgcg gcggggcgg ggggcgccct | 1560 |
| gcacccgcac cacgccgccg gcggcctgca cttcgacgac cgcttctccg acgagcagct | 1620 |
| ggtgaccatg tctgtgcgcg agctgaaccg gcagctgcgc ggggtcagca aggaggaggt | 1680 |
| gatccggctg aagcagaaga gcggaccct gaaaaaccgc ggctatgccc agtcctgccg | 1740 |
| cttcaagagg gtgcagcaga gacacgtcct ggagtcggag aagaaccagc tgctgcagca | 1800 |
| agtcgaccac ctcaagcagg agatctccag gctggtgcgc gagagggacg cgtacaagga | 1860 |
| gaaatacgag aagttggtga gcagcggctt ccgagaaaac ggctcgagca gcgacaaccc | 1920 |
| gtcctctccc gagttttca tgtgagtctg acacgcgatt ccagctagcc accctgataa | 1980 |
| gtgctccgcg ggggtccggc tcgggtgtgg gcttgctagt tctagagcca tgctcgccac | 2040 |
| cacctcacca ccccaccccc caccgagttt ggccccttg gccccctaca cacacacaaa | 2100 |
| cccgcacgca cacaccacac acacacacac acacacacac acaccccaca ccctgctcga | 2160 |
| gtttgtggtg gtggtggctg ttttaaactg gggagggaat gggtgtctgg ctcatggatt | 2220 |
| gccaatctga aattctccat aacttgctag cttgttttt ttttttttt acaccccccc | 2280 |
| gccccacccc cggacttgca caatgttcaa tgatctcagc agagttcttc atgtgaaacg | 2340 |
| ttgatcacct ttgaagcctg catcattcac atatttttc ttcttcttcc ccttcagttc | 2400 |
| atgaactggt gttcatttc tgtgtgtgtg tgtgttttat tttgtttgga ttttttttt | 2460 |
| taatttact tttagagctt gctgtgttgc ccaccttttt tccaacctcc ccctcactc | 2520 |

```
cttctcaacc catctcttcc gagatgaaag aaaaaaaaaa gcaaagttttt ttttcttct      2580
cctgagttct tcatgtgaga ttgagcttgc aaaggaaaaa aaaatgtgaa atgttataga      2640
cttgcagcgt gccgagttcc atcgggtttt tttttagca ttgttatgct aaaatagaga      2700
aaaaaatcct catgaacctt ccacaatcaa gcctgcatca accttctggg tgtgacttgt      2760
gagttttggc cttgtgatgc caaatctgag agtttagtct gccattaaaa aaactcattc      2820
tcatctcatg cattattatg cttgctactt tgtcttagca acaatgaact ataactgttt      2880
caaagacttt atggaaaaga acattatat taataaaaaa aaaaagcctg catgctggac       2940
atgtatggta taattatttt ttcctttttt tttccttttg cttggaaat ggacgttcga       3000
agacttatag catggcattc atactttgt tttattgcct catgactttt ttgagtttag       3060
aacaaaacag tgcaaccgta gagccttctt cccatgaaat tttgcatctg ctccaaaact      3120
gctttgagtt actcagaact tcaacctccc aatgcactga aggcattcct tgtcaaagat      3180
accagaatgg gttacacatt taacctggca aacattgaag aactcttaat gttttctttt     3240
taataagaat gacgcccac tttggggact aaaattgtgc tattgccgag aagcagtcta      3300
aaatttattt tttaaaaaga gaaactgccc cattattttt ggtttgtttt atttttattt     3360
tatattttt ggcttttggt cattgtcaaa tgtggaatgc tctgggtttc tagtatataa      3420
tttaattcta gttttataa tctgttagcc cagttaaaat gtatgctaca gataaaggaa      3480
tgttatagat aaatttgaaa gagttaggtc tgtttagctg tagattttt aaacgattga      3540
tgcactaaat tgtttactat tgtgatgtta aggggggtag agtttgcaag gggactgttt      3600
aaaaaaagta gcttatacag catgtgcttg caacttaaat ataagttggg tatgtgtagt      3660
ctttgctata ccactgactg tattgaaaac caaagtatta agagggggaa cgcccctgtt      3720
tatatctgta ggggtatttt acattcaaaa atgtatgttt tttttctttt tcaaaattaa     3780
agtatttggg actgaattgc actaagatat aacctgcaag catataatac aaaaaaaaat    3840
tgcaaaactg tttagaacgc taataaaatt tatgcagtta taaaaatggc attactgcac     3900
agttttaaga tgatgcagat tttttacag ttgtattgtg gtgcagaact ggattttctg      3960
taacttaaaa aaaaatccac agttttaaag gcaataatca gtaaatgtta ttttcaggga    4020
ctgacatcct gtctttaaaa agaaatgaaa agtaaatctt accacaataa atataaaaaa    4080
atcttgtcag ttacttttct tttacatatt ttgctgtgca aaattgtttt atatcttgag     4140
ttactaacta accacgcgtg ttgttcctat gtgcttttct ttcattttca attctggtta    4200
tatcaagaaa agaataatct acaataataa acggcatttt ttttgattc tgtactcagt     4260
ttcttagtgt acagtttaac tgggcccaac aacctcgtta aaagtgtaaa atgcatcctt    4320
ttctccagtg gaaggattcc tggaggaata gggagacagt aattcagggt gaaattatag    4380
gctgtttttt gaagtgagga ggctggcccc atatactgat tagcaatatt taatatagat    4440
gtaaattatg acctcatttt tttctcccca aagtttcag ttttcaaatg agttgagcca     4500
taattgccct tggtaggaaa aacaaaacaa aacagtggaa ctaggcttcc tgagcatggc    4560
cctacacttc tgatcaggag caaagccatc catagacaga ggagccggac aaatatggcg    4620
catcagaggt ggcttgcgca catatgcatt gaacggtaaa gagaaacagc gcttgccttt    4680
tcactaaagt tgactatttt tccttcttct cttacacacc gagattttct tgttagcaag    4740
gcctgacaag atttaacata aacatgacaa atcatagttg tttgttttgt tttgcttttc    4800
tctttaacac tgaagatcat ttgtcttaaa taggaaaaag aaaatccact ccttacttcc    4860
atatttccaa gtacatatct ggtttaaact atgttatcaa atcatatttc accgtgaata    4920
```

```
ttcagtggag aacttctcta cctggatgag ctagtaatga tttcagatca tgctatcccc    4980
agaaataaaa gcaaaaaata ataccctgtgt ggaatatagg ctgtgctttg atttactggt    5040
atttacccca aaataggctg tgtatggggg ctgacttaaa gatcccttgg aaagactcaa    5100
aactaccttc actagtagga ctcctaagcg ctgacctatt tttaaatgac acaaattcat    5160
gaaactaatg ttacaaattc atgcagtttg cactcttagt catcttcccc tagcacacca    5220
atagaatgtt agacaaagcc agcactgttt tgaaaataca gccaaacacg atgacttttg    5280
ttttgttttc tgccgttctt aaaagaaaaa aagataatat tgcaactctg actgaaagac    5340
ttatttttaa gaaaacaggt tgtgtttggt gctgctaagt tctggccagt ttatcatctg    5400
gccttcctgc ctattttta caaaacacga agacagtgtg taacctcgac attttgacct    5460
tcctttatgt gctagtttag acaggctcct gaatccacac ttaattttgc ttaacaaaag    5520
tcttaatagt aaacctcccc tcatgagctt gaagtcaagt gttcttgact tcagatattt    5580
ctttcctttt ttttttttt tcctcatcac aactaagaga tacacaaact ctgaagaagc    5640
agaaatggag agaatgcttt taacaaaaaa gcatctgatg aaagatttta ggcaaacatt    5700
ctcaaaataa gagtgatatt ctggatgtag ttattgcagt tatctcatga caaatgaggc    5760
ctggattgga aggaaaatat agttgtgtag aattaagcat tttgatagga atctacaagg    5820
tagttgaata taataagcag gtttgggccc ccaaacttta gaaaatcaaa tgcaaggtg    5880 ctggcaaaaa tgaggtttga gtggctggct gtaagagaag gttaactcct agtaaaggc    5940 atttttagaa ataacaatta ctgaaaactt tgaagtatag tgggagtagc aaacaaatac    6000 atgtttttt tttcttacaa agaactccta aatcctgagt aagtgccatt cattacaata    6060
agtctctaaa tttaaaaaaa aaaaaatcat atgaggaaat ctagctttcc cctttacgct    6120
gcgtttgatc tttgtctaaa tagtgttaaa attccttca ttccaattac agaactgagc    6180
ccactcgcaa gttggagcca tcagtgggat acgccacatt ttggaagccc cagcatcgtg    6240
tacttaccag tgtgttcaca aaatgaaatt tgtgtgagag ctgtacatta aaaaaaatca    6300
tcattattat tattatttgc agtcatggag aaccacctac ccctgacttc tgtttagtct    6360 ccttttaaa taaaaattac tgtgttagag aagaaggcta ttaaatgtag tagttaacta    6420
tgcctcttgt ctgggggttt catagagacc ggtaggaaag cgcactcctg cttttcgatt    6480
tatggtgtgt gcaagtaaac aggtgcattg ctttcaacct gccatactag tttaaaaat    6540 tcactgaaat tacaaagata catatatatg catatatata atggaaagtt tcccggaatg    6600
caacaattag catttaaaaa tcatatatag gcatgcacat tctaaatagt actttttcat    6660
gcttcattgt ttctctggca gataattta ctaagaagaa aaatagatat tcgactcccc    6720
ttccctaaac aaatccacgg gcagaggctc cagcggagcc gagcccctg gttttctcgt    6780 aggccctaga cggtgttgca tttatcagtg atgtcaaacg tgctcatttg tcagacatag    6840
ctgtaaatga aacaatgtg tggcaaaata caaagttaaa aaaaaa           6887
```

<210> SEQ ID NO 4
<211> LENGTH: 403
<212> TYPE: PRT
<213> ORGANISM: Homo sapiens

<400> SEQUENCE: 4

```
Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
            20                  25                  30
```

```
Lys Lys Glu Pro Val Glu Thr Asp Arg Ile Ile Ser Gln Cys Gly Arg
             35                  40                  45

Leu Ile Ala Gly Gly Ser Leu Ser Ser Thr Pro Met Ser Thr Pro Cys
 50                  55                  60

Ser Ser Val Pro Pro Ser Pro Ser Phe Ser Ala Pro Ser Pro Gly Ser
 65                  70                  75                  80

Gly Ser Glu Gln Lys Ala His Leu Glu Asp Tyr Tyr Trp Met Thr Gly
                 85                  90                  95

Tyr Pro Gln Gln Leu Asn Pro Glu Ala Leu Gly Phe Ser Pro Glu Asp
                100                 105                 110

Ala Val Glu Ala Leu Ile Ser Asn Ser His Gln Leu Gln Gly Gly Phe
            115                 120                 125

Asp Gly Tyr Ala Arg Gly Ala Gln Gln Leu Ala Ala Ala Ala Gly Ala
            130                 135                 140

Gly Ala Gly Ala Ser Leu Gly Gly Ser Gly Glu Glu Met Gly Pro Ala
145                 150                 155                 160

Ala Ala Val Val Ser Ala Val Ile Ala Ala Ala Ala Ala Gln Ser Gly
                165                 170                 175

Ala Gly Pro His Tyr His His His His His His Ala Ala Gly His His
                180                 185                 190

His His Pro Thr Ala Gly Ala Pro Gly Ala Ala Gly Ser Ala Ala Ala
            195                 200                 205

Ser Ala Gly Gly Ala Gly Gly Ala Gly Gly Gly Pro Ala Ser Ala
            210                 215                 220

Gly Gly Gly Gly Gly Gly Gly Gly Gly Gly Gly Gly Gly Gly Ala Ala
225                 230                 235                 240

Gly Ala Gly Gly Ala Leu His Pro His His Ala Ala Gly Gly Leu His
                245                 250                 255

Phe Asp Asp Arg Phe Ser Asp Glu Gln Leu Val Thr Met Ser Val Arg
            260                 265                 270

Glu Leu Asn Arg Gln Leu Arg Gly Val Ser Lys Glu Glu Val Ile Arg
            275                 280                 285

Leu Lys Gln Lys Arg Arg Thr Leu Lys Asn Arg Gly Tyr Ala Gln Ser
            290                 295                 300

Cys Arg Phe Lys Arg Val Gln Gln Arg His Val Leu Glu Ser Glu Lys
305                 310                 315                 320

Asn Gln Leu Leu Gln Gln Val Asp His Leu Lys Gln Glu Ile Ser Arg
                325                 330                 335

Leu Val Arg Glu Arg Asp Ala Tyr Lys Glu Lys Tyr Glu Lys Leu Val
            340                 345                 350

Ser Ser Gly Phe Arg Glu Asn Gly Ser Ser Ser Asp Asn Pro Ser Ser
            355                 360                 365

Pro Glu Phe Phe Ile Thr Glu Pro Thr Arg Lys Leu Glu Pro Ser Val
            370                 375                 380

Gly Tyr Ala Thr Phe Trp Lys Pro Gln His Arg Val Leu Thr Ser Val
385                 390                 395                 400

Phe Thr Lys

<210> SEQ ID NO 5
<211> LENGTH: 373
<212> TYPE: PRT
<213> ORGANISM: Homo sapiens
```

```
<400> SEQUENCE: 5

Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
            20                  25                  30

Lys Lys Glu Pro Val Glu Thr Asp Arg Ile Ile Ser Gln Cys Gly Arg
        35                  40                  45

Leu Ile Ala Gly Gly Ser Leu Ser Ser Thr Pro Met Ser Thr Pro Cys
    50                  55                  60

Ser Ser Val Pro Pro Ser Pro Ser Phe Ser Ala Pro Ser Pro Gly Ser
65                  70                  75                  80

Gly Ser Glu Gln Lys Ala His Leu Glu Asp Tyr Tyr Trp Met Thr Gly
                85                  90                  95

Tyr Pro Gln Gln Leu Asn Pro Glu Ala Leu Gly Phe Ser Pro Glu Asp
            100                 105                 110

Ala Val Glu Ala Leu Ile Ser Asn Ser His Gln Leu Gln Gly Gly Phe
        115                 120                 125

Asp Gly Tyr Ala Arg Gly Ala Gln Gln Leu Ala Ala Ala Gly Ala
    130                 135                 140

Gly Ala Gly Ala Ser Leu Gly Gly Ser Gly Glu Glu Met Gly Pro Ala
145                 150                 155                 160

Ala Ala Val Val Ser Ala Val Ile Ala Ala Ala Ala Gln Ser Gly
                165                 170                 175

Ala Gly Pro His Tyr His His His His His Ala Ala Gly His His
            180                 185                 190

His His Pro Thr Ala Gly Ala Pro Gly Ala Ala Gly Ser Ala Ala Ala
            195                 200                 205

Ser Ala Gly Gly Ala Gly Ala Gly Gly Gly Pro Ala Ser Ala
210                 215                 220

Gly Gly Gly Gly Gly Gly Gly Gly Gly Gly Gly Gly Ala Ala
225                 230                 235                 240

Gly Ala Gly Gly Ala Leu His Pro His His Ala Ala Gly Gly Leu His
            245                 250                 255

Phe Asp Asp Arg Phe Ser Asp Glu Gln Leu Val Thr Met Ser Val Arg
            260                 265                 270

Glu Leu Asn Arg Gln Leu Arg Gly Val Ser Lys Glu Glu Val Ile Arg
        275                 280                 285

Leu Lys Gln Lys Arg Arg Thr Leu Lys Asn Arg Gly Tyr Ala Gln Ser
    290                 295                 300

Cys Arg Phe Lys Arg Val Gln Gln Arg His Val Leu Glu Ser Glu Lys
305                 310                 315                 320

Asn Gln Leu Leu Gln Gln Val Asp His Leu Lys Gln Glu Ile Ser Arg
                325                 330                 335

Leu Val Arg Glu Arg Asp Ala Tyr Lys Glu Lys Tyr Glu Lys Leu Val
            340                 345                 350

Ser Ser Gly Phe Arg Glu Asn Gly Ser Ser Ser Asp Asn Pro Ser Ser
        355                 360                 365

Pro Glu Phe Phe Met
    370

<210> SEQ ID NO 6
<211> LENGTH: 19
<212> TYPE: RNA
<213> ORGANISM: Artificial Sequence
```

<220> FEATURE:
<223> OTHER INFORMATION: c-MAF specific siRNA

<400> SEQUENCE: 6
acggcucgag cagcgacaa                                         19

<210> SEQ ID NO 7
<211> LENGTH: 19
<212> TYPE: RNA
<213> ORGANISM: Artificial Sequence
<220> FEATURE:
<223> OTHER INFORMATION: c-MAF specific siRNA

<400> SEQUENCE: 7
cuuaccagug uguucacaa                                         19

<210> SEQ ID NO 8
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 8
uggaagacua cuacuggaug                                        20

<210> SEQ ID NO 9
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 9
auuugcaguc auggagaacc                                        20

<210> SEQ ID NO 10
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 10
caaggagaaa uacgagaagu                                        20

<210> SEQ ID NO 11
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 11
acaaggagaa auacgagaag                                        20

<210> SEQ ID NO 12
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 12
accuggaaga cuacuacugg                                        20

```
<210> SEQ ID NO 13
<211> LENGTH: 13878
<212> TYPE: DNA
<213> ORGANISM: Homo sapiens

<400> SEQUENCE: 13
aactatatat taaacacctc cggtctgaga ggccgtgttg ggtgtctttg tcaggtgaag      60
aaagagaaga aggctggtac accttcccag gaattctcac tgaagaaaac atctggattt     120
tttacatctc ttgtgcaaaa caacaaaga tttcattaag tgatgtatat tgttttccaa      180
ggaagaaacc tgcagagaca aaacaaata agcaaataat tgaaacaaaa atatgataaa      240
cccccaaatt cttccagtgc taatttactt gttatcatgg ttctctacaa aggcagagat     300
cactaattac aggttttttcc agaattcaca tttcacgtca agatcatcca atccaaacag    360
tgtacggaaa gcctagggcc ttcttcactt tgccccctac cccacccta cacacgccc      420 ccatctaaat gatacccttg gaaagaaacc tacacatctc atttgtctat attttgcttc     480
ctccctcgcc tcccggtaac caaatgtgag ttgttctcta actgcactgg agaatcagaa     540
tttattgtac atatgtttgt gttccactta ataaaaaaac ctatatttta agataaactt     600
tgttagtaat tcatgaggta agtgactatt tatgctaatc aggcagaaat atattctcaa     660
gcataatgca ttacataaat ttgaatgtaa aatgttcaat tatgaagtaa atacaggtaa     720
tgcaaataat aaattacctc taataaaaat tataaaagat gtgccttgaa agagagagcg     780
gctttaactt acaactgtga attgcttaaa gagaaaagaa ttaataaatg ctgaattact     840
ctgatgatta tttagcacat aattcaccta ttcataacga ctcctagtaa tcagactgtt     900
gtttcacatc ctccaacatg aggcaagact gtttcctcag caattttgcc cttatcagat     960
tatctcgtct gattctatta attttcttcc atgaatctgc taacagtgat ttgtgattta    1020
cttaccctgc taactgaaga ctgttaaaag gatttatcta acactggacc taagaacagt    1080
gtacgcctta tcgttcagtt actctgaaga actctttctc aaatcaattt agttggtttc    1140
atagtgaaat ttagtggaca ctggttagtt ctgccccata aaatcagccc ctaaacaaag    1200
agtccagaca ccatacctga tgcatcccat tctattcaga ttatggatgt ctgattccaa    1260
catgatatat ttgagttgct ataactcaca atcggggaaa atatattcct ttaagctttt    1320
aatctttgta atttggacat gaacagggt tttgttttc atttttgcat gaagtcatta     1380
tgtatgtact gacgtgaaac tataattgtg tttctgatgt tactgtgtca caatattcta    1440
tgcgatgtaa cccatgtcct cctcccctc acaaatctcc tataaatatt cattgctttc    1500
aaaaacttta atactactgg tccgaattgg tcaataatga caaatgcatg gtttctaaat    1560
tactgtatat tgttctacag agattactag agtatatata gcaaggggat gttaagcagt    1620
aagaaaacac agttcacatt gtatttggat tagattggct tggatagaag tgaaacaaac    1680
aatgttagca aagaagtcta aagacatgtg gcccactgta attgtacaga atcaaaaacc    1740
tgaatagtac tcattaaaat gagagagctc aattgttata aaagaaatgc tgctaacaga    1800
gaactgtaaa tgtttagaca cccctgtgaa tcactaaata ataatgtaaa aaggataaaa    1860
atgagaatta agttataagc ctgagagcat tactgctaca catctaaaaa aataattctg    1920
atcctctctt ttttttttcc aagagaaaat gggcgactat aaaagacctt gcaataagag    1980
aaataaaaat accatgtctt cacagcagtg tacataaata aaccataaaa atgtgcagat    2040
aataatatat ttagctgccc aaacatgggc atttaatttc tagaaatgat atataacaat    2100
gtaacaatta gatactcagc catgaatgtg tatggcacag tcttcatcat tagcaaactt    2160
```

```
tgtgtataaa atattattta ttatttatta taatactgct ttcagaggca atgatcatac    2220
cttacagctt ttaacacaaa tatgatgcaa aaggattaaa agtatatcat aaacaaacaa    2280
taaattcttt ctaaatacac ttaaattcat attttacatg aaaaatataa acttcctaca    2340
tttgtgacta ctgactttta aaaagaccta gaaaactatt gttacgggca atgttaaatg    2400
acataatgct tatgtaatgg aaagtgtgga ttttcctcta aataaactat aatcccttaa    2460
cttcattact agggaaaata ttgttaaaga gaaggaaagc aagggaattc tgctaggttg    2520
cataaatatt gacataatct tcactctttc ttccccaaac tggtaataga catagtttat    2580
tccacccaac aaaatgctct tataagacca aaactaccct tattaacaac ttctctgcag    2640
tcacgatgaa aagaaacact acttgtctga aaaataccga cagcgctgcc cttttcagat    2700
tagggtgtgc ctacgaatct tttgggaagt cttccattaa ggattcctgg gtttgctgaa    2760
actgaagtct actaggatca gagaaattaa cacaggtcta atatggtgca aggaacgagt    2820
gagagacacc tgaggttata aatagcaaag catgctgcgg ggtggggaag accattctga    2880
agtgcaatgt tcaagacgct ggcttaatat atgactaagt gtcagaagtc aggttttctg    2940
agaattactt tccagataaa caactttata gcactgcact taatcttact tactagagac    3000
atctcattta tcactgaatt acaagtaact ttaatcctat tgatattgcc ataaagcccg    3060
ttgaaaatcc atcctggcac ttttaaaggg tttggggccc tgttacatgg ggatcctctt    3120
gcaaggtctc cagccagaaa ttacaccccg agggtgtctg tatccctggg cctctttgtc    3180
aacaatcaag gagaagagga ggggcaaaaa tgatctctgc atctgccagc actttcttcg    3240 gccccttttcc tatagggtcg ggttctccca cttcagtcaa actaactttg tgtgtctctt    3300
tcctcctccc acactgggta accagctgct tttcacttca tcgacaaaac tggacacgga    3360
tcaatttcaa ctgacctttg ccgaaaggtg gcgctgttga ggtaaaaacc aactcgctcc    3420
aacaatagtt tccactcttc gatccttttg caggcttttc agaattttttt tttttttta    3480 atgcaccctc ctagcgtctc cccttctca taaagtaaaa taaatacgat aaaaacacc     3540 aaatgcattt cattaattga aggaatcaac agtcccaact tctaagcaga cgggctggtc    3600
ttccaaaggc tgggtcggtt tcaggagctt tctctccaaa taaatctctg cttcttcgac    3660
ttgcctatcg ctttaaaatc ttagaaacag agttagttgt tggtttcctt cttttttctt    3720 tttcttttt atttctttttt tgcataaact tttagagaat caatctagaa atttgaacta    3780
cttattagca tttgcaactg ggggtggggg gagcagcctc cccaccccca cccccactc    3840 tgcgtttccg gactagttcc agaaaccgcg gtttaaaatt taaccccttcg agggtagctg    3900 gtgagggctg gggtattgtt tttcccccctt gctccctgcc acgatcaagt ccgaaataat    3960
taaaggaaac gtaaaagtgc aaaggggcgcg cctgaccctg ataaacagag gtcagatttc    4020
gtaaggggac gggtgagtgt gagtgtgtgt gtgtttgtgt gtgtgtgtgt aagagagaga    4080
gagagcgagc gcgcaatatg agtctcaaag gccaaactcc ggccagtcag gagcgggaag    4140
gctgagcccg gctgacctga ctttgagctt ccccggagtt atctcgcata ggcgctcgct    4200
ctgtccaagg gcacgcgacg ccagcgggca gccggtctcc gtgaagaatg gcctctaaac    4260
aacttatttt acctcgttgt aaagagaggg ataaaatggg cttttccctct ccacggatgc    4320 ccagccttct gggcaggcgc atggccgggc ggcgcccagc ccgcagcccc gatccggaca    4380
ccccactgca tccctccctt cccggtccct tcccgcacg ggcgcccgag agacggacaa     4440
agagttgggg ccaagtttga gcgccgggca cggccaggct cagggaagga aggtccccgg    4500
cagacacctg ggtaccagag ttggtgcgag gaggaaaagc tgggaggcga attcacaatc    4560
```

```
ctggggtgg aggcaggca ggggaggga atcaggccaa tcccagccga gtgagcccc      4620
agcgagctgg ggctccggat gggaggcctg tctcgcgctc caaagaaag caaaccgccc    4680
tcccaggtcc gcccggattg ccgaagcccc tctggaaaaa ctccttcccc tcttacacca   4740
aactttgcgc cgggcctcgt tccctcccgg gtaggcagcg gcgcaggaag ggttaagcca   4800
gcccgtccca gctgacagtc agctgattgg gccctgattg acagctccga aaagtttcct   4860
tgtttctata ctattatgct aatcgcggcc gctctcgccg cctcccattg gcccggagtg   4920
ccagtcaatt tctcatttgg acctgacgtc acgagtgcta taaaactcag caattgcttt   4980
aaactcttct tgctggatca gaggctttaa aatcttttt catcttctag ctgtagctcg    5040
ggctgcttgt cggcttggcc tcccctccc ccctttgctc tctgcctcgt ctttccccag    5100
gacttcgcta ttttgctttt ttaaaaaag gcaagaaaga actaaactcc cccctccctc    5160
tcctccagtc gggctgcacc tctgccttgc actttgcaca gaggtagaga gcgcgcgagg   5220
gagagagagg aaagaaaaaa aataataaag agagccaagc agaagaggag gcgagaagca   5280
tgaagtgtta actcccccgt gccaaggccc gcgccgcccg gacagacgcc cgccgcgcct   5340
ccagccccga gcggacgccg gcgcgcgccct gcctgcagcc cgggccggcg aggcgagccc   5400
ttccttatgc aaagcgcgca gcggagcggc gagcggggga gcgccgcgcac cgggccgggc   5460
tcctccagct tcgccgccgc agccaccacc gccgccaccg cagctcgcgg aggatcttcc   5520
cgagcctgaa gccgccggct cggcgcgcaa ggaggcgagc gagcaaggag gggccggggc   5580
gagcgaggga gcacattggc gtgagcaggg gggaggagg gcgggcgcgg ggggcgcggg    5640
cagggcgggg gggtgtgtgt gtgagcgcgc tcggaggttt cggccagcc accgccgcgc   5700
aagctagaag cgccccagcc cggcaagctg gctcacccgc tggccaccca gcacagcccg   5760
ctggcccctc tcctgcagcc catctggcgg agcggcggcg gcggcggcgg cggcggcagg   5820
agaatggcat cagaactggc aatgagcaac tccgacctgc ccaccagtcc cctggccatg    5880
gaatatgtta atgacttcga tctgatgaag tttgaagtga aaaggaacc ggtgagacc     5940
gaccgcatca tcagccagtg cggccgtctc atcgcgggg gctcgctgtc ctccacccc    6000
atgagcacgc cgtgcagctc ggtgcccct tcccccagct tctcggcgcc cagcccgggc   6060
tcgggcagcg agcagaaggc gcacctggaa gactactact ggatgaccgg ctacccgcag   6120
cagctgaacc ccgaggcgct gggcttcagc cccgaggacg cggtcgaggc gctcatcagc    6180
aacagccacc agctccaggg cggcttcgat ggctacgcgc gcggggcgca gcagctggcc   6240
gcggcggccg ggggccggtgc cggcgcctcc ttgggcggca gcggcgagga gatggggcccc  6300
gccgccgccg tggtgtccgc cgtgatcgcc gcggccgccg cgcagagcgg cgcgggcccg    6360
cactaccacc accaccacca ccacgccgcc ggccaccacc accacccgac ggccggcgcg   6420
cccggcgccg cgggcagcgc ggccgcctcg gccggtggcg ctggggcgc gggcggcggt    6480
ggccccggcca gcgctggggg cggcggcggc ggcggcggcg gcggaggcgg cggggggcgcg 6540
gcggggggcgg ggggcgccct gcacccgcac cacgccgccg cgggcctgca cttcgacgac   6600
cgcttctccg acgagcagct ggtgaccatg tctgtgcgcg agctgaaccg gcagctgcgc   6660
gggggtcagca aggaggagt gatccggctg aagcagaaga ggcggaccct gaaaaaccgc   6720
ggctatgccc agtcctgccg cttcaagagg gtgcagcaga gacacgtcct ggagtcggag   6780
aagaaccagc tgctgcagca agtcgaccac ctcaagcagg gatctccag gctggtgcgc   6840
gagaggggacg cgtacaagga gaaatacgag aagttggtga gcagcggctt ccgagaaaac    6900
ggctcgagca gcgacaaccc gtcctctccc gagttttttca tgtgagtctg acacgcgatt    6960
```

```
ccagctagcc accctgataa gtgctccgcg ggggtccggc tcgggtgtgg gcttgctagt    7020
tctagagcca tgctcgccac cacctcacca cccccacccc caccgagttt ggccccttg     7080 gcccctaca cacacacaaa cccgcacgca cacaccacac acacacacac acacacacac    7140 acacccaca ccctgctcga gtttgtggtg gtggtggctg ttttaaactg gggagggaat    7200
gggtgtctgg ctcatggatt gccaatctga aattctccat aacttgctag cttgttttt    7260 ttttttttt acaccccccc gccccacccc cggacttgca caatgttcaa tgatctcagc    7320
agagttcttc atgtgaaacg ttgatcacct ttgaagcctg catcattcac atatttttc    7380 ttcttcttcc ccttcagttc atgaactggt gttcattttc tgtgtgtgtg tgtgttttat    7440
tttgtttgga tttttttttt taattttact tttagagctt gctgtgttgc ccacctttt    7500 tccaacctcc accctcactc cttctcaacc catctcttcc gagatgaaag aaaaaaaaaa   7560
gcaaagtttt ttttcttct cctgagttct tcatgtgaga ttgagcttgc aaaggaaaaa    7620
aaaatgtgaa atgttataga cttgcagcgt gccgagttcc atcgggtttt tttttagca    7680 ttgttatgct aaaatagaga aaaaaatcct catgaacctt ccacaatcaa gcctgcatca    7740
accttctggg tgtgacttgt gagttttggc cttgtgatgc caaatctgag agtttagtct    7800
gccattaaaa aaactcattc tcatctcatg cattattatg cttgctactt tgtcttagca    7860
acaatgaact ataactgttt caaagacttt atggaaaaga gacattatat taataaaaaa    7920
aaaaagcctg catgctggac atgtatggta taattatttt ttccttttt tttccttttg     7980 gcttggaaat ggacgttcga agacttatag catggcattc atactttgt tttattgcct    8040 catgactttt ttgagtttag aacaaaacag tgcaaccgta gagccttctt cccatgaaat    8100
tttgcatctg ctccaaaact gctttgagtt actcagaact tcaacctccc aatgcactga    8160
aggcattcct tgtcaaagat accagaatgg gttacacatt taacctggca aacattgaag    8220
aactcttaat gttttctttt taataagaat gacgccccac tttggggact aaaattgtgc    8280
tattgccgag aagcagtcta aaatttattt tttaaaaaga gaaactgccc cattatttt     8340 ggtttgtttt attttattt tatattttt ggcttttggt cattgtcaaa tgtggaatgc      8400
tctgggtttc tagtatataa tttaattcta gttttataa tctgttagcc cagttaaat     8460 gtatgctaca gataaaggaa tgttatagat aaatttgaaa gagttaggtc tgtttagctg    8520 tagattttt aaacgattga tgcactaaat tgtttactat tgtgatgtta aggggggtag     8580
agtttgcaag gggactgttt aaaaaaagta gcttatacag catgtgcttg caacttaaat    8640
ataagttggg tatgtgtagt ctttgctata ccactgactg tattgaaaac caaagtatta    8700 agagggaaa cgcccctgtt tatatctgta ggggtatttt acattcaaaa atgtatgttt     8760
ttttttcttt tcaaaattaa agtatttggg actgaattgc actaagatat aacctgcaag    8820
catataatac aaaaaaaaat tgcaaaactg tttagaacgc taataaaatt tatgcagtta    8880
taaaaatggc attactgcac agttttaaga tgatgcagat ttttttacag ttgtattgtg    8940
gtgcagaact ggattttctg taacttaaaa aaaaatccac agtttaaag gcaataatca    9000 gtaaatgtta ttttcaggga ctgacatcct gtctttaaaa agaaatgaaa agtaaatctt    9060
accacaataa atataaaaaa atcttgtcag ttacttttct tttacatatt ttgctgtgca    9120
aaattgtttt atatcttgag ttactaacta accacgcgtg ttgttcctat gtgcttttct    9180 ttcatttca attctggtta tatcaagaaa agaataatct acaataataa acggcatttt    9240
tttttgattc tgtactcagt ttcttagtgt acagtttaac tgggcccaac aacctcgtta    9300
aaagtgtaaa atgcatcctt ttctccagtg gaaggattcc tggaggaata gggagacagt    9360
```

```
aattcagggt gaaattatag gctgtttttt gaagtgagga ggctggcccc atatactgat    9420
tagcaatatt taatatagat gtaaattatg acctcatttt tttctcccca aagttttcag    9480
ttttcaaatg agttgagcca taattgccct tggtaggaaa aacaaaacaa aacagtggaa    9540
ctaggcttcc tgagcatggc cctacacttc tgatcaggag caaagccatc catagacaga    9600
ggagccggac aaatatggcg catcagaggt ggcttgcgca catatgcatt gaacggtaaa    9660
gagaaacagc gcttgccttt tcactaaagt tgactatttt tccttcttct cttacacacc    9720
gagattttct tgttagcaag gcctgacaag atttaacata aacatgacaa atcatagttg    9780
tttgttttgt tttgcttttc tctttaacac tgaagatcat ttgtcttaaa taggaaaaag    9840
aaaatccact ccttacttcc atatttccaa gtacatatct ggtttaaact atgttatcaa    9900
atcatatttc accgtgaata ttcagtggag aacttctcta cctggatgag ctagtaatga    9960
tttcagatca tgctatcccc agaaataaaa gcaaaaaata atacctgtgt ggaatatagg   10020
ctgtgctttg atttactggt atttacccca aaataggctg tgtatggggg ctgacttaaa   10080
gatcccttgg aaagactcaa aactaccttc actagtagga ctcctaagcg ctgacctatt   10140
tttaaatgac acaaattcat gaaactaatg ttacaaattc atgcagtttg cactcttagt   10200
catcttcccc tagcacacca atagaatgtt agacaaagcc agcactgttt tgaaaataca   10260
gccaaacacg atgactttg ttttgttttc tgccgttctt aaaagaaaaa aagataatat    10320
tgcaactctg actgaaagac ttattttaa gaaaacaggt tgtgtttggt gctgctaagt    10380
tctggccagt ttatcatctg gccttcctgc ctattttta caaaacacga agacagtgtg    10440
taacctcgac attttgacct tcctttatgt gctagtttag acaggctcct gaatccacac   10500
ttaattttgc ttaacaaaag tcttaatagt aaacctcccc tcatgagctt gaagtcaagt   10560
gttcttgact tcagatattt ctttcctttt tttttttttt tcctcatcac aactaagaga   10620
tacacaaact ctgaagaagc agaaatggag agaatgcttt taacaaaaaa gcatctgatg   10680
aaagatttta ggcaaacatt ctcaaaataa gagtgatatt ctggatgtag ttattgcagt   10740
tatctcatga caaatgaggc ctggattgga aggaaaatat agttgtgtag aattaagcat   10800
tttgatagga atctcaaagg tagttgaata taataagcag gtttgggccc ccaaacttta   10860
gaaaatcaaa tgcaaaggtg ctggcaaaaa tgaggtttga gtggctggct gtaagagaag   10920
gttaactcct agtaaaaggc attttttagaa ataacaatta ctgaaaactt tgaagtatag   10980
tgggagtagc aaacaaatac atgttttttt tttcttacaa agaactccta aatcctgagt   11040
aagtgccatt cattacaata agtctctaaa tttaaaaaaa aaaaaatcat atgaggaaat   11100
ctagctttcc cctttacgct gcgtttgatc tttgtctaaa tagtgttaaa attcctttca   11160
ttccaattac agaactgagc ccactcgcaa gttggagcca tcagtgggat acgccacatt   11220
ttggaagccc cagcatcgtg tacttaccag tgtgttcaca aaatgaaatt tgtgtgagag   11280
ctgtacatta aaaaaaatca tcattattat tattatttgc agtcatggag aaccacctac   11340
ccctgacttc tgtttagtct ccttttttaaa taaaaattac tgtgttagag aagaaggcta   11400
ttaaatgtag tagttaacta tgcctcttgt ctgggggttt catagagacc ggtaggaaag   11460
cgcactcctg cttttcgatt tatggtgtgt gcaagtaaac aggtgcattg ctttcaacct   11520
gccatactag ttttaaaaat tcactgaaat tacaaagata catatatatg catatatata   11580
atggaaagtt tcccggaatg caacaattag catttttaaaa tcatatatag gcatgcacat   11640
tctaaatagt acttttttcat gcttcattgt ttctctggca gataattttta ctaagaagaa   11700 aaatagatat tcgactcccc ttccctaaac aaatccacgg gcagaggctc cagcggagcc   11760
```

```
gagcccctg gttttctcgt aggccctaga cggtgttgca tttatcagtg atgtcaaacg   11820
tgctcatttg tcagacatag ctgtaaatga aaacaatgtg tggcaaaata caaagttagt   11880
taaatacaca ccctctgtgt gatttttgc tcccttttct tttttgctcc tactcaaaaa    11940
aaaaaaaatc acctccttta catttccctg gcttcttgca tgtttcctt ttcaaaaacc    12000 atgtaataat ttttacaat gtatctgaca cattaatata ttgacatcaa ataggcagac    12060
attctacttt tgcctggcaa ataaatctgc tacggagaca tcatttcctc actgtctcaa   12120
agccataact acctgggagt cttcaacac agacccctcc gatgggaaat gctgtttatt    12180
actgaatgca ggatgctcac gctctgatct tttctccctt gtgcctttac cccagtcatt   12240
tttacttagc aacaccaatt ctagatactt ctgttctgaa gtagaaccac ccccttgcca   12300
cactgccagt tttcctgcta aaagcagtgg acagaagaca gatcatggtc accctcacaa   12360
acatggcaca cagctgtctc ggtagctgca ttcccagcat gtcctggtct aaatatctag   12420
agttgcctat gacacgttca aaggttccca agcacagtac attgggaggc ttttgctgct   12480
gtggccgttg ttttcgttta ggccaactta cttccgtatt cacatactct tggctttacg   12540
aaatacactc ctccagtcta ctaggccaat caatatattt aaaagtctga ttgccacata   12600
agtctctctc tctctctttt tgttttttgt ttgtttgttt ttttctgttt tggctgccgg   12660
tagttaaaga ctgagatagg ttggaagact aaaatacagg agtacatgag tgacaacctt   12720
cagccgtctg atttccatgc cggtaaaaca cacaaccaag ctcttcttag cgctgctaat   12780
ataaacattc actaagaggg aataggaagt gagatttacc agcttcactt tgctgatttg   12840
caaggttccc cactacgatt cactgtcatt tgattttga aaaataattt tgtccgtctc    12900
tttgaagaaa tgtcttagtt cttttatttt gtttgtttgg ttttttttag agaagtttta   12960
tctgcagtga taggctacaa tttttatctc cgctgattat ttgtcaggat gctgaatgaa   13020
taatttggtc ctgtgccttc cttgttgttc tgaggaaaat aagagaaact tggaagtttg   13080
tttcactctt agcccatcct aaatctaaaa gaagatgtcc caggtccagg caggccatgt   13140
agtagttata aaggaggtgg tccaggtcca gccacctcaa tcaggatttg tttgttttga   13200
agcatttgct taaagcgga gcaagagtct taacccaact tgccataaca ctgcttttct    13260
cgcttttgat gtaaatcttc aaaattcaga catcaaacag ccccagaaaa ggggaattct   13320
ctccaggcat tgctccgccc cagctcctga acaaacccag ctctgtctag catttttttc   13380
cctagcgggg gtaggggaca gggtgagaga atttcagtct cccaggctgt ctcatgattg   13440
ttagggcata aagaaacaca gtcctgccac aaattgggag catctttacc ctttagagag   13500
aaacaaaaca aaactaaaca aacaaatcaa attgctttgc atgaaggcgt agcaaataaa   13560
atctcgggct ccctgttccc tgcaccattt gtaggaggtg agaaatgagg gaaacaagag   13620
aaaggggaac tttaaaagcg ggaggcccag aaataatccc tgttaccagt ctgaatttca   13680
cttgctccgt ggctaacgtc agacctagtg tgcatgtatg ccagaagtaa actaggctcg   13740
gctgtccatt tctttaaaat atgttcacat gtttcctttt tgaaacaat tttggggact    13800 aaacccaaat ggagagattt gaggaaatcg ttaatgtctt aacatttgag tatatttata   13860
aatgtatcag tctgtgat                                                  13878
```

METHOD FOR THE PROGNOSIS AND TREATMENT OF CANCER METASTASIS

CROSS-REFERENCE TO RELATED APPLICATIONS

This application is the National Stage of International Application Number PCT/IB2013/001204, filed Mar. 15, 2013, which claims the benefit of U.S. Provisional Application Nos. 61/621,949, filed on Apr. 9, 2012, 61/724.807. filed on Nov. 9, 2012, and 61/732,175, filed on Nov. 30, 2012, which are incorporated by reference herein in their entirety.

REFERENCE TO A SEQUENCE LISTING SUBMITTED ELECTRONICALLY

The content of the electronically submitted sequence listing (Name: 3190_0010003_SequenceListing.txt; Size: 48,601 bytes; and Date of Creation: Oct. 7, 2014) is herein incorporated by reference in its entirety.

BACKGROUND OF THE INVENTION

Field of the Invention

The present invention relates to the prognosis of bone metastasis in triple negative (including basal-like) breast cancer, or alternatively in ER+ breast cancer (including luminal type A and luminal type B), based on determining the levels of the c-MAF gene, 16q23 or 16q22-24 locus amplification or translocation in a primary tumor sample. Likewise, the invention also relates to a method for designing a customized therapy in a subject with triple negative (including basal-like) breast cancer, or alternatively in ER+ breast cancer, which comprises determining the c-MAF gene expression level, 16q23 or 16q22-24 locus amplification or translocation. Finally, the invention relates to the use of a c-MAF inhibitor as a therapeutic agent in the treatment of triple negative (including basal-like) breast cancer metastasis or in ER+ breast cancer metastasis, in particular bone metastasis.

Background Art

Breast cancer is the second most common type of cancer worldwide (10.4%; after lung cancer) and the fifth most common cause of death by cancer (after lung cancer, stomach cancer, liver cancer, and colon cancer). Among women, breast cancer is the most common cause of death by cancer. In 2005, breast cancer caused 502,000 deaths worldwide (7% of the deaths by cancer; almost 1% of all deaths). The number of cases worldwide has increased significantly from the 1970s, a phenomenon which is partly due to the modern lifestyle in the western world.

Breast cancer is classified into stages according to the TNM system. (See American Joint Committee on Cancer. *AJCC Cancer Staging Manual.* 6th ed. New York, N.Y.: Springer, 2002, which is incorporated herein by reference in its entirety.) The prognosis is closely related to the results of the stage classification, and the stage classification is also used to assign patients to treatments both in clinical trials and in the medical practice. The information for classifying into stages is as follow:

TX: The primary tumor cannot be assessed. T0: there is no evidence of tumor. Tis: in situ carcinoma, no invasion. T1: The tumor is 2 cm or less. T2: The tumor is more than 2 cm but less than 5 cm. T3: The tumor is more than 5 cm. T4: Tumor of any size growing in the wall of the breast or skin, or inflammatory breast cancer.

NX: The nearby lymph nodes cannot be assessed. N0: The cancer has not spread to the regional lymph nodes. N1: The cancer has spread to 1 to 3 axillary lymph nodes or to one internal mammary lymph node. N2: The cancer has spread to 4 to 9 axillary lymph nodes or to multiple internal mammary lymph nodes. N3: One of the followings applies:

The cancer has spread to 10 or more axillary lymph nodes, or the cancer has spread to the infraclavicular lymph nodes, or the cancer has spread to the supraclavicular lymph nodes or the cancer affects the axillary lymph nodes and has spread to the internal mammary lymph nodes, or the cancer affects 4 or more axillary lymph nodes and minimum amounts of cancer are in the internal mammary nodes or in sentinel lymph node biopsy.

MX: The presence of distant spread (metastasis) cannot be assessed. M0: There is no distant spread. M1: spreading to distant organs which do not include the supraclavicular lymph node has been produced.

The fact that most of the patients with solid tumor cancer die after metastasis means that it is crucial to understand the molecular and cellular mechanisms allowing a tumor to metastasize. Recent publications have demonstrated how the metastasis is caused by means of complex yet little known mechanisms and also how the different metastatic cell types have a tropism towards specific organs These tissue specific metastatic cells have a series of acquired functions allowing them to colonize specific organs.

All cells have receptors on their surface, in their cytoplasm and in the cell nucleus. Certain chemical messengers such as hormones bind to said receptors and this causes changes in the cell. There are three significant receptors which may affect the breast cancer cells: estrogen receptor (ER), progesterone receptor (PR) and HER2/neu. For the purpose of naming the cells having any of these receptors, a positive sign is placed thereto when the receptor is present and a negative sign if it is absent: ER positive (ER+), ER negative (ER−), PR positive (PR+), PR negative (PR−), HER2 positive (HER2+) and HER2 negative (HER2−). The receptor state has become a critical assessment for all breast cancers since it determines the suitability of using specific treatments, for example, tamoxifen or trastuzumab.

Unsupervised gene expression array profiling has provided biological evidence for the heterogeneity of breast cancer through the identification of intrinsic subtypes such as luminal A, luminal B, HER2+/ER− and the basal-like subtype.

Triple-negative cancers are defined as tumors that do not express the genes for estrogen receptor (ER), progesterone receptor (PR) nor HER2. This subgroup accounts for 15% of all types of breast cancer and for a higher percentage of breast cancer arising in African and African-American women who are premenopausal. Triple negative breast cancers have a relapse pattern that is very different from Estrogen Receptor positive breast cancers: the risk of relapse is much higher for the first 3-5 years but drops sharply and substantially below that of Estrogen Receptor positive breast cancers after that.

The basal-like subtype is characterized by low expression of both the ER and HER2 clusters of genes, so is typically ER-negative, PR-negative, and HER2-negative on clinical testing; for this reason, it is often referred to as "triple-negative" breast cancer (*Breast Cancer Research* 2007, 9(Suppl 1):S13). Basal-like cancers express genes usually found in "basal"/myoepithelial cells of the normal breast including high molecular weight cytokeratins (5/6, 14 and 17), P-cadherin, caveolins 1 and 2, nestin, αB crystalline and epidermal growth factor receptor (Reis-Fiho J. et al., http://www.uscap.org/site~/98th/pdf/companion03h03.pdf).

Given that there is no internationally accepted definition for basal-like breast cancers, it is not surprising that there has been a great deal of confusion as to whether triple negative and basal-like breast cancers are synonymous. Although several groups have used these terms interchangeably, it should be noted that not all basal-like cancers lack ER, PR and HER2 and not all triple negative cancers display a basal-like phenotype. The vast majority of triple negative cancers are of basal-like phenotype. Likewise, the vast majority of tumours expressing 'basal' markers are triple negative. It should be noted, however, that there is a significant number of triple negative cancers that do not express basal markers and a small, but still significant, subgroup of basal-like cancers that express either hormone receptors or HER2. Bertucci et al. (*Int J Cancer.* 2008 Jul. 1; 123(1): 236-40) have addressed this issue directly and confirmed that not all triple negative tumours when analyzed by gene expression profiling were classified as basal-like cancers (i.e. only 71% were of basal-like phenotype) and not all basal-like breast carcinomas classified by expression arrays displayed a triple negative phenotype (i.e. 77%).

The keystone for treating breast cancer is surgery when the tumor is localized with possible adjuvant hormone therapy (with tamoxifen or an aromatase inhibitor), chemotherapy, and/or radiotherapy. Currently, the suggestions for treatment after the surgery (adjuvant therapy) follow a pattern. This pattern is subject to change because every two years a world conference takes place in St. Gallen, Switzerland to discuss the actual results of the worldwide multicenter studies. Likewise, said pattern is also reviewed according to the consensus criterion of the National Institute of Health (NIH). Based on in these criteria, more than 85-90% of the patients not having metastasis in lymph nodes would be candidates to receive adjuvant systemic therapy.

Currently, PCR assays such as Oncotype DX or microarray assays such as MammaPrint can predict the risk of breast cancer relapse based on the expression of specific genes. In February 2007, the MammaPrint assay became the first breast cancer indicator in achieving official authorization from the Food and Drug Administration.

Patent application EP1961825-A1 describes a method for predicting the occurrence of breast cancer metastasis to bone, lung, liver or brain, which comprises determining in a tumor tissue sample the expression level of one or more markers with respect to their corresponding expression level in a control sample, among which include c-MAF. However, this document requires determining several genes simultaneously to enable determining the survival of breast cancer patients and the correlation between the capacities of the gene signature for predicting the survivability free from bone metastasis was not statistically significant.

Patent application US2011/0150979 describes a method for predicting a prognosis of a basal like breast cancer comprising detecting the level of FOXC1.

Patent application US2010/0210738 relates to a method for prognosing cancer in a subject with triple negative breast cancer comprising detecting in a sample the expression levels of a series of genes which are randomly up-regulated or down-regulated.

Patent application US2011/0130296 relates to the identification of marker genes useful in the diagnosis and prognosis of triple negative breast cancer.

There is the need of identifying new markers which allow predicting the probability of a subject suffering triple negative breast cancer to develop metastasis. The identification of new prognosis factors will serve as a guide in selecting the most suitable treatments.

SUMMARY OF THE INVENTION

In one aspect, the invention relates to an in vitro method for predicting bone metastasis of a triple negative (including basal-like) breast cancer, or alternatively of an ER+ breast cancer (including luminal A and B), in a subject suffering said cancer which comprises
   i) determining the expression level of the c-MAF gene in a sample of said subject and
   ii) comparing the expression level obtained in step i) with a reference value,
wherein increased expression level of said gene with respect to said reference value is indicative of increased risk of developing bone metastasis In another aspect, the invention relates to an in vitro method for predicting the clinical outcome of a patient suffering from bone metastatic triple negative (including basal-like) breast cancer, or alternatively from bone metastatic ER+ breast cancer, which comprises
   i) quantifying the expression level of the c-MAF gene in a sample of said subject and
   ii) comparing the expression level obtained in step i) with a reference value,
wherein increased expression level of said gene with respect to said reference value is indicative of a poor clinical outcome.

In another aspect, the invention relates to an in vitro method for designing a customized therapy for a subject suffering from triple negative (including basal-like) breast cancer, or alternatively from ER+ breast cancer, which comprises
   i) quantifying the c-MAF gene expression level in a sample of said subject and
   ii) comparing the expression level obtained in i) with a reference value,
wherein if the expression level is increased with respect to said reference value, then said subject is susceptible to receive a therapy aiming to prevent, inhibit and/or treat the bone metastasis. In a particular aspect of this method, the subject is then administered at least one therapeutic drug that prevents, inhibits and/or treats the bone metastasis. If the expression level is not increased with respect to said reference value, then said subject is not susceptible to receive a therapy aiming to prevent, inhibit and/or treat the bone metastasis. In a particular aspect of this method, the subject is then not administered at least one therapeutic drug that prevents, inhibits and/or treats the bone metastasis.

In another aspect, the invention relates to a method for determining the risk of bone metastasis in a subject suffering from breast cancer, for example, triple negative breast cancer or ER+ breast cancer, which comprises determining the expression level of the c-MAF gene in a sample of said subject wherein expression levels of said gene above the average value plus one standard deviation is indicative of an increased risk of early bone metastasis. In a particular aspect of this method, the subject is then administered at least one therapeutic drug that prevents or inhibits the bone metastasis.

In another aspect, the invention relates to an in vitro method for designing a customized therapy for a subject with triple negative (including basal-like) breast cancer or ER+ breast cancer with bone metastasis which comprises
i) quantifying the c-MAF gene expression level in a bone metastatic sample of said subject and
ii) comparing the expression level obtained in step (i) with a reference value,
wherein if the c-MAF gene expression level is increased with respect to said reference value, then said subject is susceptible to receive a therapy for preventing the bone degradation. In a particular aspect of this method, the subject is then administered at least one therapeutic drug that prevents, inhibits and/or treats the bone metastasis.

If the c-MAF gene expression level is not increased with respect to said reference value, then said subject is not susceptible to receive a therapy for preventing the bone degradation. In a particular aspect of this method, the subject is then not administered at least one therapeutic drug that prevents, inhibits and/or treats the bone metastasis.

In another aspect, the invention relates to an in vitro method for predicting bone metastasis of a triple negative (including basal-like) breast cancer or, alternatively, of an ER+ breast cancer, in a subject suffering said cancer which comprises determining if the c-MAF gene is amplified in a sample of said subject relative to a reference gene copy number wherein an amplification of the c-MAF gene with respect to said reference gene copy number is indicative of increased risk of developing bone metastasis. In a particular aspect of this method, the subject is then administered at least one therapeutic drug that prevents or inhibits the bone metastasis.

In another aspect, the invention relates to an in vitro method for predicting bone metastasis of breast cancer, for example triple-negative breast cancer or ER+ breast cancer, in a subject suffering said cancer which comprises determining if the c-MAF gene is translocated in a sample of said subject wherein a translocation of the c-MAF gene is indicative of increased risk of developing bone metastasis. In a particular aspect of this method, the subject is then administered at least one therapeutic drag that prevents, or inhibits the bone metastasis.

In another aspect, the invention relates to an in vitro method for predicting the clinical outcome of a patient suffering triple negative (including basal-like) breast cancer, or, alternatively, ER+ breast cancer, which comprises determining if the c-MAF gene is amplified in a sample of said subject relative to a reference gene copy number wherein an amplification of the c-MAF gene with respect to said reference gene copy number is indicative of a poor clinical outcome. In a particular aspect of this method, the subject is then administered at least one therapeutic drug that prevents, inhibits and/or treats the bone metastasis. If such amplification is not observed then the subject is then not administered at least one therapeutic drug that prevents, inhibits and/or treats the bone metastasis. In another embodiment, the invention relates to an in vitro method for predicting the clinical outcome of a patient suffering breast cancer which comprises determining if the c-MAF gene is translocated in a sample of said subject wherein a translocation of the c-MAF gene (i.e. t(14,16)) is indicative of a poor clinical outcome. In some embodiments, the invention relates to designing a customized therapy for patients with the amplification or translocation of c-MAP. In some embodiments, the customized therapy is at least one therapeutic drug that prevents, inhibits and/or treats the bone metastasis.

In another aspect, the invention relates to a c-MAF inhibitory agent for use in the prevention of bone metastasis from triple negative (including basal-like) breast cancer or from ER+ breast cancer.

In another aspect, the invention relates to a c-MAF inhibitory agent or an agent capable of avoiding or preventing bone degradation for use in the treatment of bone metastasis in a subject suffering from triple negative (including basal-like) breast cancer, or, alternatively, from ER+ breast cancer, and having elevated c-MAF levels in a metastatic sample with respect to a control sample.

In another aspect, the invention relates to a kit for predicting bone metastasis of a breast cancer in a subject suffering from said cancer, the kit comprising: a) means for quantifying the expression level of c-MAF in a sample of said subject; and b) means for comparing the quantified level of expression of c-MAF in said sample to a reference c-MAF expression level.

In another aspect, the invention relates to a kit for predicting bone metastasis of a breast cancer in a subject suffering from said cancer, the kit comprising: a) means for determining translocation of the c-MAF gene in a sample of said subject; and b) means for comparing the translocation of c-MAF in said sample to a reference c-MAF sample. The invention also relates to the use of such kit to predict bone metastasis of a breast cancer in a subject suffering from said cancer. In one embodiment, the subject is then administered or excluded at least one therapeutic drug that prevents, inhibits and/or treats the bone metastasis based on the results of using the kit.

In another aspect, the invention relates to a kit for predicting bone metastasis of a breast cancer in a subject suffering from said cancer, the kit comprising: a) means for quantifying the amplification of c-MAF gene, 16q23 or 16q22-24 locus amplification or translocation in a sample of said subject; and b) means for comparing the amplified level of c-MAF gene, 16q23 or 16q22-24 locus amplification or translocation in said sample to a reference.

In another aspect, the invention relates to a kit for predicting the clinical outcome of a subject suffering from bone metastasis from a breast cancer, the kit comprising: a) means for quantifying the expression level of c-MAF in a sample of said subject; and b) means for comparing the quantified expression level of c-MAF in said sample to a reference c-MAF expression level. The invention also relates to the use of such kit to predict the clinical outcome of a subject suffering from bone metastasis from a breast cancer. In one embodiment, the subject is then administered or excluded at least one therapeutic drug that prevents, inhibits and/or treats the bone metastasis based on the results of using the kit.

In another aspect, the invention relates to a kit for determining a therapy for a subject suffering from breast cancer, the kit comprising: a) means for quantifying the expression level of c-MAF in a sample of said subject; b) means for comparing the quantified expression level of c-MAF in said sample to a reference c-MAF expression level; and c) means for determining a therapy for preventing and/or reducing bone metastasis it said subject based on the comparison of the quantified expression level to the reference expression level. The invention also relates to the use of such kit to determine a therapy for a subject suffering from breast cancer. In one embodiment, the subject is then administered or excluded at least one therapeutic drug that prevents, inhibits and/or treats the bone metastasis based on the results of using the kit.

In another aspect, the invention relates to a kit comprising: i) a reagent for quantifying the expression level of c-MAF in a sample of a subject suffering from breast cancer, and ii) one or more c-MAF gene expression level indices that have been predetermined to correlate with the risk of bone metastasis. The invention also relates to the use of such kit to predict bone metastasis of a breast cancer in a subject suffering from said cancer. In one embodiment, the subject is then administered or excluded at least one therapeutic drug that prevents, inhibits and/or treats the bone metastasis based on the results of using the kit.

In another aspect, the invention relates to an in vitro method for typing a sample of a subject suffering from breast cancer, the method comprising:
  a) providing a sample from said subject;
  b) quantifying the expression level of c-MAF in said sample;
  c) typing said sample by comparing the quantified expression level of c-MAF to a predetermined reference level of c-MAF expression;
wherein said typing provides prognostic information related to the risk of bone metastasis in said subject. In one embodiment, the subject is administered or excluded at least one therapeutic agent based on the prognostic information provided by the typing.

In another aspect, the invention relates to a method for preventing or reducing the risk of bone metastasis in a subject suffering from triple negative (including basal-like) breast cancer, said method comprising administering to said subject an agent that prevents or reduces bone metastasis, wherein said agent is administered in accordance with a treatment regimen determined from quantifying the expression level of c-MAF in said subject.

In another aspect, the invention relates to a method of classifying a subject suffering from breast cancer into a cohort, comprising: a) determining the expression level of c-MAF in a sample of said subject; b) comparing the expression level of c-MAF in said sample to a predetermined reference level of c-MAF expression; and c) classifying said subject into a cohort based on said expression level of c-MAF in the sample. In a particular aspect, the cohort is used for conducting a clinical trial.

Kaplan-Meier curve of bone (Left), brain (Right up) and lung (Right down) metastasis-free survival in ER+ primary breast cancer patients (union of GSE2603, GSE2034 and GSE12276 data set or cohort I). Low, Med and High represent c-MAF expression levels in the following way: low (<mean−SD), medium (≥mean−SD and ≤mean+SD) and high (>mean+SD). Patients with bone metastasis have been removed from brain and lung metastasis analysis.

Figure 4:
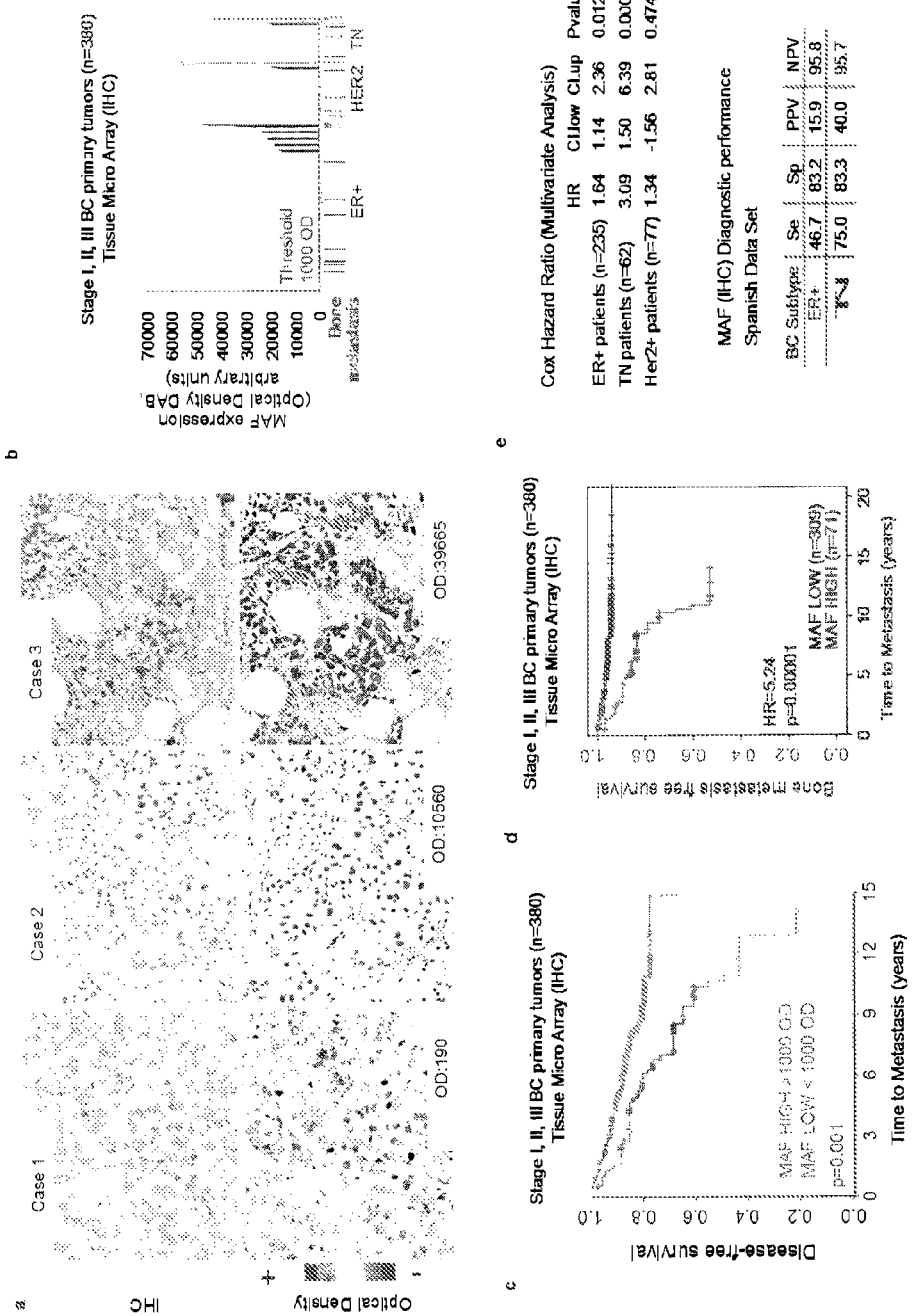

FIG. 4. c-MAF (Protein) is a clinical biomarker for breast cancer bone metastasis a) Representative c-MAF immunostainings of primary breast cancer tissues. Case 1 represents c-MAF negative tumors (OD<1000). Case 2 and Case 3 are MAF positive tumors (OD >1000 and >25000 respectively).

b) Plot depicts c-MAF protein expression (OD) in a cohort of 380 primary breast cancer tumors (cohort II). Tumors are segregated according to BC subtype (ER+, HER2+ and TN). Grey ticks at the bottom depict tumor with bone metastasis. OD-optical density based on c-MAF immunostaining.

c,d) Kaplan-Meier curve of disease-free survival (c) and bone metastasis-free survival (d) in a cohort of 380 primary breast cancer tumors (stage I, II and III). c-MAF high group (red line, OD >1000); c-MAF low group (green line, OD<1000).

e) Table depicting bone metastasis diagnostic performance of c-MAF in different BC subtypes (ER+, HER2+ and TN). CI (confidence interval); Se– sensitivity; Sp– specificity; PPV (positive prognostic value); NPV (negative prognostic value).

FIG. 5: c-MAF contribution to breast cancer cells bone metastasis.

a) Parental MCF7 cells with or without c-MAF (short and long isoforms) expression were injected into the left ventricle of a mouse and bone colonization was analyzed by in vivo bioluminescent imaging. Kaplan-Meier plot of bone metastasis free survival is shown. Images corresponding to total photon flux, HandE stainings and CT-Scans of representative bones are shown at the end point.

b) Parental T47D cells with or without c-MAF (short and long isoforms) expression were injected into the left ventricle of a mouse and bone colonization was analyzed by in vivo bioluminescent imaging. Kaplan-Meier plot of bone metastasis free survival is shown c) BoM2 bone metastatic MCF7 cell derivatives depleted or rescued for the expression of c-MAF (short and long isoforms combined or independently) were injected into the left ventricle of a mouse and bone colonization was analyzed by in vivo bioluminescent imaging. Kaplan-Meier plot of bone metastasis free survival is shown. Images corresponding to total photon flux, HandE stainings and CT-Scans of representative bones are shown at the end point.

d) Parental MCF7 cells with or without c-MAF (short and long isoforms) expression were injected via tail vein of a mouse and lung colonization was analyzed by in vivo bioluminiscent imaging. Kaplan-Meier plot of lung metastasis free survival is shown. Statistical differences were determined by Wilcoxon signed-rank test.

Figure 6:
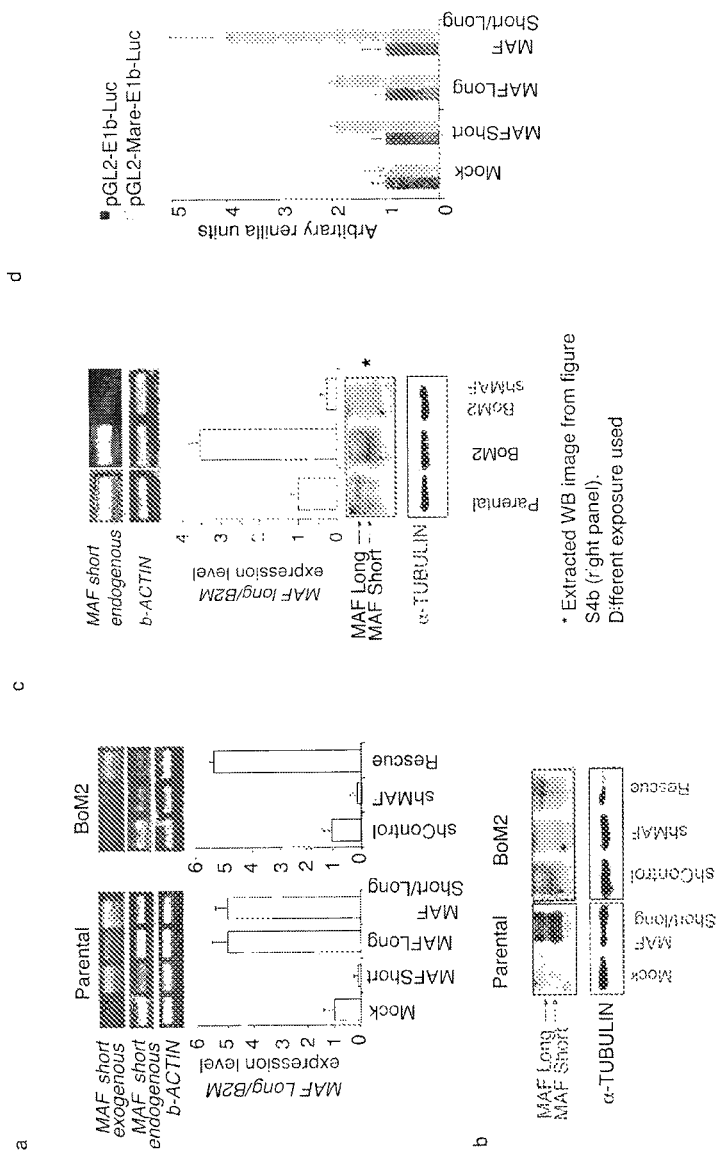

FIG. 6. MAF levels in MCF7 parental and Bone metastatic derivatives BoM2.

a) MAF expression levels in Parental cells transfected with Control, c-MAF Short, c-MAF Long or c-MAF Short and Long isoform expression constructs (Left) and in BoM2 Control, shMAF or Rescue BoM2 cells (Right). MAF long expression levels were determined using TaqMan probe and normalized to BoM2 levels. MAF short endogenous levels were determined using Syber Green reaction with indicated primers and normalized to beta ACTIN levels. Presence of ectopically expressed c-MAF short isoform was detected using PCR reaction.

b) WB depicting c-MAF protein levels in Parental Control, MAF Short and MAF Long isoform (simultaneously) overexpressing cells and in BoM2 Control, shMAF or Rescue BoM2 cells. α-TUBULIN was used as loading control.

c) Direct c-MAF mRNA and Protein expression comparison between MCF7, BoM2 and MAF-depleted BoM2 as described in a) and b).

d) Renilla activity of C-MARE (c-MAF responsive element) reporter plasmid in Parental cells transiently transfected with Control, c-MAF Short isoform, c-MAF Long Isoform or c.MAF Short and Long isoform expressing vectors. Activity of C-MARE promoter is normalized to Control condition and presented in arbitrary units. Data are mean of three independent experiments with sd.

Figure 7:
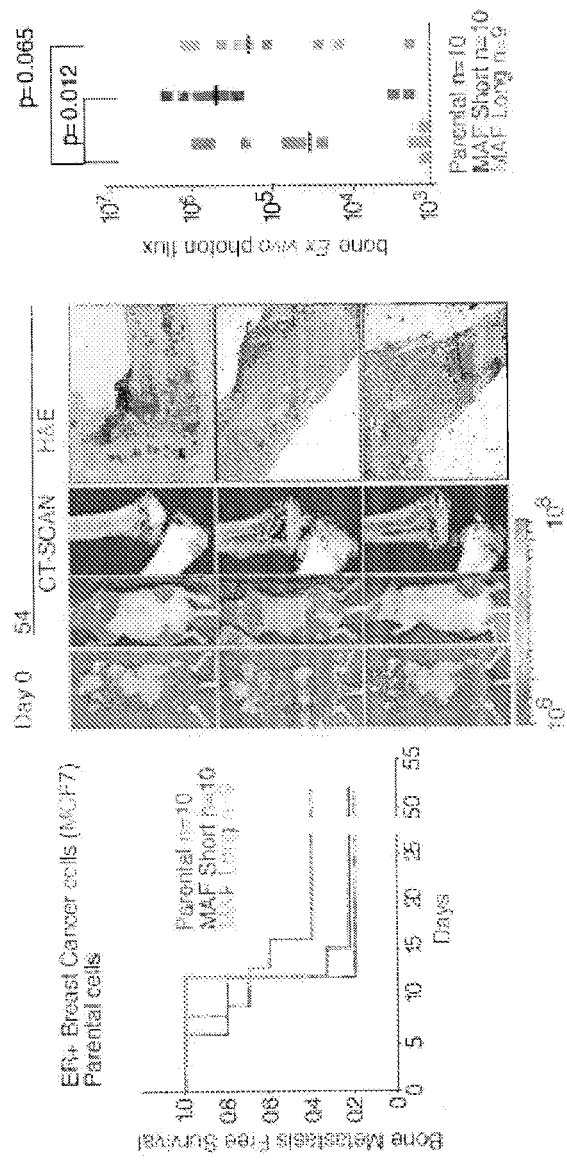

FIG. 7. MAF drives bone metastasis in experimental breast cancer metastasis mouse models (Left) Kaplan-Meier curve of bone metastasis-free survival. Parental Control and c-MAF Short and c-MAF Long isoform overexpressing cells were injected into the left ventricle and metastasis was determined by bioluminescence. (Right) Representative bioluminescent images at day 0 and at endpoint, day 54, with representative CT scans of mice hind limbs and H&E staining of bone metastasis for each group are shown. Scale bars, 100 um. Osteolytic area-yellow dashed line. (right) Total photon flux of ex vivo hind limbs was measured at endpoint, day 54, and normalized to day 0. P values were calculated by comparing Parental cells transfected with Control and both c-MAF Short and c-MAF Long expression vectors simultaneously (Left) or separately (Right).

Figure 8:
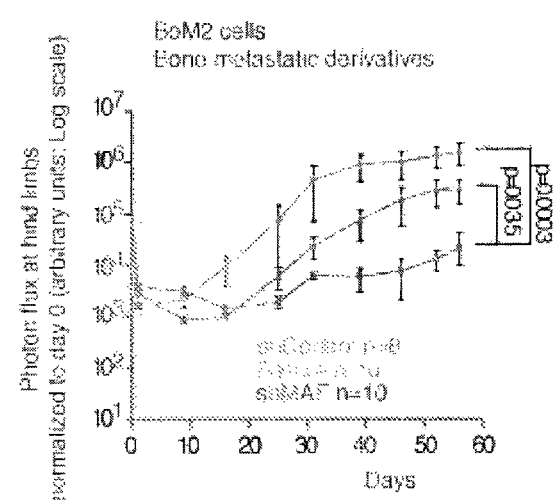

FIG. 8. c-MAF is a causal mediator of breast cancer metastasis to the bone Bioluminescence imaging plot of bone metastasis development is shown. Values are normalized to day 0. Control, shMAF or Rescue BoM2 cells were injected into left ventricle of nude mice.

Statistics were calculated including only animals that relapsed with bone metastasis.

Figure 9:
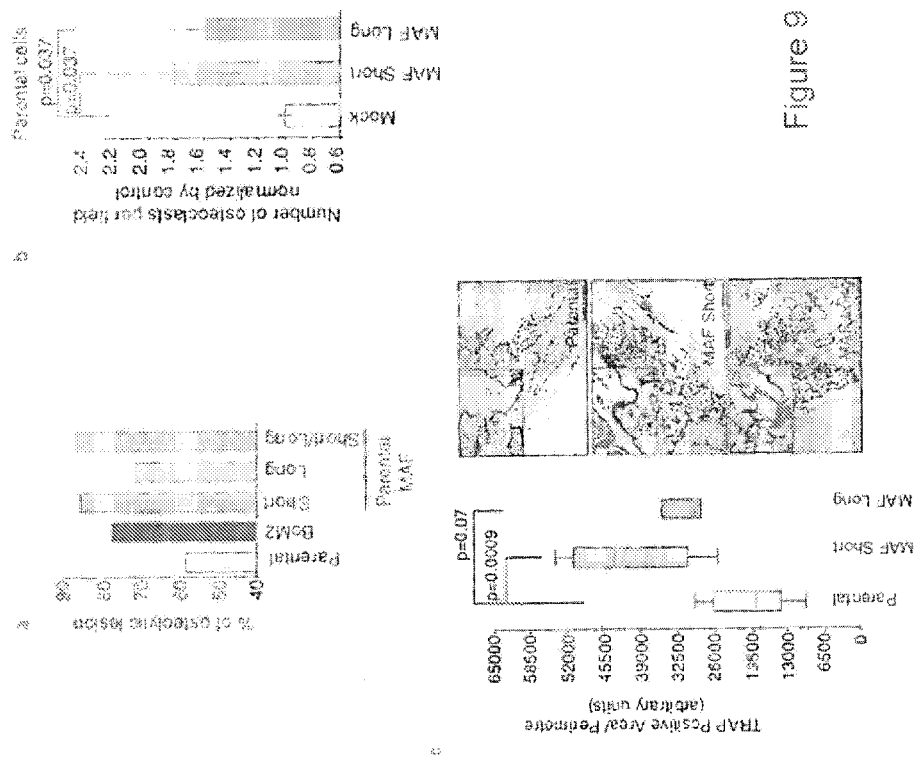
Figure 9:
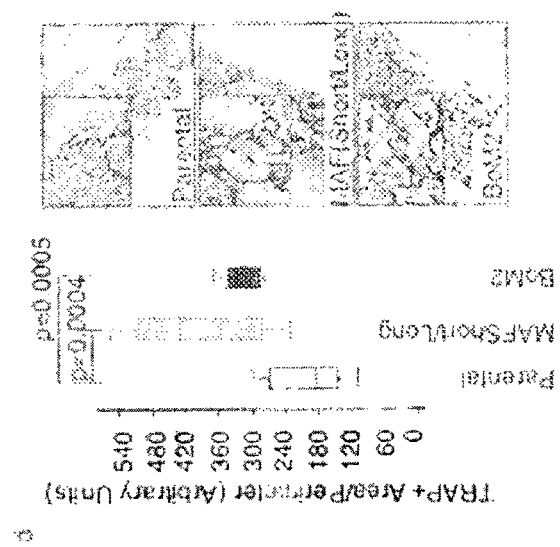

FIG. 9. c-MAF triggers osteoclast differentiation in breast cancer bone metastasis lesions.

a) Percentage of osteolytic lesions (measured by X-RAY) per total number of bone lesions (measured by luminescence). Parental, c-MAF short-, c-MAF long- and c-MAF short and Long-expressing parental cells and BoM2 bone metastatic MCF7 cell derivatives were injected into the left ventricle of a mouse and bone colonization was analyzed by in vivo bioluminescent imaging.

b) Assay of osteoclast differentiation from mouse bone marrow-derived precursor cells using conditioned medium originated from MCF7 parental cells or cells over-expressing any of the c-MAF isoforms (short—short isoform and long—long isoform). The number of osteoclasts is measured by means of the TRAP technique (>3 Multinucleated cells).

c and d) TRAP staining of representative bone metastatic lesions from mice intracardiacally injected with Parental, c-MAF short-, c-MAF long- and c-MAF short and Long-expressing parental cells and BoM2 bone metastatic MCF7 cell derivatives. TRAP positive osteoclast cells (purple) along bone tumor interface were counted in at least four different fields from four independent mice and plotted with SD values. Scale bar 50 μM. The statistical differences between groups are evaluated by means of the two-tailed wilcoxon test.

Figure 10:
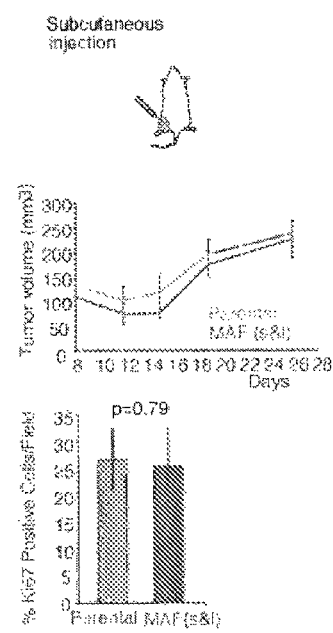

FIG. 10. c-MAF does not support breast cancer proliferation

Schematic representation of subcutaneous injection. (Upper) Growth curves of subcutaneous tumors form Parental Control or c-MAF Short and c-MAF Long isoform (simultaneously) overexpressing cells. Values represent the mean with sd. (Down) Percentage of Ki67-positive cells in subcutaneous tumors from Control or c-MAF Short and c-MAF Long isoform (simultaneously) overexpressing cells. For each tumor a minimum of ten random fields were counted for Ki67-positive cells. Values are mean with sd. (n=4)

Figure 11:
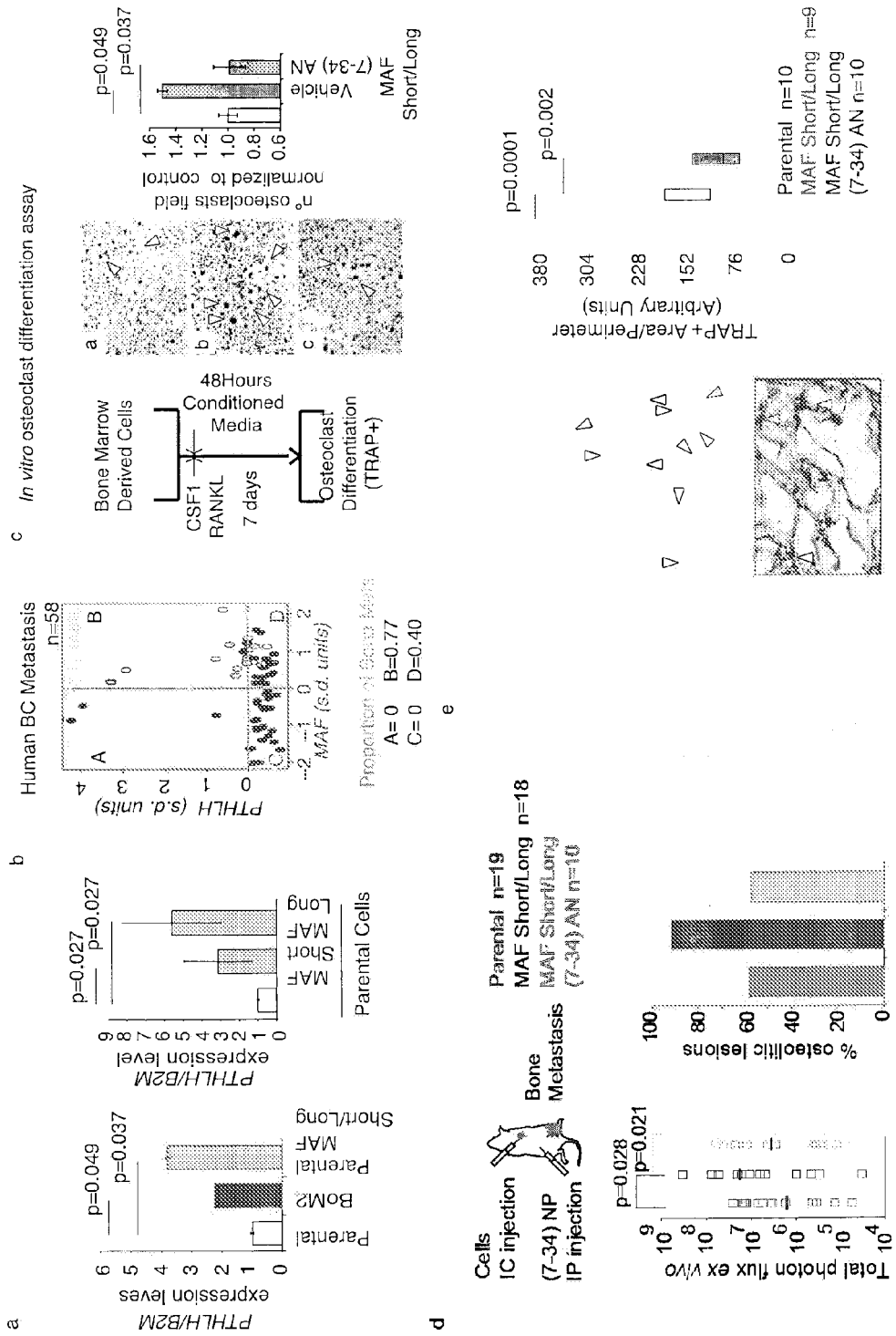

FIG. 11: PTHLH downstream of c-MAF contributes and mediates breast cancer bone metastasis a) PTHLH relative expression levels in Parental, c-MAF short-, c-MAF long- and c-MAF short and Long-expressing parental cells and BoM2 bone metastatic MCF7 cell derivatives normalized to B2M expression level. * p-value <0.05.

b) Dot chart of the standardized expression of MAF against the standardized expression of PTHLH in human breast cancer metastasis from GSE14020 data set. The red dots depict bone metastasis while the black dots depict other soft tissue mets. The dotted lines depicted the average MAF or PTHLH expression in metastasis samples.

c) Bone marrow cells treated with 50:50 osteoclast differentiation and conditioned media (CM) parental, c-MAF short and Long-expressing parental cells and BoM2 bone metastatic MCF7 cell derivatives or without CM but with human PTHLH antagonist peptide (7-34)(5 μg/ml), The number of osteoclasts is measured by means of the TRAP technique (Ostoclasts are >3 Multinucleated cells, Highlighted by white arrows) and normalized to control.

d) Parental, c-MAF short and long-expressing parental cells labeled with the luciferase gene were injected into the left ventricle of mouse and bone colonization was analyzed by in viva Bioluminescent imaging. The mice injected with c-MAF short and long expressing parental cells were treated or not with PTHLH antagonist peptide (7-34) inoculated intraperitoneally (6 μg/animal) twice a day during the course of the experiment. The plot represents the total photon flux ex viva at the experiment end point, which reflects the number of metastatic cells per lesion (left panel). Osteolytic bone metastasis lesions are depicted (right panel)

e) X-RAY (CT-scan) images of representative osteolytic lesions per group. TRAP positive osteoclast cells (black, highlighted by white arrows) along bone tumor interface were depicted for the different groups. TRAP positive osteoclast cells (Black) along bone tumor interface from lesions were counted in at least four different fields from each independent mouse and plotted with SD values. Scale bar 50 μM. The statistical differences between groups are evaluated by means of the two-tailed wilcoxon test.

Figure 12:
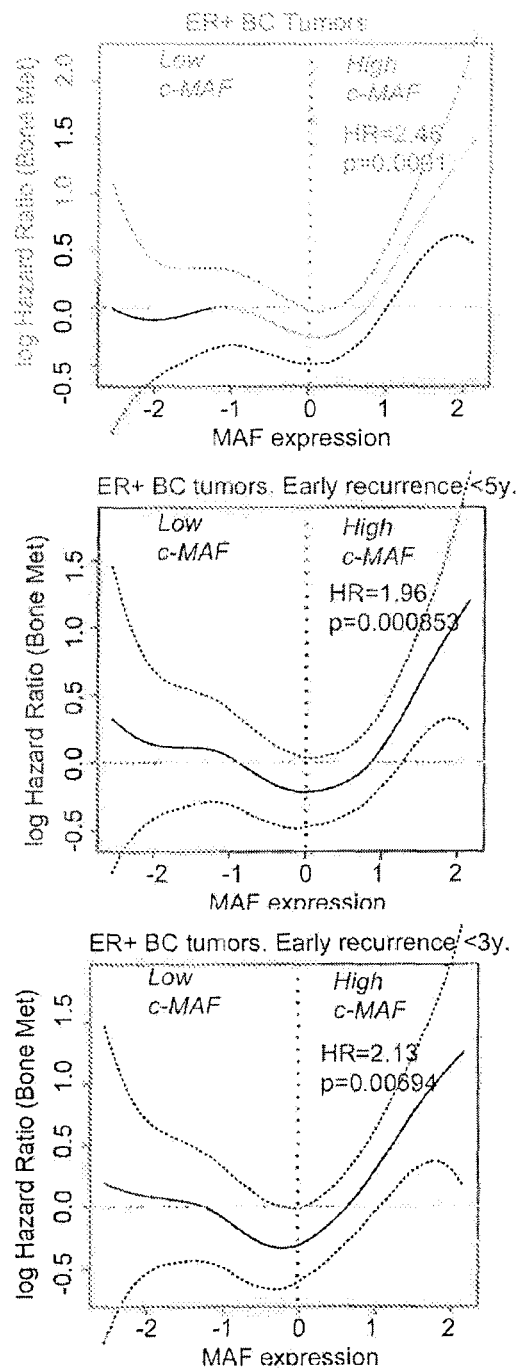
Figure 12:
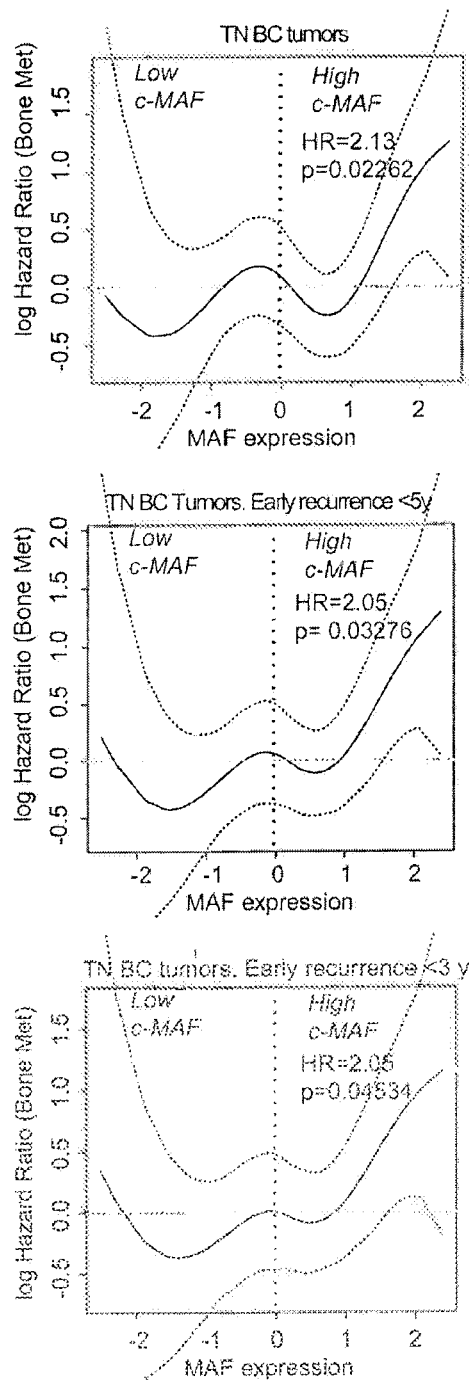

FIG. 12. Estimate of the relationship between c-MAF expression and bone metastasis hazard ratio via a Cox regression model with quartic splines (smoothCoxph function in package phenoTest). The plots correspond to the indicated groups: the HR ratio and p-value of c-MAF capacity to predict bone metastasis in tumors whose c-MAF expression levels are above the average (named 0) (union of GSE2603, GSE2034 and GSE12276 data set, cohort I). 1 at the expression levels indicates 1 standard deviation subsequently.

Figure 13:
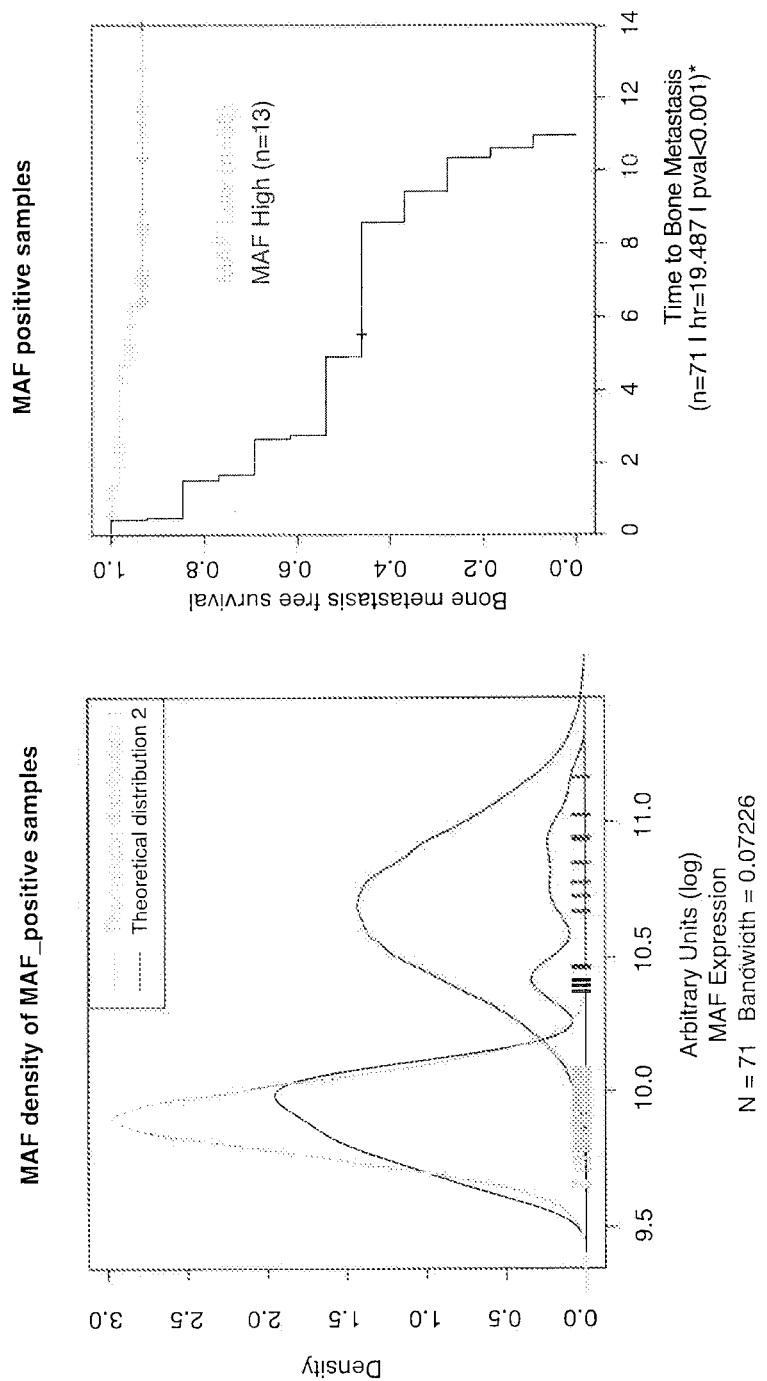

FIG. 13. Determination of c-MAF expression and bone metastasis risk. We assayed in the validation cohort II to what extend the higher the dose of c-MAF the higher the risk of bone relapse. We quantified c-MAF expression by immunohistochemistry (IHC) by means of determining the optical density of the staining using a computerized system as described above (FIG. 4a,b). Based on the two types of c-MAF positive breast cancer tumors, we can separate them in two groups as they have a bimodal behavior (left panel). Building on this two categories, we validate the observation that the higher the staining of c-MAF, the higher the risk of bone metastasis is (HR(bone mets)=19.45; p-value<0.001) and the earlier the bone metastasis occurs (right panel).

Figure 14:
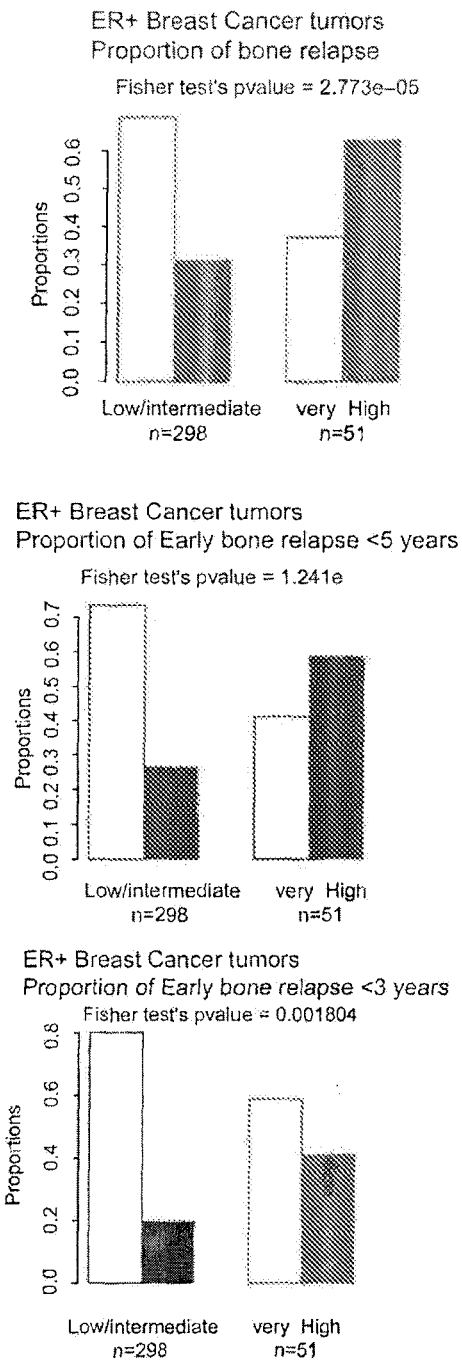

FIG. 14. Graph showing the results of a Fisher's exact test for testing the independence of c-MAF and bone metastasis at the different time points (union of GSE2603, GSE2034 and GSE12276 data set, cohort I). Proportions of the contingency table and Fisher's test p-values are indicated in each panel.

Figure 15:
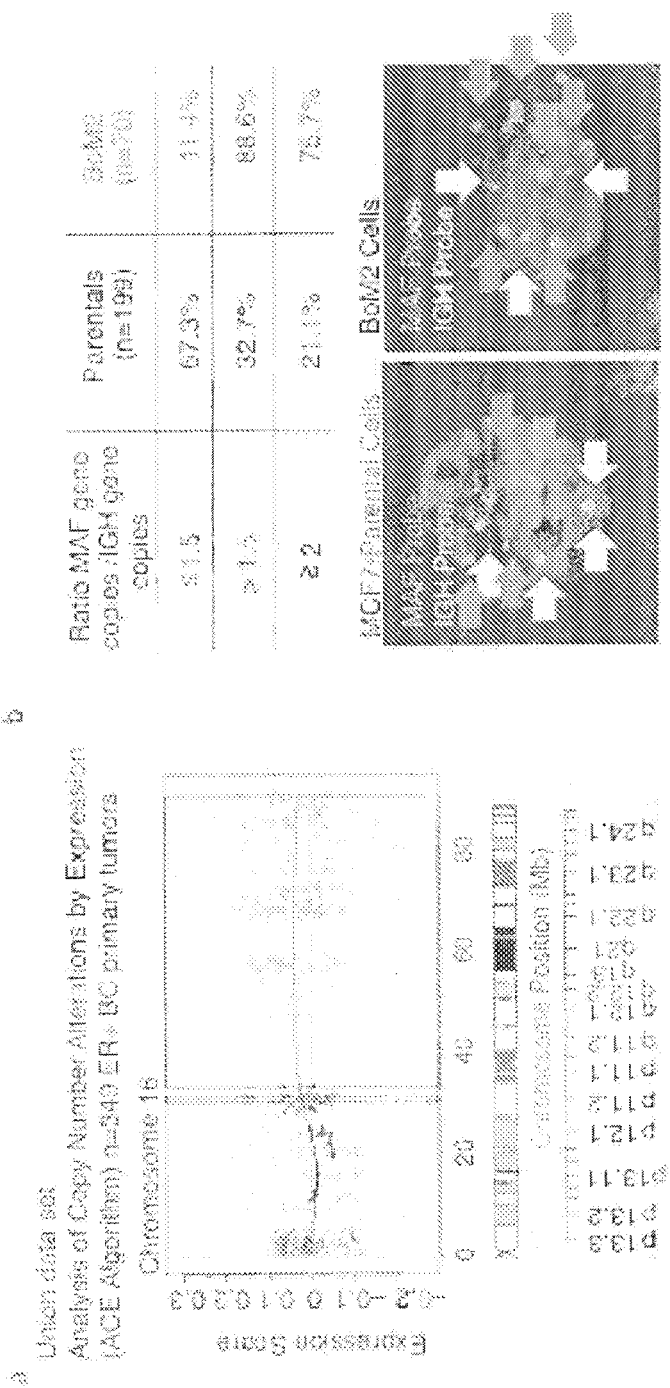
Figure 15:
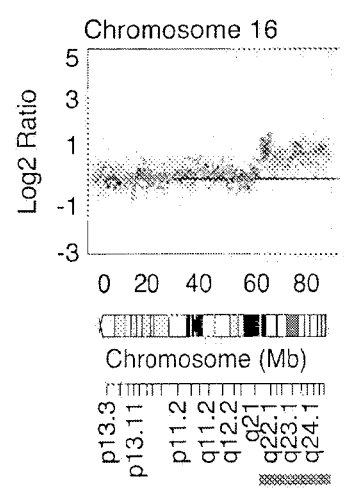

FIG. 15. c-MAF overexpression can occurs due to copy number alterations a) Analysis of copy number alteration based on gene expression (ACE Algorithm). Shaded area depicts DNA genomic amplification significantly associated with relapse in ER+ breast cancer tumors (union of GSE2603, GSE2034 and GSE12276 data set, cohort I).

b) Panel depicting percentage of Parental and BoM2 bone metastatic cells with MAF gene amplification based on ratio between MAF gene copies (16q23) and IGH (14q32) gene copies. Representative images of FISH stained Parental and BoM2 cells.

c) For chromosome 16, black dots and grey horizontal lines represent normalized log 2 intensity ratios and segments, respectively. BoM2 are compared over MCF7 parental cells. At the bottom, in grey the 16q22-24 DNA genomic amplification is highlighted.

Figure 16:
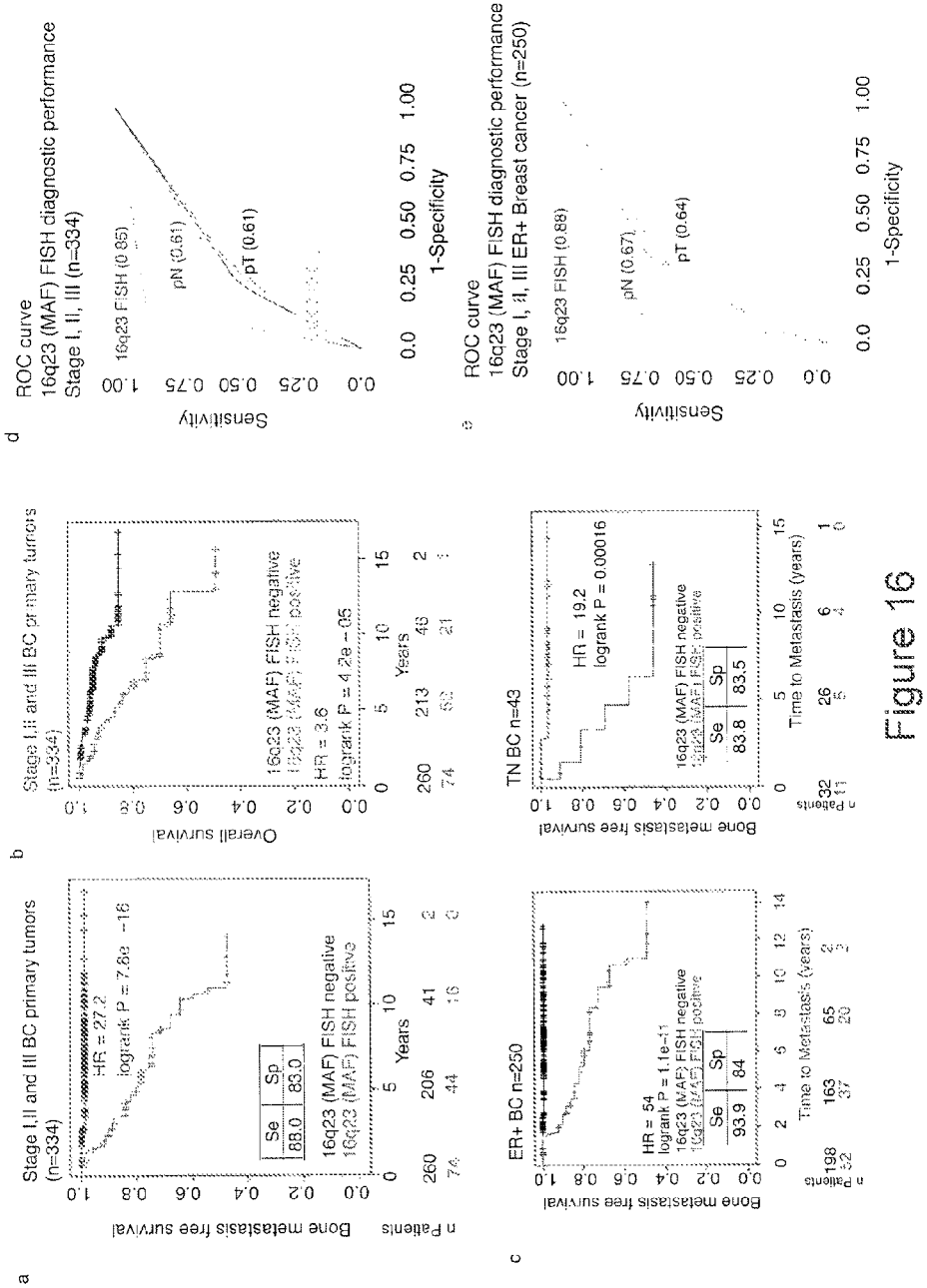

FIG. 16. Amplification of 16q22-24 genomic DNA region is associated with breast cancer bone metastasis a and b) Kaplan-Meier curve of bone (a) metastasis-free or overall (bt) survival in stage I, II, and III BC human primary tumor set (n=334)(cohort II). Patients were stratified according to 16q23 FISH negative and 16q23 FISH positive group based on cut-off of 2.5 16q23 copies per cell as an average, using 3 cores per tumor. Se-sensitivity; Sp-specificity; HR-hazard ratio.

c) Kaplan-Meier curve of bone metastasis free survival for ER-positive (left) or triple negative (right) patients in I, II, and III BC human primary tumor set (n=250 and n=43 respectively)(from cohort II). Patients were divided to 16q23 FISH negative and 16q23 FISH positive group based on cut-off of 2.5 for 16q23 copies per cell as an average, using 3 cores per tumor. HR-hazard ratio.

d, e) Receiver Operating Characteristic (ROC) curves for diagnostic performance of 16q23 amplification in overall (d) and ER+ breast cancer (e). In a ROC curve the true positive rate (Sensitivity) is plotted in function of the false positive rate (100-Specificity) for different cut-off points. Each point on the ROC curve represents a sensitivity/specificity pair corresponding to a particular decision threshold.

DETAILED DESCRIPTION OF THE INVENTION

Definitions of General Terms and Expressions

As used herein, "agent for avoiding or preventing bone degradation" refers to any molecule capable of preventing, inhibiting, treating, reducing, or stopping bone degradation either by stimulating the osteoblast proliferation or inhibiting the osteoclast proliferation or fixing the bone structure.

As used herein, the term "amplification of a gene" refers to a process through which various copies of a gene or of a gene fragment are formed in an individual cell or a cell line. The copies of the gene are not necessarily located in the same chromosome. The duplicated region is often called an "amplicon". Normally, the amount of mRNA produced, i.e., the gene expression level also increases in proportion to the copy number of a particular gene.

As used herein, the term "basal-like" "basal-like subtype," "breast cancer of the basal-like subtype" and the like, as used herein, refers to a particular subtype of breast cancer characterized by the two negative receptors ER and HER2 and at least one positive receptor of the group consisting of CK5/6, CK14, CK17 and EGFR. Thus, all sentences in the present application which cite and refer to triple negative breast cancer (ER, HER-2, PgR) can also be cited and refer also to basal-like breast cancer wherein ER and HER2 are negative and wherein at least one of CK5/6, CK14, CK17 and EGFR is positive. Alternatively, "basal-like" also refers to breast cancer characterized by a gene expression profile based on the up-regulation and/or down-regulation of the following ten genes: (1) Forkhead box CI (FOXC 1); (2) Melanoma inhibitory activity (MIA); (3) NDC80 homolog, kinetochore complex component (KNTC2); (4) Centrosomal protein 55 kDa (CEP55); (5) Anillin, actin binding protein (ANLN); (6) Maternal embryonic leucine zipper kinase (MELK); (7) G protein-coupled receptor 160 (GPR160); (8) Transmembrane protein 45B (TMEM45B); (9) Estrogen receptor 1 (ESR1); (10) Forkhead box A1 (FOXA1). Because the gene expression profile used to classify breast cancer tumors as basal-like subtype does not include the estrogen receptor, the progesterone receptor or Her2, both triple negative and non-triple negative breast cancers may be classified as basal-like subtype.

As used herein, "Triple-negative breast cancer" refers to a breast cancer which is characterized by a lack of detectable expression of both ER and PR (preferably when the measures of expression of ER and PR are carried out by the method disclosed by M. Elizabeth H et al., *Journal of Clinical Oncology*, 28(16): 2784-2795, 2010) and the tumor cells are not amplified for epidermal growth factor receptor type 2 (HER2 or ErbB2), a receptor normally located on the cell surface. Tumor cells are considered negative for expression of ER and PR if less than 5 percent of the tumor cell nuclei are stained for ER and PR expression using standard immunohistochemical techniques. As used herein, tumor cells are considered negative for HER2 overexpression if they yield a test result score of 0 or 1+, or 2+ when tested with a HercepTest™ Kit (Code K5204, Dako North America, Inc., Carpinteria, Calif.), a semi-quantitative immunohistochemical assay using a polyclonal anti-HER2 primary antibody or if they are HER2 FISH negative.

As used herein, "c-MAF gene" (v-maf musculoaponeurotic fibrosarcoma oncogene homologue (avian) also known as MAF or MGC71685) is a transcription factor containing a leucine zipper which acts like a homodimer or a heterodimer. Depending on the DNA binding site, the encoded protein can be a transcriptional activator or repressor. The DNA sequence encoding c-MAF is described in the NCBI database under accession number NG_016440 (SEQ ID NO: 1 (genomic)). The coding sequence of c-MAF is set forth in SEQ ID NO:13. The methods of the present invention may utilize either the coding sequence or the genomic DNA sequence. Two messenger RNA are transcribed from said DNA sequence, each of which will give rise to one of the two c-MAF protein isoforms, the α isoform and the β isoform. The complementary DNA sequences for each of said isoforms are described, respectively, in the NCBI database under accession numbers NM_005360.4 (SEQ ID NO: 2) and NM_001031804.2 (SEQ ID NO: 3).

As used herein, a "c-MAF inhibitory agent" refers to any molecule capable of completely or partially inhibiting the c-MAF gene expression, both by preventing the expression product of said gene from being produced (interrupting the c-MAF gene transcription and/or blocking the translation of the mRNA coming from the c-MAF gene expression) and by directly inhibiting the c-MAF protein activity. C-MAF gene expression inhibitors can be identified using methods based on the capacity of the so-called inhibitor to block the capacity of c-MAF to promote the in vitro cell proliferation, such as shown in the international patent application WO2005/046731 (the entire contents of which are hereby incorporated by reference), based on the capacity of the so-called inhibitor to block the transcription capacity of a reporter gene under the control of the cyclin D2 promoter or of a promoter containing the c-MAF response region (MARE or c-MAF responsive element) in cells which express c-MAF such as described in WO2008098351 (the entire contents of which are hereby incorporated by reference) or based on the capacity of the so-called inhibitor to block the expression of a reporter gene under the control of the IL-4 promoter in response to the stimulation with PMA/ionomycin in cells which express NFATc2 and c-MAF such as described in US2009048117A (the entire contents of which is hereby incorporated by reference).

As used herein, Mammalian target of rapamycin (mTOR) or "mTor" refers to those proteins that correspond to EC 2.7.11.1. mTor enzymes are serine/threonine protein kinases and regulate cell proliferation, cell motility, cell growth, cell survival, and transcription.

As used herein, an "mTor inhibitor" refers to any molecule capable of completely or partially inhibiting the mTor gene expression, both by preventing the expression product of said gene from being produced (interrupting the mTor gene transcription and/or blocking the translation of the mRNA coming from the mTor gene expression) and by directly inhibiting the mTor protein activity. Including inhibitors that have a dual or more targets and among them mTor protein activity.

As used herein, "Src" refers to those proteins that correspond to EC 2.7.10.2. Src is a non-receptor tyrosine kinase and a proto-oncogene. Src may play a role in cell growth and embryonic development.

As used herein, a "Src inhibitor" refers to any molecule capable of completely or partially inhibiting the Src gene expression, both by preventing the expression product of said gene from being produced (interrupting the Src gene transcription and/or blocking the translation of the mRNA coining from the Src gene expression) and by directly inhibiting the Src protein activity.

As used herein, "Prostaglandin-endoperoxide synthase 2", "cyclooxygenase-2" or "COX-2" refers to those proteins that correspond to EC 1.14.99.1. COX-2 is responsible for converting arachidonic acid to prostaglandin endoperoxide H2.

As used herein, a "COX-2 inhibitor" refers to any molecule capable of completely or partially inhibiting the COX-2 gene expression, both by preventing the expression product of said gene from being produced (interrupting the COX-2 gene transcription and/or blocking the translation of the mRNA coming from the COX-2 gene expression) and by directly inhibiting the COX-2 protein activity.

As used herein "outcome" or "clinical outcome" refers to the resulting course of disease and/or disease progression and can be characterized for example by recurrence, period of time until recurrence, metastasis, period of time until metastasis, number of metastases, number of sites of metastasis and/or death due to disease. For example a good clinical outcome includes cure, prevention of recurrence, prevention of metastasis and/or survival within a fixed period of time (without recurrence), and a poor clinical outcome includes disease progression, metastasis and/or death within a fixed period of time.

As used herein, "ER+ breast cancer" is understood as breast cancer the tumor cells of which express the estrogen receptor (ER). This makes said tumors sensitive to estrogen, meaning that the estrogen makes the cancerous breast tumor grow. In contrast, "ER− breast cancer" is understood as breast cancer the tumor cells of which do not express the estrogen receptor (ER). Among the ER+ breast cancer are included luminal A and B subtypes.

As used herein, the term "expression level" of a gene as used herein refers to the measurable quantity of gene product produced by the gene in a sample of the subject, wherein the gene product can be a transcriptional product or a translational product. Accordingly, the expression level can pertain to a nucleic acid gene product such as mRNA or cDNA or a polypeptide gene product. The expression level is derived from a subject's sample and/or a reference sample or samples, and can for example be detected de novo or correspond to a previous determination. The expression level can be determined or measured, for example, using microarray methods, PCR methods (such as qPCR), and/or antibody based methods, as is known to a person of skill in the art.

As used herein, the term "gene copy number" refers to the copy number of a nucleic acid molecule in a cell. The gene copy number includes the gene copy number in the genomic (chromosomal) DNA of a cell. In a normal cell (non-tumoral cell), the gene copy number is normally two copies (one copy in each member of the chromosome pair). The gene copy number sometimes includes half of the gene copy number taken from samples of a cell population.

"Increased expression level" is understood as the expression level when it refers to the levels of the c-MAF gene greater than those in a reference sample or control sample. This increased levels can be caused without excluding other mechanisms by a gene or 16q23 or 16q22-24 chromosomal locus amplification or translocation. Particularly, a sample can be considered to have high c-MAF expression level when the expression level in the sample isolated from the patient is at least about 1.1 times, 1.5 times, 5 times, 10 times, 20 times, 30 times, 40 times, 50 times, 60 times, 70 times, 80 times, 90 times, 100 times or even more with respect to the reference or control.

"Probe", as used herein, refers to an oligonucleotide sequence that is complementary to a specific nucleic acid sequence of interest. In some embodiments, the probes may be specific to regions of chromosomes which are known to undergo translocations. In some embodiments, the probes have a specific label or tag. In some embodiments, the tag is a fluorophore. In some embodiments, the probe is a DNA in situ hybridization probe whose labeling is based on the stable coordinative binding of platinum to nucleic acids and proteins. In some embodiments, the probe is described in U.S. patent application Ser. No. 12/067,532 and U.S. patent application Ser. No. 12/181,399, which are incorporated by reference in their entirety, or as described in Swennenhuis et al. "Construction of repeat-free fluorescence in situ hybridization probes" *Nucleic Acids Research* 40(3):e20 (2012).

"Tag" or "label", as used herein, refers to any physical molecule which is directly or indirectly associated with a probe, allowing the probe or the location of the probed to be visualized, marked, or otherwise captured.

"Translocation", as used herein, refers to the exchange of chromosomal material in unequal or equal amounts between chromosomes. In some cases, the translocation is on the same chromosome. In some cases, the translocation is between different chromosomes. Translocations occur at a high frequency in many types of cancer, including breast cancer and leukemia. Translocations can be either primary reciprocal translocations or the more complex secondary translocations. There are several primary translocations that involve the immunoglobin heavy chain (IgH) locus that are believed to constitute the initiating event in many cancers. (Eychène, A., Rocques, N., and Puoponnot, C., A new MAFia in cancer. 2008. *Nature Reviews: Cancer.* 8: 683-693.)

"Polyploid" or "polyploidy", as used herein, indicates that the cell contains more than two copies of a gene of interest. In some instances, the gene of interest is MAP. In some embodiments, polyploidy is associated with an accumulation of expression of the gene of interest. In some embodiments, polyploidy is associated with genomic instability. In some embodiments, the genomic instability may lead to chromosome translocations.

"Whole genome sequencing", as used herein, is a process by which the entire genome of an organism is sequenced at a single time. See, e.g., Ng., P. C. and Kirkness, E. F., Whole Genome Sequencing. 2010. *Methods in Molecular Biology.* 628: 215-226.

"Exome sequencing", as used herein, is a process by which the entire coding region of the DNA of an organism is sequenced. In exome sequencing, the mRNA is sequenced. The untranslated regions of the genome are not included in exome sequencing. See, e.g., Choi, M. et al., Genetic diagnosis by whole exome capture and massively parallel DNA sequencing. 2009. *PNAS.* 106(45): 19096-19101.

"Metastasis", as used herein, is understood as the propagation of a cancer from the organ where it started to a different organ. It generally occurs through the blood or lymphatic system. When the cancer cells spread and form a new tumor, the latter is called a secondary or metastatic tumor. The cancer cells forming the secondary tumor are like those of the original tumor. If a breast cancer, for example, spreads (metastasizes) to the lung, the secondary tumor is formed of malignant breast cancer cells. The disease in the lung is metastatic breast cancer and not lung cancer. In a particular embodiment of the method of the invention, the metastasis is triple negative breast cancer, or, alternatively ER+ breast cancer (including luminal type A and type B) which has spread (metastasized) to the bone.

"Predicting", as used herein, refers to the determination of the likelihood that the subject suffering from triple negative (including basal-like) breast cancer, or alternatively ER+ breast cancer will develop metastasis to a distant organ. As used herein, "good prognosis" indicates that the subject is expected (e.g. predicted) to survive and/or have no, or is at low risk of having, recurrence or distant metastases within a set time period. The term "low" is a relative term and, in the context of this application, refers to the risk of the "low" expression group with respect to a clinical outcome (recurrence, distant metastases, etc.). A "low" risk can be considered as a risk lower than the average risk for an heterogeneous cancer patient population. In the study of Paik et al. (2004), an overall "low" risk of recurrence was considered to be lower than 15 percent. The risk will also vary in function of the time period. The time period can be, for example, five years, ten years, fifteen years or even twenty years after initial diagnosis of cancer or after the prognosis was made.

As used herein, "poor prognosis" indicates that the subject is expected e.g. predicted to not survive and/or to have, or is at high risk of having, recurrence or distant metastases within a set time period. The term "high" is a relative term and, in the context of this application, refers to the risk of the "high" expression group with respect to a clinical outcome (recurrence, distant metastases, etc.). A "high" risk can be considered as a risk higher than the average risk for a heterogeneous cancer patient population. In the study of Paik et al. (2004), an overall "high" risk of recurrence was considered to be higher than 15 percent. The risk will also vary in function of the time period. The time period can be, for example, five years, ten years, fifteen years or even twenty years of initial diagnosis of cancer or after the prognosis was made.

"Reference value", as used herein, refers to a laboratory value used as a reference for values/data obtained by laboratory examinations of patients or samples collected from patients. The reference value or reference level can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from a population of subjects of the chronological age matched group, or based on a pool of samples including or excluding the sample to be tested.

As used herein, "Subject" or "patient" refers to all animals classified as mammals and includes but is not limited to domestic and farm animals, primates and humans, for example, human beings, non-human primates, cows, horses, pigs, sheep, goats, dogs, cats, or rodents. Preferably, the subject is a human man or woman of any age or race.

The term "treatment", as used herein, refers to any type of therapy, which aims at terminating, preventing, ameliorating or reducing the susceptibility to a clinical condition as described herein. In a preferred embodiment, the term treatment relates to prophylactic treatment (i.e. a therapy to reduce the susceptibility to a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, or immune deficiency.

As used herein, "sample" or "biological sample" means biological material isolated from a subject. The biological sample may contain any biological material suitable for determining the expression level of the c-MAF gene. The sample can be isolated from any suitable biological tissue or fluid such as, for example, tumor tissue, blood, blood plasma, serum, urine or cerebral spinal fluid (CSF).

"Tumor tissue sample" is understood as the tissue sample originating from the primary triple negative (including basal-like) breast cancer tumor, or alternatively from an ER+ breast cancer tumor. Said sample can be obtained by conventional methods, for example biopsy, using methods well known by the persons skilled in related medical techniques.

"Osteolytic bone metastasis" refers to a type of metastasis in which bone resorption (progressive loss of the bone density) is produced in the proximity of the metastasis resulting from the stimulation of the osteoclast activity by the tumor cells and is characterized by severe pain, pathological fractures, hypercalcaemia, spinal cord compression and other syndromes resulting from nerve compression.

Method for Predicting Bone Metastasis of a Triple Negative (Including Basal-like) Breast Cancer, or of an ER+ Breast Cancer, Based on the Expression Level of c-MAF It was surprisingly found that the expression level of c-MAF in samples of a triple negative (including basal-like) breast cancer, and in samples of ER+ breast cancer, correlated with the risk of suffering bone metastasis. Moreover, gene expression of c-MAF in triple negative (including basal-like) primary tumors, and in ER+ primary tumors, correlated significantly with bone metastasis recurrence, and inversely with bone metastasis-free survival and survival. Moreover, it has been found that the c-MAF expression levels predict bone metastasis in a dose-dependent manner.

In a first aspect, the invention relates to an in vitro method (hereinafter first method of the invention) for predicting bone metastasis of a triple negative (including basal-like) breast cancer, or, alternatively an ER+ breast cancer, in a subject suffering said cancer which comprises:

i) determining the expression level of the c-MAF gene in a sample of said subject and ii) comparing the expression level obtained in step i) with a reference value, wherein increased expression level of said gene with respect to said reference value is indicative of increased risk of developing bone metastasis.

The method of the invention comprises in a first step determining the c-MAF gene expression level in a sample from a subject. In a preferred embodiment, the sample is a tumor tissue sample.

The methods for obtaining a biopsy sample include splitting a tumor into large pieces, or microdissection, or other cell separating methods known in the art. The tumor cells can additionally be obtained by means of cytology through aspiration with a small gauge needle. To simplify sample preservation and handling, samples can be fixed in formalin and soaked in paraffin or first frozen and then soaked in a tissue freezing medium such as OCT compound by means of immersion in a highly cryogenic medium which allows rapid freezing.

In a preferred embodiment, the first method of the invention comprises quantifying only the c-MAF gene expression level as a single marker, i.e., the method does not involve determining the expression level of any additional marker.

As understood by the person skilled in the art, the gene expression level can be quantified by measuring the messenger RNA levels of said gene or of the protein encoded by said gene, as well as the number of genomic region copies or translocations containing said gene.

For this purpose, the biological sample can be treated to physically or mechanically break up the tissue or cell structure, releasing the intracellular components into an aqueous or organic solution for preparing nucleic acids. The nucleic acids are extracted by means of commercially available methods known by the person skilled in the art (Sambrook, J., et al., "Molecular cloning: a Laboratory Manual", 3rd ed., Cold Spring Harbor Laboratory Press, N.Y., Vol. 1-3.)

Thus, the c-MAF gene expression level can be quantified from the RNA resulting from the transcription of said gene (messenger RNA or mRNA) or, alternatively, from the complementary DNA (cDNA) of said gene. Therefore, in a particular embodiment of the invention, the quantification of the c-MAF gene expression level comprises the quantification of the messenger RNA of the c-MAF gene or a fragment of said mRNA, complementary DNA of the c-MAF gene or a fragment of said cDNA or the mixtures thereof.

Virtually any conventional method can be used within the scope of the invention for detecting and quantifying the mRNA levels encoded by the c-MAF gene or of the corresponding cDNA thereof. By way of non-limiting illustration, the mRNA levels encoded by said gene can be quantified using conventional methods, for example, methods comprising mRNA amplification and the quantification of said mRNA amplification product, such as electrophoresis and staining, or alternatively, by Southern blot and using suitable probes, Northern blot and using specific probes of the mRNA of the gene of interest (c-MAF) or of the corresponding cDNA thereof, mapping with S1 nuclease, RT-PCR, hybridization, microarrays, etc., preferably by means of real time quantitative PCR using a suitable marker. Likewise, the cDNA levels corresponding to said mRNA encoded by the c-MAF gene can also be quantified by means of using conventional techniques; in this case, the method of the invention includes a step for synthesizing the corresponding cDNA by means of reverse transcription (RT) of the corresponding mRNA followed by the amplification and quantification of said cDNA amplification product. Conventional methods for quantifying expression level can be found, for example, in Sambrook et al., 2001. (cited ad supra). These methods are known in the art and a person skilled in the art would be familiar with the normalizations necessary for each technique. For example, the expression measurements generated using multiplex PCR should be normalized by comparing the expression of the genes being measured to so called "housekeeping" genes, the expression of which should be constant over all samples, thus providing a baseline expression to compare against or other control genes whose expression are known to be modulated with cancer.

In a particular embodiment, the c-MAF gene expression level is quantified by means of quantitative polymerase chain reaction (PCR) or a DNA/RNA array or nucleotide hybridization technique.

In addition, the c-MAF gene expression level can also be quantified by means of quantifying the expression level of the protein encoded by said gene, i.e., the c-MAF protein (c-MAF) [NCBI, accession number O75444], or any functionally equivalent variant of the c-MAF protein. There are two c-MAF protein isoforms, the α isoform (NCBI, NP_005351.2) made up of 403 amino acids (SEQ ID NO: 4) and the β isoform (NCBI, NP_001026974.1) made up of 373 amino acids (SEQ ID NO: 5). The c-MAF gene expression level can be quantified by means of quantifying the expression level of any of the c-MAF protein isoforms. Thus, in a particular embodiment, the quantification of the level of the protein encoded by the c-MAF gene comprises the quantification of the c-MAF protein.

In the context of the present invention, "functionally equivalent variant of the c-MAF protein" is understood as (i) variants of the c-MAF protein (SEQ ID NO: 4 or SEQ ID NO: 5) in which one or more of the amino acid residues are substituted by a conserved or non-conserved amino acid residue (preferably a conserved amino acid residue), wherein such substituted amino acid residue may or may not be one encoded by the genetic code, or (ii) variants comprising an insertion or a deletion of one or more amino acids and having the same function as the c-MAF protein, i.e., to act as a DNA binding transcription factor. Variants of the c-MAF protein can be identified using methods based on the capacity of c-MAF for promoting in vitro cell proliferation as shown in international patent application WO20051046731 (incorporated herein by reference in its entirety), based on the capacity of the so-called inhibitor for blocking the transcription capacity of a reporter gene under the control of cyclin D2 promoter or of a promoter containing the c-MAF responsive region (MARE or c-MAF responsive element) in cells expressing c-MAF as described in WO2008098351 (incorporated herein by reference in its entirety), or based on the capacity of the so-called inhibitor for blocking reporter gene expression under the control of the IL-4 promoter in response to the stimulation with PMA/ionomycin in cells expressing NFATc2 and c-MAF as described in US2009048117A (incorporated herein by reference in its entirety).

The variants according to the invention preferably have a sequence similarity with the amino acid sequence of any of the c-MAF protein isoforms (SEQ ID NO: 4 or SEQ ID NO: 5) of at least about 50%, at least about 60%, at least about 70%, at least about 80%, at least about 90%, at least about 91%, at least about 92%, at least about 93%, at least about 94%, at least about 95%, at least about 96%, at least about 97%, at least about 98% or at least about 99%. The degree of similarity between the variants and the specific c-MAF protein sequences defined previously is determined using algorithms and computer processes which are widely known by the persons skilled in the art. The similarity between two amino acid sequences is preferably determined using the BLASTP algorithm [BLAST Manual, Altschul, S., et al., NCBI NLM NIH Bethesda, Md. 20894, Altschul, S., et al., J. Mol. Biol. 215: 403-410 (1990)].

The c-MAF protein expression level can be quantified by any conventional method which allows detecting and quantifying said protein in a sample from a subject. By way of non-limiting illustration, said protein levels can be quantified, for example, by using antibodies with c-MAF binding capacity (or a fragment thereof containing an antigenic determinant) and the subsequent quantification of the complexes formed. The antibodies used in these assays may or may not be labeled. Illustrative examples of markers that can be used include radioactive isotopes, enzymes, fluorophores, chemiluminescence reagents, enzyme substrates or cofactors, enzyme inhibitors, particles, dyes, etc. There is a wide range of known assays that can be used in the present invention which use unlabeled antibodies (primary antibody) and labeled antibodies (secondary antibody); these techniques include Western-blot or Western transfer, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of protein microarrays or biochips including specific antibodies or assays based on colloidal precipitation in formats such as dipsticks. Other ways for detecting and quantifying said c-MAF protein include affinity chromatography techniques, ligand binding assays, etc. When an immunological method is used, any antibody or reagent that is known to bind to the c-MAF protein with a high affinity can be used for detecting the amount thereof. Nevertheless, the use of an antibody, for example, polyclonal sera, supernatants of hybridomas or monoclonal antibodies, antibody fragments, Fv, Fab, Fab' and F(ab')2, scFv, humanized diabodies, triabodies, tetrabodies, nanobodies, alphabodies, stapled peptides, cyclopeptides and antibodies is preferred. There are commercial anti-c-MAF protein antibodies on the market which can be used in the context of the present invention, such as for example antibodies ab427, ab55502, ab55502, ab72584, ab76817, ab77071 (Abcam plc, 330 Science Park, Cambridge CB4 0FL, United Kingdom), the 075444 monoclonal antibody (Mouse Anti-Human MAF Azide free Monoclonal antibody, Unconjugated, Clone 6b8) of AbD Serotec, etc. There are many commercial companies offering anti-c-MAF antibodies, such as Abnova Corporation, Bethyl Laboratories, Santa Cruz Biotechnology, Bioworld Technology, GeneTex, etc.

In a particular embodiment, the c-MAF protein levels are quantified by means of western blot, ELISA or a protein array.

In another particular embodiment, the c-MAF protein levels are quantified from exosomes or circulating DNA. Exosomes are 40-100 nm membrane vesicles secreted by most cell types in vivo and in vitro. Exosomes form in a particular population of endosomes, called multivesicular bodies (MVBs) by inward budding into the lumen of the compartment. Upon fusion of MVBs with the plasma membrane, these internal vesicles are secreted. Exosomes can be isolated from diverse cell lines or body fluids by several methods well known in the art (Théry C. et al., *Curr Protoc Cell Biol.* 2006 April; Chapter 3:Unit 3.22) (the entire contents of which are incorporated by reference herein). Several commercial kits are available for the isolation of exosomes such as ExoQuick™ or ExoTest™.

The first method of the invention comprises in a second step comparing the c-MAF gene expression level obtained in the sample (e.g., tumor sample) from the subject with a reference value.

Once the c-MAF gene expression level in a sample from a subject with breast cancer, for example triple negative (including basal-like) breast cancer or, alternatively, ER+ breast cancer, have been measured and compared with the reference value, if the expression level of said gene is increased with respect to said reference value, then it can be concluded that said subject has a greater tendency to develop bone metastasis.

The determination of the c-MAF gene expression level must be correlated with the reference value.

In an embodiment, reference value(s) as intended herein may convey absolute quantities of c-MAF. In another embodiment, the quantity of any one or more biomarkers in a sample from a tested subject may be determined directly relative to the reference value (e.g., in terms of increase or decrease, or fold-increase or fold-decrease). Advantageously, this may allow to compare the quantity of any one or more biomarkers in the sample from the subject with the reference value (in other words to measure the relative quantity of any one or more biomarkers in the sample from the subject vis-a-vis the reference value) without the need to first determine the respective absolute quantities of said one or more biomarkers.

In a preferred embodiment, the reference value is the c-MAF gene expression level in a control sample or reference sample. Depending on the type of tumor to be analyzed, the exact nature of the control or reference sample may vary. Thus, in the event that a prognosis is to be evaluated, then the reference sample is a sample from a subject with triple negative (including basal-like) breast cancer or, alternatively, ER+ breast cancer, that has not metastasized or that corresponds to the median value of the c-MAF gene expression level measured in a tumor tissue collection in biopsy samples from subjects with triple negative (including basal-like) breast cancer or, alternatively ER+ breast cancer, which have not metastasized.

Said reference sample is typically obtained by combining equal amounts of samples from a subject population. Generally, the typical reference samples will be obtained from subjects who are clinically well documented and in whom the absence of metastasis is well characterized. In such samples, the normal concentrations (reference concentration) of the biomarker (c-MAF gene) can be determined, for example by providing the mean concentration over the reference population. Various considerations are taken into account when determining the reference concentration of the marker. Among such considerations are the age, weight, sex, general physical condition of the patient and the like. For example, equal amounts of a group of at least about 2, at least about 10, at least about 100 to preferably more than about 1000 subjects, preferably classified according to the foregoing considerations, for example according to various age categories, are taken as the reference group. The sample collection from which the reference level is derived will preferably be formed by subjects suffering from the same type of cancer as the patient object of the study.

In a particular embodiment the reference values for "increased" or "reduced" expression of the c-MAF expression are determined by calculating the percentiles by conventional means which involves performing assays in one or several samples isolated from subjects whose disease is well documented by any of the methods mentioned above the c-MAF expression level. The "reduced" level of c-MAF can then preferably be assigned to samples wherein the c-MAF expression level is equal to or lower than $50^{th}$ percentile in the normal population including, for example, expression level equal to or lower than the $60^{th}$ percentile in the normal population, equal to or lower than the $70^{th}$ percentile in the normal population, equal to or lower than the $80^{th}$ percentile in the normal population, equal to or lower than the $90^{th}$ percentile in the normal population, and equal to or lower than the $95^{th}$ percentile in the normal population. The "increased" c-MAF gene expression level can then preferably be assigned to samples wherein the c-MAF gene expression level is equal to or greater than the $50^{th}$ percentile in the normal population including, for example, expression level equal to or greater than the $60^{th}$ percentile in the normal population, equal to or greater than the $70^{th}$ percentile in the normal population, equal to or greater than the $80^{th}$ percentile in the normal population, equal to or greater than the $90^{th}$ percentile in the normal population, and equal to or greater than the $95^{th}$ percentile in the normal population.

The person skilled in the art will understand that the prediction of the tendency for a primary breast tumor to metastasize is not needed to be correct for all the subjects to be identified (i.e., for 100% of the subjects). Nevertheless, the term requires enabling the identification of a statistically significant part of the subjects (for example, a cohort in a cohort study). Whether a part is statistically significant can be determined in a simple manner by the person skilled in the art using various well known statistical evaluation tools, for example, the determination of confidence intervals, determination of p values, Student's T test, Mann-Whitney test, etc. Details are provided in Dowdy and Wearden, Statistics for Research, John Wiley and Sons, New York 1983. The preferred confidence intervals are at least 90%, at least 95%, at least 97%, at least 98% or at least 99%. The p values are preferably 0.1, 0.05, 0.01, 0.005 or 0.0001. More preferably, at least 60%, at least 70%, at least 80% or at least 90% of the subjects of a population can be suitably identified by the method of the present invention.

In yet another embodiment, the metastasis to bone is an osteolytic bone metastasis.

In yet another embodiment, an expression level of c-MAF which is above the average indicates increased risk of bone metastasis, being said risk is proportional to the levels of c-MAF expression, Thus, the risk of bone metastasis in a subject suffering breast cancer is dose-dependent.

Method for Predicting the Clinical Outcome of a Patient Suffering Bone Metastasis from Triple Negative (Including Basal-like) Breast Cancer, or, Alternatively from ER+ Breast Cancer, Based on the Expression Level of c-MAF In another aspect, the invention relates to an in vitro method (hereinafter second method of the invention) for predicting the clinical outcome of a patient suffering bone metastatic triple negative (including basal-like) breast cancer or, alternatively, bone metastatic ER+ bone cancer which comprises:
 i) quantifying the expression level of the c-MAF gene in a sample of said subject and
 ii) comparing the expression level obtained in step i) with a reference value,
wherein increased expression level of said gene with respect to said reference value is indicative of a poor clinical outcome.

The second method of the invention comprises in a first step, quantifying the c-MAF gene expression level in a sample of a subject suffering triple negative (including basal-like) breast cancer, or alternatively ER+ breast cancer. In a preferred embodiment, the sample is a tumor tissue sample.

In a preferred embodiment, the second method of the invention comprises quantifying only the c-MAF gene expression level as a single marker, i.e., the method does not involve determining the expression level of any additional marker.

In a second step, the c-MAF gene expression level obtained in the tumor sample of the subject is compared with a reference value. In a preferred embodiment, the reference value is the expression level of said gene in a control sample. The determination of the c-MAF gene expression level must be correlated to values of a control sample or reference sample. Depending on the type of tumor to be analyzed, the exact nature of the control sample may vary. Thus, in the case involving the second method of the invention, then the reference sample is a sample of subject with breast cancer who has not suffered bone metastasis or that corresponds to the median value of the c-MAF gene expression level measured in a tumor tissue collection in biopsy samples of subjects with breast cancer who have not suffered metastasis.

Once the c-MAF gene expression level in the sample is measured and compared with the control sample, if the expression level of said gene is increased with respect to its expression level in the control sample, then it is indicative of a poor clinical outcome.

In a specific embodiment, the bone metastasis is osteolytic metastasis.

In another specific embodiment, the quantification of the c-MAF gene expression level comprises quantifying the messenger RNA (mRNA) of said gene, or a fragment of said mRNA, the complementary DNA (cDNA) of said gene, or a fragment of said cDNA. In a more preferred embodiment, the expression level is quantified by means of a quantitative polymerase chain reaction (PCR) or a DNA or RNA array.

In another embodiment, the quantification of the c-MAF gene expression level comprises quantifying the level of protein encoded by said gene or of a variant thereof. In a yet more preferred embodiment, the protein level is determined by means of Western blot, immunohistochemistry, ELISA or a protein array.

In another embodiment, the reference sample is a tumor tissue sample of a triple negative (including basal-like) breast cancer or, alternatively ER+ breast cancer, from a subject who has not suffered metastasis.

Any parameter which is widely accepted for determining clinical outcome of a patient can be used in the present invention including, without limitation:

disease-free progression which, as used herein, describes the proportion of subjects in complete remission who have had no recurrence of disease during the time period under study.

disease-free survival (DFS), as used herewith, is understood as the length of time after treatment for a disease during which a subject survives with no sign of the disease.

objective response which, as used in the present invention, describes the proportion of treated subjects in whom a complete or partial response is observed.

tumour control which, as used in the present invention, relates to the proportion of treated subjects in whom complete response, partial response, minor response or stable disease ≥6 months is observed.

progression free survival which, as used herein, is defined as the time from start of treatment to the first measurement of cancer growth.

Time to progression (TTP), as used herein, relates to the time after a disease is treated until the disease starts to get worse. The term "progression" has been previously defined.

six-month progression free survival or "PFS6" rate which, as used herein, relates to the percentage of subjects who are free of progression in the first six months after the initiation of the therapy and median survival which, as used herein, relates to the time at which half of the subjects enrolled in the study are still alive.

The terms "poor" or "good", as used herein to refer to a clinical outcome, mean that the subject will show a favourable or unfavourable outcome. As will be understood by those skilled in the art, such the assessment of the probability, although preferred to be, may not be correct for 100% of the subjects to be diagnosed. The term, however, requires that a statistically significant portion of subjects can be identified as having a predisposition for a given outcome. Whether a portion is statistically significant can be determined readily by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least about 50%, at least about 60%, at least about 70%, at least about 80%, at least about 90% at least about 95%. The p-values are, preferably, 0.05, 0.01, 0.005, or 0.0001 or less. More preferably, at least about 60 percent, at least about 70 percent, at least about 80 percent or at least about 90 percent of the subjects of a population can be properly identified by the method of the present invention.

Method for Designing Customized Therapy—in Patients with Triple Negative (Including Basal-like) Breast Tumors or, Alternatively ER+ Breast Tumors, or SrcResponsiveSignature+ or HER2+Breast Tumors As is known in the state of the art, the treatment to be administered to a subject suffering from cancer depends on whether the latter is a malignant tumor, i.e., whether it has high probabilities of undergoing metastasis, or whether the latter is a benign tumor. In the first assumption, the treatment of choice is a systemic treatment such as chemotherapy and in the second assumption, the treatment of choice is a localized treatment such as radiotherapy.

Therefore, as described in the present invention, given that c-MAF gene overexpression in triple negative (including basal-like) breast cancer cells or, alternatively ER+ breast cancer cells is related to the presence of bone metastasis, the expression level of the c-MAF gene is useful for making decisions in terms of the most suitable therapy for the subject suffering said cancer.

Thus, in another aspect the invention relates to an in vitro method (hereinafter third method of the invention) for designing a customized therapy for a subject suffering triple negative (including basal-like) breast cancer or, alternatively ER+ breast cancer, which comprises i) quantifying the c-MAF gene expression level in a sample of said subject and ii) comparing the expression level obtained in i) with a reference value, wherein if the expression level is increased with respect to said reference value, then said subject is susceptible to receive a therapy aiming to prevent and/or treat the bone metastasis. If the expression level is not increased with respect to said reference value, then said subject is not susceptible to receive a therapy aiming to prevent and/or treat the bone metastasis.

In a particular embodiment, the bone metastasis is osteolytic metastasis.

The third method of the invention comprises in a first step quantifying the c-MAF gene expression level in a sample in a subject suffering from triple negative (including basal-like) breast cancer or, alternatively ER+ breast cancer. In a preferred embodiment, the sample is a tumor tissue sample.

In another particular embodiment, the third method of the invention comprises quantifying only the c-MAF gene expression level as a single marker, i.e., the method does not involve determining the expression level of any additional marker.

In the case of the third method of the invention the sample can be a primary tumor tissue sample of the subject.

In a second step, the c-MAF gene expression level obtained in the tumor sample of the subject is compared with a reference value. In a preferred embodiment, the reference value is the c-MAF gene expression level of said gene in a control sample. The determination of the c-MAF gene expression level must be related to values of a control sample or reference sample. Depending on the type of tumor to be analyzed, the exact nature of the control sample may vary. Thus preferably the reference sample is a sample of a subject with triple negative (including basal-like) breast cancer or, alternatively ER+ breast cancer, that has not metastasized or that corresponds to the median value of the c-MAF gene expression level measured in a tumor tissue collection in biopsy samples of subjects with triple negative (including basal-like) breast cancer or, alternatively ER+ breast cancer, which has not metastasized.

Once the c-MAF gene expression level in the sample has been measured and compared with the reference value, if the expression level of said gene is increased with respect to the reference value, then it can be concluded that said subject is susceptible to receiving therapy aiming to prevent (if the subject has yet to undergo metastasis) and/or treat metastasis (if the subject has already experienced metastasis).

When the cancer has metastasized, systemic treatments including but not limited to chemotherapy, hormone treatment, immunotherapy, or a combination thereof can be used. Additionally, radiotherapy and/or surgery can be used. The choice of treatment generally depends on the type of primary cancer, the size, the location of the metastasis, the age, the general health of the patient and the types of treatments used previously.

The systemic treatments are those that reach the entire body, such as:

Chemotherapy is the use of medicaments to destroy cancer cells. The medicaments are generally administered through oral or intravenous route. Sometimes, chemotherapy is used together with radiation treatment. Suitable chemotherapeutic treatments for breast cancer include, without limitation, anthracyclines (doxorubicin, epirubicin, pegylated liposomal doxorubicin), Taxanes (paclitaxel, docetaxel, albumin nano-particle bound paclitaxel), 5-fluorouracil (continuous infusion 5-FU, capecitabine), Vinca alkaloids (vinorelbine, vinblastine), Gemcitabine, Platinum salts (cisplatin, carboplatin), cyclophosphamide, Etoposide and combinations of one or more of the above such as Cyclophosphamide/anthracycline+/−5-fluorouracil regimens (such as doxorubicin/cyclophosphamide (AC), epirubicin/cyclophosphamide, (EC) cyclophosphamide/epirubicin/5-fluorouracil (CEF), cyclophosphamide/doxorubicin/5-fluorouracil (CAF), 5-fluorouracil/epirubicin/cyclophosphamide (FEC)), cyclophosphamide/metothrexate/5-fluorouracil (CMF), anthracyclines/taxanes (such as doxorubicin/paclitaxel or doxorubicin/docetaxel), Docetaxel/capecitabine, Gemcitabine/paclitaxel, Taxane/platinum regimens (such as paclitaxel/carboplatin or docetaxel/carboplatin).

Immunotherapy is a treatment that aids the immune system itself of the patient to combat cancer. There are several types of immunotherapy which are used to treat metastasis in patients. These include but are not limited to cytokines, monoclonal antibodies and antitumor vaccines.

In another aspect, the treatment is Alpharadin (radium-223 dichloride). Alpharadin uses alpha radiation from radium-223 decay to kill cancer cells. Radium-223 naturally self-targets to bone metastases by virtue of its properties as a calcium-mimic. Alpha radiation has a very short range of 2-10 cells (when compared to current radiation therapy which is based on beta or gamma radiation), and therefore causes less damage to surrounding healthy tissues (particularly bone marrow). With similar properties to calcium, radium-223 is drawn to places where calcium is used to build bone in the body, including the site of faster, abnormal bone growth—such as that seen in the skeletal metastases of men with advanced, castration-resistant prostate cancer. Radium-223, after injection, is carried in the bloodstream to sites of abnormal bone growth. The place where a cancer starts in the body is known as the primary tumor. Some of these cells may break away and be carried in the bloodstream to another part of the body. The cancer cells may then settle in that part of the body and form a new tumor. If this happens it is called a secondary cancer or a metastasis. Most patients with late stage prostate cancer suffer the maximum burden of disease in their bones. The aim with radium-223 is to selectively target this secondary cancer. Any radium-223 not taken-up in the bones is quickly routed to the gut and excreted.

In another aspect, the treatment is an mTor inhibitor. In some aspects, the mTor inhibitor is a dual mTor/PI3kinase inhibitor. In some aspects, the mTor inhibitor is used to prevent or inhibit metastasis. In some aspects the mTor inhibitor is selected from the group consisting of: ABI009 (sirolimus), rapamycin (sirolimus), Abraxane (paclitaxel), Absorb (everolimus), Afinitor (everolimus), Afinitor with Gleevec, AS703026 (pimasertib), Axxess (umirolimus), AZD2014, BEZ235, Biofreedom (umirolimus), BioMatrix (umirolimus), BioMatrix flex (umirolimus), CC115, CC223, Combo Bio-engineered Sirolimus Eluting Stent ORBUS-NEICH (sirolimus), Curaxin CBLC102 (mepacrine), DE109 (sirolimus), DS3078, Endeavor DES (zotarolimus), Endeavor Resolute (zotarolimus), Femara (letrozole), Hocena (antroquinonol), INK128, Inspiron (sirolimus), IPI504 (retaspimycin hydrochloride), KRN951 (tivozanib), ME344, MGA031 (teplizumab), MiStent SES (sirolimus), MKC1, Nobori (umirolimus), OSI027, OVI123 (cordycepin), Palomid 529, PF04691502, Promus Element (everolimus), PWT33597, Rapamune (sirolimus), Resolute DES (zotarolimus), RG7422, SAR245409, SF1126, SGN75 (vorsetuzumab mafodotin), Synergy (everolimus), Taltorvic (ridaforolimus), Tarceva (erlotinib), Torisel (temsirolimus), Xience Prime (everolimus), Xience V (everolimus), Zomaxx (zotarolimus), Zortress (everolimus), Zotarolimus Eluting Peripheral Stent MEDTRONIC (zotarolimus), AP23841, AP24170, ARmTOR26, BN107, BN108, Canstatin GENZYME (canstatin), CU906, EC0371, EC0565, KI1004, LOR220, NV128, Rapamycin ONCOIMMUNE (sirolimus), SB2602, Sirolimus PNP SAMYANG BIOPHARMACEUTICALS (sirolimus), TOP216, VLI27, VS5584, WYE125132, XL388, Advacan (everolimus), AZD8055, Cypher Select Plus Sirolimus eluting Coronary Stent (sirolimus), Cypher Sirolimus eluting coronary stent (sirolimus), Drug Coated Balloon (sirolimus), E-Magic Plus (sirolimus), Emtor (sirolimus), Esprit (everolimus), Evertor (everolimus), HBF0079, LCP-Siro (sirolimus), Limus CLARIS (sirolimus), mTOR Inhibitor CELLZOME, Nevo Sirolimus eluting Coronary Stent (sirolimus), nPT-mTOR, Rapacan (sirolimus), Renacept (sirolimus), ReZolve (sirolimus), Rocas (sirolimus), SF1126, Sirolim (sirolimus), Sirolimus NORTH CHINA (sirolimus), Sirolimus RANBAXY (sirolimus), Sirolimus WATSON (sirolimus) Siropan (sirolimus), Sirova (sirolirrus), Supralimus (sirolimus), Supralimus-Core (sirolimus), Tacrolimus WATSON (tacrolimus), TAFA93, Temsirolimus ACCORD (temsirolimus), Temsirolimus SANDOZ (temsirolimus), TOP216, Xience Prime (everolimus), Xience V (everolimus). In a specific aspect the mTor inhibitor is Afinitor (everolimus) (http://www.afinitor.com/indexjsp?usertrack.filter_applied=true&NovaId=40294620643 38207963; last accessed Nov. 28, 2012). In another aspect, everolimus is combined with an aromatase inhibitor. (See. e.g., Baselga, J., el al., Everolimus in Postmenopausal Hormone-Receptor Positive Advanced Breast Cancer. 2012. *N. Engl. J. Med.* 366(6): 520-529, which is herein incorporated by reference). In another aspect, mTor inhibitors can be identified through methods known in the art. (See, e.g., Zhou, H. et al. Updates of mTor inhibitors. 2010. *Anticancer Agents Med. Chem.* 10(7): 571-81, which is herein incorporated by reference). In some aspects, the mTor inhibitor is used to treat or prevent or inhibit metastasis in a patient that is positive for a hormone receptor. (See. e.g., Baselga, J., et al., Everolimus in Postmenopausal Hormone-Receptor Positive Advanced Breast Cancer. 2012. *N. Engl. J. Med.* 366(6): 520-529). In some embodiments, the patient is ER+. In some aspects, the mTor inhibitor is used to treat or prevent or inhibit metastasis in a patient with advanced breast cancer. In some aspects, the mTor inhibitor is used in combination with a second treatment. In some aspects, the second treatment is any treatment described herein.

In another aspect, the treatment is a Src kinase inhibitor. In some aspects, the Src inhibitor is used to prevent or inhibit metastasis. In some aspects, the Src kinase inhibitor is selected from the group: AZD0530 (saracatinib), Bosulif (bosutinib), ENMD981693, KD020, KX01, Sprycel (dasatinib), Yervoy (ipilimumab), AP23464, AP23485, AP23588, AZD0424, c-Src Kinase Inhibitor KISSEI, CU201, KX2361, SKS927, SRN004, SUNK706, TG100435, TG100948, AP23451, Dasatinib HETERO (dasatinib), Dasatinib VALEANT (dasatinib), Fontrax (dasatinib), Src Kinase Inhibitor KINEX, VX680, (tozasertib lactate), XL228, and SUNK706. In some embodiments, the Src kinase inhibitor is dasatinib. In another aspect, Src kinase inhibitors can be identified through methods known in the art (See, e.g., Sen, B. and Johnson, F. M. Regulation of Src Family Kinases in Human Cancers. 2011. *J. Signal Transduction.* 2011: 14 pages, which is herein incorporated by reference). In some aspects, the Src kinase inhibitor is used to treat or prevent or inhibit metastasis in a patient that is positive for the SRC-responsive signature (SRS). In some aspects, the patient is SRS+ and ER−. (See. e.g., Zhang, CH.-F, et al. Latent Bone Metastasis in Breast Cancer Tied to Src-Dependent survival signals. 2009. *Cancer Cell.* 16: 67-78, which is herein incorporated by reference.) In some aspects, the Src kinase inhibitor is used to treat or prevent or inhibit metastasis in a patient with advanced breast cancer. In some aspects, the Src kinase inhibitor is used in combination with a second treatment. In some aspects, the second treatment is any treatment described herein.

In another aspect, the treatment is a COX-2 inhibitor. In some aspects, the COX-2 inhibitor is used to prevent or inhibit metastasis. In some aspects, the COX-2 inhibitor is selected from the group: ABT963, Acetaminophen ER JOHNSON (acetaminophen), Acular X (ketorolac tromethamine), BAY1019036 (aspirin), BAY987111 (diphenhydramine, naproxen sodium), BAY11902 (piroxicam), BCIBUCH001 (ibuprofen), Capoxigem (apricoxib), CS502, CS670 (pelubiprofen), Diclofenac HPBCD (diclofenac), Diractin (ketoprofen), GW406381, HCT1026 (nitroflurbiprofen), Hyanalgese-D (diclofenac), HydrocoDex (acetaminophen, dextromethorphan, hydrocodone), Ibuprofen Sodium PFIZER (ibuprofen sodium), Ibuprofen with Acetaminophen PFIZER (acetaminophen, ibuprofen), Impracor (ketoprofen), IP880 (diclofenac), IP940 (indomethacin), ISV205 (diclofenac sodium), JNS013 (acetaminophen, tramadol hydrochloride), Ketoprofen TDS (ketoprofen), LTNS001 (naproxen etemesil), Mesalamine SALIX (mesalamine), Mesalamine SOFAR (mesalamine), Mesalazine (mesalamine), ML3000 (licofelone), MRX7EAT (etodolac), Naproxen IROKO (naproxen), NCX4016 (nitroaspirin), NCX701 (nitroacetaminophen), Nuprin SCOLR (ibuprofen), OMS103HP (amitriptyline hydrochloride, ketoprofen, oxymetazoline hydrochloride), Oralease (diclofenac), OxycoDex (dextromethorphan, oxycodone), P54, PercoDex (acetaminophen, dextromethorphan, oxycodone), PL3100 (naproxen, phosphatidyl choline), PSD508, R-Ketoprofen (ketoprofen), Remura (bromfenac sodium), ROX828 (ketorolac tromethamine), RP19583 (ketoprofen lysine), RQ00317076, SDX101 (R-etodolac), TDS943 (diclofenac sodium), TDT070 (ketoprofen), TPR100, TQ1011 (ketoprofen), TT063 (S-flurbiprofen), UR8880 (cimicoxib), V0498TA01A (ibuprofen), VT122 (etodolac, propranolol), XP20B (acetaminophen, dextropropoxyphene), XP21B (diclofenac potassium), XP21L (diclofenac potassium), Zoenasa (acetylcysteine, mesalamine), Acephen, Actifed Plus, Actifed-P, Acular, Acular LS, Acular PF, Acular X, Acuvail, Advil, Advil Allergy Sinus, Advil Cold and Sinus, Advil Congestion Relief, Advil PM, Advil PM Capsule, Air Salonpas, Airtal, Alcohol-Free NyQuil Cold & Flu Relief, Aleve, Aleve ABDI IBRAHIM, Aleve-D, Alka-Seltzer, Alka-Seltzer BAYER, Alka-Seltzer Extra Strength, Alka-Seltzer Lemon-Lime, Alka-Seltzer Original, Alka-Seltzer Plus, Alka-Seltzer plus Cold and Cough, Alka-Seltzer plus Cold and Cough Formula, Alka-Seltzer Plus Day and Night Cold Formula, Alka-Seltzer Plus Day Non-Drowsy Cold Formula, Alka-Seltzer Plus Flu Formula, Alka-Seltzer Plus Night Cold Formula, Alka-Seltzer Plus Sinus Formula, Alka-Seltzer Plus Sparkling Original Cold Formula, Alka-Seltzer PM, Alka-Seltzer Wake-Up Call, Anacin, Anaprox, Anaprox MINERVA, Ansaid, Apitoxin, Apranax, Apranax abdi, Arcoxia, Arthritis Formula Bengay, Arthrotec, Asacol, Asacol HD, Asacol MEDUNA ARZNEIMITTEL, Asacol ORIFARM, Aspirin BAYER, Aspirin Complex, Aspirin Migran, AZD3582, Azulfidine, Baralgan M, BAY1019036, BAY987111, BAY11902, BCIBUCH001, Benadryl Allergy, Benadryl Day and Night, Benylin 4 Flu, Benylin Cold and Flu, Benylin Cold and Flu Day and Night, Benylin Cold and Sinus Day and Night, Benylin Cold and Sinus Plus, Benylin Day and Night Cold and Flu Relief, Benylin1 All-In-One, Brexin, Brexin ANGELLNI, Bromday, Bufferin, Buscopan Plus, Caldolor, Calmatel, Cambia, Canasa, Capoxigem, Cataflam, Celebrex, Celebrex ORIFARM, Children's Advil Allergy Sinus, Children's Tylenol, Children's Tylenol Cough and Runny Nose, Children's Tylenol plus cold, Children's Tylenol plus Cold and Cough, Children's Tylenol plus cold and stuffy nose, Children's Tylenol plus Flu, Children's Tylenol plus cold & allergy, Children's Tylenol plus Cough & Runny Nose, Children's Tylenol plus Cough & Sore Throat, Children's Tylenol plus multi symptom cold, Clinoril, Codral Cold and Flu, Codral Day and Night Day Tablets, Codral Day and Night Night Tablets, Codral Nightime, Colazal, Combunox, Contac Cold plus Flu, Contac Cold plus Flu Non-Drowsy, Coricidin D, Coricidin HBP Cold and Flu, Coricidin FIBP Day and Night Multi-Symptom Cold, Coricidin HBP Maximum Strength Flu, Coricidin HBP Nighttime Multi-Symptom Cold, Coricidin II Extra Strength Cold and Flu, CS502, CS670, Daypro, Daypro Alta, DDS06C, Demazin Cold and Flu, Demazin Cough, Cold and Flu, Demazin day/night Cold and Flu, Demazin PE Cold and Flu, Demazin PE day/night Cold and Flu, Diclofenac HPBCD, Dimetapp Day Relief, Dimetapp Multi-Symptom Cold and Flu, Dimetapp Night Relief, Dimetapp Pain and Fever Relief, Dimetapp PE Sinus Pain, Dimetapp PE Sinus Pain plus Allergy, Dipentum, Diractin, Disprin Cold 'n' Fever, Disprin Extra, Disprin Forte. Disprin Plus, Dristan Cold, Dristan Junior, Drixoral Plus, Duexis, Dynastat, Efferalgan, Efferalgan Plus Vitamin C, Efferalgan Vitamin C, Elixsure IB, Excedrin Back and Body, Excedrin Migraine, Excedrin PM, Excedrin Sinus Headache, Excedrin Tension Headache, Falcol, Fansamac, Feldene, Fever-All, Fiorinal, Fiorinal with Codeine, Flanax, Flector Patch, Flucam, Fortagesic, Gerbin, Giazo, Gladio, Goody's Back and Body Pain, Goody's Cool Orange, Goody's Extra Strength, Goody's PM, Greaseless Bengay, GW406381, HCT1026, He Xing Yi, Hyanalgese-D, HydrocoDex, Ibuprofen Sodium PFIZER, Ibuprofen with, Acetaminophen PFIZER, Icy Hot SANOFI AVENTIS, Impracor, Indocin, Indomethacin APP PHARMA, Indomethacin MYLAN, Infants' Tylenol, IP880, IP940, Iremod, ISV205, JNS013, Jr. Tylenol, Junifen, Junior Strength Advil, Junior Strength Motrin, Ketoprofen TDS, Lemsip Max, Lemsip Max All in One, Lemsip Max All Night, Lemsip Max Cold and Flu, Lialda, Listerine Mouth Wash, Lloyds Cream, Lodine, Lorfit P, Loxonin, LTNS001, Mersyndol, Mesalarnine SALIX, Mesalamine SOFAR, Mesalazine, Mesasal GLAXO, Mesasal SANOFI, Mesulid, Metsal Heat Rub, Midol Complete, Midol Extended Relief, Midol Liquid Gels, Midol PM, Midol Teen Formula, Migranin COATED TABLETS, ML3000, Mobic, Mohrus, Motrin, Motrin Cold and Sinus Pain, Motrin PM, Movalis ASPEN, IVIRX7EAT, Nalfon, Nalfon PEDINOL, Naprelan, Naprosyn, Naprosyn RPG LIFE SCIENCE, Naproxen IROKO, NCX4016, NCX701, NeoProfen LUNDBECK, Nevanac, Nexcede, Niflan, Norgesic MEDICIS, Novalgin, Nuprin SCOLR, Nurofen, Nurofen Cold and Flu, Nurofen Max Strength Migraine, Nurofen Plus, Nuromol, NyQuil with Vitamin C, Ocufen, OMS103HP, Oralease, Orudis ABBOTT JAPAN, Oruvail, Osteluc, OxycoDex, P54, Panadol, Panadol Actifast, Paradine, Paramax, Parfenac, Pedea, Pennsaid, Pentasa, Pentasa ORIFARM, Peon, Percodan, Percodan-Demi, PercoDex, Percogesic, Perfalgan, PL2200, PL3100, Ponstel, Prexige, Prolensa, PSD508, R-Ketoprofen, Rantudil, Relafen, Remura, Robaxisal, Rotec, Rowasa, ROX828, RP19583, RQ00317076, Rubor, Salofalk, Salonpas, Saridon, SDX101, Seltouch, sfRowasa, Shinbaro, Sinumax, Sinutab, Sinutab, sinus, Spalt, Sprix, Strefen, Sudafed Cold and Cough, Sudafed Head Cold and Sinus, Sudafed PE Cold plus Cough, Sudafed PE Pressure plus Pain, Sudafed PE, Severe Cold, Sudafed PE Sinus Day plus Night Relief Day Tablets, Sudafed PE Sinus Day plus Night Relief Night Tablets, Sudafed PE Sinus plus Anti-inflammatory Pain Relief, Sudafed Sinus Advance, Surgam, Synalgos-DC, Synflex, Tavist allergy/sinus/headache, TDS943, TDT070, Theraflu Cold and Sore Throat, Theraflu Daytime Severe Cold and Cough, Theraflu Daytime Warming Relief, Theraflu Warming Relief Caplets Daytime Multi-Symptom Cold, Theraflu Warming Relief Cold and Chest Congestion, Thomapyrin, Thomapyrin C, Thomapyrin Effervescent, Thomapyrin Medium, Tilcotil, Tispol, Tolectin, Toradol, TPR100, TQ1011, Trauma-Salbe, Trauma-Salbe Kwizda, Treo, Treximet, Trovex, TT063, Tylenol, Tylenol Allergy Multi-Symptom, Tylenol Back Pain, Tylenol Cold & Cough Daytime, Tylenol Cold & Cough Nighttime, Tylenol Cold and Sinus Daytime, Tylenol Cold and Sinus Nighttime, Tylenol Cold Head Congestion Severe, Tylenol Cold Multi Symptom Daytime, Tylenol Cold Multi Symptom Nighttime Liquid, Tylenol Cold Multi Symptom Severe, Tylenol Cold Non-Drowsiness Formula, Tylenol Cold Severe Congestion Daytime, Tylenol Complete Cold, Cough and Flu Night time, Tylenol Flu Nighttime, Tylenol Menstrual, Tylenol PM, Tylenol Sinus Congestion & Pain Daytime, Tylenol Sinus Congestion & Pain Nighttime, Tylenol Sinus Congestion & Pain Severe, Tylenol Sinus Severe Congestion Daytime, Tylenol Ultra Relief, Tylenol with Caffeine and Codeine phosphate, Tylenol with Codeine phosphate, Ultra Strength Bengay Cream, Ultracet, UR8880, V0498TA01A, Vicks NyQuil Cold and Flu Relief, Vicoprofen, Vimovo, Voltaren Emulgel, Voltaren GEL, Voltaren NOVARTIS CONSUMER HEALTH GMBH, Voltaren XR, VT122, Xefo, Xefo Rapid, Xefocam, Xibrom, XL3, Xodol, XP20B, XP21B, XP21L, Zipsor, and Zoenasa. In another aspect, COX-2 inhibitors can be identified through methods known in the art (See, e.g., Dannhardt, G. and Kiefer, W. Cyclooxygenase inhibitors—current status and future prospects. 2001. *Eur. J. Med. Chem.* 36: 109-126, which is herein incorporated by reference). In some aspects, the COX-2 inhibitor is used to treat or prevent or inhibit metastasis in a patient with advanced breast cancer. In some aspects, the COX-2 inhibitor is used in combination with a second treatment. In some aspects, the second treatment is any treatment described herein. In some aspects, the COX-2 inhibitor is used in combination with a second treatment selected from the group consisting of: Denosumab, Zometa (http://www.us.zometa.com/index. jsp?usertrack.filter_applied=true&NovaId=293537693 4467633633; last accessed Dec. 2, 2012), Carbozantinib or Cabozantinib, Antibody or peptide blocking PTHLH (parathyroid hormone like hormone) or PTHrP (parathyroid hormone related protein) and Everolimus.

In another aspect, the treatment agents used for avoiding and/or preventing bone degradation include, but are not limited to:

Parathyroid hormone (PTH) and Parathyroid like hormone (PTHLH) inhibitors (including blocking antibodies) or recombinant forms thereof (teriparatide corresponding to the amino acids 7-34 of PTH). This hormone acts by stimulating the osteoclasts and increasing their activity.

Strontium ranelate: is an alternative oral treatment, and forms part of the group of drugs called "dual action bone agents" (DABAs) because they stimulate the osteoblast proliferation and inhibit the osteoclast proliferation.

"Estrogen receptor modulators" (SERM) refers to compounds which interfere with or inhibit the binding of estrogens to the receptor, regardless of the mechanism. Examples of estrogen receptor modulators include, among others, estrogens, progestagen, estradiol, droloxifene, raloxifene, lasofoxifene, TSE-424, tamoxifen, idoxifene, LY353381, LY117081, toremifene, fluvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate 4,4'dihydroxybenzophenone-2,4-dinitrophenylhydrazone and SH646.

Calcitonin: directly inhibits the osteoclast activity through the calcitonin receptor. The calcitonin receptors have been identified on the surface of the osteoclasts.

Bisphosphonates: are a group of medicinal products used for the prevention and the treatment of diseases with bone resorption and reabsorption such as osteoporosis and cancer with bone metastasis, the latter being with or without hypercalcaemia, associated to breast cancer and prostate cancer. Examples of bisphosphonates which can be used in the therapy designed by means of the fifth method of the invention include, although not limited to, nitrogenous bisphosphonates (such as pamidronate, neridronate, olpadronate, alendronate, ibandronate, risedronate, incadronate, zoledronate or zoledronic acid, etc.) and non-nitrogenous bisphosphonates (such as etidronate, clodronate, tiludronate, etc.).

"Cathepsin K inhibitors" refers to compounds which interfere in the cathepsin K cysteine protease activity. Non-limiting examples of cathepsin K inhibitors include 4-amino-pyrimidine-2-carbonitrile derivatives (described in the International patent application WO 03/020278 under the name of Novartis Pharma GMBH), pyrrolo-pyrimidines described in the publication WO 03/020721 (Novartis Pharma GMBH) and the publication WO 04/000843 (ASTRAZENECA AB) as well as the inhibitors described in the publications PCT WO 00/55126 of Axys Pharmaceuticals, WO 01/49288 of Merck Frosst Canada & Co. and Axys Pharmaceuticals.

"DKK-1 (Dickkopf-1) inhibitor" as used herein refers to any compound which is capable of reducing DKK-1 activity. DKK-1 is a soluble Wnt pathway antagonist expressed predominantly in adult bone and upregulated in myeloma patients with osteolytic lesions. Agents targeting DKK-1 may play a role in preventing osteolytic bone disease in multiple myeloma patients. BHQ880 from Novartis is a first-in-class, fully human, anti-DKK-1 neutralizing antibody. Preclinical studies support the hypothesis that BHQ880 promotes bone formation and thereby inhibits tumor-induced osteolytic disease (Ettenberg S. et al., American Association for Cancer Research Annual Meeting. Apr. 12-16, 2008; San Diego, Calif. Abstract).

"Dual MET and VEGFR2 inhibitor" as used herein refers to any compound which is a potent dual inhibitor of the MET and VEGF pathways designed to block MET driven tumor escape. MET is expressed not only in tumor cells and endothelial cells, but also in osteoblasts (bone-forming cells) and osteoclasts (bone-removing cells). HGF binds to MET on all of these cell types, giving the MET pathway an important role in multiple autocrine and paracrine loops. Activation of MET in tumor cells appears to be important in the establishment of metastatic bone lesions. At the same time, activation of the MET pathway in osteoblasts and osteoclasts may lead to pathological features of bone metastases, including abnormal bone growth (i.e., blastic lesions) or destruction (i.e., lytic lesion. Thus, targeting the MET pathway may be a viable strategy in preventing the establishment and progression of metastatic bone lesions. Cabozantinib (Exelixis, Inc), formerly known as XL184 (CAS 849217-68-1), is a potent dual inhibitor of the MET and VEGF pathways designed to block MET driven tumor escape. In multiple preclinical studies cabozantinib has been shown to kill tumor cells, reduce metastases, and inhibit angiogenesis (the formation of new blood vessels necessary to support tumor growth). Another suitable dual inhibitors are E7050 (N-[2-Fluoro-4-({2-[4-(4-methylpiperazin-1-yl)piperidin-1-yl]carbonylaminopyridin-4-yl}oxy)phenyl]-N'-(4-fluorophenyl)cyclopropane-1,1-dicarboxamide (2R,3R)-tartrate) (CAS 928037-13-2) or Foretinib (also known as GSK1363089, XL880, CAS 849217-64-7).

"RANKL inhibitors" as used herein refer to any compound which is capable of reducing the RANK activity. RANKL is found on the surface of the osteoblast membrane of the stroma and T-lymphocyte cells, and these T-lymphocyte cells are the only ones which have demonstrated the capacity for secreting it. Its main function is the activation of the osteoclasts, cells involved in the bone resorption. The RANKL inhibitors can act by blocking the binding of RANKL to its receptor (RANK), blocking the RANK-mediated signaling or reducing the expression of RANKL by blocking the transcription or the translation of RANKL. RANKL antagonists or inhibitors suitable for use in the present invention include, without limitation:

a suitable RANK protein which is capable of binding RANKL and which comprises the entire or a fragment of the extracellular domain of a RANK protein. The soluble RANK may comprise the signal peptide and the extracellular domain of the murine or human RANK polypeptides, or alternatively, the mature form of the protein with the signal peptide removed can be used.

Osteoprotegerin or a variant thereof with RANKL-binding capacity.

RANKL-specific antisense molecules

Ribozymes capable of processing the transcribed products of RANKL

Specific anti-RANKL antibodies. "Anti-RANKL antibody or antibody directed against RANKL" is understood herein as all that antibody which is capable of binding specifically to the ligand of the activating receptor for the nuclear factor κB (RANKL) inhibiting one or more RANKL functions. The antibodies can be prepared using any of the methods which are known by the person skilled in the art. Thus, the polyclonal antibodies are prepared by means of immunizing an animal with the protein to be inhibited. The monoclonal antibodies are prepared using the method described by Kohler, Milstein et al. (Nature, 1975, 256: 495). Antibodies suitable in the context of the present invention include intact antibodies which comprise a variable antigen binding region and a constant region, fragments "Fab", "F(ab')2" and "Fab'", Fv, scFv, diabodies and bispecific antibodies.

Specific anti-RANKL nanobodies. Nanobodies are antibody-derived therapeutic proteins that contain the unique structural and functional properties of naturally-occurring heavy-chain antibodies. The Nanobody technology was originally developed following the discovery that camelidae (camels and llamas) possess fully functional antibodies that lack light chains. The general structure of nanobodies is FR1-CDR1-FR2-CDR2-FR3-CDR3-FR4 wherein FR1 to FR4 are the framework regions 1 to 4 CDR1 to CDR3 are the complementarity determining regions 1 to 3. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. These newly discovered VHH domains with their unique structural and functional properties form the basis of a new generation of therapeutic antibodies which Ablynx has named Nanobodies.

In one embodiment, the RANKL inhibitor is selected from the group consisting of a RANKL specific antibody, a RANKL specific nanobody and osteoprotegerin. In a specific embodiment, the anti-RANKL antibody is a monoclonal antibody. In a yet more specific embodiment, the anti-RANKL antibody is Denosumab (Pageau, Steven C. (2009). mAbs 1 (3): 210-215, CAS number 615258-40-7) (the entire contents of which are hereby incorporated by reference). Denosumab is a fully human monoclonal antibody which binds to RANKL and prevents its activation (it does not bind to the RANK receptor). Various aspects of Denosumab are covered by U.S. Pat. Nos. 6,740,522; 7,411,050; 7,097,834; 7,364,736 (the entire contents of each of which are hereby incorporated by reference in their entirety). In another embodiment, the RANKL inhibitor an antibody, antibody fragment, or fusion construct that binds the same epitope as Denosumab.

In a preferred embodiment, the anti-RANKL nanobody is any of the nanobodies as described in WO2008142164, (the contents of which are incorporated in the present application by reference). In a still more preferred embodiment, the anti-RANKL antibody is the ALX-0141 (Ablynx). ALX-0141 has been designed to inhibit bone loss associated with post-menopausal osteoporosis, rheumatoid arthritis, cancer and certain medications, and to restore the balance of healthy bone metabolism.

In a preferred embodiment, the agent preventing the bone degradation is selected from the group consisting of a bisphosphonate, a RANKL inhibitor, PTH and PTHLH inhibitor or a PRG analog, strontium ranelate, a DKK-1 inhibitor, a dual MET and VEGFR2 inhibitor, an estrogen receptor modulator, Radium-223 calcitonin, and a cathepsin K inhibitor. In a more preferred embodiment the agent preventing the bone degradation is a bisphosphonate. In a yet more preferred embodiment, the bisphosphonate is the zoledronic acid.

In one embodiment, a CCR5 antagonist is administered to prevent or inhibit metastasis of the primary breast cancer tumor to bone. In one embodiment, the CCR5 antagonist is a large molecule. In another embodiment, the CCR5 antagonist is a small molecule. In some embodiments, the CCR5 antagonist is Maraviroc (Velasco-Veláquez, M. at al. 2012. CCR5 Antagonist Blocks Metastasis of Basal Breast Cancer Cells. *Cancer Research*. 72:3839-3850.). In some embodiments, the CCR5 antagonist is Vicriviroc. Velasco-Veláquez, M. et al. 2012. CCR5 Antagonist Blocks Metastasis of Basal Breast Cancer Cells. *Cancer Research*. 72:3839-3850.). In some aspects, the CCR5 antagonist is Aplaviroc (Demarest J. F. at al. 2005. Update on Aplaviroc: An HIV Entry Inhibitor Targeting CCR5. *Retrovirology* 2(Suppl. 1): S13). In some aspects, the CCR5 antagonist is a spiropiperidine CCR5 antagonist. (Rotstein D. M. et al. 2009. Spiropiperidine CCR5 antagonists. *Bioorganic & Medicinal Chemistry Letters*. 19 (18): 5401-5406. In some embodiments, the CCR5 antagonist is INCB009471 (Kuritzkes, D. R. 2009. HIV-1 entry inhibitors: an overview. *Curr. Opin. HIV AIDS.* 4(2): 82-7).

In a preferred embodiment the dual MET and VEGFR2 inhibitor is selected from the group consisting of Cabozantinib, Foretinib and E7050.

In a preferred embodiment the Radium 223 therapy is alpharadin.

Alternatively a combined treatment can be carried out in which more than one agent from those mentioned above are combined to treat and/or prevent the metastasis or said agents can be combined with other supplements, such as calcium or vitamin D or with a hormone treatment.

Method for Predicting Early Bone Metastasis in Breast Cancer Patients.

In another aspect, the invention relates to an in vitro method for determining the risk of bone metastasis in a subject suffering breast cancer, such as triple negative (including basal-like) breast cancer or, alternatively ER+ breast cancer, which comprises determining the expression level of the c-MAF gene in a sample of said subject wherein an expression level of said gene above the average value plus one standard deviation is indicative of an increased risk of early bone metastasis.

In a preferred embodiment, the bone metastasis is very early bone metastasis.

In a preferred embodiment, the bone metastasis is osteolytic metastasis.

"Early bone metastasis" as used herein, relates to a bone metastasis that appears before 5 years post surgery in a patient with breast cancer.

"Very early bone metastasis" as used herein, relates to a bone metastasis that appears before 3 years post surgery in a patient with breast cancer.

The fourth method of the invention comprises in a first step, quantifying the c-MAF gene expression level in a sample of a subject suffering breast cancer, such as triple-negative (basal-like) breast cancer or, alternatively ER+ breast cancer. In a preferred embodiment, the sample is a tumor tissue sample.

In a preferred embodiment, the fourth method of the invention comprises quantifying only the c-MAF gene expression level as a single marker, i.e., The method does not involve determining the expression level of any additional marker. The c-MAF gene expression level can be quantified as previously disclosed for the first method of the invention.

In a preferred embodiment, the breast cancer is triple negative breast cancer, including basal-like breast cancer, or, alternatively ER+ breast cancer, including luminal A and B.

In a second step, an expression level of said gene above the average value plus one standard deviation is indicative of an increased risk of early bone metastasis.

"Average level" as used herein relates to a single value of c-MAF expression level (as a mean, mode, or median) that summarizes or represents the general significance of a set of unequal values. In a preferred embodiment the average level corresponds to the average of expression levels obtained from a representative cohort of breast cancer tumors. The patient cohort is defined by age that is representative of the individual patient that one is attempting to evaluate.

"Standard deviation" as used herein relates to a measure of the dispersion of a collection of numbers. For example, the standard deviation for the average normal level of c-MAF is the dispersion of a collection of the c-MAF levels found in breast tumor samples The more spread apart the data, the higher the deviation. Standard deviation can be obtained by extracting the square root of the mean of squared deviations of observed values from their mean in a frequency distribution.

Once the c-MAF gene expression level in a sample from a subject with breast cancer, such as triple-negative (including basal-like) breast cancer or, alternatively ER+ breast cancer, has been measured and compared with the average level, if the expression level of said gene is above the average plus one standard deviation with respect to the average level, then it can be concluded that said subject has a greater tendency to develop early bone metastasis.

Method for Designing Customized Therapy in Triple Negative (Including Basal-like) Breast Cancer Patients, or, Alternatively ER+ Breast Cancer, Patients, with Bone Metastasis In another aspect, the invention relates to an in vitro method for designing a customized therapy for a subject with triple negative (including basal-like) breast cancer with bone metastasis or, alternatively ER+ breast cancer with bone metastasis (hereinafter fifth method of the invention) which comprises i) quantifying the c-MAF gene expression level in a bone metastatic sample of said subject and ii) comparing the expression level obtained in step (i) with a reference value, wherein if the c-MAF gene expression level is increased with respect to said reference value, then said subject is susceptible to receive a therapy aiming to prevent the bone degradation.

In a preferred embodiment, the bone metastasis is osteolytic metastasis.

The fifth method of the invention comprises in a first step, quantifying the c-MAF gene expression level (or c-MAF translocation or amplification) in a sample in a subject suffering breast cancer. In the case of the fifth method of the invention, the sample can be a tissue sample from bone metastasis.

In a preferred embodiment, the fifth method of the invention comprises quantifying only the c-MAF gene expression level as a single marker, i.e., the method does not involve determining the expression level of any additional marker.

In a second step the c-MAF gene expression level (or c-MAF translocation or amplification) obtained in the tumor sample of the subject is compared with the reference value. In a preferred embodiment, the reference value is the c-MAF gene expression level in a control sample. Depending on the type of tumor to be analyzed, the exact nature of the control sample may vary. Thus, in the case involving the fifth method of the invention, then the reference sample is a sample of a subject with breast cancer who has not suffered metastasis or that corresponds to the median value of the c-MAF gene expression level measured in a tumor tissue collection in biopsy samples of subjects with breast cancer who have not suffered metastasis.

Once the c-MAF gene expression level in the sample is measured and compared with the reference value (e.g. the c-MAF gene expression level of a control sample), if the expression level of said gene is increased with respect to the reference value, then this is indicative that said subject is susceptible to receive a therapy aiming to avoid or prevent bone degradation.

Illustrative examples of agents used for avoiding and/or preventing bone degradation include, although not limited to:
  Parathyroid hormone (PTH) and Parathyroid like hormone (PTHLH) inhibitors (including blocking antibodies) or recombinant forms thereof (teriparatide corresponding to the amino acids 7-34 of PTH). This hormone acts by stimulating the osteoclasts and increasing their activity.
  Strontium ranelate: is an alternative oral treatment, and forms part of the group of drugs called "dual action bone agents" (DABAs) because they stimulate the osteoblast proliferation and inhibit the osteoclast proliferation.
  "Estrogen receptor modulators" (SERM) refers to compounds which interfere with or inhibit the binding of estrogens to the receptor, regardless of the mechanism. Examples of estrogen receptor modulators include, among others, estrogens, progestagen, estradiol, droloxifene, raloxifene, lasofoxifene, TSE-424, tamoxifen, idoxifene, LY353381, LY117081, toremifene, fluvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate 4,4'dihydroxybenzophenone-2,4-dinitrophenylhydrazone and SH646.
  Calcitonin: directly inhibits the osteoclast activity through the calcitonin receptor. The calcitonin receptors have been identified on the surface of the osteoclasts.
  Bisphosphonates: are a group of medicinal products used for the prevention and the treatment of diseases with bone resorption and reabsorption such as osteoporosis and cancer with bone metastasis, the latter being with or without hypercalcaemia, associated to breast cancer and prostate cancer. Examples of bisphosphonates which can be used in the therapy designed by means of the fifth method of the invention include, although not limited to, nitrogenous bisphosphonates (such as pamidronate, neridronate, olpadronate, alendronate, ibandronate, risedronate, incadronate, zoledronate or zoledronic acid, etc.) and non-nitrogenous bisphosphonates (such as etidronate, clodronate, tiludronate, etc.).
  Alpharadin (radium-223 dichloride). Alpharadin uses alpha radiation from radium-223 decay to kill cancer cells. Radium-223 naturally self-targets to bone metastases by virtue of its properties as a calcium-mimic. Alpha radiation has a very short range of 2-10 cells (when compared to current radiation therapy which is based on beta or gamma radiation), and therefore causes less damage to surrounding healthy tissues (particularly bone marrow). With similar properties to calcium, radium-223 is drawn to places where calcium is used to build bone in the body, including the site of faster, abnormal bone growth—such as that seen in the skeletal metastases of men with advanced, castration-resistant prostate cancer. Radium-223, after injection, is carried in the bloodstream to sites of abnormal bone growth. The place where a cancer starts in the body is known as the primary tumor. Some of these cells may break away and be carried in the bloodstream to another part of the body. The cancer cells may then settle in that part of the body and form a new tumor. If this happens it is called a secondary cancer or a metastasis. Most patients with late stage prostate cancer suffer the maximum burden of disease in their bones. The aim with radium-223 is to selectively target this secondary cancer. Any radium-223 not taken-up in the bones is quickly routed to the gut and excreted.
  "Cathepsin K inhibitors" refers to compounds which interfere in the cathepsin K cysteine protease activity. Non-limiting examples of cathepsin K inhibitors include 4-amino-pyrimidine-2-carbonitrile derivatives (described in the International patent application WO 03/020278 under the name of Novartis Pharma GMBH), pyrrolo-pyrimidines described in the publication WO 03/020721 (Novartis Pharma GMBH) and the publication WO 04/000843 (ASTRAZENECA AB) as well as the inhibitors described in the publications PCT WO 00/55126 of Axys Pharmaceuticals, WO 01/49288 of Merck Frosst Canada & Co. and Axys Pharmaceuticals.
  "DKK-1(Dickkopf-1) inhibitor" as used herein refers to any compound which is capable of reducing DKK-1 activity. DKK-1 is a soluble Wnt pathway antagonist expressed predominantly in adult bone and upregulated in myeloma patients with osteolytic lesions. Agents targeting DKK-1 may play a role in preventing osteolytic bone disease in multiple myeloma patients. BHQ880 from Novartis is a first-in-class, fully human, anti-DKK-1 neutralizing antibody. Preclinical studies support the hypothesis that BHQ880 promotes bone formation and thereby inhibits tumor-induced osteolytic disease (Ettenberg S. et al., American Association for Cancer Research Annual Meeting. Apr. 12-16, 2008; San Diego, Calif. Abstract).
  "Dual MET and VEGFR2 inhibitor" as used herein refers to any compound which is a potent dual inhibitor of the MET and VEGF pathways designed to block MET driven tumor escape. MET is expressed not only in tumor cells and endothelial cells, but also in osteoblasts (bone-forming cells) and osteoclasts (bone-removing cells). HGF binds to MET on all of these cell types, giving the MET pathway an important role in multiple autocrine and paracrine loops. Activation of MET in tumor cells appears to be important in the establishment of metastatic bone lesions. At the same time, activation of the MET pathway in osteoblasts and osteoclasts may lead to pathological features of bone metastases, including abnormal bone growth (i.e., blastic lesions) or destruction (i.e., lytic lesion. Thus, targeting the MET pathway may be a viable strategy in preventing the establishment and progression of metastatic bone lesions. Cabozantinib (Exelixis, Inc), formerly known as XL184 (CAS 849217-68-1), is a potent dual inhibitor of the MET and VEGF pathways designed to block MET driven tumor escape. In multiple preclinical studies cabozantinib has been shown to kill tumor cells, reduce metastases, and inhibit angiogenesis (the formation of new blood vessels necessary to support tumor growth). Another suitable dual inhibitors are E7050 (N-[2-Fluoro-4-({2-[4-(4-methylpiperazin-1-yl)piperidin-1-yl]carbonylaminopyridin-4-yl}oxy)phenyl]-N'-(4-fluorophenyl)cyclopropane-1,1-dicarboxamide (2R,3R)-tartrate) (CAS 928037-13-2) or Foretinib (also known as GSK1363089, XL880, CAS 849217-64-7).

"RANKL inhibitors" as used herein refer to any compound which is capable of reducing the RANK activity. RANKL is found on the surface of the osteoblast membrane of the stroma and T-lymphocyte cells, and these T-lymphocyte cells are the only ones which have demonstrated the capacity for secreting it. Its main function is the activation of the osteoclasts, cells involved in the bone resorption. The RANKL inhibitors can act by blocking the binding of RANKL to its receptor (RANK), blocking the RANK-mediated signaling or reducing the expression of RANKL by blocking the transcription or the translation of RANKL. RANKL antagonists or inhibitors suitable for use in the present invention include, without limitation:

a suitable RANK protein which is capable of binding RANKL and which comprises the entire or a fragment of the extracellular domain of a RANK protein. The soluble RANK may comprise the signal peptide and the extracellular domain of the murine or human RANK polypeptides, or alternatively, the mature form of the protein with the signal peptide removed can be used.

Osteoprotegerin or a variant thereof with RANKL-binding capacity.

RANKL-specific antisense molecules

Ribozymes capable of processing the transcribed products of RANKL

Specific anti-RANKL antibodies. "Anti-RANKL antibody or antibody directed against RANKL" is understood herein as all that antibody which is capable of binding specifically to the ligand of the activating receptor for the nuclear factor κB (RANKL) inhibiting one or more RANKL functions. The antibodies can be prepared using any of the methods which are known by the person skilled in the art. Thus, the polyclonal antibodies are prepared by means of immunizing an animal with the protein to be inhibited. The monoclonal antibodies are prepared using the method described by Kohler, Milstein et al. (Nature, 1975, 256: 495). Antibodies suitable in the context of the present invention include intact antibodies which comprise a variable antigen binding region and a constant region, fragments "Fab", "F(ab')2" and "Fab'", Fv, scFv, diabodies and bispecific antibodies.

Specific anti-RANKL nanobodies. Nanobodies are antibody-derived therapeutic proteins that contain the unique structural and functional properties of naturally-occurring heavy-chain antibodies. The Nanobody technology was originally developed following the discovery that camelidae (camels and llamas) possess fully functional antibodies that lack light chains. The general structure of nanobodies is FR1-CDR1-FR2-CDR2-FR3-CDR3-FR4 wherein FR1 to FR4 are the framework regions 1 to 4 CDR1 to CDR3 are the complementarity determining regions 1 to 3. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. These newly discovered VHH domains with their unique structural and functional properties form the basis of a new generation of therapeutic antibodies which Ablynx has named Nanobodies.

In one embodiment, the RANKL inhibitor is selected from the group consisting of a RANKL specific antibody, a RANKL specific nanobody and osteoprotegerin. In a specific embodiment, the anti-RANKL antibody is a monoclonal antibody. In a yet more specific embodiment, the anti-RANKL antibody is Denosumab (Pageau, Steven C. (2009). mAbs 1 (3): 210-215, CAS number 615258-40-7) (the entire contents of which are hereby incorporated by reference). Denosumab is a fully human monoclonal antibody which binds to RANKL and prevents its activation (it does not bind to the RANK receptor). Various aspects of Denosumab are covered by U.S. Pat. Nos. 6,740,522; 7,411,050; 7,097,834; 7,364,736 (the entire contents of each of which are hereby incorporated by reference in their entirety). In another embodiment, the RANKL inhibitor an antibody, antibody fragment, or fusion construct that binds the same epitope as Denosumab.

In a preferred embodiment, the anti-RANKL nanobody is any of the nanobodies as described in WO2008142164, (the contents of which are incorporated in the present application by reference). In a still more preferred embodiment, the anti-RANKL antibody is the ALX-0141 (Ablynx). ALX-0141 has been designed to inhibit bone loss associated with post-menopausal osteoporosis, rheumatoid arthritis, cancer and certain medications, and to restore the balance of healthy bone metabolism.

In a preferred embodiment, the agent preventing the bone degradation is selected from the group consisting of a bisphosphonate, a RANKL inhibitor, PTH and PTHLH inhibitor or a PRG analog, strontium ranelate, a DKK-1 inhibitor, a dual MET and VEGFR2 inhibitor, an estrogen receptor modulator, Radium-223, calcitonin, and a cathepsin K inhibitor. In a more preferred embodiment the agent preventing the bone degradation is a bisphosphonate. In a yet more preferred embodiment, the bisphosphonate is the zoledronic acid.

In one embodiment, a CCR5 antagonist is administered to prevent or inhibit metastasis of the primary breast cancer tumor to bone. In one embodiment, the CCR5 antagonist is a large molecule. In another embodiment, the CCR5 antagonist is a small molecule. In some embodiments, the CCR5 antagonist is Maraviroc (Velasco-Veláquez, M. et al. 2012. CCR5 Antagonist Blocks Metastasis of Basal Breast Cancer Cells. *Cancer Research.* 72:3839-3850.). In some embodiments, the CCR5 antagonist is Vicriviroc. Velasco-Veláquez, M. et al. 2012. CCR5 Antagonist Blocks Metastasis of Basal Breast Cancer Cells. *Cancer Research.* 72:3839-3850.). In some aspects, the CCR5 antagonist is Aplaviroc (Demarest J. F. et al. 2005. Update on Aplaviroc: An HIV Entry Inhibitor Targeting CCR5. *Retrovirology* 2(Suppl. 1): S13).

In some aspects, the CCR5 antagonist is a spiropiperidine CCR5 antagonist. (Rotstein D. M. et al. 2009. Spiropiperidine CCR5 antagonists. *Bioorganic & Medicinal Chemistry Letters*. 19 (18): 5401-5406. In some embodiments, the CCR5 antagonist is INCB009471 (Kuritzkes, D. A. 2009. HIV-1 entry inhibitors: an overview. *Curr. Opin. HIV AIDS.* 4(2): 82-7).

In a preferred embodiment the dual MET and VEGFR2 inhibitor is selected from the group consisting of Cabozantinib, Foretinib and E7050.

In a preferred embodiment the Radium 223 therapy is alpharadin.

Alternatively a combined treatment can be carried out in which more than one agent from those mentioned above are combined to treat and/or prevent the metastasis or said agents can be combined with other supplements, such as calcium or vitamin D or with a hormone treatment.

Method of Prognosis of Metastasis in Triple Negative (Including Basal-like) Breast Cancer or, Alternatively ER+ Breast Cancer, Based on Detecting the Amplification of the c-MAF Gene In another aspect, the invention relates to an in vitro method (hereinafter sixth method of the invention) for predicting bone metastasis of a triple negative (including basal-like) breast cancer or, alternatively ER+ breast cancer, in a subject suffering said cancer which comprises determining if the c-MAF gene is amplified in a sample of said subject relative to a reference gene copy number wherein an amplification of the c-MAF gene with respect to said reference gene copy number is indicative of increased risk of developing bone metastasis.

In some embodiments, the amplification is in region at the 16q23 locus. In some embodiments, the amplification is in any part of the chromosomal region between about Chr. 16-about 79,392,959 bp to about 79,663,806 bp (from centromere to telomere). In some embodiments, the amplification is in the genomic region between about Chr. 16-79,392,959 bp to about 79,663,806 bp, but excluding DNA repeating elements. In some embodiments, amplification is measured using a probe specific for that region.

In a particular embodiment, the degree of amplification of the c-MAF gene can be determined by means of determining the amplification of a chromosome region containing said gene. Preferably, the chromosome region the amplification of which is indicative of the existence of amplification of the c-MAF gene is the locus 16q22-q24 which includes the c-MAF gene. The locus 16q22-q24 is located in chromosome 16, in the long arm of said chromosome and in a range between band 22 and band 24. This region corresponds in the NCBI database with the contigs NT_010498.15 and NT_010542.15. In another preferred embodiment, the degree of amplification of the c-MAF gene can be determined by means of using a probe specific for said gene. In another preferred embodiment, the amplification of the c-MAF gene is determined by means of using the Vysis LSI IGH/MAF Dual Color dual fusion probe, that comprises a probe against 14q32 and 16q23.

The sixth method of the invention comprises, in a first step, determining if the c-MAF gene is amplified in a sample of a subject. In a preferred embodiment, the sample is a tumor tissue sample. To that end, the amplification of the c-MAF gene in the tumor sample is compared with respect to a control sample.

In a particular embodiment, the sixth method of the invention for the prognosis of the tendency to develop bone metastasis in a subject with breast cancer, comprises determining the c-MAF gene copy number in a sample of said subject and comparing said copy number with the copy number of a control or reference sample, wherein if the c-MAF copy number is greater with respect to the c-MAF copy number of a control sample, then the subject has a greater tendency to develop bone metastasis.

The control sample refers to a sample of a subject with triple negative (including basal-like) breast cancer or, alternatively ER+ breast cancer, who has not suffered metastasis or that correspond to the median value of the c-MAF gene copy number measured in a tumor tissue collection in biopsy samples of subjects with triple negative (including basal-like) breast cancer or ER+ breast cancer, respectively, who have not suffered metastasis. Said reference sample is typically obtained by combining equal amounts of samples from a subject population. If the c-MAF gene copy number is increased with respect to the copy number of said gene in the control sample, then the subject has a greater tendency to develop metastasis.

In a preferred embodiment, the c-MAF gene is amplified with respect to a reference gene copy number when the c-MAF gene copy number is higher than the copy number that a reference sample or control sample has. In one example, the c-MAF gene is said to be "amplified" if the genomic copy number of the c-MAF gene is increased by at least 2-(i.e., 6 copies), 3- (i.e., 8 copies), 4-, 5-, 6-, 7-, 8-, 9-, 10-, 15-, 20-, 25-, 30-, 35-, 40-, 45-, or 50-fold in a test sample relative to a control sample. In another example, a c-MAF gene is said to be "amplified" if the genomic copy number of the c-MAF gene per cell is at least 3, 4, 5, 6, 7, 8, 9, 10, 11, 12, 13, 14, 15, 16, 17, 18, 19, 20, 21, 22, 23, 24, 25, 26, 27, 28, 29, 30, and the like.

In a particular embodiment, the amplification or the copy number is determined by means of in situ hybridization or PCR.

Methods for determining whether the c-MAF gene or the chromosome region 16q22-q24 is amplified are widely known in the state of the art. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification or the copy number can be determined by counting the number of fluorescent points, colored points or points with silver in the chromosomes or in the nucleus.

The fluorescence in situ hybridization (FISH) is a cytogenetic technique which is used for detecting and locating the presence or absence of specific DNA sequences in chromosomes. FISH uses fluorescence probes which only bind to some parts of the chromosome with which they show a high degree of sequence similarity. In a typical FISH method, the DNA probe is labeled with a fluorescent molecule or a hapten, typically in the form of fluor-dUTP, digoxigenin-dUTP, biotin-dUTP or hapten-dUTP which is incorporated in the DNA using enzymatic reactions, such as nick translation or PCR. The sample containing the genetic material (the chromosomes) is placed on glass slides and is denatured by a formamide treatment. The labeled probe is then hybridized with the sample containing the genetic material under suitable conditions which will be determined by the person skilled in the art. After the hybridization, the sample is viewed either directly (in the case of a probe labeled with fluorine) or indirectly (using fluorescently labeled antibodies to detect the hapten).

In the case of CISH, the probe is labeled with digoxigenin, biotin or fluorescein and is hybridized with the sample containing the genetic material in suitable conditions.

Any marking or labeling molecule which can bind to a DNA can be used to label the probes used in the fourth method of the invention, thus allowing the detection of nucleic acid molecules. Examples of labels for the labeling include, although not limited to, radioactive isotopes, enzyme substrates, cofactors, ligands, chemiluminescence agents, fluorophores, haptens, enzymes and combinations thereof. Methods for labeling and guidelines for selecting suitable labels for different purposes can be found, for example, in Sambrook et al. (Molecular Cloning: A Laboratory Manual, Cold Spring Harbor, N.Y., 1989) and Ausubel et al. (In Current Protocols in Molecular Biology, John Wiley and Sons, New York, 1998).

Once the existence of amplification is determined, either by directly determining the amplification of the c-MAF gene, the amplification of the 16q23 locus or by determining the amplification of the locus 16q22-q24, and after being compared with the amplification of said gene in the control sample, if amplification in the c-MAF gene is detected, it is indicative of the fact that the subject has a greater tendency to develop bone metastasis.

The determination of the amplification of the c-MAF gene needs to be correlated with values of a control sample or reference sample that correspond to the level of amplification of the c-MAF gene measured in a sample of a subject with breast cancer who has not suffered metastasis or that correspond to the median value of the amplification of the c-MAF gene measured in a tumor tissue collection in biopsy samples of subjects with breast cancer who have not suffered metastasis. Said reference sample is typically obtained by combining equal amounts of samples from a subject population. In general, the typical reference samples will be obtained from subjects who are clinically well documented and in whom the absence of metastasis is well characterized. The sample collection from which the reference level is derived will preferably be made up of subjects suffering the same type of cancer as the patient object of the study. Once this median value has been established, the level of amplification of c-MAF in tumor tissues of patients can be compared with this median value, and thus, if there is amplification, the subject has a greater tendency to develop metastasis.

In a preferred embodiment, the bone metastasis is osteolytic bone metastasis. As used herein, the expression "osteolytic bone metastasis" refers to a type of metastasis in which bone resorption (progressive loss of bone density) is produced in the proximity of the metastasis resulting from the stimulation of the osteoclast activity by the tumor cells and is characterized by severe pain, pathological fractures, hypercalcaemia, spinal cord compression and other syndromes resulting from nerve compression.

Method of Prognosis of Metastasis in Triple Negative (Including Basal-like) Breast Cancer, or Alternatively ER+ Breast Cancer Based on Detecting the Translocation of the c-MAF Gene In another aspect, the invention relates to an in vitro method for predicting the clinical outcome of a patient suffering from triple-negative (including basal-like) breast cancer or, alternatively ER+ breast cancer, which comprises determining if the c-MAF gene is translocated in a sample of said subject wherein a translocation of the c-MAF gene is indicative of a poor clinical outcome.

In another aspect, the invention relates to an in vitro method for predicting the clinical outcome of a patient suffering triple-negative (including basal-like) breast cancer or, alternatively ER+ breast cancer, which comprises determining if the c-MAF gene is translocated in a sample of said subject wherein a translocation of the c-MAF gene is indicative of a poor clinical outcome.

In some embodiments, the translocated gene is from the region at the 16q23 locus. In some embodiments, the translocated gene is from any part of the chromosomal region between about Chr. 16—about 79,392,959 bp to 79,663,806 bp (from centromere to telomere). In some embodiments, the translocated gene is from the genomic region between about Chr. 16—about 79,392,959 bp to 79,663,806 bp, but excluding DNA repeating elements. In some embodiments, the translocation is measured using a probe specific for that region.

In a particular embodiment, the translocation of the c-MAF gene can be determined by means of determining the translocation of a chromosome region containing said gene. In one embodiment, the translocation is the t(14,16) translocation. In another embodiment, the chromosome region that is translocated is from locus 16q22-q24. The locus 16q22-q24 is located in chromosome 16, in the long arm of said chromosome and in a range between band 22 and band 24. This region corresponds in the NCBI database with the contigs NT_010498.15 and NT_010542.15. In a preferred embodiment, the c-MAF gene translocates to chromosome 14 at the locus 14q32, resulting in the translocation t(14, 16)(q32,q23). This translocation places the MAF gene next to the strong enhancers in the IgH locus, which, in some cases, leads to overexpression of MAF. (Eychène, A., Rocques, N., and Puoponnot, C., A new MAFia in cancer. 2008. *Nature Reviews: Cancer.* 8: 683-693.)

In a preferred embodiment, the translocation of the c-MAF gene can be determined by means of using a probe specific for said translocation. In some embodiments, the translocation is measured using a dual color probe. In some embodiments, the translocation is measured using a dual fusion probe. In some embodiments, the translocation is measured using a dual color, dual fusion probe. In some embodiments, the translocation is measured using two separate probes.

In another preferred embodiment, the translocation of the c-MAF gene is determined using the Vysis LSI IGH/MAF Dual Color dual fusion probe (http://www.abbottmolecular.com/us/products/analyte-specific-reagent/fish/vysis-lsi-igh-maf-dual-color-dual-fusion-probe.html; last accessed Nov. 5, 2012), which comprises a probe against 14q32 and 16q23. In another preferred embodiment, the translocation of the c-MAF gene is determined using a Kreatech diagnostics MAF/IGH gt(14;16) Fusion probe (http://www.kreatech.com/products/repeat-freetm-poseidontm-fish-probes/hematology/maf-igh-gt1416-fusion-probe.html; last accessed Nov. 5, 2012), an Abnova MAF FISH probe (http://www.abnova.com/products/products_detail.asp?Catalog_id=FA0375; last accessed Nov. 5, 2012), a Cancer Genetics Italia IGH/MAF Two Color, Two Fusion translocation probe (http://www.cancergeneticsitalia.com/dna-fish-probe/igh-maf/; last accessed Nov. 5, 2012), a Creative Bioarray IGH/MAF-t(14;16)(q32;q23) FISH probe (http://www.creative-bioarray.com/products.asp?cid=35&page=10; last accessed Nov. 5, 2012), a Arup Laboratories multiple myeloma panel by FISH (http://www.aruplab.com/files/technical-bulletins/Multiple%20Myeloma%20%28MM%29%20by%20FISH.pdf; last accessed Nov. 5, 2012), an Agilent probe specific to 16q23 or 14q32 (http://www.genomics.agilent.com/ProductSearch.aspx?chr16&start=79483700&end=7 9754340; last accessed Nov. 5, 2012; http://www.genomics.agilent.com/ProductSearch.aspx?Pageid=3000&ProductID-637; last accessed Nov. 5, 2012), a Dako probe specific to 16q23 or 14q32 (http://www.

dako.com/us/ar42/psg42806000/baseproducts_sure-fish.htm?setCountry=true&purl=ar42/psg42806000/baseproducts_surefish.htm!undefined&submit=Accept%20country; last accessed Nov. 5, 2012), a Cytocell IGH/MAF Translocation, Dual Fusion Probe (http://www.zentech.be/uploads/docs/products_info/prenatalogy/cytocell%202012-2013%20catalogue%5B3%5D.pdf; last accessed Nov. 5, 2012), a Metasystems XL IGH/MAF Translocation-Dual Fusion Probe (http://www.metasystems-international.com/index.php?option=com_joodb&view=article&joobase=5&id=12%3Ad-5029-100-og&Itemid=272; last accessed Nov. 5, 2012), a Zeiss FISH Probes XL, 100 µl, IGH/MAFB (https://www.micro-shop.zeiss.com/?s=440675675dedc6&l=en&p=uk&f=r&i=5000&o=&h=25&n=l&sd=00 0000-0528-231-uk; last accessed Nov. 5, 2012) or a Genycell Biotech IGH/MAF Dual Fusion Probe (http://www.google.com/url?sa=t&rct=j&q=&esrc=s&source=web&cd=1&ved=0CCQQFjAA&url=http%3A%2F%2Fwww.genycell.es%2Fimages%2Fproductos%2Fbrochures%2Flphmie6_86.ppt&ei=MhGYUOi3GKWH0QGlt4DoDw&usg=AFQjCNEqQMbT8vQGjJbi9riEf3lVgoFTFQ&sig2=V5IS8juEMVHB18Mv2Xx_Ww; last accessed Nov. 5, 2012)

In some embodiments, the label on the probe is a fluorophore. In some embodiments, the fluorophore on the probe is orange. In some embodiments, the fluorophore on the probe is green. In some embodiments, the fluorophore on the probe is red. In some cases, the fluorophore on the probe is yellow. In some embodiments, one probe is labeled with a red fluorophore, and one with a green fluorophore. In some embodiments, one probe is labeled with a green fluorophore and one with an orange fluorophore. In some cases, the fluorophore on the probe is yellow. For instance, if the MAF-specific probe is labeled with a red fluorophore, and the IGH-specific probe is labeled with a green fluorophore, if white is seen it indicates that the signals overlap and translocation has occurred.

In some embodiments, the fluorophore is SpectrumOrange. In some embodiments, the fluorophore is SpectrumGreen. In some embodiments, the fluorophore is DAPI. In some embodiments, the fluorophore is PlatinumBright405 In some embodiments, the fluorophore is PlatinumBright415. In some embodiments, the fluorophore is PlatinumBright495. In some embodiments, the fluorophore is PlatinumBright505. In some embodiments, the fluorophore is PlatinumBright550. In some embodiments, the fluorophore is PlatinumBright547. In some embodiments, the fluorophore is PlatinumBright570. In some embodiments, the fluorophore is PlatinumBright590. In some embodiments, the fluorophore is PlatinumBright647. In some embodiments, the fluorophore is PlatinumBright495/550. In some embodiments, the fluorophore is PlatinumBright415/495/550. In some embodiments, the fluorophore is DAPI/PlatinumBright495/550. In some embodiments, the fluorophore is FITC. In some embodiments, the fluorophore is Texas Red. In some embodiments, the fluorophore is DEAC. In some embodiments, the fluorophore is R6G. In some embodiments, the fluorophore is Cy5. In some embodiments, the fluorophore is FITC, Texas Red and DAPI. In some embodiments, a DAPI counterstain is used to visualize the translocation, amplification or copy number alteration.

One embodiment of the invention comprises a method in which in a first step it is determined if the c-MAF gene is translocated in a sample of a subject. In a preferred embodiment, the sample is a tumor tissue sample.

In a particular embodiment, a method of the invention for the prognosis of the tendency to develop bone metastasis in a subject with breast cancer comprises determining the c-MAF gene copy number in a sample of said subject wherein the c-MAF gene is translocated and comparing said copy number with the copy number of a control or reference sample, wherein if the c-MAF copy number is greater with respect to the c-MAF copy number of a control sample, then the subject has a greater tendency to develop bone metastasis.

Methods for determining whether the c-MAF gene or the chromosome region 16q22-q24 is translocated are widely known in the state of the art and include those described previously for the amplification of c-MAF. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification, the copy number, or the translocation can be determined by counting the number of fluorescent points, colored points or points with silver in the chromosomes or in the nucleus. In other embodiments, the detection of copy number alterations and translocations can be detected through the use of whole genome sequencing, exome sequencing or by the use of any PCR derived technology. For instance, PCR can be performed on samples of genomic DNA to detect translocation. In one embodiment, quantitative PCR is used. In one embodiment, PCR is performed with a primer specific to the c-MAF gene and a primer specific to the IGH promoter region; if a product is produced, translocation has occurred.

In some embodiments, the amplification and copy number of the c-MAF gene are determined after translocation of the c-MAF gene is determined. In some embodiments, the probe is used to determine if the cell is polyploid for the c-MAF gene. In some embodiments, a determination of polyploidy is made by determining if there are more than 2 signals from the gene of interest. In some embodiments, polyploidy is determined by measuring the signal from the probe specific for the gene of interest and comparing it with a centromeric probe or other probe.

Method of Prognosis of Clinical Outcome in a Triple Negative (Including Basal-like) Breast Cancer, or Alternatively ER+ Breast Cancer, Based on Detecting the Amplification of the c-MAP Gene In another aspect, the invention relates to an in vitro method (hereinafter seventh method of the invention) for predicting the clinical outcome of a patient suffering triple negative (including basal-like) breast cancer or, alternatively ER+ breast cancer, which comprises determining if the c-MAF gene is amplified in a sample of said subject relative to a reference gene copy number wherein an amplification of the c-MAF gene with respect to said reference gene copy number is indicative of a poor clinical outcome.

The seventh method of the invention comprises, in a first step, determining if the c-MAF gene is amplified in a sample of a subject. The determination of the amplification of the c-MAF is carried out essentially as described in the fifth method of the invention. In a preferred embodiment the sample is a tumor tissue sample. In a preferred embodiment, the amplification of the c-MAF gene is determined by means of determining the amplification of the locus 16q23 or 16q22-q24. In another preferred embodiment, the amplification of the c-MAF gene is determined by means of using a c-MAF gene-specific probe.

In a second step, the seventh method of the invention comprises comparing said copy number with the copy number of a control or reference sample, wherein if the c-MAF copy number is greater with respect to the c-MAP copy number of a control sample, then this is indicative of a poor clinical outcome.

In a preferred embodiment, the c-MAF gene is amplified with respect to a reference gene copy number when the c-MAF gene copy number is higher than the copy number that a reference sample or control sample has. In one example, the c-MAF gene is said to be "amplified" if the genomic copy number of the c-MAF gene is increased by at least 2-(i.e., 6 copies), 3- (i.e., 8 copies), 4-, 5-, 6-, 7-, 8-, 9-, 10-, 15-, 20-, 25-, 30-, 35-, 40-, 45-, or 50-fold in a test sample relative to a control sample. In another example, a c-MAF gene is said to be "amplified" if the genomic copy number of the c-MAF gene per cell is at least 3, 4, 5, 6, 7, 8, 9, 10, 11, 12, 13, 14, 15, 16, 17, 18, 19, 20, 21, 22, 23, 24, 25, 26, 27, 28, 29, 30, and the like.

In another embodiment, the reference gene copy number is the gene copy number in a sample of triple negative (including basal-like) breast cancer or, alternatively ER+ breast cancer, from a subject who has not suffered bone metastasis.

In another embodiment, the amplification is determined by means of in situ hybridization or PCR.

Method for Designing Customized Therapy—in Patients with Triple Negative (Including Basal-like) Breast Tumors or, Alternatively ER+ Breast Tumors or HER2+ Breast Tumors As is known in the state of the art, the treatment to be administered to a subject suffering from cancer depends on whether the latter is a malignant tumor, i.e., whether it has high probabilities of undergoing metastasis, or whether the latter is a benign tumor. In the first assumption, the treatment of choice is a systemic treatment such as chemotherapy and in the second assumption, the treatment of choice is a localized treatment such as radiotherapy.

Therefore, as described in the present application, given that c-MAF gene amplification or translocation in triple negative (including basal-like) breast cancer cells or, alternatively ER+ breast cancer cells is related to the presence of bone metastasis, the c-MAF gene amplification or translocation is useful for making decisions in terms of the most suitable therapy for the subject suffering said cancer. In a preferred embodiment, the amplification of the c-MAF gene is determined by means of determining the amplification of the locus 16q23 or 16q22-q24. In another preferred embodiment, the amplification of the c-MAF gene is determined by means of using a c-MAF gene-specific probe.

Thus, in another aspect the invention relates to an in vitro method (hereinafter third method of the invention) for designing a customized therapy for a subject suffering triple negative (including basal-like) breast cancer or, alternatively ER+ breast cancer, which comprises
  iii) quantifying the c-MAF gene amplification or translocation in a sample of said subject and
  iv) comparing the gene amplification or translocation obtained in i) with a reference value,
wherein if the c-MAF gene amplification or translocation is increased with respect to said reference value, then said subject is susceptible to receive a therapy aiming to prevent and/or treat the bone metastasis. If the c-MAF gene amplification or translocation is not increased with respect to said reference value, then said subject is not susceptible to receive a therapy aiming to prevent and/or treat the bone metastasis.

In a preferred embodiment, the amplification of the c-MAF gene is determined by means of determining the amplification of the locus 16q23 or 16q22-q24. In another preferred embodiment, the amplification of the c-MAF gene is determined by means of using a c-MAF gene-specific probe.

In a particular embodiment, the bone metastasis is osteolytic metastasis.

Another method of the invention comprises quantifying the c-MAF gene amplification or translocation in a sample in a subject suffering from triple negative (including basal-like) breast cancer or, alternatively ER+ breast cancer. In a preferred embodiment, the sample is a tumor tissue sample.

In another particular embodiment, the method of the invention comprises quantifying only the c-MAF gene amplification or translocation as a single marker, i.e., the method does not involve determining the expression level of any additional marker.

In the case of this particular method of the invention the sample can be a primary tumor tissue sample of the subject.

In a second step, the c-MAF gene amplification or translocation obtained in the tumor sample of the subject is compared with a reference value. In a preferred embodiment, the reference value is the c-MAF gene amplification or translocation of said gene in a control sample. The determination of the c-MAF gene amplification or translocation must be related to values of a control sample or reference sample. Depending on the type of tumor to be analyzed, the exact nature of the control sample may vary. Thus preferably the reference sample is a sample of a subject with triple negative (including basal-like) breast cancer or, alternatively ER+ breast cancer, that has not metastasized or that corresponds to c-MAF gene amplification or translocation measured in a tumor tissue collection in biopsy samples of subjects with triple negative (including basal-like) breast cancer or, alternatively ER+ breast cancer, which has not metastasized.

Once the c-MAF gene amplification or translocation in the sample has been measured and compared with the reference value, if the gene amplification or translocation of said gene is increased with respect to the reference value, then it can be concluded that said subject is susceptible to receiving therapy aiming to prevent (if the subject has yet to undergo metastasis) and/or treat metastasis (if the subject has already experienced metastasis).

When the cancer has metastasized, systemic treatments including but not limited to chemotherapy, hormone treatment, immunotherapy, or a combination thereof can be used. Additionally, radiotherapy and/or surgery can be used. The choice of treatment generally depends on the type of primary cancer, the size, the location of the metastasis, the age, the general health of the patient and the types of treatments used previously.

The systemic treatments are those that reach the entire body, such as:
  Chemotherapy is the use of medicaments to destroy cancer cells. The medicaments are generally administered through oral or intravenous route. Sometimes, chemotherapy is used together with radiation treatment. Suitable chemotherapeutic treatments for breast cancer include, without limitation, anthracyclines (doxorubicin, epirubicin, pegylated liposomal doxorubicin), Taxanes (paclitaxel, docetaxel, albumin nano-particle bound paclitaxel), 5-fluorouracil (continuous infusion 5-FU, capecitabine), Vinca alkaloids (vinorelbine, vinblastine), Gemcitabine, Platinum salts (cisplatin, carboplatin), cyclophosphamide, Etoposide and combinations of one or more of the above such as Cyclophosphamide/anthracycline+/−5-fluorouracil regimens (such as doxorubicin/cyclophosphamide (AC), epirubicin/cyclophosphamide, (EC) cyclophosphamide/epirubicin/5-fluorouracil (CEF), cyclophosphamide/doxorubicin/5-fluorouracil (CAF), 5-fluorouracil/epirubicin/cyclophosphamide (FEC)), cyclophosphamide/metothrexate/5-fluorouracil (CMF), anthracyclines/taxanes (such as doxorubicin/paclitaxel or doxorubicin/docetaxel), Docetaxel/capecitabine, Gemcitabine/paclitaxel, Taxane/platinum regimens (such as paclitaxel/carboplatin or docetaxel/carboplatin).

Immunotherapy is a treatment that aids the immune system itself of the patient to combat cancer. There are several types of immunotherapy which are used to treat metastasis in patients. These include but are not limited to cytokines, monoclonal antibodies and antitumor vaccines.

In another aspect, the treatment is Alpharadin (radium-223 dichloride). Alpharadin uses alpha radiation from radium-223 decay to kill cancer cells. Radium-223 naturally self-targets to bone metastases by virtue of its properties as a calcium-mimic. Alpha radiation has a very short range of 2-10 cells (when compared to current radiation therapy which is based on beta or gamma radiation), and therefore causes less damage to surrounding healthy tissues (particularly bone marrow). With similar properties to calcium, radium-223 is drawn to places where calcium is used to build bone in the body, including the site of faster, abnormal bone growth—such as that seen in the skeletal metastases of men with advanced, castration-resistant prostate cancer. Radium-223, after injection, is carried in the bloodstream to sites of abnormal bone growth. The place where a cancer starts in the body is known as the primary tumor. Some of these cells may break away and be carried in the bloodstream to another part of the body. The cancer cells may then settle in that part of the body and form a new tumor. If this happens it is called a secondary cancer or a metastasis. Most patients with late stage prostate cancer suffer the maximum burden of disease in their bones. The aim with radium-223 is to selectively target this secondary cancer. Any radium-223 not taken-up in the bones is quickly routed to the gut and excreted.

In another aspect, the treatment is an mTor inhibitor. In some aspects, the mTor inhibitor is a dual mTor/PI3kinase inhibitor. In some aspects, the mTor inhibitor is used to prevent or inhibit metastasis. In some aspects the mTor inhibitor is selected from the group consisting of: ABI009 (sirolimus), rapamycin (sirolimus), Abraxane (paclitaxel), Absorb (everolimus), Afinitor (everolimus), Afinitor with Gleevec, AS703026 (pimasertib), Axxess (umirolimus), AZD2014, BEZ235, Biofreedom (umirolimus), BioMatrix (umirolimus), BioMatrix flex (umirolimus), CC115, CC223, Combo Bio-engineered Sirolimus Eluting Stent ORBUS-NEICH (sirolimus), Curaxin CBLC102 (mepacrine), DE109 (sirolimus), DS3078, Endeavor DES (zotarolimus), Endeavor Resolute (zotarolimus), Ferrara (letrozole), Hocena (antroquinonol), INK128, Inspiron (sirolimus), IPI504 (retaspimycin hydrochloride), KRN951 (tivozanib), ME344, MGA031 (teplizumab), MiStent SES (sirolimus), MKC1, Nobori (umirolimus), OSI027, OVI123 (cordycepin), Palomid 529, PF04691502, Promus Element (everolimus), PWT33597, Rapamune (sirolimus), Resolute DES (zotarolimus), RG7422, SAR245409, SF1126, SGN75 (vorsetuzumab mafodotin), Synergy (everolimus), Taltorvic (ridaforolimus), Tarceva (erlotinib), Torisel (temsirolimus), Xience Prime (everolimus), Xience V (everolimus), Zomaxx (zotarolimus), Zortress (everolimus), Zotarolimus Eluting Peripheral Stent MEDTRONIC (zotarolimus), AP23841, AP24170, ARmTOR26, BN107, BN108, Canstatin GENZYME (canstatin), CU906, EC0371, EC0565, KI1004, LOR220, NV128, Rapamycin ONCOIMMUNE (sirolimus), SB2602, Sirolimus PNP SAMYANG BIOPHARMACEUTICALS (sirolimus), TOP216, VLI27, VS5584, WYE125132, XL388, Advacan (everolimus), AZD8055, Cypher Select Plus Sirolimus eluting Coronary Stent (sirolimus), Cypher Sirolimus eluting coronary stent (sirolimus), Drug Coated Balloon (sirolimus), E-Magic Plus (sirolimus), Emtor (sirolimus), Esprit (everolimus), Evertor (everolimus), HBF0079, LCP-Siro (sirolimus), Limus CLARIS (sirolimus), mTOR Inhibitor CELLZOME, Nevo Sirolimus eluting Coronary Stent (sirolimus), nPT-mTOR, Rapacan (sirolimus), Renacept (sirolimus), ReZolve (sirolimus), Rocas (sirolimus), SF1126, Sirolim (sirolimus), Sirolimus NORTH CHINA (sirolimus), Sirolimus RANBAXY (sirolimus), Sirolimus WATSON (sirolimus) Siropan (sirolimus), Sirova (sirolimus), Supralimus (sirolimus), Supralimus-Core (sirolimus), Tacrolimus WATSON (tacrolimus), TAFA93, Temsirolimus ACCORD (temsirolimus), Temsirolimus SANDOZ (temsirolimus), TOP216, Xience Prime (everolimus), Xience V (everolimus). In a specific aspect the mTor inhibitor is Afinitor (everolimus) (http://www.afinitor.com/index.jsp?usertrack.filter_applied=true&NovaId= 40294620643 38207963; last accessed Nov. 28, 2012). In another aspect, everolimus is combined with an aromatase inhibitor. (See. e.g., Baselga, J., el al., Everolimus in Postmenopausal Hormone-Receptor Positive Advanced Breast Cancer. 2012. *N. Engl. J. Med.* 366(6): 520-529, which is herein incorporated by reference). In another aspect, mTor inhibitors can be identified through methods known in the art. (See, e.g., Zhou, H. et al. Updates of mTor inhibitors. 2010. *Anticancer Agents Med. Chem.* 10(7): 571-81, which is herein incorporated by reference). In some aspects, the mTor inhibitor is used to treat or prevent or inhibit metastasis in a patient that is positive for a hormone receptor. (See. e.g., Baselga, J., et al., Everolimus in Postmenopausal Hormone-Receptor Positive Advanced Breast Cancer. 2012. *N. Engl. J. Med.* 366(6): 520-529). In some embodiments, the patient is ER+. In some aspects, the mTor inhibitor is used to treat or prevent or inhibit metastasis in a patient with advanced breast cancer. In some aspects, the mTor inhibitor is used in combination with a second treatment. In some aspects, the second treatment is any treatment described herein.

In another aspect, the treatment is a Src kinase inhibitor. In some aspects, the Src inhibitor is used to prevent or inhibit metastasis. In some aspects, the Src kinase inhibitor is selected from the group: AZD0530 (saracatinib), Bosulif (bosutinib), ENMD981693, KD020, KX01, Sprycel (dasatinib), Yervoy (ipilimumab), AP23464, AP23485, AP23588, AZD0424, c-Src Kinase Inhibitor KISSEI, CU201, KX2361, SKS927, SRN004, SUNK706, TG100435, TG100948, AP23451, Dasatinib HETERO (dasatinib), Dasatinib VALEANT (dasatinib), Fontrax (dasatinib), Src Kinase Inhibitor KINEX, VX680, (tozasertib lactate), XL228, and SUNK706. In some embodiments, the Src kinase inhibitor is dasatinib. In another aspect, Src kinase inhibitors can be identified through methods known in the art (See, e.g., Sen, B. and Johnson, F. M. Regulation of Src Family Kinases in Human Cancers. 2011. *J. Signal Transduction.* 2011: 14 pages, which is herein incorporated by reference). In some aspects, the Src kinase inhibitor is used to treat or prevent or inhibit metastasis in a patient that is positive for the SRC-responsive signature (SRS). In some aspects, the patient is SRS+ and ER–. (See. e.g., Zhang, CH.-F, et al. Latent Bone Metastasis in Breast Cancer Tied to Src-Dependent survival signals. 2009. *Cancer Cell*. 16: 67-78, which is herein incorporated by reference.) In some aspects, the Src kinase inhibitor is used to treat or prevent or inhibit metastasis in a patient with advanced breast cancer. In some aspects, the Src kinase inhibitor is used in combination with a second treatment. In some aspects, the second treatment is any treatment described herein.

In another aspect, the treatment is a COX-2 inhibitor. In some aspects, the COX-2 inhibitor is used to prevent or inhibit metastasis. In some aspects, the COX-2 inhibitor is selected from the group: ABT963, Acetaminophen ER JOHNSON (acetaminophen), Acular X (ketorolac tromethamine), BAY1019036 (aspirin), BAY987111 (diphenhydramine, naproxen sodium), BAY11902 (piroxicam), BCIBUCH001 (ibuprofen), Capoxigem (apricoxib), CS502, CS670 (pelubiprofen), Diclofenac HPBCD (diclofenac), Diractin (ketoprofen), GW406381, HCT1026 (nitroflurbiprofen), Hyanalgese-D (diclofenac), HydrocoDex (acetaminophen, dextromethorphan, hydrocodone), Ibuprofen Sodium PFIZER (ibuprofen sodium), Ibuprofen with Acetaminophen PFIZER (acetaminophen, ibuprofen), Impracor (ketoprofen), IP880 (diclofenac), IP940 (indomethacin), ISV205 (diclofenac sodium), JNS013 (acetaminophen, tramadol hydrochloride), Ketoprofen TDS (ketoprofen), LTNS001 (naproxen etemesil), Mesalamine SALIX (mesalamine), Mesalamine SOFAR (mesalamine), Mesalazine (mesalamine), ML3000 (licofelone), MRX7EAT (etodolac), Naproxen IROKO (naproxen), NCX4016 (nitroaspirin), NCX701 (nitroacetaminophen), Nuprin SCOLR (ibuprofen), OMS103HP (amitriptyline hydrochloride, ketoprofen, oxymetazoline hydrochloride), Oralease (diclofenac), OxycoDex (dextromethorphan, oxycodone), P54, PercoDex (acetaminophen, dextromethorphan, oxycodone), PL3100 (naproxen, phosphatidyl choline), PSD508, R-Ketoprofen (ketoprofen), Remura (bromfenac sodium), ROX828 (ketorolac tromethamine), RP19583 (ketoprofen lysine), RQ00317076, SDX101 (R-etodolac), TDS943 (diclofenac sodium), TDT070 (ketoprofen), TPR100, TQ1011 (ketoprofen), TT063 (S-flurbiprofen), UR8880 (cimicoxib), V0498TA01A (ibuprofen), VT122 (etodolac, propranolol), XP20B (acetaminophen, dextropropoxyphene), XP21B (diclofenac potassium), XP21L (diclofenac potassium), Zoenasa (acetylcysteine, mesalamine), Acephen, Actifed Plus, Actifed-P, Acular, Acular LS, Acular PF, Acular X, Acuvail, Advil, Advil Allergy Sinus, Advil Cold and Sinus, Advil Congestion Relief, Advil PM, Advil PM Capsule, Air Salonpas, Airtal, Alcohol-Free NyQuil Cold & Flu Relief, Aleve, Aleve ABDI IBRAHIM, Aleve-D, Alka-Seltzer, Alka-Seltzer BAYER, Alka-Seltzer Extra Strength, Alka-Seltzer Lemon-Lime, Alka-Seltzer Original, Alka-Seltzer Plus, Alka-Seltzer plus Cold and Cough, Alka-Seltzer plus Cold and Cough Formula, Alka-Seltzer Plus Day and Night Cold Formula, Alka-Seltzer Plus Day Non-Drowsy Cold Formula, Alka-Seltzer Plus Flu Formula, Alka-Seltzer Plus Night Cold Formula, Alka-Seltzer Plus Sinus Formula, Alka-Seltzer Plus Sparkling Original Cold Formula, Alka-Seltzer PM, Alka-Seltzer Wake-Up Call, Anacin, Anaprox, Anaprox MINERVA, Ansaid, Apitoxin, Apranax, Apranax abdi, Arcoxia, Arthritis Formula Bengay, Arthrotec, Asacol, Asacol HD, Asacol MEDUNA ARZNEIMITTEL, Asacol ORIFARM, Aspirin BAYER, Aspirin Complex, Aspirin Migran, AZD3582, Azulfidine, Baralgan M, BAY1019036, BAY987111, BAY11902, BCIBUCH001, Benadryl Allergy, Benadryl Day and Night, Benylin 4 Flu, Benylin Cold and Flu, Benylin Cold and Flu Day and Night, Benylin Cold and Sinus Day and Night, Benylin Cold and Sinus Plus, Benylin Day and Night Cold and Flu Relief, Benylin1 All-In-One, Brexin, Brexin ANGELINI, Bromday, Bufferin, Buscopan Plus, Caldolor, Calmatel, Cambia, Canasa, Capoxigem, Cataflam, Celebrex, Celebrex ORIFARM, Children's Advil Allergy Sinus, Children's Tylenol, Children's Tylenol Cough and Runny Nose, Children's Tylenol plus cold, Children's Tylenol plus Cold and Cough, Children's Tylenol plus cold and stuffy nose, Children's Tylenol plus Flu, Children's Tylenol plus cold & allergy, Children's Tylenol plus Cough & Runny Nose, Children's Tylenol plus Cough & Sore Throat, Children's Tylenol plus multi symptom cold, Clinoril, Codral Cold and Flu, Codral Day and Night Day Tablets, Codral Day and Night Night Tablets, Codral Nightime, Colazal, Combunox, Contac Cold plus Flu, Contac Cold plus Flu Non-Drowsy, Coricidin D, Coricidin HBP Cold and Flu, Coricidin HBP Day and Night Multi-Symptom Cold, Coricidin HBP Maximum Strength Flu, Coricidin HBP Nighttime Multi-Symptom Cold, Coricidin II Extra Strength Cold and Flu, CS502, CS670, Daypro, Daypro Alta, DDS06C, Demazin Cold and Flu, Demazin Cough, Cold and Flu, Demazin day/night Cold and Flu, Demazin PE Cold and Flu, Demazin PE day/night Cold and Flu, Diclofenac HPBCD, Dimetapp Day Relief, Dimetapp Multi-Symptom Cold and Flu, Dimetapp Night Relief, Dimetapp Pain and Fever Relief, Dimetapp PE Sinus Pain, Dimetapp PE Sinus Pain plus Allergy, Dipentum, Diractin, Disprin Cold 'n' Fever, Disprin Extra, Disprin Forte. Disprin Plus, Dristan Cold, Dristan Junior, Drixoral Plus, Duexis, Dynastat, Efferalgan, Efferalgan Plus Vitamin C, Efferalgan Vitamin C, Elixsure IB, Excedrin Back and Body, Excedrin Migraine, Excedrin PM, Excedrin Sinus Headache, Excedrin Tension Headache, Falcol, Fansamac, Feldene, Fever-All, Fiorinal, Fiorinal with Codeine, Flanax, Elector Patch, Flucam, Fortagesic, Gerbin, Giazo, Gladio, Goody's Back and Body Pain, Goody's Cool Orange, Goody's Extra Strength, Goody's PM, Greaseless Bengay, GW406381, HCT1026, He Xing Yi, Hyanalgese-D, HydrocoDex, Ibuprofen Sodium PFIZER, Ibuprofen with, Acetaminophen PFIZER, Icy Hot SANOFI AVENTIS, Impracor, Indocin, Indomethacin APP PHARMA, Indomethacin MYLAN, Infants' Tylenol, IP880, IP940, Iremod, ISV205, JNS013, Jr. Tylenol, Junifen, Junior Strength Advil, Junior Strength Motrin, Ketoprofen TDS, Lemsip Max, Lemsip Max All in One, Lemsip Max All Night, Lemsip Max Cold and Flu, Lialda, Listerine Mouth Wash, Lloyds Cream, Lodine, Lorfit P, Loxonin, LTNS001, Mersyndol, Mesalamine SALIX, Mesalamine SOFAR, Mesalazine, Mesasal GLAXO, Mesasal SANOFI, Mesulid, Metsal Heat Rub, Midol Complete, Midol Extended Relief, Midol Liquid Gels, Midol PM, Midol Teen Formula, Migranin COATED TABLETS, ML3000, Mobic, Mohrus, Motrin, Motrin Cold and Sinus Pain, Motrin PM, Movalis ASPEN, MRX7EAT, Nalfon, Nalfon PEDINOL, Naprelan, Naprosyn, Naprosyn RPG LIFE SCIENCE, Naproxen IROKO, NCX4016, NCX701, NeoProfen LUNDBECK, Nevanac, Nexcede, Niflan, Norgesic MEDICIS, Novalgin, Nuprin SCOLR, Nurofen, Nurofen Cold and Flu, Nurofen Max Strength Migraine, Nurofen Plus, Nuromol, NyQuil with Vitamin C, Ocufen, OMS103HP, Oralease, Orudis ABBOTT JAPAN, Oruvail, Osteluc, OxycoDex, P54, Panadol, Panadol Actifast, Paradine, Paramax, Parfenac, Pedea, Pennsaid, Pentasa, Pentasa ORIFARM, Peon, Percodan, Percodan-Demi, PercoDex, Percogesic, Perfalgan, PL2200, PL3100, Ponstel, Prexige, Prolensa, PSD508, R-Ketoprofen, Rantudil, Relafen, Remura, Robaxisal, Rotec, Rowasa, ROX828, RP19583, RQ00317076, Rubor, Salofalk, Salorpas, Saridon, SDX101, Seltouch, sfRowasa, Shinbaro, Sinumax, Sinutab, Sinutab, sinus, Spalt, Sprix, Strefen, Sudafed Cold and Cough, Sudafed Head Cold and Sinus, Sudafed PE Cold plus Cough, Sudafed PE Pressure plus Pain, Sudafed PE, Severe Cold, Sudafed PE Sinus Day plus Night Relief Day Tablets, Sudafed PE Sinus Day plus Night Relief Night Tablets, Sudafed PE Sinus plus Anti-inflammatory Pain Relief, Sudafed Sinus Advance, Surgam, Synalgos-DC, Synflex, Tavist allergy/sinus/headache, TDS943, TDT070, Theraflu Cold and Sore Throat, Theraflu Daytime Severe Cold and Cough, Theraflu Daytime Warming Relief, Theraflu Warming Relief Caplets Daytime Multi-Symptom Cold, Theraflu Warming Relief Cold and Chest Congestion, Thomapyrin, Thomapyrin C, Thomapyrin Effervescent, Thomapyrin Medium, Tilcotil, Tispol, Tolectin, Toradol, TPR100, TQ1011, Trauma-Salbe, Trauma-Salbe Kwizda, Treo, Treximet, Trovex, TT063, Tylenol, Tylenol Allergy Multi-Symptom, Tylenol Back Pain, Tylenol Cold & Cough Daytime, Tylenol Cold & Cough Nighttime, Tylenol Cold and Sinus Daytime, Tylenol Cold and Sinus Nighttime, Tylenol Cold Head Congestion Severe, Tylenol Cold Multi Symptom Daytime, Tylenol Cold Multi Symptom Nighttime Liquid, Tylenol Cold Multi Symptom Severe, Tylenol Cold Non-Drowsiness Formula, Tylenol Cold Severe Congestion Daytime, Tylenol Complete Cold, Cough and Flu Night time, Tylenol Flu Nighttime, Tylenol Menstrual, Tylenol PM, Tylenol Sinus Congestion & Pain Daytime, Tylenol Sinus Congestion & Pain Nighttime, Tylenol Sinus Congestion & Pain Severe, Tylenol Sinus Severe Congestion Daytime, Tylenol Ultra Relief, Tylenol with Caffeine and Codeine phosphate, Tylenol with Codeine phosphate, Ultra Strength Bengay Cream, Ultracet, UR8880, V0498TA01A, Vicks NyQuil Cold and Flu Relief, Vicoprofen, Vimovo, Voltaren Emulgel, Voltaren GEL, Voltaren NOVARTIS CONSUMER HEALTH GMBH, Voltaren XR, VT122, Xefo, Xefo Rapid, Xefocam, Xibrom, XL3, Xodol, XP20B, XP21B, XP21L, Zipsor, and Zoenasa. In another aspect, COX-2 inhibitors can be identified through methods known in the art (See, e.g., Dannhardt, G. and Kiefer, W. Cyclooxygenase inhibitors—current status and future prospects. 2001. *Eur. J. Med. Chem.* 36: 109-126, which is herein incorporated by reference). In some aspects, the COX-2 inhibitor is used to treat or prevent or inhibit metastasis in a patient with advanced breast cancer. In some aspects, the COX-2 inhibitor is used in combination with a second treatment. In some aspects, the second treatment is any treatment described herein. In some aspects, the COX-2 inhibitor is used in combination with a second treatment selected from the group consisting of: Denosumab, Zometa (http://www.us.zometa.com/index.jsp?usertrack.filter_applied=true&NovaId=293 537693 4467633633; last accessed Dec. 2, 2012), Carbozantinib or Cabozantinib, Antibody or peptide blocking PTHLH (parathyroid hormone like hormone) or PTHrP (parathyroid hormone related protein) and Everolimus.

In another aspect, the treatment agents used for avoiding and/or preventing bone degradation include, although not limited to:

Parathyroid hormone (PTH) and Parathyroid like hormone (PTHLH) inhibitors (including blocking antibodies) or recombinant forms thereof (teriparatide corresponding to the amino acids 7-34 of PTH). This hormone acts by stimulating the osteoclasts and increasing their activity.

Strontium ranelate: is an alternative oral treatment, and forms part of the group of drugs called "dual action bone agents" (DABAs) because they stimulate the osteoblast proliferation and inhibit the osteoclast proliferation.

"Estrogen receptor modulators" (SERM) refers to compounds which interfere with or inhibit the binding of estrogens to the receptor, regardless of the mechanism. Examples of estrogen receptor modulators include, among others, estrogens, progestagen, estradiol, droloxifene, raloxifene, lasofoxifene, TSE-424, tamoxifen, idoxifene, LY353381, LY117081, toremifene, fluvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate 4,4'dihydroxybenzophenone-2,4-dinitrophenylhydrazone and SH646.

Calcitonin: directly inhibits the osteoclast activity through the calcitonin receptor. The calcitonin receptors have been identified on the surface of the osteoclasts.

Bisphosphonates: are a group of medicinal products used for the prevention and the treatment of diseases with bone resorption and reabsorption such as osteoporosis and cancer with bone metastasis, the latter being with or without hypercalcaemia, associated to breast cancer and prostate cancer. Examples of bisphosphonates which can be used in the therapy designed by means of the fifth method of the invention include, although not limited to, nitrogenous bisphosphonates (such as pamidronate, neridronate, olpadronate, alendronate, ibandronate, risedronate, incadronate, zoledronate or zoledronic acid, etc.) and non-nitrogenous bisphosphonates (such as etidronate, clodronate, tiludronate, etc.).

"Cathepsin K inhibitors" refers to compounds which interfere in the cathepsin K cysteine protease activity. Non-limiting examples of cathepsin K inhibitors include 4-amino-pyrimidine-2-carbonitrile derivatives (described in the International patent application WO 03/020278 under the name of Novartis Pharma GMBH), pyrrolo-pyrimidines described in the publication WO 03/020721 (Novartis Pharma GMBH) and the publication WO 04/000843 (ASTRAZENECA AB) as well as the inhibitors described in the publications PCT WO 00/55126 of Axys Pharmaceuticals, WO 01/49288 of Merck Frosst Canada & Co. and Axys Pharmaceuticals.

"DKK-1(Dickkopf-1) inhibitor" as used herein refers to any compound which is capable of reducing DKK-1 activity. DKK-1 is a soluble Wnt pathway antagonist expressed predominantly in adult bone and upregulated in myeloma patients with osteolytic lesions. Agents targeting DKK-1 may play a role in preventing osteolytic bone disease in multiple myeloma patients. BHQ880 from Novartis is a first-in-class, fully human, anti-DKK-1 neutralizing antibody. Preclinical studies support the hypothesis that BHQ880 promotes bone formation and thereby inhibits tumor-induced osteolytic disease (Ettenberg S. et al., American Association for Cancer Research Annual Meeting. Apr. 12-16, 2008; San Diego, Calif. Abstract).

"Dual MET and VEGFR2 inhibitor" as used herein refers to any compound which is a potent dual inhibitor of the MET and VEGF pathways designed to block MET driven tumor escape. MET is expressed not only in tumor cells and endothelial cells, but also in osteoblasts (bone-forming cells) and osteoclasts (bone-removing cells). HGF binds to MET on all of these cell types, giving the MET pathway an important role in multiple autocrine and paracrine loops. Activation of MET in tumor cells appears to be important in the establishment of metastatic bone lesions. At the same time, activation of the MET pathway in osteoblasts and osteoclasts may lead to pathological features of bone metastases, including abnormal bone growth (i.e., blastic lesions) or destruction (i.e., lytic lesion. Thus, targeting the MET pathway may be a viable strategy in preventing the establishment and progression of metastatic bone lesions. Cabozantinib (Exelixis, Inc), formerly known as XL184 (CAS 849217-68-1), is a potent dual inhibitor of the MET and VEGF pathways designed to block MET driven tumor escape. In multiple preclinical studies cabozantinib has been shown to kill tumor cells, reduce metastases, and inhibit angiogenesis (the formation of new blood vessels necessary to support tumor growth). Another suitable dual inhibitors are E7050 (N-[2-Fluoro-4-({2[4-(4-methylpiperazin-1-yl)piperidin-1-yl]carbonylaminopyridin-4-yl}oxy)phenyl]-N'-(4-fluorophenyl)cyclopropane-1,1-dicarboxamide (2R,3R)-tartrate) (CAS 928037-13-2) or Foretinib (also known as GSK1363089, XL880, CAS 849217-64-7).

"RANKL inhibitors" as used herein refer to any compound which is capable of reducing the RANK activity. RANKL is found on the surface of the osteoblast membrane of the stroma and T-lymphocyte cells, and these T-lymphocyte cells are the only ones which have demonstrated the capacity for secreting it. Its main function is the activation of the osteoclasts, cells involved in the bone resorption. The RANKL inhibitors can act by blocking the binding of RANKL to its receptor (RANK), blocking the RANK-mediated signaling or reducing the expression of RANKL by blocking the transcription or the translation of RANKL. RANKL antagonists or inhibitors suitable for use in the present invention include, without limitation:

a suitable RANK protein which is capable of binding RANKL and which comprises the entire or a fragment of the extracellular domain of a RANK protein. The soluble RANK may comprise the signal peptide and the extracellular domain of the murine or human RANK polypeptides, or alternatively, the mature form of the protein with the signal peptide removed can be used.

Osteoprotegerin or a variant thereof with RANKL-binding capacity.

RANKL-specific antisense molecules

Ribozymes capable of processing the transcribed products of RANKL

Specific anti-RANKL antibodies. "Anti-RANKL antibody or antibody directed against RANKL" is understood herein as all that antibody which is capable of binding specifically to the ligand of the activating receptor for the nuclear factor κB (RANKL) inhibiting one or more RANKL functions. The antibodies can be prepared using any of the methods which are known by the person skilled in the art. Thus, the polyclonal antibodies are prepared by means of immunizing an animal with the protein to be inhibited. The monoclonal antibodies are prepared using the method described by Kohler, Milstein at al. (Nature, 1975, 256: 495). Antibodies suitable in the context of the present invention include intact antibodies which comprise a variable antigen binding region and a constant region, fragments "Fab", "F(ab')2" and "Fab'", Fv, scFv, diabodies and bispecific antibodies.

Specific anti-RANKL nanobodies. Nanobodies are antibody-derived therapeutic proteins that contain the unique structural and functional properties of naturally-occurring heavy-chain antibodies. The Nanobody technology was originally developed following the discovery that camelidae (camels and llamas) possess fully functional antibodies that lack light chains. The general structure of nanobodies is FR1-CDR1-FR2-CDR2-FR3-CDR3-FR4 wherein FR1 to FR4 are the framework regions 1 to 4 CDR1 to CDR3 are the complementarity determining regions 1 to 3. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. These newly discovered VHH domains with their unique structural and functional properties form the basis of a new generation of therapeutic antibodies which Ablynx has named Nanobodies.

In one embodiment, the RANKL inhibitor is selected from the group consisting of a RANKL specific antibody, a RANKL specific nanobody and osteoprotegerin. In a specific embodiment, the anti-RANKL antibody is a monoclonal antibody. In a yet more specific embodiment, the anti-RANKL antibody is Denosumab (Pageau, Steven C. (2009). mAbs 1 (3): 210-215, CAS number 615258-40-7) (the entire contents of which are hereby incorporated by reference). Denosumab is a fully human monoclonal antibody which binds to RANKL and prevents its activation (it does not bind to the RANK receptor). Various aspects of Denosumab are covered by U.S. Pat. Nos. 6,740,522; 7,411,050; 7,097,834; 7,364,736 (the entire contents of each of which are hereby incorporated by reference in their entirety). In another embodiment, the RANKL inhibitor an antibody, antibody fragment, or fusion construct that binds the same epitope as Denosumab.

In a preferred embodiment, the anti-RANKL nanobody is any of the nanobodies as described in WO2008142164, (the contents of which are incorporated in the present application by reference). In a still more preferred embodiment, the anti-RANKL antibody is the ALX-0141 (Ablynx). ALX-0141 has been designed to inhibit bone loss associated with post-menopausal osteoporosis, rheumatoid arthritis, cancer and certain medications, and to restore the balance of healthy bone metabolism.

In a preferred embodiment, the agent preventing the bone degradation is selected from the group consisting of a bisphosphonate, a RANKL inhibitor, PTH and PTHLH inhibitor or a PRG analog, strontium ranelate, a DKK-1 inhibitor, a dual MET and VEGFR2 inhibitor, an estrogen receptor modulator, Radium-223 calcitonin, and a cathepsin K inhibitor. In a more preferred embodiment the agent preventing the bone degradation is a bisphosphonate. In a yet more preferred embodiment, the bisphosphonate is the zoledronic acid.

In one embodiment, a CCR5 antagonist is administered to prevent or inhibit metastasis of the primary breast cancer tumor to bone. In one embodiment, the CCR5 antagonist is a large molecule. In another embodiment, the CCR5 antagonist is a small molecule. In some embodiments, the CCR5 antagonist is Maraviroc (Velasco-Veláquez, M. et al. 2012. CCR5 Antagonist Blocks Metastasis of Basal Breast Cancer Cells. *Cancer Research.* 72:3839-3850.). In some embodiments, the CCR5 antagonist is Vicriviroc. Velasco-Veláquez, M. et al. 2012. CCR5 Antagonist Blocks Metastasis of Basal Breast Cancer Cells. *Cancer Research.* 72:3839-3850.). In some aspects, the CCR5 antagonist is Aplaviroc (Demarest J. F. et al. 2005. Update on Aplaviroc: An HIV Entry Inhibitor Targeting CCR5. *Retrovirology* 2(Suppl. 1): S13).

In some aspects, the CCR5 antagonist is a spiropiperidine CCR5 antagonist. (Rotstein D. M. et al. 2009. Spiropiperidine CCR5 antagonists. *Bioorganic & Medicinal Chemistry Letters*. 19 (18): 5401-5406. In. some embodiments, the CCR5 antagonist is INCB009471 (Kuritzkes, D. R. 2009. HIV-1 entry inhibitors: an overview. *Curr. Opin. HIV AIDS.* 4(2): 82-7).

In a preferred embodiment the dual MET and VEGFR2 inhibitor is selected from the group consisting of Cabozantinib, Foretinib and E7050.

In a preferred embodiment the Radium 223 therapy is alpharadin.

Alternatively a combined treatment can be carried out in which more than one agent from those mentioned above are combined to treat and/or prevent the metastasis or said agents can be combined with other supplements, such as calcium or vitamin D or with a hormone treatment.

Methods for Treating Bone Metastasis from Triple Negative (Including Basal-like) Breast Cancer, or Alternatively ER+ Breast Cancer, Using c-MAF Inhibitory Agents In another aspect, the invention relates to a c-MAF inhibitory agent (hereinafter, inhibitory agent of the invention) for use in the treatment or prevention of bone metastasis from triple negative (including basal-like) breast cancer or, alternatively ER+ breast cancer.

In another aspect, the invention relates to the use of a c-MAF inhibitory agent for the manufacture of a medicament for the treatment or prevention of bone metastasis from triple negative (including basal-like) breast cancer or, alternatively ER+ breast cancer.

In another aspect, the invention relates to a method for the treatment or prevention of the bone metastasis from triple negative (including basal-like) breast cancer or, alternatively ER+ breast cancer, in a subject in need thereof comprising the administration to said subject of a c-MAF inhibitory agent.

In another aspect, the invention relates to a method for preventing or reducing the risk of bone metastasis in a subject suffering from triple negative (including basal-like) breast cancer or, alternatively ER+ breast cancer, said method comprising administering to said subject an agent that prevents or reduces bone metastasis, wherein said agent is administered in accordance with a treatment regimen determined from quantifying the expression level of c-MAF in said subject.

By way of non-limiting illustration, c-MAF inhibitory agents suitable for use in the present invention include antisense oligonucleotides, interference RNAs (siRNAs), catalytic RNAs, specific ribozymes, inhibitory antibodies or nanobodies, a dominant negative c-MAF variant or a compound from Table 1 or 2.

Antisense Oligonucleotides

An additional aspect of the invention relates to the use of isolated "antisense" nucleic acids to inhibit expression, for example, for inhibiting transcription and/or translation of a nucleic acid which encodes c-MAF the activity of which is to be inhibited. The antisense nucleic acids can be bound to the potential target of the drug by means of conventional base complementarity or, for example, in the case of binding to Double stranded DNA through specific interaction in the large groove of the double helix. Generally, these methods refer to a range of techniques generally used in the art and they include any method which is based on the specific binding to oligonucleotide sequences.

An antisense construct of the present invention can be distributed, for example, as an expression plasmid which, when it is transcribed in a cell, produces RNA complementary to at least one unique part of the cellular mRNA encoding c-MAF. Alternatively, the antisense construct is a oligonucleotide probe generated ex vivo which, when introduced into the cell, produces inhibition of gene expression hybridizing with the mRNA and/or gene sequences of a target nucleic acid. Such oligonucleotide probes are preferably modified oligonucleotides which are resistant to endogenous nucleases, for example, exonucleases and/or endonucleases and are therefore stable in vivo. Examples of nucleic acids molecules for use thereof as antisense oligonucleotides are DNA analogs of phosphoramidate, phosphothionate and methylphosphonate (see also U.S. Pat. Nos. 5,176,996; 5,264,564; and 5,256,775) (each of which is incorporated herein by reference in its entirety). Additionally, the general approximations for constructing oligomers useful in the antisense therapy have been reviewed, for example, in Van der Krol et al., BioTechniques 6: 958-976, 1988; and Stein et al., Cancer Res 48: 2659-2668, 1988.

With respect to the antisense oligonucleotide, the oligodeoxyribonucleotide regions derived from the starting site of the translation, for example, between −10 and +10 of the target gene are preferred. The antisense approximations involve the oligonucleotide design (either DNA or RNA) that are complementary to the mRNA encoding the target polypeptide. The antisense oligonucleotide will be bound to the transcribed mRNA and translation will be prevented.

The oligonucleotides which are complementary to the 5' end of the mRNA, for example the non translated 5' sequence up to and including the start codon AUG must function in the most efficient manner to inhibit translation. Nevertheless, it has been shown recently that the sequences complementary to the non translated 3' sequences of the mRNA are also efficient for inhibiting mRNA translation (Wagner, Nature 372: 333, 1994). Therefore, complementary oligonucleotides could be used at the non translated 5' or 3' regions, non coding regions of a gene in an antisense approximation to inhibit the translation of that mRNA. The oligonucleotides complementary to the non translated 5' region of the mRNA must include the complement of the start codon AUG. The oligonucleotides complementary to the coding region of the mRNA are less efficient translation inhibitors but they could also be used according to the invention. If they are designed to hybridize with the 5' region, 3' region or the coding region of the mRNA, the antisense nucleic acids must have at least six nucleotides long and preferably have less than approximately 100 and more preferably less than approximately 50, 25, 17 or 10 nucleotides long.

Preferably, in vitro studies are performed first to quantify the capacity of the antisense oligonucleotides for inhibiting gene expression. Preferably these studies use controls which distinguish between antisense gene inhibition and non specific biological effects of the oligonucleotides. Also preferably these studies compared the levels of target RNA or protein with that of an internal control of RNA or protein. The results obtained using the antisense oligonucleotides can be compared with those obtained using a control oligonucleotide. Preferably the control oligonucleotide is approximately of the same length as the oligonucleotide to be assayed and the oligonucleotide sequence does not differ from the antisense sequence more than it is deemed necessary to prevent the specific hybridization to the target sequence.

The antisense oligonucleotide can be a single or double stranded DNA or RNA or chimeric mixtures or derivatives or modified versions thereof. The oligonucleotide can be modified in the base group, the sugar group or the phosphate backbone, for example, to improve the stability of the molecule, its hybridization capacity etc. The oligonucleotide may include other bound groups, such as peptides (for example, for directing them to the receptors of the host cells) or agents for facilitating transport through the cell membrane (see, for example, Letsinger et al., *Proc. Natl. Acad. Sci. U.S.A.* 86: 6553-6556, 1989; Lemaitre et al., *Proc. Natl. Acad. Sci.* 84: 648-652, 1987; PCT Publication No. WO 88/09810) or the blood-brain barrier (see, for example, PCT Publication No. WO 89/10134), intercalating agents (see, for example, Zon, *Pharm. Res.* 5: 539-549, 1988). For this purpose, the oligonucleotide can be conjugated to another molecule, for example, a peptide, a transporting agent, hybridization triggered cleaving agent, etc.

The antisense oligonucleotides may comprise at least one group of modified base. The antisense oligonucleotide may also comprise at least a modified sugar group selected from the group including but not limited to arabinose, 2-fluoro-arabinose, xylulose, and hexose. The antisense oligonucleotide may also contain a backbone similar to a neutral peptide. Such molecules are known as peptide nucleic acid (PNA) oligomers and are described, for example, in Perry-O'Keefe et al., *Proc. Natl. Acad. Sci. U.S.A.* 93: 14670, 1996, and in Eglom et al., *Nature* 365: 566, 1993.

In yet another embodiment, the antisense oligonucleotide comprises at least one modified phosphate backbone. In yet another embodiment, the antisense oligonucleotide is an alpha-anomeric oligonucleotide.

While antisense oligonucleotides complementary to the coding region of the target mRNA sequence can be used, those complementary to the transcribed non translated region can also be used.

In some cases, it may be difficult to reach the sufficient intracellular concentrations of the antisense to suppress the endogenous mRNA translation. Therefore, a preferred approximation uses a recombinant DNA construct in which the antisense oligonucleotide is placed under the control of a strong pol III or pol II promoter.

Alternatively, the target gene expression can be reduced by directing deoxyribonucleotide sequences complementary to the gene regulating region (i.e., the promoter and/or enhancers) to form triple helix structures preventing gene transcription in the target cells in the body (see in general, Helene, *Anticancer Drug Des.* 6(6): 569-84, 1991). In certain embodiments, the antisense oligonucleotides are antisense morpholines.

siRNA

Small interfering RNA or siRNA are agents which are capable of inhibiting the expression of a target gene by means of RNA interference. A siRNA can be chemically synthesized, can be obtained by means of in vitro transcription or can be synthesized in vivo in the target cell. Typically, the siRNA consist of a double stranded RNA between 15 and 40 nucleotide long and may contain a 3' and/or 5' protruding region of 1 to 6 nucleotides. The length of the protruding region is independent of the total length of the siRNA molecule. The siRNA acts by means of degrading or silencing the target messenger after transcription.

The siRNA of the invention are substantially homologous to the mRNA of the c-MAF encoding gene or to the gene sequence which encodes said protein. "Substantially homologous" is understood as having a sequence which is sufficiently complementary or similar to the target mRNA such that the siRNA is capable of degrading the latter through RNA interference. The siRNA suitable for causing said interference include siRNA formed by RNA, as well as siRNA containing different chemical modifications such as:

siRNA in which the bonds between the nucleotides are different than those that appear in nature, such as phosphorothionate bonds.

Conjugates of the RNA strand with a functional reagent, such as a fluorophore.

Modifications of the ends of the RNA strands, particularly of the 3' end by means of the modification with different hydroxyl functional groups in 2' position.

Nucleotides with modified sugars such as O-alkylated residues on 2' position like 2'-O-methylribose or 2'-O-fluororibose.

Nucleotides with modified bases such as halogenated bases (for example 5-bromouracil and 5-iodouracil), alkylated bases (for example 7-methylguanosine).

The siRNA can be used as is, i.e., in the form of a double stranded RNA with the aforementioned characteristics. Alternatively, the use of vectors containing the sense and antisense strand sequence of the siRNA is possible under the control of suitable promoters for the expression thereof in the cell of interest.

Vectors suitable for expressing siRNA are those in which the two DNA regions encoding the two strands of siRNA are arranged in tandem in one and the same DNA strand separated by a spacer region which, upon transcription, forms a loop and wherein a single promoter directs the transcription of the DNA molecule giving rise to shRNA.

Alternatively, the use of vectors in which each of the strands forming the siRNA is formed from the transcription of a different transcriptional unit is possible. These vectors are in turn divided into divergent and convergent transcription vectors. In divergent transcription vectors, the transcriptional units encoding each of the DNA strands forming the siRNA are located in tandem in a vector such that the transcription of each DNA strand depends on its own promoter which may be the same or different (Wang, J. et al., 2003, *Proc. Natl. Acad. Sci. USA.*, 100:5103-5106 and Lee, N. S., et al., 2002, *Nat. Biotechnol.*, 20:500-505). In convergent transcription vectors, the DNA regions giving rise to the siRNA form the sense and antisense strands of a DNA region which are flanked by two reverse promoters. After the transcription of the sense and antisense RNA strands, the latter will form the hybrid for forming a functional siRNA. Vectors with reverse promoter systems in which 2 U6 promoters (Tran, N. et al., 2003, *BMC Biotechnol.*, 3:21), a mouse U6 promoter and a human H1 promoter (Zheng, L., et al., 2004, *Proc. Natl. Acad. Sci. USA.*, 135-140 and WO 2005026322) and a human U6 promoter and a mouse H1 promoter (Kaykas, A. and Moon, R., 2004, *BMC Cell Biol.*, 5:16) are used have been described.

Promoters suitable for use thereof in the expression of siRNA from convergent or divergent expression vectors include any promoter or pair of promoters compatible with the cells in which the siRNA is to be expressed. Thus, promoters suitable for the present invention include but are not necessarily limited to constitutive promoters such as those derived from the genomes of eukaryotic viruses such as the polyoma virus, adenovirus, SV40, CMV, avian sarcoma virus, hepatitis B virus, the metallothionein gene promoter, the thymidine kinase gene promoter of the herpes simplex virus, retrovirus LTR regions, the immunoglobulin gene promoter, the actin gene promoter, the EF-1alpha gene promoter as well as inducible promoters in which the protein expression depends on the addition of a molecule or an exogenous signal such as the tetracycline system, the NFkappaB/UV light system, the Cre/Lox system and the heat shock gene promoter, the regulatable RNA polymerase II promoters described in WO/2006/135436 as well as specific tissue promoters (for example, the PSA promoter described in WO2006012221). In a preferred embodiment, the promoters are RNA polymerase III promoters which act constitutively. The RNA polymerase III promoters are found in a limited number of genes such as 5S RNA, tRNA, 7SL RNA and U6 snRNA. Unlike other RNA polymerase III promoters, type III promoters do not require any intragenic sequence but rather need sequences in 5' direction comprising a TATA box in positions −34 and −24, a proximal sequence element or PSE between −66 and −47 and, in some cases, a distal sequence element or DSE between positions −265 and −149. In a preferred embodiment, the type III RNA polymerase III promoters are the human or murine H1 and U6 gene promoters. In a yet more preferred embodiment, the promoters are 2 human or murine U6 promoters, a mouse U6 promoter and a human H1 promoter or a human U6 promoter and a mouse H1 promoter. In the context of the present invention, the ER alpha gene promoters or cyclin D1 gene promoters are especially suitable and therefore they are especially preferred to specifically express the genes of interest in breast tumors, preferably in triple negative (including basal-like) breast tumors.

The siRNA can be generated intracellularly from the so called shRNA (short hairpin RNA) characterized in that the antiparallel strands forming the siRNA are connected by a loop or hairpin region. The shRNAs can be encoded by plasmids or viruses, particularly retroviruses, and are under the control of a promoter. Promoters suitable for expressing shRNA are those indicated in the paragraph above for expressing siRNA.

Vectors suitable for expressing siRNA and shRNA include prokaryotic expression vectors such as pUC18, pUC19, Bluescript and the derivatives thereof, mp18, mp19, pBR322, pMB9, CoIE1, pCR1, RP4, phages and shuttle vectors such as pSA3 and pAT28, yeast expression vectors such as 2-micron plasmid type vectors, integration plasmids, YEP vectors, centromeric plasmids and the like, insect cell expression vectors such as pAC series vectors and pVL series vectors, plant expression vectors such as pIBI, pEarleyGate, pAVA, pCAMBIA, pGSA, pGWB, pMDC, pMY, pORE series vectors and the like and viral vector-based (adenovirus, viruses associated with adenoviruses as well as retroviruses and particularly lentiviruses) higher eukaryotic cell expression vectors or non-viral vectors such as pcDNA3, pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1. In a preferred embodiment, the vectors are lentiviral vectors.

The siRNA and shRNA of the invention can be obtained using a series of techniques known by the person skilled in the art. The region of the nucleotide sequence taken as a basis for designing the siRNA is not limiting and it may contain a region of the coding sequence (between the start codon and the end codon) or it may alternatively contain sequences of the non-translated 5' or 3' region preferably between 25 and 50 nucleotides long and in any position in 3' direction position with respect to the start codon. One way of designing an siRNA involves the identification of the AA(N19)TT motifs wherein N can be any nucleotide in the c-MAF gene sequence, and the selection of those having a high G/C content. If said motif is not found, it is possible to identify the NA(N21) motif wherein N can be any nucleotide.

c-MAF specific siRNAs include the siRNA described in WO2005046731, one of the strands of which is ACGGCUCGAGCAGCGACAA (SEQ ID NO: 6). Other c-MAF specific siRNA sequences include, but are not limited to, CUUACCAGUGUGUUCACAA (SEQ ID NO: 7), UGGAAGACUACUACUGGAUG (SEQ ID NO: 8), AUUUGCAGUCAUGGAGAACC (SEQ ID NO: 9), CAAGGAGAAAUACGAGAAGU (SEQ ID NO: 10), ACAAGGAGAAAUACGAGAAG (SEQ ID NO: 11) and ACCUGGAAGACUACUACUGG (SEQ ID NO: 12).

DNA Enzymes

On the other hand, the invention also contemplates the use of DNA enzymes to inhibit the expression of the c-MAF gene of the invention. DNA enzymes incorporate some of the mechanistic features of both antisense and ribozyme technologies. DNA enzymes are designed such that they recognize a particular target nucleic acid sequence similar to the antisense oligonucleotide, nevertheless like the ribozyme they are catalytic and specifically cleave the target nucleic acid.

Ribozymes

Ribozyme molecules designed for catalytically cleaving transcription products of a target mRNA to prevent the translation of the mRNA which encodes c-MAF the activity of which is to be inhibited, can also be used. Ribozymes are enzymatic RNA molecules capable of catalyzing specific RNA cleaving (For a review, see, Rossi, *Current Biology* 4: 469-471, 1994). The mechanism of ribozyme action involves a specific hybridization of a ribozyme molecule sequence to a complementary target RNA followed by an endonucleolytic cleavage event. The composition of the ribozyme molecules preferably includes one or more sequences complementary to the target mRNA and the well known sequence responsible for cleaving the mRNA or a functionally equivalent sequence (see, for example, U.S. Pat. No. 5,093,246).

The ribozymes used in the present invention include hammer-head ribozymes, endoribonuclease RNA (hereinafter "Cech type ribozymes") (Zaug et al., *Science* 224:574-578, 1984.

The ribozymes can be formed by modified oligonucleotides (for example to improve the stability, targeting, etc.) and they should be distributed to cells expressing the target gene in vivo. A preferred distribution method involves using a DNA construct which "encodes" the ribozyme under the control of a strong constitutive pol III or pol II promoter such that the transfected cells will produce sufficient amounts of the ribozyme to destroy the endogenous target messengers and to inhibit translation. Since the ribozymes are catalytic, unlike other antisense molecules, a low intracellular concentration is required for its efficiency.

Inhibitory Antibodies

In the context of the present invention, "inhibitory antibody" is understood as any antibody capable of binding specifically to the c-MAF protein and inhibiting one or more of the functions of said protein, preferably those related to transcription. The antibodies can be prepared using any of the methods which are known by the person skilled in the art, some of which have been mentioned above. Thus, the polyclonal antibodies are prepared by means of immunizing an animal with the protein to be inhibited. The monoclonal antibodies are prepared using the method described by Kohler, Milstein et al. (*Nature*, 1975, 256: 495). In the context of the present invention, suitable antibodies include intact antibodies comprising a variable antigen binding region and a constant region, "Fab", "F(ab')2" and "Fab'", Fv, scFv fragments, diabodies, bispecific antibodies, alphabodies, cyclopeptides and stapled peptides. Once antibodies with c-MAF protein binding capacity are identified, those capable of inhibiting the activity of this protein will be selected using an inhibitory agent identification assay.

Inhibitory Peptides

As used herein, the term "inhibitory peptide" refers to those peptides capable of binding to the c-MAF protein and inhibiting its activity as has been explained above, i.e., preventing the c-MAF from being able to activate gene transcription.

Negative c-MAF Dominants

Since the proteins from the MAF family are capable of homodimerizing and heterodimerizing with other members of the AP-1 family such as Fos and Jun, one way of inhibiting c-MAF activity is by means of using negative dominants capable of dimerizing with c-MAF but lacking the capacity for activating transcription. Thus, the negative c-MAF dominants can be any of the small maf proteins existing in the cell and lacking two-thirds of the amino terminal end containing the transactivation domain (for example, mafK, mafF, mafg and pi 8) (Fujiwara et al (1993) Oncogene 8, 2371-2380; Igarashi et al. (1995) *J. Biol. Chem.* 270, 7615-7624; Andrews et al. (1993) *Proc. Natl. Acad. Sci. USA* 90, 11488-11492; Kataoka et al. (1995) *Mol. Cell. Biol.* 15, 2180-2190) (Kataoka et al. (1996) *Oncogene* 12, 53-62).

Alternatively, the negative c-MAF dominants include c-MAF variants which maintain the capacity for dimerizing with other proteins but lack the capacity for activating transcription. These variants are, for example, those lacking the c-MAF transactivation domain located at the N-terminal end of the protein. Thus, negative c-MAF dominant variants include in an illustrative manner the variants in which at least amino acids 1 to 122, at least amino acids 1-187 or at least amino acids 1 to 257 (by considering the numbering of human c-MAF as described in U.S. Pat. No. 6,274,338) have been removed.

The invention contemplates the use of both the negative c-MAF dominant variants and of polynucleotides encoding c-MAF under the operative control of a promoter suitable for expression in target cell. The promoters that can be used for regulating the polynucleotide transcription of the invention can be constitutive promoters, i.e., promoters directing the transcription at a basal level, or inducible promoters in which the transcriptional activity requires an external signal. Constitutive promoters suitable for regulating transcription are, among others, the CMV promoter, the SV40 promoter, the DHFR promoter, the mouse mammary tumor virus (MMTV) promoter, the Ia elongation factor (EFla) promoter, the albumin promoter, the ApoA1 promoter, the keratin promoter, the CD3 promoter, the immunoglobulin heavy or light chain promoter, the neurofilament promoter, the neuron specific enolase promoter, the L7 promoter, the CD2 promoter, the myosin light chain kinase promoter, the HOX gene promoter, the thymidine kinase promoter, the RNA polymerase II promoter, the MyoD gene promoter, the phosphoglyceratekinase (PGK) gene promoter, the low density lipoprotein (LDL) promoter, the actin gene promoter. In a preferred embodiment, the promoter regulating the expression of the transactivator is the PGK gene promoter. In a preferred embodiment, the promoter regulating the polynucleotide transcription of the invention is the RNA polymerase promoter of the T7 phage.

Preferably, the inducible promoters that can be used in the context of the present invention are those responding to an inducer agent showing zero or negligible basal expression in the absence of an inducer agent and are capable of promoting the activation of gene located in the 3' position. Depending on the type of inducer agent, the inducible promoters are classified as Tet on/off promoters (Gossen, M. and H. Bujard (1992) *Proc. Natl. Acad. Sci. USA*, 89:5547-5551; Gossen, M. et al., 1995, *Science* 268:1766-1769; Rossi, F. M. V. and H. M. Blau, 1998, *Curr. Opin. Biotechnol.* 9:451-456); Pip on/off promoters (U.S. Pat. No. 6,287,813); antiprogestin-dependent promoters (US 2004132086), ecdysone-dependent promoters (Christopherson et al., 1992, *Proc. Natl. Acad. Sci. USA*, 89:6314-6318; No et al., 1996, *Proc. Natl. Acad. Sci. USA*, 93:3346-3351, Suhr et al., 1998, *Proc. Natl. Acad. Sci. USA*, 95:7999-8004 and WO9738117), a metallothionein-dependent promoter (WO8604920) and rapamycin-dependent promoters (Rivera et al., 1996, *Nat. Med.* 2:1028-32).

Vectors suitable for expressing the polynucleotide encoding the negative c-MAF dominant variant include vectors derived from prokaryotic expression vectors such as pUC18, pUC19, Bluescript and derivatives thereof, mp18, mp19, pBR322, pMB9, ColE1, pCR1, RP4, phages and shuttle vectors such as pSA3 and pAT28, yeast expression vectors such as 2-micron type plasmid vectors, integration plasmids, YEP vectors, centromeric plasmids and the like, insect cell expression vectors such as pAC series vectors and pVL series vectors, plant expression vectors such as pIBI, pEarleyGate, pAVA, pCAMBIA, pGSA, pGWB, pMDC, pMY, pORE series vectors and the like and viral vector-based (adenoviruses, viruses associated with adenoviruses as well as retroviruses and particularly lentiviruses) higher eukaryotic cell expression vectors OR non-viral vectors such as pSilencer 4.1-CMV (Ambion), pcDNA3, pcDNA3.1/hyg pHCMV/Zeo, pCR3.1, pEF1/His, pIND/GS, pRc/HCMV2, pSV40/Zeo2, pTRACER-TICMV, pUB6N5-His, pVAX1, pZeoSV2, pCI, pSVL and pKSV-10, pBPV-1, pML2d and pTDT1.

Small Molecules

Other c-MAF inhibitory compounds suitable for use in the present invention include:

TABLE 1

Small molecules with c-MAF inhibiting capacity

I  Endiandric acid H derivatives such as those described in WO2004014888 corresponding to the general formula

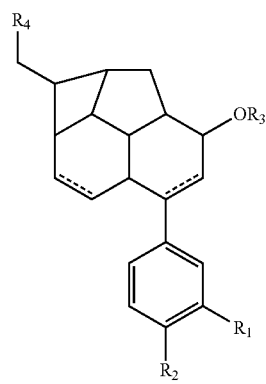

wherein
$R_1$ and $R_2$ are, independently of one another,
1.0 H or
2.0 a O—$C_1$-$C_6$-alkyl, —O—$C_2$-$C_6$-alkenyl, —O—$C_2$-$C_6$-alkynyl or —O—$C_6$-$C_{10}$-aryl group, in which alkyl, alkenyl and alkynyl are straight-chain or branched, and in which the alkyl, alkenyl and alkynyl groups are mono- or disubstituted with:
2.1 —OH,
2.2 =O,
2.3 —O—$C_1$-C6-alkyl, in which alkyl is straight-chain or branched, TABLE 1-continued Small molecules with c-MAF inhibiting capacity 2.4 —O—C$_2$-C$_6$-alkenyl, in which alkenyl is straight-chain or branched,
2.5 C$_6$-C$_{10}$-aryl,
2.6 —NH—C$_1$-C$_6$-alkyl, in which alkyl is straight-chain or branched,
2.7 —NH—C$_2$-C$_6$-alkenyl, in which alkenyl is straight-chain or branched,
2.8 —NH$_2$ or
2.9 halogen,
and in which the aryl group, is optionally mono- or disubstituted with the substituent 2.1 or 2.3 to 2.9,
in which the substituents 2.3, 2.4, 2.6 and 2.7 may be further substituted with —CN, -amide or -oxime functions, and 2.5 may be further substituted with —CN or amide functions, or
R$_1$ and R$_2$ together form a ring, wherein R$_1$ and R$_2$ mean a —O—[(C$_1$-C$_6$)-alkylene]-O— group,
R$_3$ is
1.0 H or
2.0 a —O—C$_1$-C$_6$-alkyl, —O—C$_2$-C$_6$-alkenyl, —O—C$_2$-C$_6$-alkynyl or —O—C$_6$-C$_{10}$-aryl group, in which alkyl, alkenyl and alkynyl are straight-chain or branched, and in which the alkyl, alkenyl and alkynyl groups are mono- or disubstituted with:
2.1 —OH,
2.2 =O,
2.3 —O—C$_1$-C$_6$-alkyl, in which alkyl is straight-chain or branched,
2.4 —O—C$_2$-C$_6$-alkenyl, in which alkenyl is straight-chain or branched,
2.5 —C$_6$-C$_{10}$-aryl,
2.6 —NH—C$_1$-C$_6$-alkyl, in which alkyl is straight-chain or branched,
2.7 —NH—C$_2$-C$_6$-alkenyl, in which alkenyl is straight-chain or branched,
2.8 —NH$_2$ or
2.9 halogen,
and in which the aryl group, is optionally mono- or disubstituted with the substituent 2.1 or 2.3 to 2.9,
in which the substituents 2.3, 2.4, 2.6 and 2.7 may be further substituted with —CN, -amide or -oxime functions, and 2.5 may be further substituted with —CN or amide functions
R$_4$ is CO$_2$R$_3$, CO$_2$NHR$_3$, CHO, CH$_2$OR$_3$, CH$_2$OSi(R$_3$)$_3$, CH$_2$Br, CH$_2$CN, in which R$_3$ is as defined above,
and, in particular, the compounds II  8-hydroxyquinoline derivatives such as those described in WO2009146546 of general formula

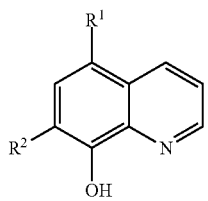

wherein
R$_1$ is selected from the group consisting of NO$_2$, NH$_2$, NH(C$_1$-C$_6$-alkyl) and N(C$_1$-C$_6$-alkyl)(C$_1$-C$_6$-alkyl);
R$_2$ is selected from H, halogen, C$_1$-C$_6$ alkyl, and fluoro-substituted C$_1$-C$_6$ alkyl,
or
R$_1$ is Cl and R$_2$ is Br or H,
and, preferably, the compounds III Clioquinol (5-chloro-7-iodoquinolin-8-ol) as described in WO09049410
IV Compounds such as those described in WO08098351 of general formula wherein
+Z,42 is a single or double bond,
R$^1$ is selected from the group consisting of H, C$_1$-C$_4$ alkyl, C(O)O C$_1$-C$_4$ alkyl, C(O) C$_1$-C$_4$ alkyl and C(O)NH C$_1$-C$_4$ alkyl;
R$^2$ is selected from H and C$_1$-C$_4$ alkyl;
R$^3$ is selected from H and C$_1$-C$_4$ alkyl;
or R$^2$ and R$^3$ are bound together along with the carbon and nitrogen atoms to which they are bound to form a piperidine ring,
R$^4$ and R$^5$ are independently selected from H, halogen, hydroxy, C$_1$-C$_4$ alkyl, fluoro-substituted C$_1$-C$_4$ alkyl and C$_1$-C$_4$ alkoxy; and
X is selected from C and N,
and preferred compounds such as
Cyproheptadine (4-(5H-dibenzo-[a,d]cyclohepten-5-ylidene)-1-methylpiperidine hydrochloride),
Amitriptyline (3-(10,11-dihydro-5H-dibenzo[[a,d]]cycloheptene-5-ylidene)-N,N-dimethyl-1-propanamine),
Loratadine (Ethyl 4-(8-chloro-5,6-dihydro-11H-benzo[5,6]-cyclohepta[1,2-b]pyridin-11-ylidene)-1-piperidinecarboxylate,
Cyclobenzrapine (3-(5H-dibenzo[a,d]cyclohepten-5-ylidene)-N,N-dimethyl-1-propanamine).
V Nivalenol (12,13-epoxy-3,4,7,15-tetrahydroxytrichothec-9-en-8-one) as described in WO0359249

Other c-MAF inhibitors are described in the patent application WO2005063252 (incorporated by reference herein in its entirety), such as shown in the following table (Table 2).

TABLE 2

| c-MAF inhibitors | |
|---|---|
| Antagonist | Reference for cdk2 inhibitory activity |
| *Purine Analogs* | |
| Purvalanols such as 2-(1R-Isopropyl-2-hydroxyethylamino)-6-(3-chloroanilino)-9-isopropylpurine having a molecular formula $C_{19}H_{25}ClN_6O$ available from Sigma-Aldrich under the trade name Purvalanol A (#P4484, Sigma-Aldrich, St. Louis, MO), Purvalanol B, aminopurvalanol, compound 52 (where isopropyl of purvalanol A is replaced with II) | Gray, N. S. et al., Science, 281, 533-538 (1998); Chang, Y. T. et al., Chem. Biol., 6, 361-375 (1999). |
| 2-(Hydroxyethylamino)-6-benzylamino-9-methylpurine having a molecular formula $C_{15}H_{18}N_6O$ available from Sigma-Aldrich under the trade name Olomoucine (#O0886), 2-(2'-Hydroxyethylamino)-6-benzylamino-9-isopropylpurine having a molecular formula $C_{17}H_{22}N_6O$ available from Sigma-Aldrich under the trade name $N^9$-isopropylolomoucine (#I0763); CVT-313 | Vesely, J., et al., (1994) Eur. J. Biochem., 224, 771-86, 11; Brooks, E. B., et al., (1997) J. Biol. Chem., 272, 29207-11 |
| 6-(Benzylamino)-2(R)-[[1-(hydroxymethyl)propyl]amino]-9-isopropylpurine 2-(R)-[[9-(1-methylethyl)-6-[(phenylmethyl)amino]-9H-purin-2-yl]amino]-1-butanol having a molecular formula of $C_{19}H_{26}N_6O$ available from Sigma-Aldrich under the trade name Roscovitine (#R7772), methoxyroscovitine | Wang, D. et al., J. Virol., 75, 7266-7279 (2001); McClue, S. J. et al., Int. J. Cancer, 102, 463-468 (2002); Meijer, L., et al., (1997) Eur. J. Biochem., 243, 527-36 |
| Purine analog N2-(cis-2-Aminocyclohexyl)-N6-(3-chlorophenyl)-9-ethyl-9H-purine-2,6-diamine having a molecular formula of $C_{19}H_{24}ClN_7$ available from Sigma-Aldrich under the trade name CGP74514 (#C3353) | Imbach, P. et al., Bioorg. Med. Chem. Lett., 9, 91-96 (1999); Dreyer, M. K. et al., J. Med. Chem., 44, 524-530 (2001). |
| CGP79807, a purine analog of CGP74514 (supra) where Cl is replaced with CN, OH is removed, and the ortho position of cyclohexane ring is $NH_2$ | Imbach, P. et al., Bioorg. Med. Chem. Lett., 9, 91-96 (1999); Dreyer, M. K. et al., J. Med. Chem., 44, 524-530 (2001). |
| purine analog such as O6-cyclohexylmethyl guanine NU2058 | Arris, C. E. et al., J. Med. Chem., 43, 2797-2804 (2000); Davies et al, *Nature Structural Biology*, 9:10, 745-749, 2002 |
| purine analog such as NU6102 | Arris, C. E. at al., J. Med. Chem., 43, 2797-2804 (2000); Davies, T. G. et al., Nat. Struct. Biol., 9, 745-749 (2002). |
| isopentenyl-adenine | Vesely, J., et al., (1994) Eur. J. Biochem., 224, 771-86 |
| *Nonpurine based agents* | |
| Indirubins such as indirubin-3'-monoxime having a molecular formula of $C_{16}H_{11}N_3O_2$ available from Sigma-Aldrich under the trade name (#I0404), indirubin 5-sulfonate, 5-chloro indirubin | Davies, T. G. et al., Structure, 9, 389-397 (2001); Marko, D. et al., Br. J. Cancer, 84, 283-289 (2001); Hoessal, R., et al., (1999) Nat. Cell Biol., 1, 60-7; PCT/US02/30059 to Hellberg et al., published as WO 03/027275. |
| Oxindole 1 of Fischer as referenced in column 2 of this table, (#IN118, JMAR Chemical, Indenopyrazoles | Porcs-Makkay, M., et al., *Tetrahedron* 2000, 56, 5893; *Org. Process Res. Dev.* 2000, 4, 10 Nugiel, D. A. et al., J. Med. Chem., 44, 1334-1336 (2001); Nugiel, D. A. et al., J. Med. Chem., 45, 5224-5232 (2002); Yue, R. W. et al., J. Med, Chem., 45, 5233-5248 (2002). |
| Pyrido(2,3-d)pyrimidine-7-ones, compound 3 of Fischer | Barvian, M. et al., J. Med. Chem., 43, 4606-4616 (2000); Toogood, P. L., Med. Res. Rev., 21, 487-498 (2001). |
| Quinazolines such as anilinoquinazoline | Sielecki, T. M. et al., Bioorg. Med. Chem. Lett., 11, 1157-1160 (2001); Mettey et al., *J. Med. Chem.* 2003, 46, 222-236. |
| Thiazoles such as fused thiazole, 4-{[(7-Oxo-6,7-dihydro-8H-[1,3]thiazolo[5,4-e]indol-8- | Davis, S. T. et al., Science, 291, 134-137 (2001); |

TABLE 2-continued c-MAF inhibitors

| Antagonist | Reference for cdk2 inhibitory activity |
|---|---|
| ylidene)methyl]amino}-N-(2-pyridyl)benzenesulfonamide having a molecular formula of $C_2H_{15}N_5O_3S_2$ available from Sigma-Aldrich under the trade name GW8510 (#G7791) | PCT/US02/30059 to Hellberg et al., published as WO 03/027275. |
| Flavopiridols such as flavopiridol (L86 8275; NCS 649890, National Cancer Institute, Bethesda, MD) and a dechloro derivative. | Carlson, B. A., et al., (1996) Cancer Res., 56, 2973-8 |
| Alkaloids such as Staurosporine (#S1016, A.G. Scientific, San Diego, CA) or UCN-01 (7-hydroxystaurosporine) National Cancer institute, Bethesda, MD | Rialet, V., et al., (1991) Anticancer Res., 11, 1581-90; Wang, Q., et al., (1995) Cell Growth Differ., 6, 927-36, Akiyama, T., et al., (1997) Cancer Res., 57, 1495-501, Kawakami, K., et al., (1996) Biochem. Biophys. Res. Commun., 219, 778-83 |
| Paullones such as 9-Bromo-7,12-dihydro-indolo[3,2-d][1]benzazepin-6(5H)-one having a molecular formula of $C_{16}H_{11}BrN_2O$ available from Sigma-Aldrich under the trade name kenpaullone (#K3888), or 9-Nitro-7,12-dihydroindolo-[3,2-d][1]benzazepin-6(5)-one having a molecular formula of $C_{16}H_{11}N_3O_3$ available from Sigma-Aldrich under the trade name alsterpaullone (#A4847) | Zaharevitz, D. W. et al., Cancer Res., 59, 2566-2569 (1999); Schultz, C. et al., J. Med. Chem., 42, 2909-2919 (1999); Zaharevitz, D. W., et al., (1999) Cancer Res., 59, 2566-9; PCT/US02/30059 to Hellberg et al., published as WO 03/027275. |
| CGP 41251, an alkaloid | Begemann, M., et al., (1998) Anticancer Res., 18, 2275-82; Fabbro et al., Pharmacol Ther. 1999 May-June; 82(2-3): 293-301 |
| Hymenialdisines such as 10z-hymenialdisine having a molecular formula of $C_{11}H_{10}BrN_5O_2$ available Biochemicals.net, a division of A.G. Scientific, Inc. (San Diego, CA) (H-1150) | Meijer, L., et al., (1999) Chemistry & Biology, 7, 51-63; PCT/US02/30059 to Hellberg et al., published as WO 03/027275, |
| CGP60474, a phenylaminopyrimidine | 21; WO95/09853, Zimmermann et al., Sep. 21, 1994 |
| Thiazolopyrimidine 2 | Attaby et al., Z. Naturforsch. 54b, 788-798 (1999) |
| Diarylurea | Honma, T. et al., J. Med. Chem., 44, 4628-4640 (2001), Honma, T. et al., J. Med. Chem., 44, 4615-4627 (2001). |
| (2R)-2,5-Dihydro-4-hydroxy-2-[(4-hydroxy-3-(3-methyl-2-butenyl)phenyl)methyl]-3-(4-hydroxyphenyl)-5-oxo-2-furancarboxylic acid methyl ester having a molecular formula of $C_{24}H_{24}O_7$ available from Sigma-Aldrich under the trade name Butyrolactonc-I (B7930) | Kitagawa, M. et al., Oncogene, 8, 2425-2432 (1993). |
| Aloisine A, Cat. No, 128125 (Calbiochem, San Diego, CA) | Mettey et al., J. Med. Chem. 2003, 46, 222-236 |

In a preferred embodiment, the bone metastasis is osteolytic metastasis.

The c-MAF inhibitory agents are typically administered in combination with a pharmaceutically acceptable carrier.

The term "carrier" refers to a diluent or an excipient whereby the active ingredient is administered. Such pharmaceutical carriers can be sterile liquids such as water and oil, including those of a petroleum, animal, plant or synthetic origin such as peanut oil, soy oil, mineral oil, sesame oil and the like. Water or aqueous saline solutions and aqueous dextrose and glycerol solutions, particularly for injectable solutions, are preferably used as carriers. Suitable pharmaceutical carriers are described in "Remington's Pharmaceutical Sciences" by E.W. Martin, 1995. Preferably, the carriers of the invention are approved by the state or federal government regulatory agency or are listed in the United States Pharmacopeia or other pharmacopeia generally recognized for use thereof in animals and more particularly in human beings.

The carriers and auxiliary substances necessary for manufacturing the desired pharmaceutical dosage form of the pharmaceutical composition of the invention will depend, among other factors, on the pharmaceutical dosage form chosen. Said pharmaceutical dosage forms of the pharmaceutical composition will be manufactured according to the conventional methods known by the person skilled in the art. A review of the different methods for administering active ingredients, excipients to be used and processes for producing them can be found in "Tratado de Farmacia Galénica", C. Faulí i Trillo, Luzán 5, S.A. 1993 Edition. Examples of pharmaceutical compositions include any solid composition (tablets, pills, capsules, granules, etc.) or liquid composition (solutions, suspensions or emulsions) for oral, topical or parenteral administration. Furthermore, the pharmaceutical composition may contain, as deemed necessary, stabilizers, suspensions, preservatives, surfactants and the like.

For use in medicine, the c-MAF inhibitory agents can be found in the form of a prodrug, salt, solvate or clathrate, either isolated or in combination with additional active agents and can be formulated together with a pharmaceutically acceptable excipient. Excipients preferred for use thereof in the present invention include sugars, starches, celluloses, rubbers and proteins. In a particular embodiment, the pharmaceutical composition of the invention will be formulated in a solid pharmaceutical dosage form (for example tablets, capsules, pills, granules, suppositories, sterile crystal or amorphous solids that can be reconstituted to provide liquid forms, etc.), liquid pharmaceutical dosage form (for example solutions, suspensions, emulsions, elixirs, lotions, ointments, etc.) or semisolid pharmaceutical dosage form (gels, ointments, creams and the like). The pharmaceutical compositions of the invention can be administered by any route, including but not limited to the oral route, intravenous route, intramuscular route, intraarterial route, intramedularry route, intrathecal route, intraventricular router, transdermal route, subcutaneous route, intraperitoneal route, intranasal route, enteric route, topical route, sublingual route or rectal route. A review of the different ways for administering active ingredients, of the excipients to be used and of the manufacturing processes thereof can be found in Tratado de Farmacia Galénica, C. Faulí i Trillo, Luzán 5, S.A., 1993 Edition and in Remington's Pharmaceutical Sciences (A.R. Gennaro, Ed.), $20^{th}$ edition, Williams & Wilkins Pa., USA (2000). Examples of pharmaceutically acceptable carriers are known in the state of the art and include phosphate buffered saline solutions, water, emulsions such as oil/water emulsions, different types of wetting agents, sterile solutions, etc. The compositions comprising said carriers can be formulated by conventional processes known in the state of the art.

In the event that nucleic acids (siRNA, polynucleotides encoding siRNA or shRNA or polynucleotides encoding negative c-MAF dominants) are administered, the invention contemplates pharmaceutical compositions particularly prepared for administering said nucleic acids. The pharmaceutical compositions can comprise said naked nucleic acids, i.e., in the absence of compounds protecting the nucleic acids from degradation by the nucleases of the body, which entails the advantage that the toxicity associated with the reagents used for transfection is eliminated. Administration routes suitable for naked compounds include the intravascular route, intratumor route, intracranial route, intraperitoneal route, intrasplenic route, intramuscular route, subretinal route, subcutaneous route, mucosal route, topical route and oral route (Templeton, 2002, *DNA Cell Biol.*, 21:857-867). Alternatively, the nucleic acids can be administered forming part of liposomes conjugated to cholesterol or conjugated to compounds capable of promoting the translocation through cell membranes such as the Tat peptide derived from the HIV-1 TAT protein, the third helix of the homeodomain of the *D. melanogaster* antennapedia protein, the herpes simplex virus VP22 protein, arginine oligomers and peptides as described in WO07069090 (Lindgren, A. et al., 2000, *Trends Pharmacol. Sci*, 21:99-103, Schwarze, S. R. et al., 2000, *Trends Pharmacol. Set.*, 21:45-48, Lundberg, M et al., 2003, *Mol Therapy* 8:143-150 and Snyder, E. L. and Dowdy, S. F., 2004, *Pharm. Res.* 21:389-393). Alternatively, the polynucleotide can be administered forming part of a plasmid vector or viral vector, preferably adenovirus-based vectors, in adeno-associated viruses or in retroviruses such as viruses based on murine leukemia virus (MLV) or on lentivirus (HIV, FIV, EIAV).

The c-MAF inhibitory agents or the pharmaceutical compositions containing them can be administered at a dose of less than 10 mg per kilogram of body weight, preferably less than 5, 2, 1, 0.5, 0.1, 0.05, 0.01, 0.005, 0.001, 0.0005, 0.0001, 0.00005 or 0.00001 mg per kg of body weight. The unit dose can be administered by injection, inhalation or topical administration.

The dose depends on the severity and the response of the condition to be treated and it may vary between several days and months or until the condition subsides. The optimal dosage can be determined by periodically measuring the concentrations of the agent in the body of the patient. The optimal dose can be determined from the EC50 values obtained by means of previous in vitro or in vivo assays in animal models. The unit dose can be administered once a day or less than once a day, preferably less than once every 2, 4, 8 or 30 days. Alternatively, it is possible to administer a starting dose followed by one or several maintenance doses, generally of a lesser amount than the starting dose. The maintenance regimen may involve treating the patient with a dose ranging between 0.01 μg and 1.4 mg/kg of body weight per day, for example 10, 1, 0.1, 0.01, 0.001, or 0.00001 mg per kg of body weight per day. The maintenance doses are preferably administered at the most once every 5, 10 or 30 days. The treatment must be continued for a time that will vary according to the type of disorder the patient suffers, the severity thereof and the condition of the patient. After treatment, the progress of the patient must be monitored to determine if the dose should be increased in the event that the disease does not respond to the treatment or the dose is reduced if an improvement of the disease is observed or if unwanted side effects are observed.

Treatment or Prevention of the Bone Degradation in Breast Cancer Patients with Bone Metastasis Having Elevated c-MAF Levels In another aspect, the invention relates to a c-MAF inhibitory agent or an agent capable of avoiding or preventing bone degradation for use in the treatment of bone metastasis in a subject suffering triple negative (including basal-like) breast cancer or, alternatively ER+ breast cancer, and having elevated c-MAF levels in a metastatic sample with respect to a control sample.

In another aspect, the invention relates to the use of a c-MAF inhibitory agent or an agent capable of avoiding or preventing bone degradation for the manufacture of a medicament for the treatment of bone metastasis in a subject suffering triple negative (including basal-like) breast cancer or, alternatively ER+ breast cancer, and having elevated c-MAF levels in a metastatic sample with respect to a control sample.

Alternatively, the invention relates to a method of prevention and/or treatment of the degradation in a subject suffering breast cancer and has elevated c-MAF levels in a metastatic sample with respect to a control sample, which comprises administering a c-MAF inhibitory agent or an agent for avoiding or preventing bone degradation to said subject.

In a particular embodiment the bone metastasis is osteolytic metastasis.

c-MAF inhibitory agents and agents capable of avoiding or preventing bone degradation suitable for the therapeutic method described in the present invention have been described in detail above in the context of the customized therapy method.

The reference or control sample is a sample of a subject with triple negative (including basal-like) breast cancer or, alternatively ER+ breast cancer, who has not suffered metastasis or that correspond to the median value of the c-MAF gene expression level measured in a tumor tissue collection in biopsy samples of subjects with triple negative (including basal-like) breast cancer who have not suffered metastasis.

Methods for determining or quantifying if the c-MAF levels are elevated with respect to a control sample have been described in detail in relation with the first method of the invention and are equally applicable to the agent for avoiding or preventing bone degradation.

Alternatively a combined treatment can be carried out, in which more than one agent for avoiding or preventing bone degradation from those mentioned above are combined to treat and/or prevent the metastasis or said agents can be combined with other supplements, such as calcium or vitamin D or with a hormone.

The agents for avoiding or preventing bone degradation are typically administered in combination with a pharmaceutically acceptable carrier. The term "carrier" and the types of carriers have been defined above for the c-MAF inhibitory agent, as well as the form and the dose in which they can be administered and are equally applicable to the agent for avoiding or preventing bone degradation.

The following examples illustrate the invention and do not limit the scope thereof.

Kits of the Invention

In another aspect, the invention relates to a kit for predicting bone metastasis of a triple negative (including basal-like) breast cancer or, alternatively ER+ breast cancer, in a subject suffering from said cancer, the kit comprising: a) means for quantifying the expression level of c-MAF in a sample of said subject; and b) means for comparing the quantified level of expression of c-MAF in said sample to a reference c-MAF expression level.

In another aspect, the invention relates to a kit for predicting the clinical outcome of a subject suffering from bone metastasis from a triple negative of basal-like breast cancer or, alternatively ER+ breast cancer, the kit comprising: a) means for quantifying the expression level of c-MAF in a sample of said subject; and b) means for comparing the quantified expression level of c-MAF in said sample to a reference c-MAF expression level.

In another aspect the invention relates to a kit for determining a therapy for a subject suffering from triple negative (including basal-like) breast cancer or, alternatively ER+ breast cancer, the kit comprising: a) means for quantifying the expression level of c-MAF in a sample of said subject; b) means for comparing the quantified expression level of c-MAF in said sample to a reference c-MAF expression level; and c) means for determining a therapy for preventing and/or reducing bone metastasis in said subject based on the comparison of the quantified expression level to the reference expression level.

In another aspect the invention relates to a kit comprising: i) a reagent for quantifying the expression level of c-MAF in a sample of a subject suffering from triple negative (including basal-like) breast cancer or, alternatively ER+ breast cancer, and ii) one or more c-MAF gene expression level indices that have been predetermined to correlate with the risk of bone metastasis.

Means for quantifying the expression level of c-MAF in a sample of said subject have been previously described in detail including 16q23 and 16q22-24 locus amplification and translocation.

In a preferred embodiment, means for quantifying expression comprise a set of probes and/or primers that specifically bind and/or amplify the c-MAF gene.

In particular embodiment the breast cancer is triple negative (including basal-like) or ER+ (including luminal A and B) breast cancer.

All the particular embodiments of the methods of the present invention are applicable to the kits of the invention and to their uses.

Method for Typing a Sample of a Subject Suffering Breast Cancer.

In another aspect, the invention relates to an in vitro method for typing a sample of a subject suffering from breast cancer, the method comprising:
a) providing a sample from said subject;
b) quantifying the expression level of c-MAF in said sample;
c) typing said sample by comparing the quantified expression level of c-MAF to a predetermined reference level of c-MAF expression;
wherein said typing provides prognostic information related to the risk of bone metastasis in said subject Means for quantifying the expression level of c-MAF in a sample of said subject have been previously described in detail including 16q23 and 16q22-24 locus amplification and translocation.

In particular embodiment the breast cancer is triple negative (including basal-like) or ER+(including luminal A and B) breast cancer.

In a preferred embodiment the sample is a tumor tissue sample.

Method for Classifying a Subject Suffering from Breast Cancer.

In another aspect, the invention relates to a method for classifying a subject suffering from breast cancer into a cohort, comprising: a) determining the expression level of c-MAF in a sample of said subject; b) comparing the expression level of c-MAF in said sample to a predetermined reference level of c-MAF expression; and c) classifying said subject into a cohort based on said expression level of c-MAF in the sample.

Means for quantifying the expression level of c-MAF in a sample of said subject have been previously described in detail including 16q23 and 16q22-24 locus amplification and translocation.

In particular embodiment the breast cancer is triple negative (including basal-like) or ER+ (including luminal A and B) breast cancer.

In a preferred embodiment the sample is a tumor tissue sample.

In a preferred embodiment said cohort comprises at least one other individual who has been determined to have a comparable expression level of c-MAF in comparison to said reference expression level.

In another preferred embodiment said expression level of c-MAF in said sample is increased relative to said predetermined reference level, and wherein the members of the cohort are classified as having increased risk of bone metastasis.

In another preferred embodiment said cohort is for conducting a clinical trial. In a preferred embodiment, the sample is a tumor tissue sample.

EXAMPLES

Cohort I. Discovery Breast Cancer Primary Tumor Cohort

Human breast tumors were classified in 5 subtypes as they are described in the PAM50 Breast Cancel Intrinsic Classifier and then the appropriate statistical analysis was performed to see if c-MAF (MAF) expression in these tumors correlates with bone metastasis events in some of the given subtypes. PAM50 has a subtype named Basal-like. The group Triple negative was used instead. The patients' information was downloaded from GEO (T. Barrett, D. B. Troup, S. E. Wilhite, P. Ledoux, D. Rudnev, C. Evangelista, I. F. Kim, A. Soboleva, M. Tomashevsky, and R. Edgar. NCBI GEO: mining tens of millions of expression profiles—database and tools update. Nucleic Acids Research, 35, January 2007. ISSN 1362-4962)). The following set of data was used: union of GSE2603, GSE2034 and GSE12276. This union cohort had 560 patients. In order to remove systematic biases, prior to merging the expression measurements were converted to z-scores for all genes. All statistical analyses were performed using Bioconductor (R. C. Gentleman, V. J. Carey, D. M. Bates, B. Bolstad, M. Dettling, oS. Du-doit, B. Ellis, L. Gautier, Y. Ge, J. Gentry, K. Hornik, T. Hothorn, W. Huber, S. Iacus, R. Irizarry, F. Leisch, C. Li, M. Maechler, A. J. Rossini, G. Sawitzki, C. Smith, G. Smyth, L. Tierney, J. Y. H. Yang, and J. Zhang. Bioconductor: Open software development for computational biology and bioinformatics. Genome Biology, 5:R80, 2004. URL http://genomebiology.com/2004/5/10/R80).

Cohort II. Validation Breast Cancer Primary Tumor Sample Cohort:

A second human breast tumor cohort was used to validate the hypothesis discovered with the above patient tumor sample cohort I. The independent validation set is composed of more than 380 primary breast cancer specimens from patients with stage I, II or III BC and annotated follow up (Rojo F., *Ann Oncol* (2012) 23 (5): 1156-1164). Tissue microarrays were processed as per standard procedures. Tumors were classified in 3 subtypes according to ER+, Triple Negative and HER2+ and then the appropriate statistical analysis were performed to see if c-MAF (MAF) expression and the 16q22-24 amplification in these tumors correlates with bone metastasis events in some of the given subtypes.

Statistical analyses in this second cohort were based on the following premises:

i) Comparison of baseline characteristics (Table 3 and 6).

Equality of variances of age is tested with the Folded F test. Differences in the mean of age are tested with the pooled or Satterhwaite t-test (ANOVA or Kruskal-Wallis for multiple categories comparison) depending on equality of variances. Categorical variables are compared with a chi-square or Fisher test when applicable.

ii) Diagnostic performance FISH and IHC

Multivariate analysis is done via stepwise selection with a p-value criterion for entering the variable of p<0:2 and a criterion for retaining the variable in the model after adjusting of p<0.10. Diagnostic performance will be evaluated by comparing the AUC of the ROC curves. Goodness of fit of the model will be assessed with the Hosmer-Lemeshow test (if significant, no further analysis will be done).

Sensitivity (Se), specificity (Sp), positive predictive value (PPV) and negative predictive value (NPV) will be computed for each of the classification categories based on the most predictive variables (16q23 FISH and MAF IHC). To overcome the data over-fitting issue, bootstrapping of the PPV and NPV will be done.

iii) Prognostic role

Cox regression modeling of the outcome time to bone metastasis will be done, with an "efron" management of ties. The number of events will drive the number of variables that are entered in the models (about one variable for each 5-10 events).

Proportional hazard assumption will be checked using the supremum test for proportional hazards assumption as implemented in SAS 9.3. This test yields a significant p-value if this assumption is violated.

Classification of Breast Cancer Subtypes

PAM50 genes of the union cohort (discovery cohort I) were normalized according to the genes described as control genes in the PAM50 gene signature. For each patient, the expression estimates were normalized by subtracting the average of the control genes for that same patient.

Figure 1:
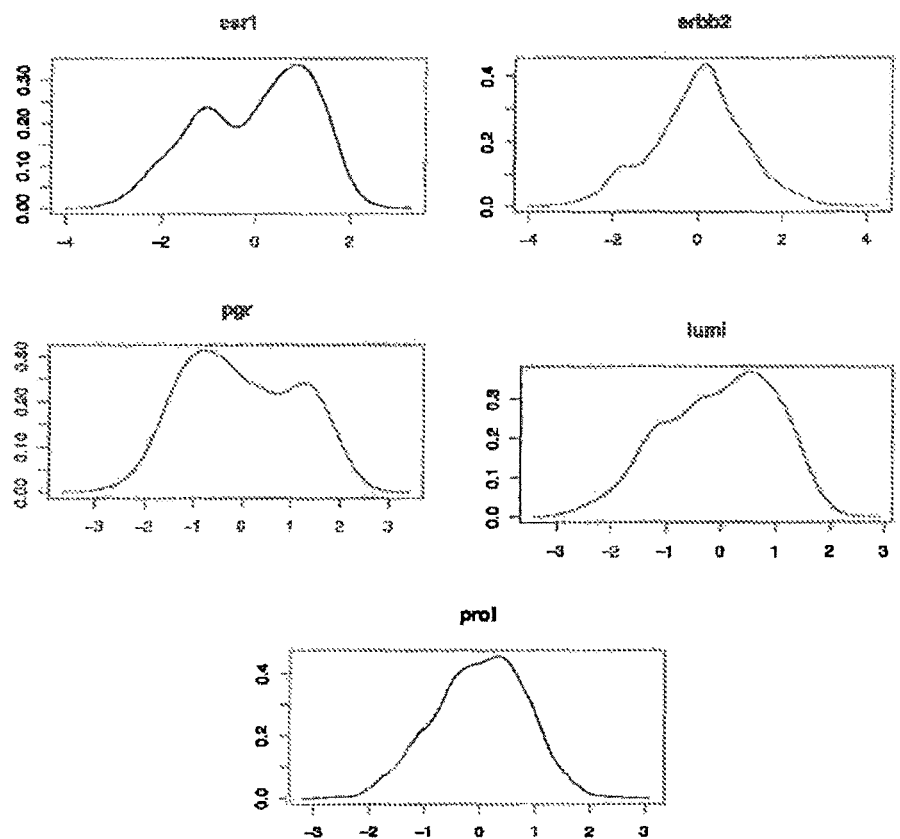
FIG. 1: Density plots of each score. ESR1, ERBB2, PGR, LUMINAL, PROLIFERATION.

5 scores were computed to classify the patients:

ESR1 status: The distribution of gene ESR1 exhibited bimodality (FIG. 1). The two modes identify ESR1 low and ESR1 high patients. Package "mclust" was used to fit a mixture of normal distributions with 2 components and obtain the posterior probability that each patient belongs to the ESR1 low and ESR1 high components. A patient was considered ESR1 low if the posterior probability of belonging to this group was bigger than 80%. The same criterion was used for ESR1 high. When a patient was neither ESR1 high nor ESR1 low it was considered ESR1 intermediate.

Luminal status: For each patient a luminal score was computed by averaging the expression of all genes hi the luminal gene list. The distribution of the luminal score exhibited bimodality (FIG. 1), therefore the luminal status was described in the same way as the ESR1 status.

Proliferation status; For each patient a proliferation score was computed by averaging the expression of all genes in the luminal gene list. The means of proliferation genes did not exhibit bimodality (FIG. 1). Therefore half of the patients with lowest mean values were considered proliferation low. The rest were considered proliferation high.

PGR1 status: Gene PGR1 shows bimodality (FIG. 1), therefore the PGR1 status was described in the same way as the luminal status.

ERBB2 status: Gene ERBB2 does not show bimodality (FIG. 1). A sample was described as ERBB2 high when the ERBB2 expression value was higher than the ERBB2 mean plus one standard deviation of ERBB2. A sample was considered ERBB2 low otherwise.

Two luminal genes and one proliferation gene did not exist in the union cohort. They were not used. Every patient was assigned to a subtype according to PAM50.

There were 58 patients that could not be assigned to any subtype according to PAM50's classification. We did not find patients that belonged to more than one subtype.

Estrogen Receptor positive (ER+) tumors are defined as ESR1 high.

Triple Negative tumors are defined as ESR1, PGR1 and ERBB2 low.

For validation cohort II, patient classification was based on routine pathologist score as per diagnostic purposes. ER+ tumors were defined as tumors that express ESR1, Triple negative breast cancer tumors were defined as tumors that do not express ESR1, PR and HER2. HER2+ tumors were defined as 2+ and 3+ HER2 tumors according to pathologist score. There were 6 patients that could not be assigned to any of the above subtype. We did not find patients that belonged to more than one subtype.

Analysis of c-MAF Gene Expression Capacity to Predict Metastasis, Bone Metastasis, in a Cohort of Triple Negative Breast Cancer When analyzing bone metastasis in cohort I, 33 patients were removed due to having bone metastasis and another metastasis at the same time while only one time to event was reported. We are interested in the first metastasis and given that there was no way to know which of the metastasis was first we removed the patients with two metastatic site annotations from the analysis.

Once we identified the subtype of interest, Triple Negative (which includes a large proportion of basal-like breast cancers), and selected the patients we adjusted Cox Proportional Hazards Models (using the R function coxph from Packaged survival) to see if we could explain each phenotype (bone metastasis) through subtype and c-MAF expression, including the cohort as an adjustment variable. c-MAF had a statistically significant interaction effect with subtype (p=0.043). This told us that the association between c-MAF and survival differed significantly according to the patient subtype. Gene expression of c-MAF in Triple Negative breast cancer primary tumors correlated significantly with bone metastasis. (Table 3 and FIG. 2).

TABLE 3

Survival analysis

Figure 2:
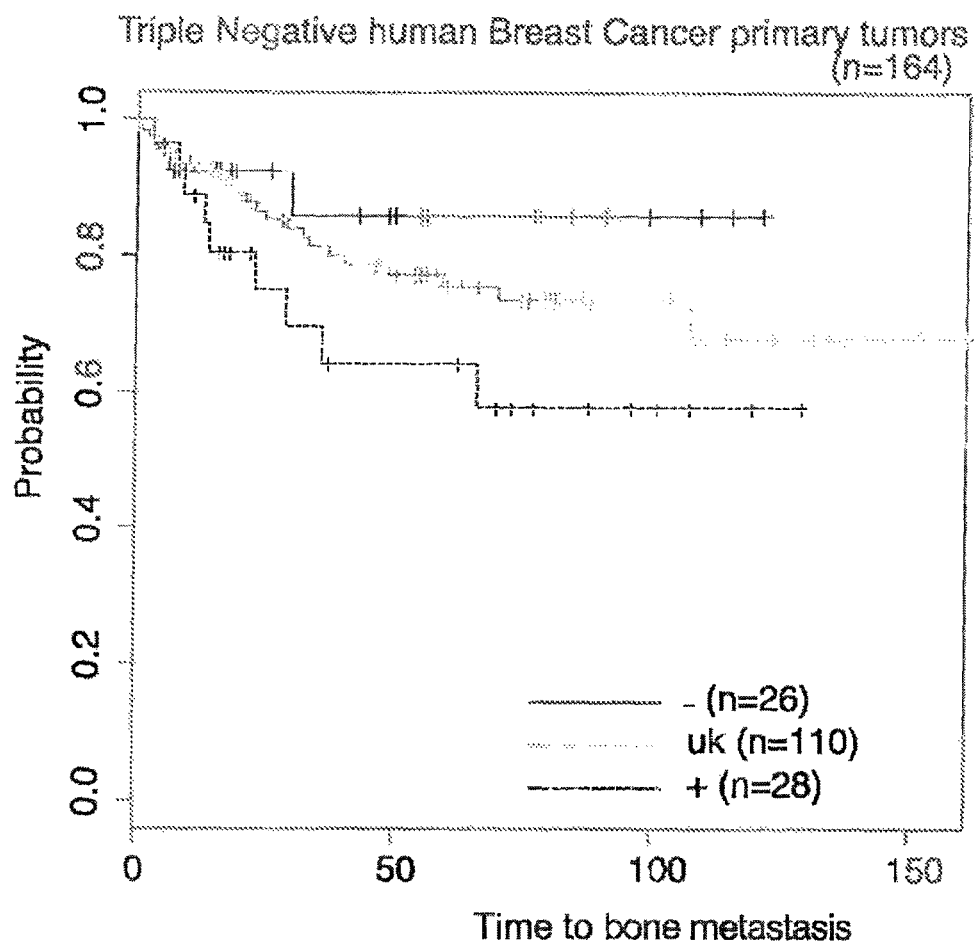
FIG. 2: Time to Bone metastasis Kaplan-Meier graphs for patients with Triple Negative (triple negative) breast cancer (p-value 0.04). Groups of each graph are defined by levels of c-MAF. (−), (uk) and (+) represent c-MAF expression levels in the following way: (−) (<mean−SD), (uk) (≥mean−SD and ≤mean+SD) and (+) (>mean+SD). SD stands for standard deviation.

| Subtype | n | Hazard ratio | 95% confidence interval | p-value |
| --- | --- | --- | --- | --- |
| Triple Negative | 164 | 1.444 | [1.016-2.054] | 0.040 | c-MAF can be used to determine the prognosis of the tendency to develop metastasis in a subject with Triple Negative (which includes a large proportion of basal-like breast cancers) breast cancer (Table 3 and FIG. 2).

Analysis of c-MAF Gene Expression Capacity to Predict Metastasis, Bone Metastasis, in ER+ Breast Cancer Tumors.

We focused on ER+ breast cancers (which includes a large proportion of luminal, including A and B subtypes, breast cancers). We adjusted Cox Proportional Hazards Models (using the R function coxph from Packaged survival) to see if we could explain each phenotype (bone metastasis, lung metastasis or brain metastasis) through c-MAF expression. Gene expression of c-MAF in ER+ breast cancer primary tumors correlated significantly with bone metastasis. (Table 4 and FIG. 3).

TABLE 4

Survival analysis

Figure 3:
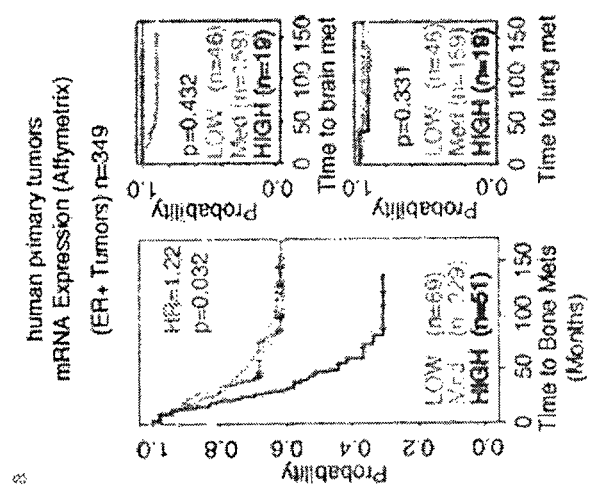
FIG. 3. c-MAF (mRNA) is a clinical biomarker for breast cancer bone metastasis in ER+ breast cancer.

| Subtype | n | Hazard ratio | 95% confidence interval | p-value |
| --- | --- | --- | --- | --- |
| Estrogen Receptor Positive | 349 | 1.22 | [1.014-1.473] | 0.032 | c-MAF can be used to determine the prognosis of the tendency to develop metastasis in a subject with ER+ breast cancers (which includes a large proportion of luminal, including A and B subtypes, breast cancers) (Table 4 and FIG. 3).

Validation that c-MAF is a clinical biomarker for breast cancer bone metastasis in cohort II by means of Immunohistochemistry, in particular in ER+ and TN c-MAF immunostaining was performed using 3 μm human BC tumor tissue sections, placed on plus charged glass slides in a Dako Link platform. After deparafinization, heat antigen retrieval was performed in pH6.1, 0.01 mol/L citrate-based buffered solution (Dako). Endogenous peroxidase was quenched. A rabbit polyclonal anti-MAF antibody was used for 30 minutes at room temperature, 1:100 dilution, followed by incubation with an anti-rabbit Ig dextran polymer coupled with peroxidase (Flex+, Dako). Sections were then visualized with 3,3'-diaminobenzidine (DAB) and counterstained with Hematoxylin.

c-MAF antibody sensitivity (1:100) had been calculated in a range of crescent dilutions of primary antibody from 1:10 to 1:1000. Specificity was determined using parental and c-MAF-overexpressing (plus c-MAF long/short) MCF7 and T47D human BC cells.

Formalin-fixed cell pellets were processed as described for IHC and results confirmed by western blot from whole lysates. Specificity was also shown in heterotopic MCF7 and c-MAF-overexpressing MCF7 xenoimplants in BALB-c nude mice. Sections from the same specimens incubated with normal rabbit IgG2 (IS600, Dako) instead primary antibodies were used as negative controls.

MAF immunostaining was scored by a computerized measurement. Nine representative images from each specimen were acquired at 10-nm wavelength intervals between 420 and 700 nm, using a DM2000 Leica microscope equipped with the Nuance FX Multispectral Imaging System (CRI Inc). Before acquiring a spectral dataset of an image, an autoexposure routine was performed while imaging a blank area of slides to determine the exposure time necessary to approximately 90% fill the device wells at each wavelength to compensate for variations in source intensity, filter transmission efficiency and camera sensitivity. A library of pure DAB and Hematoxylin dye colors was created and used to unmix the colors using the Nuance 1.6.4 software. A cube (stack of images taken at the different wavelengths) of reference was then acquired for each new case, followed by spectral imaging of three representative tissue fields using the same exposure times. After deconvolution of the images, the spectral data was flat fielded to compensate for unevenness in illumination and background was filtered. The positive signals were converted from transmission to optical density units by taking the negative log of the ratio of the sample divided by the reference cube using a Beer law conversion. A computer-aided threshold was set, which creates a pseudo-color image that highlights all of the positive signals. Analysis yielded quantitative data of c-MAF from the average intensity of regions of interest. Only the nuclei of epithelial cells (normal and malignant), but not stromal cells or lymphocytes, were automatically detected by setting distinct size threshold and confirmed by a pathologist. Each case was calculated for the mean value of the signal intensity of all regions of interest for statistical analysis. The output of the computerized measurement produced a continuous data ranging from 56 to 70,367 for c-MAF expression.

Representative c-MAF immunostainings (IHC) of primary breast cancer tissues are shown (FIG. 4a). Case 1 represents c-MAF negative tumors (OD<1000). Case 2 and 3 are c-MAF positive tumors (OD >1000 and >25000 respectively) (FIG. 4a). Following, a plot depicting c-MAF protein expression (computerized measurement and expressed as optical density arbitrary units, OD) in a cohort of 380 primary breast cancer tumors summarized all tumor IHC signal quantitation. Tumors were segregated according to BC subtype (ER+, HER2+ and TN)(FIG. 4b). Based on the above IHC stainings, a Kaplan-Meier curve of disease-free survival (FIG. 4c) and bone metastasis-free survival (FIG. 4d) in the cohort of 380 primary breast cancer tumors (stage I, II and III) according to the c-MAF (Positive or negative) stratification was draw. The diagnostic performance of c-MAF in different BC subtypes (ER+, HER2+ and TN) (FIG. 4e) was also calculated. Baseline characteristics and Cox multivariate analysis were performed as defined above to determine the influence on c-MAF as a stratification criteria for bone metastasis prediction in primary breast cancer tumors of any other clinical pathological parameter (Table 5 and 6). As shown, there is no significant association with any other parameter with the exception of having more than 9 lymph node positive.

TABLE 5

Baseline Characteristics According to c-MAF IHC expression

| Characteristics | Complete series (n = 380) | | c-MAF non-overexpression (n = 309) | | c-MAF overexpression (n = 71) | | P |
|---|---|---|---|---|---|---|---|
| | No. of patients | % | No. of patients | % | No. of patients | % | |
| Age (median, range) | 58, 26-90 | | 58, 31-90 | | 59, 26-90 | | |
| Menopausal status | | | | | | | 0.726 |
| Premenopausal | 111 | 29.2 | 89 | 28.8 | 22 | 31.0 | |
| Postmenopausal | 269 | 70.8 | 220 | 71.2 | 49 | 69.0 | |
| Tumor size, mm | | | | | | | 0.447 |
| ≤20 | 209 | 55.0 | 168 | 54.4 | 41 | 57.7 | |
| 21-50 | 113 | 35.0 | 112 | 36.2 | 21 | 29.6 | |
| >50 | 38 | 10.0 | 29 | 9.4 | 9 | 12.7 | |
| Tumor grade | | | | | | | 0.782 |
| I | 67 | 17.6 | 56 | 18.1 | 11 | 15.5 | |
| II | 184 | 48.4 | 150 | 48.5 | 34 | 47.9 | |
| III | 129 | 33.9 | 103 | 32.9 | 26 | 36.6 | |
| Lymph nodes | | | | | | | 0.622 |
| None | 227 | 59.7 | 182 | 58.9 | 45 | 63.4 | |
| 1-3 | 90 | 23.7 | 78 | 25.2 | 12 | 16.9 | |
| 4-9 | 40 | 10.5 | 31 | 10.0 | 9 | 12.7 | |
| >9 | 23 | 5.1 | 18 | 5.8 | 5 | 7.0 | |
| Estrogen receptor status | | | | | | | 0.807 |
| Negative | 97 | 25.5 | 78 | 25.2 | 19 | 26.8 | |
| Positive | 283 | 74.5 | 231 | 74.8 | 52 | 73.2 | |
| Progesterone receptor status | | | | | | | 0.481 |
| Negative | 133 | 35.0 | 106 | 34.3 | 27 | 38.0 | |
| Positive | 247 | 65.0 | 203 | 65.7 | 44 | 62.0 | |
| HER2 status | | | | | | | 0.358 |
| Negative | 303 | 79.7 | 243 | 78.6 | 60 | 84.5 | |
| Positive | 77 | 20.3 | 66 | 21.4 | 11 | 15.5 | |
| Proliferation (Ki-67) | | | | | | | 0.105 |
| Low proliferation (<15%) | 278 | 73.2 | 232 | 75.1 | 46 | 64.8 | |
| High proliferation (≥15%) | 102 | 26.8 | 77 | 24.9 | 25 | 35.2 | |

Abbreviations:
HER2, human epidermal growth receptor 2

TABLE 6

BDFS analysis in patients with c-MAF IHC expression

| Variable | Univariate (n = 380) | | | Multivariate (n = 380) | | |
|---|---|---|---|---|---|---|
| | HR | 95% CI | P | HR | 95% CI | P |
| Menopausal status | | | 0.818 | | | — |
| Premenopausal | — | | | — | | |
| Postmenopausal | 1.00 | 0.42 to 1.97 | | — | — | |
| Tumor size, mm | 0.91 | | 0.067 | | | — |
| ≤20 | | | | | | |
| 21-50 | 1.00 | 1.08 to 5.41 | | — | — | |
| >50 | 2.42 | 0.76 to 7.70 | | — | — | |
| Tumor grade | 2.41 | | 0.062 | | | 0.130 |
| I | | | | 1.00 | | |
| II | 1.00 | 0.81 to 45.8 | | 4.41 | 0.58 to 33.503 | |
| III | 5.71 | 0.74 to 44.27 | | 2.61 | 0.31 to 21.57 | |
| Lymph nodes | | | 0.005 | | | 0.006 |
| None | 1.00 | | | 1.00 | | |
| 1-3 | 1.59 | 0.65 to 3.90 | | 1.47 | 0.59 to 3.68 | |
| 4-9 | 0.88 | 0.20 to 4.09 | | 0.96 | 0.21 to 4.35 | |
| >9 | 6.72 | 2.64 to 17.10 | | 6.89 | 2.56 to 18.56 | |
| Hormonal receptor status | | | 0.124 | | | |
| Negative | 1.00 | | | — | | |
| Positive | 0.54 | 0.25 to 1.15 | | — | | |
| HER2 status | | | 0.775 | | | — |
| Negative | 1.00 | | | — | | |
| Positive | 0.87 | 0.33 to 2.28 | | — | | |
| Proliferation (Ki-67) | | | 0.029 | | | 0.133 |
| Low proliferation (<15%) | 1.00 | | | 1.00 | | |

TABLE 6-continued

BDFS analysis in patients with c-MAF IHC expression

| Variable | Univariate (n = 380) | | | Multivariate (n = 380) | | |
| --- | --- | --- | --- | --- | --- | --- |
| | HR | 95% CI | P | HR | 95% CI | P |
| High proliferation (≥15%) | 2.32 | 1.11 to 4.82 | | 1.85 | 0.84 to 4.06 | |
| c-MAF (IHC) | | | <0.001 | | | 1e−05 |
| Non-overexpression | 1.00 | | | 1.00 | | |
| Overexpression | 5.24 | 2.53 to 10.87 | | 5.62 | 2.65 to 11.95 | |

Abbreviations:
BDFS, bone disease free survival;
HR, hazard ratio;
CI, confidence interval;
HER2, human epidermal growth factor receptor 2

Functional Validation of c-MAF in a Bone Metastasis Colonization Assay

The causal contribution of c-MAF has been functionally validated in a bone metastasis colonization assay using preclinical experimental xenograft mouse models. ER+ human breast cell lines, namely MCF7 and T47D labeled with the GFP/luciferase vector were used and inoculated into immunodeficient mice by means of intra-ventricular or tail-vein injection. These mice must carry estrogen pellets to warrant hormone supply for tumor cells contiguous in the xenograft model.

The standard approach was loss and gain of function experiments. c-MAF was expressed or silenced in MCF7 parental, T47D or highly bone metastatic cell derivatives that selected for high levels of c-MAF expression (BoM2) to validate its function in metastasis (FIGS. 5 and 6). c-MAF gene bone metastasis functions were determined in vivo using bioluminescence detection of metastatic cells inoculated in the mouse intracardiacally. We generated shRNA-mediated c-MAF knockdown in BoM2 cells that reduced the level of endogenous c-MAF by more than 80%, and could be rescued by c-MAF exogenous overexpression (FIG. 6). Moreover, we also generated cells expressing each c-MAF isoform individually or collectively, and tested its functionality as a transcriptional activator in reporter assays (FIG. 6). Parental MCF7 cells, Parental T47D cells with or without c-MAF (short and long isoforms collectively or independently) and BoM2 bone metastatic MCF7 cell derivatives depleted or rescued for the expression of c-MAF (short and long isoforms) were injected into the left ventricle of a mouse and bone colonization was analyzed by in vivo bioluminescent imaging. In all cases, the corresponding controls were inoculated (FIGS. 5, 6, 7 and 8).

Figure 5A:
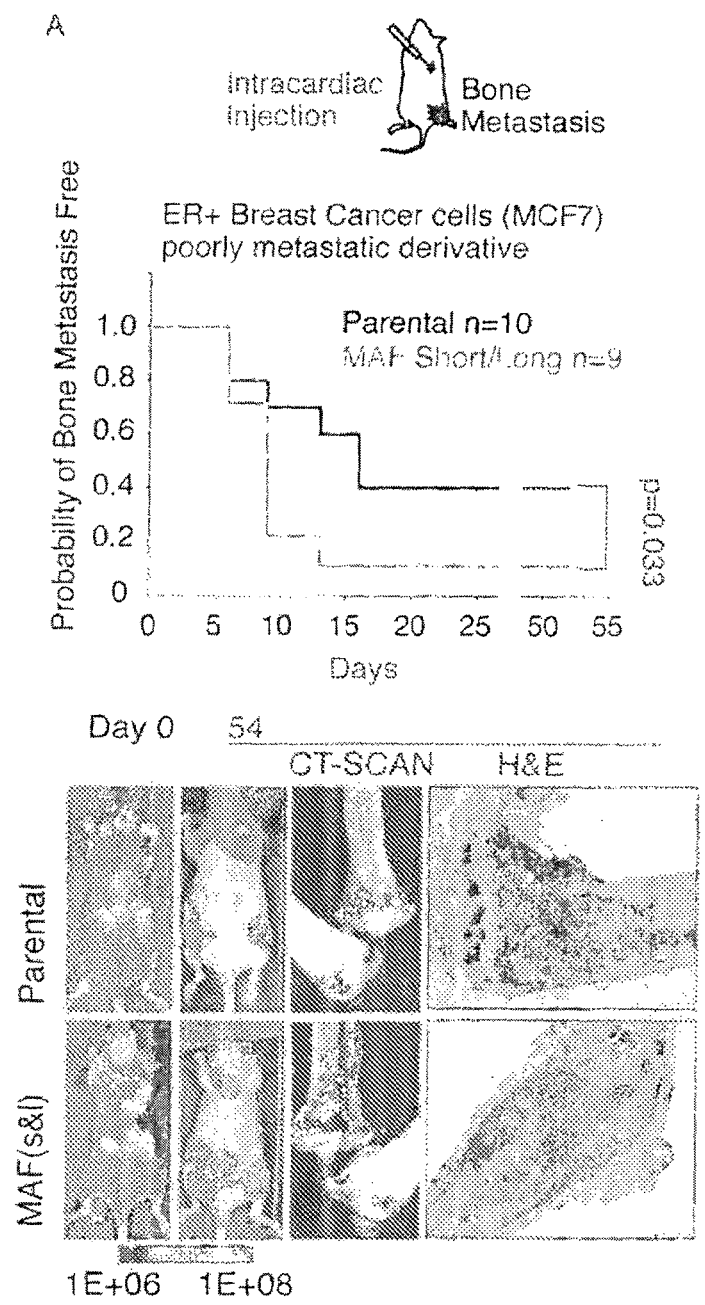
Figure 5B:
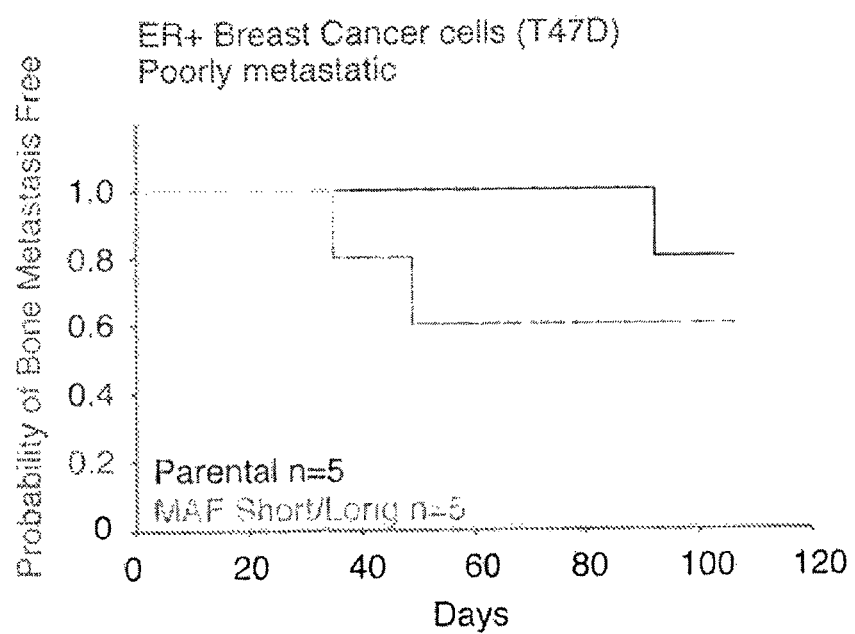
Figure 5C:
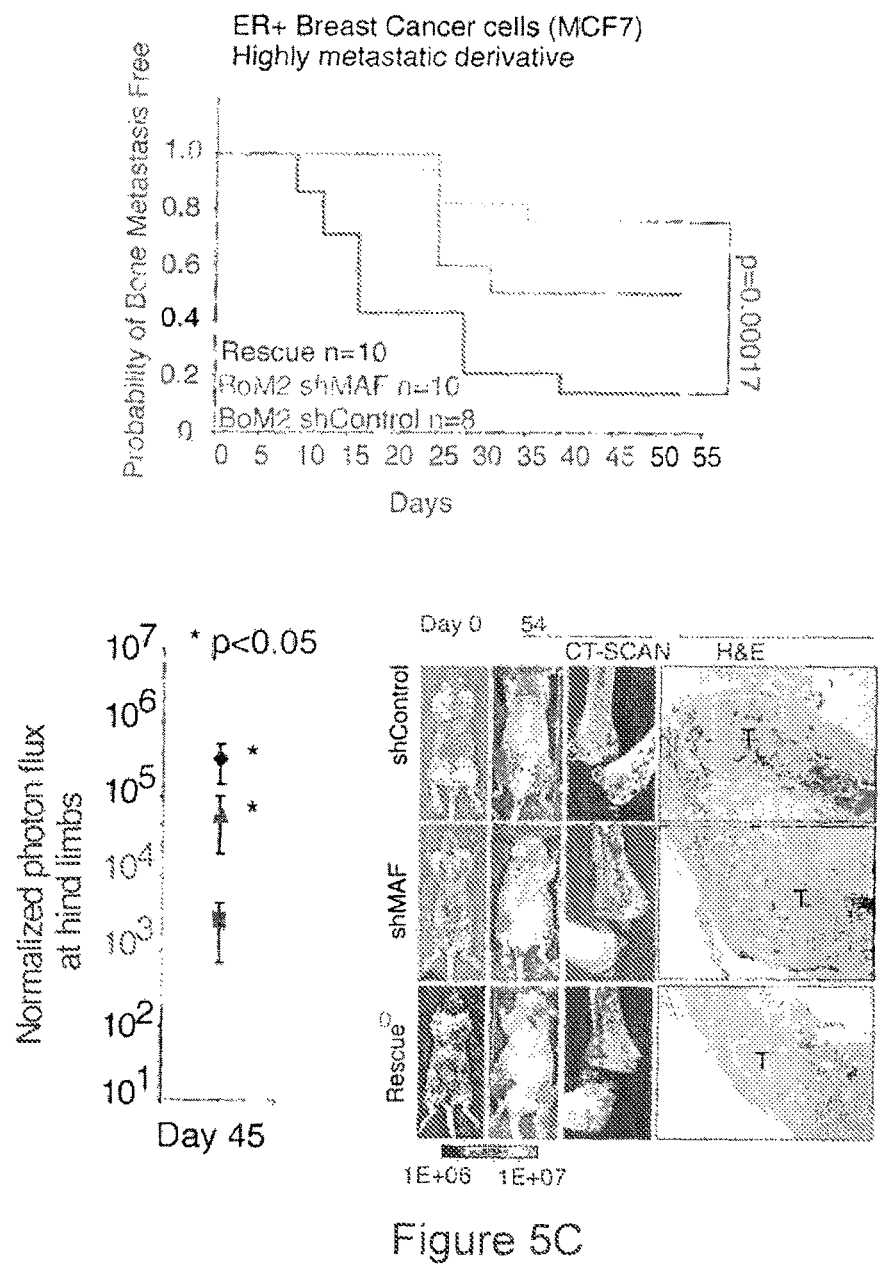
Figure 5D:
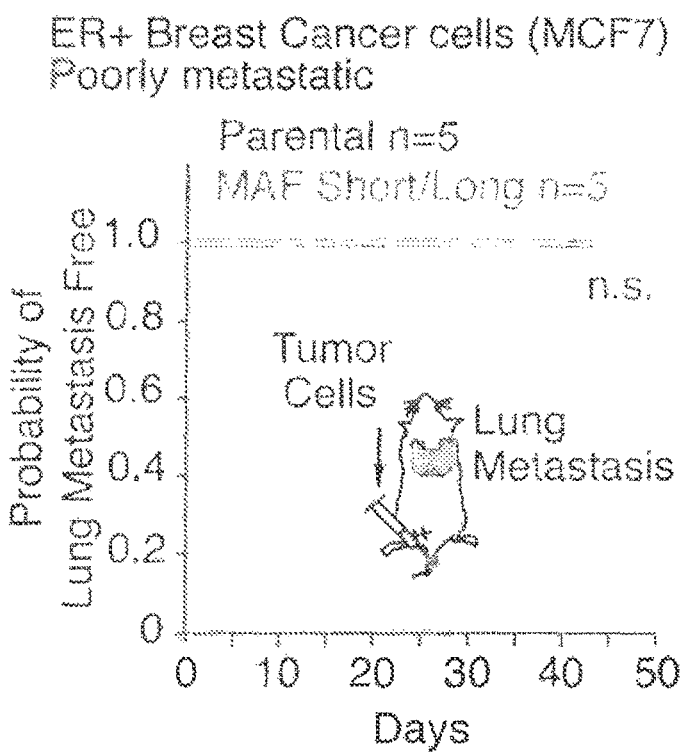

Only 23% of mice inoculated with BoM2 c-MAF knockdown cells developed bone metastasis, compared to 90% in shControl BoM2 cells (i.e. c-MAF expressing) or 50% in the rescue group (FIGS. 5c and 8) at day 52 post injection. Bone metastasis reduction in c-MAF-depleted cells was accompanied with a sharp reduction in the extent of the hind limb osteolytic lesions (FIG. 5c). On the contrary, MAF overexpression, either each isoform individually or collectively, enhanced the capacity and the metastatic burden of ER+ breast cancer cells (MCF7 and T47D) to metastasize the bone after intracardiac injection (FIG. 5a,b and 7). Interestingly, MAF expressing cells render more osteolytic bone metastasis compared to parental MCF7 cells (FIGS. 5a, 6 and 9a), and increased the number of tartrate-resistant acid phosphatase (TRAP+) osteoclast at the metastatic lesion perimeter could be detected (FIG. 9b,c,d). MAF overexpression did not increase the intrinsic proliferative activity of parental MCF7 cells when implanted subcutaneously (FIG. 10). High levels of MAF expression did not support lung colonization (FIG. 5d).

The loss and gain of function experiments altogether with the clinical validation in breast cancer primary tumors have led to the functional validation of c-MAF as a prognostic and predictive marker and causal target gene in bone metastasis processes in Estrogen Receptor Positive (including luminal A and B molecular subtypes) and Triple Negative (including basal-like molecular subtype) breast cancer subtypes.

MAF Mediates Osteolytic Bone Metastasis Through Tumor Cell Stimulation of Osteoclast Differentiation, For Example, Through The Transcriptional Control Of Pthlh Cytokine.

Without a direct activity of c-MAF in providing bone metastasis functions to breast cancer cells, c-MAF may instead transcriptionally control the activity of genes promoting homing and bone remodeling capabilities to colonize the bone. PTHLH expression was under the control of c-MAF. An observation confirmed by qPCR analysis (FIG. 11a). Further, patient breast cancer metastasis (GSE14020) growing in the bone retained c-MAF expression compared to metastasis elsewhere (FIG. 11b). Moreover, 77% of metastasis expressing MAF and PTHLH above the average were bone metastasis (FIG. 11b). PTHLH was identified as the factor responsible for humoral hypercalcaemia of malignancy. Moreover it has been shown to play a fundamental role in osteolytic bone metastasis due to stimulation, in part, of osteoclast differentiation. Indeed, conditioned media from cells expressing c-MAF enhanced the induction of osteoclast differentiation in vitro, a process that is prevented upon co-incubation with PTHLH antagonist peptide (7-34Aa, PTHLH-AN) (FIG. 11c).

To test whether PTHLH mediates c-MAF driven bone metastasis in breast cancer cells, we injected c-MAF expressing MCF7 breast cancer cells intracardiacally and evaluated its capacity to establish and grow bone metastasis in the presence or absence of PTHLH-AN during the span of 47 days. In order to block PTHLH activity in vivo, animals were administered, twice a day, with 6 μg of (7-34 Aa) PTHLH-AN dissolved in PBS. Control groups were treated with PBS. c-MAF expressing cells produce bone metastasis with similar penetrance, yet treatment with PTHLH-AN cause a dramatic reduction in the in the extent of the hind limb osteolytic lesions (FIG. 11d,e). This reduction was accompanied by a reduction in the number of osteoclast (TRAP+ cells) at the metastatic lesion perimeter (FIG. 11d,e). These results indicate that c-MAF drives breast cancer osteolytic bone metastasis. Moreover, PTHLH expression is a necessary factor for c-MAF driven osteolytic breast cancer bone metastasis. Finally, blockade of osteoclast differentiation process prevents c-MAF-driven breast cancer bone metastasis.

c-MAF Capacity to Predict Metastasis to the Bone is Dose-dependent

First, we evaluated whether c-MAF expression capacity to predict bone metastasis was dose-dependent.

The patients' information had been downloaded from GEO (Barrett et al. (2007)). The following set of data was used: union of GSE2603, GSE2034 and GSE12276. This union cohort had 560 patients. In order to remove systematic biases prior to merging, the expression measurements were converted to z-scores for all genes.

All statistical analyses were performed using Bioconductor (Gentleman R C et al. *Genome Biology*, 5:R80, 2004. URL http://genomebiology.com/2004/5/101R80).

We obtained a smooth estimate of the relationship between c-MAF expression and bone metastasis hazard ratio via a Cox regression model with quartic splines (smoothCoxph function in package phenoTest). The smoothCoxph function in package phenoTest Plots the Cox proportional hazard smoothed by gene expression level. Thus, builds a plot showing how hazard behaves over different levels of expression of a given gene. Confidence intervals are also provided (Usage: smoothCoxph (time, event, x, xlim, ylim, others . . . ). Arguments: time) variable where time to survival is stored; event) variable where survival event is stored; x) numeric containing the expression levels of a given gene; Xlim) xlim for the plot; Ylim) ylim for the plot; Others . . . ) other arguments that will be passed to plot.).

The relationship between c-MAF expression and bone metastasis hazard ratio via a Cox regression model with quartic splines can be seen in FIG. 12. All breast cancer tumors present in the union cohort, Estrogen Receptor positive breast cancer tumors in the union cohort and the triple negative tumors at the union cohort. The analysis was run and indicated the hazard ratio (HR) and p-value of c-MAF capacity to predict bone metastasis in tumors whose c-MAF expression level was above the average (named 0). 1 at the expression level indicates 1 standard deviation and then subsequently, etc.

We defined "high c-MAF" expressing breast cancer primary tumors as the group of tumors that express c-MAF above the average expression in a representative cohort of breast cancer primary tumors. We defined "low c-MAF" expressing breast cancer primary tumors as the group of tumors that express c-MAF below the average obtained in a representative cohort of breast cancer primary tumors.

In breast cancer tumors with high c-MAF expressing level, c-MAF expression predicts the risk of bone metastasis in a dose-dependent manner (FIG. 12). Similarly, in ER positive (including luminal A and B molecular subtypes) and Triple Negative (including basal-like molecular subtype) breast cancer subtypes we observed the same behavior (FIG. 12).

In conclusion, the higher the c-MAF expression level is, the higher the Hazard Risk for bone metastasis is in ER+ and TN breast cancer tumors that expressed c-MAF levels above the average of a representative set of breast cancer tumors.

We assayed in the validation cohort II to what extend the higher the dose of c-MAF the higher the risk of bone relapse. To this end we quantified c-MAF expression by immunohistochemistry (IHC) by means of determining the optical density of the staining using a computerized system as described above (FIG. 4*a,b*). c-MAF staining is specific of the tumor cells (FIG. 4*a*). Based on the staining we can observe two types of c-MAF positive breast cancer tumors (case 2 and 3, FIG. 4*a, b*). According to these two types of c-MAF IHC staining in c-MAF positive breast cancer tumors, we can separate them in two groups as they have a bimodal behavior (FIG. 13, left panel). Building on these two categories, we validated the observation that the higher the staining of c-MAF, the higher the risk of bone metastasis is (HR(bone mets)=19.45; p-value<0.001) and the earlier the bone metastasis occurs (FIG. 13, right panel).

c-MAF Capacity to Predict Early Bone Metastasis

Breast cancer tumors were classified between early (<5 years) and late (>5 years) recurrent tumors depending on the span of time between primary tumor detection and surgical resection and the time of observation of distant relapse. Indeed, under certain circumstances early distant relapse was even limited to a shorter time period. This classification is of clinical importance given that ER positive and negative tumors were described to behave differently in terms of early bone relapse. In detail, ER negative, including Triple Negative and Basal-like, tumors recur at early time points while ER positive tumors have the same tendency to recur at late and early time points (Knight W A, et al *Cancer Research* 1997: 37, 4669-4671, Goss P E *Nature Rev Cancer* 2010: 10, 871-877).

We evaluated whether c-MAF expression can predict early bone metastasis in breast cancer, in ER positive (including luminal A and B) and Triple negative (including basal-like) breast cancer primary tumors.

The patients' information had been downloaded from GEO. The following set of data was used: union of GSE2603, GSE2034 and GSE12276. This union cohort has 560 patients. In order to remove systematic biases prior to merging, the expression measurements were converted to z-scores for all genes. All statistical analyses were performed using Bioconductor.

We performed a Fisher's exact test for testing the independence of c-MAF and bone metastasis at the different time points. Proportions of the contingency table and Fisher's test p-values can be seen in FIG. 14.

We define "very high c-MAF" expressing breast cancer primary tumors as the group of tumors that express c-MAF above the average plus one standard deviation. We defined "low c-MAF" expressing breast cancer primary tumors as the group of tumors that express c-MAF below the average plus one standard deviation in a representative cohort of breast cancer primary tumors.

In breast cancer primary tumors, very high c-MAF levels (RNA or Protein) predict early bone metastasis (FIG. 14) both at 3 and 5 years post surgery of breast cancer primary tumors.

In particular, it is shown that in Estrogen Receptor Positive (including luminal A and B molecular subtypes), c-MAF levels (RNA or Protein) significantly define the proportion of tumors with early bone metastasis (FIG. 14) both 3 and 5 years post surgery, respectively.

In conclusion, high levels of c-MAF expression can be used to discriminate or predict breast cancer primary tumors that are at high risk of bone metastasis, including of early breast cancer bone metastasis.

Table 7 shows the prediction of bone metastasis, early bone metastasis and very early bone metastasis in breast cancer primary tumors (union of GSE2603, GSE2034 and GSE12276), Estrogen Receptor Positive (including luminal A and B molecular subtypes) breast cancer primary tumors and Triple Negative (including basal-like molecular subtype) breast cancer subtypes.

TABLE 7

| HR | | CI.low | CI.up | Pvalue |
|---|---|---|---|---|
| ER+ Breast Cancer primary tumors (c-MAF >) | | | | |
| Bone Metastasis | | 1.56 | 3.87 | 0.00017 |
| Early Bone Metastasis (<5 years) | | 1.20 | 3.20 | 0.00853 |
| Very Early Bone Metastasis (<3 years) | | 1.25 | 3.62 | 0.00694 |
| Triple Negative Breast Cancer primary tumors (c-MAF > Average, n = 96) | | | | |
| Bone Metastasis | | 1.15 | 3.97 | 0.02262 |
| Early Bone Metastasis (<5 years) | | 1.04 | 4.02 | 0.04534 |
| Very Early Bone Metastasis (<3 years) | | 1.09 | 3.87 | 0.03276 |

HR (Hazard Ratio), CI (Confidence Interval)

Amplification of the Chromosomal Region Located in 16q22-q24 Including c-MAF is Associated with Bone Metastasis We identified copy number alterations (CNA) in primary breast cancer specimens associated to risk of metastasis by means of an adaptation of the ACE algorithm (analysis of CNAs by expression data) (FIG. 15a). Among them, an amplified region located in chromosome 16q22-q24 was significantly (p<0.05) associated with risk of metastasis and included c-MAF, a gene whose increased expression was individually and independently associated with risk of bone metastasis in ER+ human Breast Cancer (HR=1.22 p=0.032, breast cancer primary tumor data set based on the union of GSE2603, GSE2034 and GSE12276). Similarly, when comparing Parental MCF7 (ER+) to Bone metastatic MCF7 derivatives (BoM2) cells by FISH(16q23) and Comparative Genomic Hybridization (CGH), we confirmed a gain in the 16q22-24 chromosomal region (FIG. 15b,c). A subset of parental cells (32.7%) carried this genomic amplification, yet the in vivo bone metastasis selection led this residual population to take over the rest (88.6%). Thus, we show that the 16q22-q24 is amplified in breast cancers with risk of metastasis, particularly bone metastasis and corroborated in vivo selected cells for their ability to metastasis to the bone.

Validation in Cohort II of the Prognostic Capacity to Predict Bone Metastasis of the 16q22-24 DNA Genomic Amplification by FISH Determination.

To further validate the ability of 16q22-24 genomic amplification to specifically predict bone metastasis risk, we analyzed 16q22-24 chromosome region genomic gain by means of FISH (we used a commercially available diagnostic probe that determines the 16q23 genomic region, IGH/MAF Abbot Vysis probe) in an independent validation set composed of 334 primary breast cancer specimens from patients with stage I, II or III BC and annotated follow up (Rojo F., Ann Oncol (2012) 23 (5): 1156-1164). Tissue microarrays were processed as per standard procedures. The slides were incubated with MAF (16q23) and IGH (1402) probe mixture (Abbot vysis probe). DAPI counterstain was applied and images were acquired with adequate microscope.

Kaplan-Meier curve of bone (FIG. 16a) metastasis-free or overall (FIG. 16b) survival in stage I, II, and III BC human primary tumor set (n=334) was determined. Patients were stratified according to 16q23 FISH negative and 16q23 FISH positive group based on cut-off of 2.5 16q23 copies per cell as an average, using 3 cores per tumor (FIGS. 16a and b).

Hazard ration (Bone Metastasis), specificity and sensitivity of the marker to predict bone metastasis was calculated. Baseline characteristics of the data set and Cox multivariate analysis for overall breast cancers were performed as described above (Table 8 and 9).

Kaplan-Meier curve of bone metastasis free survival for ER-positive (left) or triple negative (right) patients in I, II, and III BC human primary tumor set (n=250 and n=43 respectively) (FIG. 16c) were also determined. Patients were divided to 16q23 FISH negative and 16q23 FISH positive group based on cut-off of 2.5 for 16q23 copies per cell as an average, using 3 cores per tumor. Cox multivariate analysis for ER+ breast cancers were performed as described above (Table 10)

TABLE 8

Comparison of baseline characteristics by 16q23 (MAF) FISH > 2.5 copies per cell. Measured in 3 cores per tumor.
(*Percentages computed over the patients without missing values on this variable)

| | 16q23 (MAF) FISH ≤2.5 (n = 262) | 16q23 (MAF) FISH >2.5 (n = 75) | p-value |
|---|---|---|---|
| Median age (IQR), years | 58 (17) | 58 (21) | 0.32 |
| Postmenopausal (%) | 187 (71.4) | 46 (61.3) | 0.10 |
| ER+ (%) | 200 (76.4) | 53 (70.7) | 0.32 |
| PR+ (%) | 172 (65.7) | 45 (60.0) | 0.37 |
| High grade (%) | 83 (31.7) | 35 (36.7) | 0.016 |
| Ki67* (%) | 55 (22.3) | 29 (41.4) | 0.0014 |
| Subtype* (%) | | | 0.58 |
| Luminal | 151 (66.5) | 39 (66.1) | |
| Her2 | 44 (19.4) | 9 (15.3) | |
| T N | 32 (14.1) | 11 (18.6) | |
| HER2+ (%) | 51 (19.5) | 13 (17.3) | 0.68 |
| pT (%) | | | 0.21 |
| 1 | 164 (62.6) | 41 (54.7) | |
| 2-4 | 98 (37.4) | 34 (45.3) | |
| pN (%) | | | 0.27 |
| 0 | 163 (62.2) | 42 (56.0) | |
| 1-2 | 89 (34.0) | 27 (36.0) | |
| 3 | 10 (3.8) | 6 (8.0) | |

TABLE 9

Stage I, II, III Breast Cancer
Cox regression of time to bone metastasis as first site of relapse.
16q23(MAF) FISH > 2.5 copies per cell.
Measured 3 cores per tumor

| | Univariate | | Multivariate | |
|---|---|---|---|---|
| Variable | HR (95% CI) | p-value | HR (95% CI) | p-value |
| 16q23Fish > 2.5 | 27.2 (8.1-91.0) | <0.0001 | 26.1 (7.8-87.4) | <0.0001 |
| Ki67 | 2.8 (1.2-6.4) | 0.014 | | |
| pT | | | | |
| 1 | Ref | | Ref | |
| 2-4 | 2.4 (1.1-5.3) | 0.035 | 2.1 (0.9-4.6) | 0.077 |
| pN | | | | |
| 0 | Ref | | | |
| 1-2 | 1.4 (0.6-3.3) | 0.44 | | |
| 3 | 4.8 (1.5-15.1) | 0.0076 | | |

TABLE 10

Stage I, II, III ER+ Breast Cancer
Cox regression of time to bone metastasis as first site of relapse.
16q23(MAF) FISH > 2.5 copies per cell.
Measured 3 cores per tumor

| Variable | Univariate | | Multivariate | |
|---|---|---|---|---|
| | HR (95% CI) | p-value | HR (95% CI) | p-value |
| 16q23 Fish | 53.5 (7.0-406.7) | 0.0001 | 49.5 (6.5-376.3) | 0.0002 |
| pT | | | | |
| 1 | Ref | | Ref | |
| 2-4 | 3.4 (1.2-9.4) | 0.018 | 2.8 (1.0-7.9) | 0.047 |
| pN | | | | |
| 0 | Ref | | | |
| 1-2 | 2.6 (0.8-8.0) | 0.094 | | |
| 3 | 6.8 (1.6-28.8) | 0.0089 | | |

Receiver Operating Characteristic (ROC) curves for diagnostic performance of 16q23 amplification in overall (FIG. 16d) and ER+ breast cancer (FIG. 16e) were also calculated to estimate the diagnostic performance. In a ROC curve the true positive rate (Sensitivity) is plotted in function of the false positive rate (100-Specificity) for different cut-off points. Each point on the ROC curve represents a sensitivity/specificity pair corresponding to a particular decision threshold.

In summary, the 16q22-24 amplification measured herein using a 16q23 FISH probe significantly predicts risk of bone metastasis in breast cancer primary tumors, particularly in TN and ER+ breast cancer subtypes.

Determination of Treatment Regimen in Subject Diagnosed with Triple Negative Breast Cancer Based on c-MAF Expression Levels A tumor tissue sample is obtained from a subject diagnosed as having triple negative breast cancer. The sample is sectioned into thin slices of tissue and embedded in paraffin. Each paraffin section is mounted on a slide. The slides are incubated with anti-MAF antibody. For visualization and detection of antibodies bound to MAF, antibodies conjugated with fluorescent dye are used. The slides are visualized by providing excitation beams to the fluorescent dyes. Images of fluorescent signals are taken by fluorescent microscopes. The relative expression level of c-MAF in the tumor sample is obtained by comparing the fluorescent signal in the tumor sample to that of a reference sample. The intensity in the tumor sample is correlated with the intensity in the reference sample, wherein a higher intensity in the tumor sample compared to the reference sample correlates with an increased risk of the subject having primary breast cancer metastasis to the bone. Alternatively, 16q22-24 locus, 16q23 locus or c-MAP gene amplification or translocation determined using an in situ hybridization technique or similar Based on the prognosis of increased risk of bone metastasis, the subject is administered the anti-RANKL antibody Denosumab as a prophylactic treatment for bone metastasis. 120 mg of Denosumab is administered to the subject subcutaneously (SC) once monthly for 6 months. 120 mg SC every 3 months for the next 4 and a half years. Oral calcium (at least 500 mg) and vitamin D (at least 400 IU) for 5 years. After 5 years, the subject is free of any evidence of bone-metastasis. Based on the prognosis of not increase risk of bone metastasis the patient is not administered this anti-RANKL antibody.

It is understood that the examples and embodiments described herein are for illustrative purposes only and that various modifications or changes in light thereof will be suggested to persons skilled in the art and are to be included with the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

What is claimed is:

1. An in vitro method for diagnosing a subject with an increased risk of bone metastasis or recurrence of a triple negative (including basal-like) breast cancer in a subject suffering said cancer and treating said subject to inhibit or prevent said bone metastasis or recurrence, comprising detecting amplification and/or gain of the c-MAF gene in a sample of said subject relative to a reference gene copy number, wherein an amplification and/or gain of the c-MAF gene with respect to said reference gene copy number is indicative of increased risk of developing bone metastasis or recurrence, and administering a therapeutically effective amount of a c-MAF inhibitor, a therapy aiming to prevent and/or treat bone metastasis selected from the group consisting of an mTor inhibitor, a Src kinase inhibitor, a COX-2 inhibitor, a CCR-5 antagonist and/or Radium-223, and/or an agent capable of avoiding and/or preventing bone degradation to said subject with an increased risk of bone metastasis or recurrence.

2. An in vitro method for diagnosing a subject with an increased risk of bone metastasis or recurrence of a triple negative (including basal-like) breast cancer in a subject suffering said cancer and treating said subject to inhibit or prevent said bone metastasis or recurrence, comprising detecting translocation of the c-MAF gene in a sample of said subject, wherein a translocation of the c-MAF gene is indicative of an increased risk of developing bone metastasis or recurrence, and administering a therapeutically effective amount of a c-MAF inhibitor, a therapy aiming to prevent and/or treat bone metastasis selected from the group consisting of an mTor inhibitor, a Src kinase inhibitor, a COX-2 inhibitor, a CCR-5 antagonist and/or Radium-223, and/or an agent capable of avoiding and/or preventing bone degradation to said subject with an increased risk of bone metastasis or recurrence.

3. The method according to any one of claims 1-2, wherein the bone metastasis is osteolytic metastasis.

4. An in vitro method for predicting the clinical outcome of a subject suffering triple negative (including basal-like) breast cancer and further treating said subject, comprising detecting amplification and/or gain of the c-MAF gene in a sample of said subject relative to a reference gene copy number, wherein an amplification and/or gain of the c-MAF gene with respect to said reference gene copy number is indicative of a poor clinical outcome, and administering a therapeutically effective amount of a c-MAF inhibitor, a therapy aiming to prevent and/or treat bone metastasis selected from the group consisting of an mTor inhibitor, a Src kinase inhibitor, a COX-2 inhibitor, a CCR-5 antagonist and/or Radium-223, and/or an agent capable of avoiding and/or preventing bone degradation to said subject.

5. An in vitro method for predicting the clinical outcome of a subject suffering from triple negative (including basal-like) breast cancer and further treating said subject comprising detecting translocation of the c-MAF gene in a sample of said subject, wherein a translocation of the c-MAF gene is indicative of a poor clinical outcome, and administering a therapeutically effective amount of a c-MAF inhibitor, a therapy aiming to prevent and/or treat bone metastasis selected from the group consisting of an mTor inhibitor, a Src kinase inhibitor, a COX-2 inhibitor, a CCR-5 antagonist and/or Radium-223, and/or an agent capable of avoiding and/or preventing bone degradation to said subject.

6. The method of either of claims 2 and 5, wherein locus 16q23 or 16q22-q24 is translocated.

7. The method of any of claim 2 or 5, wherein locus 16q23 or 16q22-q24 is translocated to chromosome 14 at locus 14q32.

8. The method of any of claim 2 or 5, comprising further determining if the c-MAF gene is amplified/gained in the sample of the subject suffering said cancer relative to a reference gene copy number wherein an amplification and/or gain of the c-MAF gene with respect to said reference gene copy number is indicative of increased risk of developing bone metastasis.

9. The method according to any of claim 1, 2, 4 or 5, wherein the amplification and/or gain and translocation of the c-MAF gene is determined by means of determining the amplification or translocation of the locus 16q23 or 16q22-q24.

10. The method according to any of claim 1, 2, 4, or 5, wherein the amplification and/or gain or the translocation of the c-MAF gene is determined by means of using a c-MAF gene-specific probe.

11. The method according to any of claim 1, 2, 4, or 5, wherein the reference gene copy number is the gene copy number in a tumor tissue sample of triple negative breast cancer from a subject who has not suffered metastasis.

12. The method of any of claim 1, 2, 4 or 5, comprising further determining if the subject sample is polyploid for the c-MAF gene.

13. The method according to claim 1, 2, 4 or 5, wherein said c-MAF inhibitory agent is selected from the group consisting of a c-MAF specific siRNA, a c-MAF specific antisense oligonucleotide, a c-MAF specific ribozyme, a c-MAF inhibitory antibody or nanobody, a dominant negative c-MAF variant, a compound from Table 1 or from Table 2, catalytic RNAs, DNA enzymes, inhibitory antibodies, inhibitory peptides, a c-MAF specific small molecule, a c-MAF specific antibody, a c-MAF specific antibody-like molecule, a c-MAF specific structurally constrained (cyclical) peptide, a c-MAF specific stapled peptide, or a c-MAF specific alphabody.

14. The method according to claim 1, 2, 4 or 5, wherein the agent preventing the bone degradation is selected from the group consisting of a bisphosphonate, a RANKL inhibitor, a PTH or a PTHLH inhibitor or a PRG analog, strontium ranelate, a DKK-1 inhibitor, a dual MET and VEGFR2 inhibitor, an estrogen receptor modulator, calcitonin, Radium-223 and a cathepsin K inhibitor.

15. The method according to claim 14, wherein the RANKL inhibitor is selected from the group consisting of a RANKL specific antibody, a RANKL-specific nanobody and osteoprotegerin, the bisphosphonate is zoledronic acid, the dual MET and VEGFR2 inhibitor is Cabozantinib, and/or the Radium-223 is alpharadin.

16. The method according to claim 15, wherein the RANKL specific antibody is denosumab and/or the RANKL specific nanobody is ALX-0141.

17. The method of any one of claim 1, 2, 4 or 5, wherein the mTor inhibitor is Everolimus, the Src kinase inhibitor is dasatinib and/or a second treatment is used in combination with the COX-2 inhibitor.

18. The method of claim 1, 2, 4 or 5, wherein the c-MAF amplification and/or gain or the translocation is quantified by means of western blot, ELISA, FISH, immunohistochemistry or a protein array.

19. The method of claim 1 or 2, wherein the subject is diagnosed with an increased risk of bone metastasis.

* * * * *